US010954193B2

(12) United States Patent
Lee et al.

(10) Patent No.: US 10,954,193 B2
(45) Date of Patent: Mar. 23, 2021

(54) SUBSTITUTED INDOLE MCL-1 INHIBITORS

(71) Applicant: Vanderbilt University, Nashville, TN (US)

(72) Inventors: Taekyu Lee, Brentwood, TN (US); Kwangho Kim, Nashville, TN (US); Plamen P. Christov, Mount Juliet, TN (US); Johannes Belmar, Nashville, TN (US); Jason P. Burke, Houston, TX (US); Edward T. Olejniczak, Nashville, TN (US); Stephen W. Fesik, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/975,854

(22) Filed: May 10, 2018

(65) Prior Publication Data
US 2018/0258039 A1   Sep. 13, 2018

Related U.S. Application Data

(63) Continuation of application No. 14/914,307, filed as application No. PCT/US2014/053148 on Aug. 28, 2014, now Pat. No. 10,005,728.

(60) Provisional application No. 61/871,280, filed on Aug. 28, 2013.

(51) Int. Cl.
*C07D 209/26* (2006.01)
*A61K 31/4045* (2006.01)
*C07D 401/14* (2006.01)
*C07D 401/04* (2006.01)
*C07D 403/04* (2006.01)
*C07D 413/04* (2006.01)
*C07D 209/24* (2006.01)
*A61K 31/404* (2006.01)
*A61K 31/4155* (2006.01)
*A61K 31/422* (2006.01)
*A61K 31/4439* (2006.01)
*A61K 31/5377* (2006.01)
*A61K 45/06* (2006.01)

(52) U.S. Cl.
CPC .......... *C07D 209/26* (2013.01); *A61K 31/404* (2013.01); *A61K 31/4045* (2013.01); *A61K 31/4155* (2013.01); *A61K 31/422* (2013.01); *A61K 31/4439* (2013.01); *A61K 31/5377* (2013.01); *A61K 45/06* (2013.01); *C07D 209/24* (2013.01); *C07D 401/04* (2013.01); *C07D 401/14* (2013.01); *C07D 403/04* (2013.01); *C07D 413/04* (2013.01)

(58) Field of Classification Search
CPC .................................................. C07D 209/26
See application file for complete search history.

(56) References Cited

U.S. PATENT DOCUMENTS

| | | | |
|---|---|---|---|
| 4,703,053 A | 10/1987 | Connor et al. | |
| 4,980,368 A | 12/1990 | Thielke et al. | |
| 4,994,477 A | 2/1991 | Kempf et al. | |
| 5,324,725 A | 6/1994 | Jasserand et al. | |
| 5,436,264 A | 7/1995 | Pfister et al. | |
| 6,500,853 B1 * | 12/2002 | Seehra | C07D 209/18 514/339 |
| 6,787,651 B2 | 9/2004 | Stolle et al. | |
| 2003/0109533 A1 | 6/2003 | Lavielle et al. | |
| 2005/0124675 A1 | 6/2005 | Hsich et al. | |
| 2009/0054402 A1 | 2/2009 | Wang et al. | |
| 2009/0270497 A1 | 10/2009 | Buggy | |
| 2010/0009986 A1 | 1/2010 | Zemolka et al. | |
| 2010/0009991 A1 | 1/2010 | Terasaka et al. | |
| 2011/0263599 A1 | 10/2011 | Song et al. | |
| 2012/0172285 A1 | 7/2012 | Walensky et al. | |
| 2014/0005386 A1 | 1/2014 | Doemling | |
| 2015/0336925 A1 | 11/2015 | Lee et al. | |

FOREIGN PATENT DOCUMENTS

| | | |
|---|---|---|
| EP | 639573 | 2/1995 |
| EP | 2161266 | 3/2010 |
| JP | S62181252 A | 8/1987 |
| JP | 3739432 | 1/2006 |
| JP | 2013537191 A | 9/2013 |
| WO | WO 9742188 | 11/1997 |
| WO | WO 9810778 | 3/1998 |
| WO | 2006034391 A2 | 3/2006 |
| WO | WO 2007112322 | 10/2007 |

(Continued)

OTHER PUBLICATIONS

Hsieh, et al. Document No. 143:43770, retrieved from STN; entered in STN on Jun. 10, 2005.*
Leow, et al., Document No. 146:287658, retrieved from STN; 2007.*
Casey, et al. Document No. 166:272475, retrieved from STN; 2011.*
Beigelman, et al. Document No. 149:307661, retrieved from STN; entered in STN on Aug. 21, 2008.*
Seehra, et al. Document No. 138:55866, retrieved from STN; entered in STN on Jan. 2, 2003.*
Andreani, et al. Document No. 116:75869, retrieved from STN; entered in STN on Mar. 6, 1992.*

(Continued)

*Primary Examiner* — Shawquia Jackson
(74) *Attorney, Agent, or Firm* — Michael Best & Friedrich LLP

(57) ABSTRACT

The present application, among other things, provides compounds that are capable of inhibiting the activity of anti-apoptotic Bcl-2 family proteins, for example, myeloid cell leukemia-1 (Mcl-1) protein. The present invention also provides pharmaceutical compositions as well as methods for using provided compounds for treatment of diseases and conditions (e.g., cancer) characterized by the over-expression or dysregulation of Mcl-1 protein. In some embodiments, a provided compound has the structure of formula I. In some embodiments, a provided compound has the structure of formula II.

19 Claims, No Drawings

(56) References Cited

FOREIGN PATENT DOCUMENTS

| WO | WO 2010123507 | 10/2010 |
|---|---|---|
| WO | WO 2011157668 | 12/2011 |
| WO | WO 2013112878 | 8/2013 |
| WO | WO 2014047427 | 3/2014 |
| WO | WO 2015031608 | 3/2015 |

OTHER PUBLICATIONS

EP14839887.8 Extended European Search Report dated May 30, 2017 (13 pages).
EP14839887.8 Extended European Search Report dated Sep. 5, 2017 (11 pages).
PCT/US2013/060881 International Search Report and Written Opinion dated May 5, 2014 (11 pages).
PCT/US2014/053148 International Search Report and Written Opinion dated Jan. 27, 2015 (12 pages).
PCT/US2014/053148 International Preliminary Report on Patentability dated Mar. 1, 2016 (2 pages).
PCT/US2015/022841 International Search Report and Written Opinion dated Jun. 29, 2015 (12 pages).
Lavielle et al. Document No. 138:89686, retrieved from STN; Jan. 15, 2003.
Chan et al., "Document No. 150:563639," retrieved from STN; May 22, 2009.
Friberg, "Discovery of Potent Myeloid Cell Leukemia 1 (Mcl 1) Inhibitors Using Fragment Based Methods and Structure Based Design," manuscript (2014) pp. 1-38, National Institutes of Health.
Hung et al, "Document No. 152:66468, Caplus," retrieved from STN; Oct. 28, 2009.
Jansen et al., "Document No. 140:111233, Caplus," retrieved from STN; Oct. 22, 2009.
Wahyuningsih, et al. Document No. 147:235137, retrieved from STN; entered in STN on Jun. 11, 2007.
Medline Plus, "Cancer" retrieved from http://www.nlm.nih.gov/medlineplus/cancer.html on Jul. 6, 2007.
Golub et al., "Molecular classification of cancer: class discovery and class prediction by gene expression monitoring," Science (1999), vol. 286, 531-537.
Lala et al., "Role of nitric oxide in tumor progression: lessons from experimental tumors," Cancer and Metastasis Reviews (1998), 17(1), 91-106.
Shultz et al. "Optimization of the in vitro cardiac safety of hydroxamate-based histone deacetylase inhibitors." Journal of medicinal chemistry. Jun. 17, 2011;54(13):4752-72.
Tabatabaeian et al., "Solvent-free, ruthenium-catalyzed, regioselective ring-opening of epoxides, an efficient route to various 3-alkylated indoles." Tetrahedron Letters. Feb. 25, 2008;49(9):1450-4.
Kalaus et al., "Synthesis of vinca alkaloids and related compounds. 63. A new synthetic pathway for preparing alkaloids and related compounds with the aspidosperma skeleton. Total syntheses of (.+−.)-vincadifformine,(.+−.)-tabersonine, and (.+−.)-oxotabersonine." The Journal of Organic Chemistry. Mar. 1993;58(6):1434-42.
Vago et al., "Synthesis of vinca alkaloids and related compounds 95. Attempted build-up of the aspidospermidine skeleton by [4+2] cycloaddition. Some unexpected reactions, and formation of a new ring system." Heterocycles. May 1, 2001;55(5):873-80.
Shaw et al., "Optimization of potent and selective tricyclic indole diazepinone myeloid cell leukemia-1 inhibitors using structure-based design." Journal of medicinal chemistry. Jan. 11, 2018;61(6):2410-21.
Japanese Patent Office Action for Application No. 2017502932 dated Dec. 6, 2018, with translation, 15 pages.
Canadian Patent Office Action for Application No. 2,922,341 dated Oct. 15, 2020 (14 pages).

* cited by examiner

SUBSTITUTED INDOLE MCL-1 INHIBITORS

CROSS REFERENCE TO RELATED APPLICATIONS

The present application is a continuation of U.S. patent application Ser. No. 14/914,307, filed Feb. 25, 2016, which application is the U.S. national stage entry, under 35 U.S.C. § 371, of international application number PCT/US2014/053148, filed Aug. 28, 2014, which claims priority to U.S. Provisional Application Ser. No. 61/871,280, filed Aug. 28, 2013, the entirety of which are incorporated herein by reference.

STATEMENT REGARDING FEDERALLY SPONSORED RESEARCH OR DEVELOPMENT

This invention was made with government support under grants CA098131 and CA174419 awarded by the National Institutes of Health. The government has certain rights in the invention.

FIELD OF THE INVENTION

The present invention pertains to compounds that inhibit the activity of an anti-apoptotic Bcl-2 family member Myeloid cell leukemia-1 (Mcl-1) protein, compositions containing the compounds, and methods of treating cancer involving over-expressed or dysregulated Mcl-1 protein.

BACKGROUND OF THE INVENTION

Abnormal regulation of apoptosis is now recognized to play an important role in the development of cancer. The Apoptosis pathway can be initiated by various extracellular and intracellular stresses, including growth factor deprivation, DNA damage, oncogene induction, and cytotoxic drugs (Danial, N. N. and Korsmeyer, S J. *Cell* (2004) 116, 205-219). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. Recent data suggests that the anti-apoptotic Bcl-2 proteins function to protect the cell from apoptotic insults, primarily by preventing disruption of mitochondrial outer membrane integrity by binding to the pro-apoptotic proteins as described in Adams, J. M. and Cory S. *Oncogene* (2007) 26, 1324-1337; Willis, S. N. et al. *Science* (2007) 315, 856-859. Because tumor cells are under stress, alterations in their apoptotic signaling pathways are believed to be crucial for survival. Recent data implicates down-regulated apoptosis in the onset of cancer. Research has shown, for example, that anti-apoptotic proteins, are over-expressed in many cancer cell types as described in Beroukhim, R. et al. *Nature* (2010) 463, 899-905, Zhang J. Y, *Nature Reviews/Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy which is a major cause of treatment failure and poor prognosis in many cancers can be caused by the upregulation of anti-apoptotic Bcl-2 family proteins.

An important anti-apoptotic member of the Bcl-2 family is Myeloid cell leukemia-1 (Mcl-1). Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) (Beroukhim et al. *Nature* (2010) 463, 899-905). Moreover, its overexpression is implicated as a resistance factor for multiple therapies including widely prescribed microtubule-targeted agents for breast cancers, such as paclitaxel and vincristine as well as Gemcitabine, a first-line treatment option for pancreatic cancer (Wei et al. *Cancer Chemother Pharmacol* (2008) 62, 1055-1064 and Wertz et al. *Nature* (2011) 471, 110-114). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

SUMMARY OF THE INVENTION

It has now been found that compounds of this invention, and pharmaceutically acceptable compositions thereof, are effective as inhibitors of Mcl-1. Such compounds have the general formula I or II:

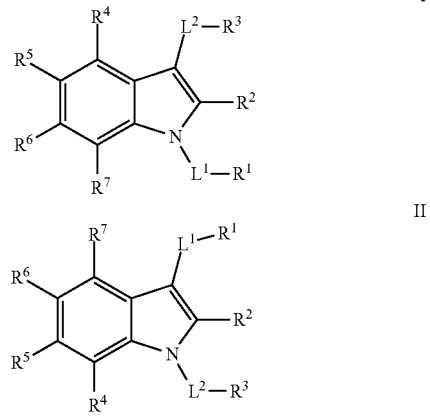

or a pharmaceutically acceptable salt thereof, wherein each of $L^1$, $L^2$, $R^1$, $R^2$, $R^3$, $R^4$, $R^5$, $R^6$, and $R^7$ is as defined and described in embodiments herein.

Compounds of the present invention, and pharmaceutically acceptable compositions thereof, are useful for treating a variety of diseases, disorders or conditions, associated with Mcl-1. Such diseases, disorders, or conditions include those described herein.

Compounds provided by this invention are also useful for the study of Mcl-1 in biological and pathological phenomena and the comparative evaluation of new Mcl-1 inhibitors in vitro or in vivo.

DETAILED DESCRIPTION OF CERTAIN EMBODIMENTS OF THE INVENTION

1. General Description of Compounds of the Invention

In certain embodiments, the present invention provides inhibitors of Mcl-1. In some embodiments, such compounds include those of formula I:

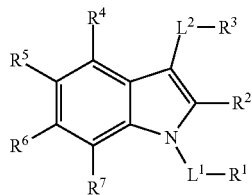

I or a pharmaceutically acceptable salt thereof, wherein:

$L^1$ is an optionally substituted bivalent $C_{1-6}$ hydrocarbon chain wherein one or more methylene units are optionally replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is —OR, —SR, —S(O)R, —S(O)$_2$R, —S(O)$_2$N(R)$_2$, —N(R)$_2$, —C(O)N(R)$_2$, —C(O)R, —NRC(O)R, —NRC(O)OR, —NRC(O)N(R)$_2$, —NRS(O)$_2$R, —NRS(O)$_2$N(R)$_2$, —C(O)OH, —C(O)$R^x$, —S(O)$_2$OH, or —S(O)$_2R^y$, or is selected from

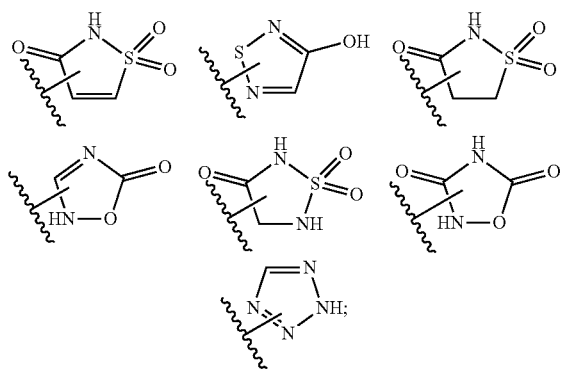

$R^x$ is selected from —C(O)OR, —NRS(O)$_2$CF$_3$, —NRC(O)R, —NRC(O)OR, —NRC(O)N(R)$_2$, or —NRS(O)$_2$R;
$R^y$ is selected from —NRC(O)CF$_3$, —NRC(O)R, or —NRC(O)N(R)$_2$;

$R^2$ is selected from R, halo, —NH$_2$, —CN, —NO$_2$, and —CF$_3$;

each R is independently selected from hydrogen or an optionally substituted group selected from $C_{1-6}$ aliphatic or a ring selected from a 3-8 membered saturated or partially unsaturated carbocyclic ring, phenyl, a 8-10 membered bicyclic aryl ring, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is an optionally substituted bivalent $C_{3-6}$ hydrocarbon chain wherein one or two methylene units of $L^2$ are optionally and independently replaced with —O—, —S—, or —NR'—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted $C_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

each of $R^4$, $R^5$, and $R^6$ is independently selected from R, halo, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

$R^7$ is hydrogen, halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur.

In certain embodiments, the present invention provides a compound of formula II:

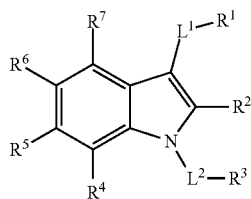

or a pharmaceutically acceptable salt thereof, wherein:

$L^1$ is an optionally substituted bivalent $C_{1-6}$ hydrocarbon chain wherein one or more methylene units are optionally replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is —OR, —SR, —S(O)R, —S(O)$_2$R, —S(O)$_2$N(R)$_2$, —N(R)$_2$, —C(O)N(R)$_2$, —C(O)R, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

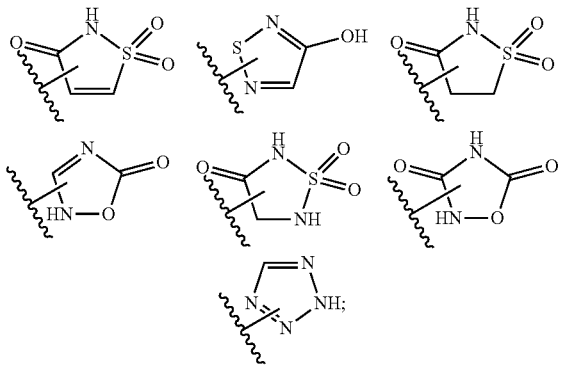

$R^x$ is selected from —C(O)OR, —NRS(O)$_2$CF$_3$, —NRC(O)R, —NRC(O)OR, —NRC(O)N(R)$_2$, or —NRS(O)$_2$R;

$R^y$ is selected from —NRC(O)CF$_3$, —NRC(O)R, or —NRC(O)N(R)$_2$;

$R^2$ is selected from R, halo, —NH$_2$, —CN, —NO$_2$, and —CF$_3$;

each R is independently selected from hydrogen or an optionally substituted group selected from $C_{1-6}$ aliphatic or a ring selected from a 3-8 membered saturated or partially unsaturated carbocyclic ring, phenyl, a 8-10 membered bicyclic aryl ring, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is an optionally substituted bivalent $C_{3-6}$ hydrocarbon chain wherein one or two methylene units of $L^2$ are optionally and independently replaced with —O—, —S—, or —NR'—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted $C_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

each of $R^4$, $R^5$, and $R^6$ is independently selected from R, halo, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

$R^7$ is hydrogen, halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a C1-4 straight or branched alkyl group. Exemplary lower alkyl groups are methyl, ethyl, propyl, isopropyl, butyl, isobutyl, and tert-butyl.

The term "lower haloalkyl" refers to a C1-4 straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent C1-8 (or C1-6) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)n-, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, naphthyl, anthracyl and the like, which may be optionally substituted. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH2)$_{0-4}$N(R)C(O)OR°; —N(R°)N(R°)C(O)R°; —N(R°)N(R)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR, —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)R°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C1- 4 straight or branched alkylene)O—N(R°)$_2$; or —(C1-4 straight or branched alkylene)C(O)O—N(R°)$_2$, wherein each R° may be substituted as defined below and is independently hydrogen, C1-6 aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$S(O)R$^\bullet$, —(CH$_2$)$_{0-2}$S(O)$_2$R$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR', or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a suitable carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)R$^\bullet$, —C(O)OH, —C(O)OR$^\bullet$, —C(O)NR$^\bullet$$_2$, —SR$^\bullet$, —S(O)R$^\bullet$, —S(O)$_2$R$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^t$ are independently halogen, —R●, -(haloR●), —OH, —OR●, —O(haloR●), —CN, —C(O)OH, —C(O)OR●, —C(O)NR●$_2$, —SR●, —S(O)R●, —S(O)$_2$R●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention.

Such compounds are useful, for example, as analytical tools, as probes in biological assays, or as therapeutic agents in accordance with the present invention.

3. Description of Exemplary Embodiments

In some embodiments, the present invention provides a compound of formula I:

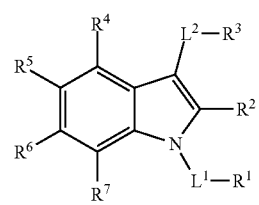

I or a pharmaceutically acceptable salt thereof, wherein:

$L^1$ is an optionally substituted bivalent $C_{1-6}$ hydrocarbon chain wherein one or more methylene units are optionally replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is —OR, —SR, —S(O)R, —S(O)$_2$R, —S(O)$_2$N(R)$_2$, —N(R)$_2$, —C(O)N(R)$_2$, —C(O)R, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH or —S(O)$_2$R$^y$, or is selected from

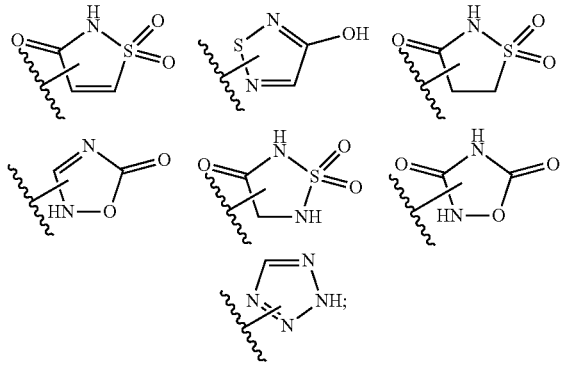

$R^x$ is selected from —C(O)OR, —NRS(O)$_2$CF$_3$, —NRC(O)R, —NRC(O)OR, —NRC(O)N(R)$_2$, or —NRS(O)$_2$R;

$R^y$ is selected from —NRC(O)CF$_3$, —NRC(O)R, or —NRC(O)N(R)$_2$;

$R^2$ is selected from R, halo, —NH$_2$, —CN, —NO$_2$, and —CF$_3$;

each R is independently selected from hydrogen or an optionally substituted group selected from $C_{1-6}$ aliphatic or a ring selected from a 3-8 membered saturated or partially unsaturated carbocyclic ring, phenyl, a 8-10 membered bicyclic aryl ring, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is an optionally substituted bivalent $C_{3-6}$ hydrocarbon chain wherein one or two methylene units of $L^2$ are optionally and independently replaced with —O—, —S—, or —NR'—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted $C_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

each of $R^4$, $R^5$, and $R^6$ is independently selected from R, halo, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

$R^7$ is hydrogen, halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur.

In certain embodiments, the present invention provides a compound of formula II:

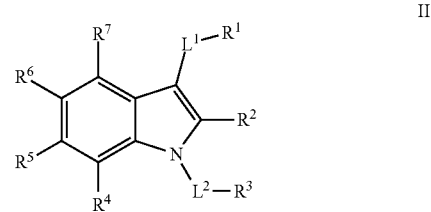

or a pharmaceutically acceptable salt thereof, wherein:

$L^1$ is an optionally substituted bivalent $C_{1-6}$ hydrocarbon chain wherein one or more methylene units are optionally replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is —OR, —SR, —S(O)R, —S(O)$_2$R, —S(O)$_2$N(R)$_2$, —N(R)$_2$, —C(O)N(R)$_2$, —C(O)R, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

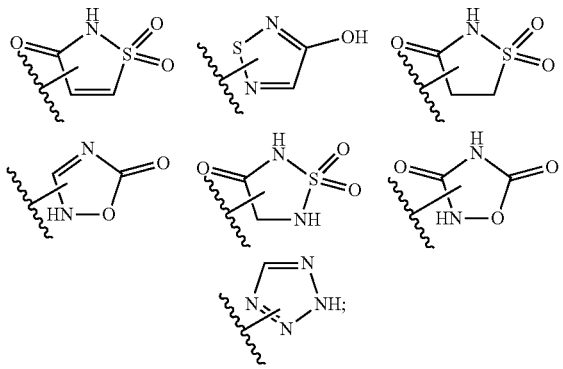

$R^x$ is selected from —C(O)OR, —NRS(O)$_2$CF$_3$, —NRC(O)R, —NRC(O)OR, —NRC(O)N(R)$_2$, or —NRS(O)$_2$R;

$R^y$ is selected from —NRC(O)CF$_3$, —NRC(O)R, or —NRC(O)N(R)$_2$;

$R^2$ is selected from R, halo, —NH$_2$, —CN, —NO$_2$, and —CF$_3$;

each R is independently selected from hydrogen or an optionally substituted group selected from $C_{1-6}$ aliphatic or a ring selected from a 3-8 membered saturated or partially unsaturated carbocyclic ring, phenyl, a 8-10 membered bicyclic aryl ring, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is an optionally substituted bivalent $C_{3-6}$ hydrocarbon chain wherein one or two methylene units of $L^2$ are optionally and independently replaced with —O—, —S—, or —NR'—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted $C_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

each of $R^4$, $R^5$, and $R^6$ is independently selected from R, halo, —CN, —NO₂, —C(O)OR', —OR', —SR', —C(O)N(R')₂—N(R')₂, —S(O)₂N(R)₂, —N(R')S(O)₂CF₃, —C(O)R', —N(R')C(O)R', —S(O)R', —S(O)₂R', —N(R')C(O)OR', and —N(R')S(O)₂R';

$R^7$ is hydrogen, halo, —CN, —NO₂, —C(O)OR, —OCF₃, —OR, —SR, —S(O)₂OR, —P(O)(OH)₂, —C(O)N(R)₂, —N(R)₂, —S(O)₂N(R)₂, —NRS(O)₂CF₃, —C(O)NRS(O)₂R, —S(O)₂NRC(O)OR, —S(O)₂NRC(O)N(R)₂, —C(O)R, —C(O)NRS(O)₂CF₃, —NRC(O)R, —OC(O)R, —OC(O)N(R)₂, —C(NR)N(R)₂, —NRC(NR)N(R)₂, —S(O)R, —S(O)₂R, —NRC(O)OR, or —NRS(O)₂R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur.

As defined generally above, $L^1$ is an optionally substituted bivalent $C_{1-6}$ hydrocarbon chain wherein one or more methylene units are optionally replaced with -Cy-. In some embodiments, $L^1$ is an optionally substituted bivalent $C_{1-6}$ hydrocarbon chain wherein one methylene unit is replaced with -Cy-. In some embodiments, $L^1$ is an optionally substituted bivalent $C_{1-6}$ hydrocarbon chain wherein two or more methylene units are replaced with -Cy-. In some embodiments, $L^1$ is an optionally substituted bivalent $C_{1-6}$ hydrocarbon chain wherein no methylene units are replaced with -Cy-.

In some embodiments, $L^1$ is an optionally substituted bivalent $C_{1-6}$ hydrocarbon chain. In some embodiments, $L^1$ is an optionally substituted bivalent $C_{2-6}$ hydrocarbon chain. In some embodiments, $L^1$ is an optionally substituted bivalent $C_{3-6}$ hydrocarbon chain. In some embodiments, $L^1$ is an optionally substituted bivalent $C_{4-6}$ hydrocarbon chain. In some embodiments, $L^1$ is an optionally substituted bivalent $C_{5-6}$ hydrocarbon chain. In some embodiments, $L^1$ is an optionally substituted bivalent $C_{1-2}$ hydrocarbon chain. In some embodiments, $L^1$ is an optionally substituted bivalent $C_{1-3}$ hydrocarbon chain. In some embodiments, $L^1$ is an optionally substituted bivalent $C_{1-4}$ hydrocarbon chain. In some embodiments, $L^1$ is an optionally substituted bivalent $C_{2-3}$ hydrocarbon chain. In some embodiments, $L^1$ is an optionally substituted bivalent $C_{2-4}$ hydrocarbon chain. In some embodiments, $L^1$ is an optionally substituted methylene group. In some embodiments, $L^1$ is an optionally substituted bivalent $C_2$ hydrocarbon chain. In some embodiments, $L^1$ is an optionally substituted bivalent $C_3$ hydrocarbon chain. In some embodiments, $L^1$ is an optionally substituted bivalent $C_4$ hydrocarbon chain. In some embodiments, $L^1$ is an optionally substituted bivalent $C_5$ hydrocarbon chain. In some embodiments, $L^1$ is an optionally substituted bivalent $C_6$ hydrocarbon chain.

In some embodiments, $L^1$ is an unsubstituted bivalent $C_{1-6}$ hydrocarbon chain. In some embodiments, $L^1$ is an unsubstituted bivalent $C_{2-6}$ hydrocarbon chain. In some embodiments, $L^1$ is an unsubstituted bivalent $C_{3-6}$ hydrocarbon chain. In some embodiments, $L^1$ is an unsubstituted bivalent $C_{4-6}$ hydrocarbon chain. In some embodiments, $L^1$ is an unsubstituted bivalent $C_{5-6}$ hydrocarbon chain. In some embodiments, $L^1$ is an unsubstituted bivalent $C_{1-2}$ hydrocarbon chain. In some embodiments, $L^1$ is an unsubstituted bivalent $C_{1-3}$ hydrocarbon chain. In some embodiments, $L^1$ is an unsubstituted bivalent $C_{1-4}$ hydrocarbon chain. In some embodiments, $L^1$ is an unsubstituted bivalent $C_{2-3}$ hydrocarbon chain. In some embodiments, $L^1$ is an unsubstituted bivalent $C_{2-4}$ hydrocarbon chain. In some embodiments, $L^1$ is an unsubstituted methylene group. In some embodiments, $L^1$ is an unsubstituted bivalent $C_2$ hydrocarbon chain. In some embodiments, $L^1$ is an unsubstituted bivalent $C_3$ hydrocarbon chain. In some embodiments, $L^1$ is an unsubstituted bivalent $C_4$ hydrocarbon chain. In some embodiments, $L^1$ is an unsubstituted bivalent $C_5$ hydrocarbon chain. In some embodiments, $L^1$ is an unsubstituted bivalent $C_6$ hydrocarbon chain.

In some embodiments, $L^1$ is a substituted bivalent $C_{1-6}$ hydrocarbon chain. In some embodiments, $L^1$ is a substituted bivalent $C_{2-6}$ hydrocarbon chain. In some embodiments, $L^1$ is a substituted bivalent $C_{3-6}$ hydrocarbon chain. In some embodiments, $L^1$ is a substituted bivalent $C_{4-6}$ hydrocarbon chain. In some embodiments, $L^1$ is a substituted bivalent $C_{5-6}$ hydrocarbon chain. In some embodiments, $L^1$ is a substituted bivalent $C_{1-2}$ hydrocarbon chain. In some embodiments, $L^1$ is a substituted bivalent $C_{1-3}$ hydrocarbon chain. In some embodiments, $L^1$ is a substituted bivalent $C_{1-4}$ hydrocarbon chain. In some embodiments, $L^1$ is a substituted bivalent $C_{2-3}$ hydrocarbon chain. In some embodiments, $L^1$ is a substituted bivalent $C_{2-4}$ hydrocarbon chain. In some embodiments, $L^1$ is a substituted methylene group. In some embodiments, $L^1$ is a substituted bivalent $C_2$ hydrocarbon chain. In some embodiments, $L^1$ is a substituted bivalent $C_3$ hydrocarbon chain. In some embodiments, $L^1$ is a substituted bivalent $C_4$ hydrocarbon chain. In some embodiments, $L^1$ is a substituted bivalent $C_5$ hydrocarbon chain. In some embodiments, $L^1$ is a substituted bivalent $C_6$ hydrocarbon chain.

In some embodiments, $L^1$ is a substituted bivalent $C_{1-6}$ hydrocarbon chain wherein none of the substituents are —N(R)$_2$ or —N(R)C(O)R. In some embodiments, $L^1$ is a substituted bivalent $C_{1-6}$ hydrocarbon chain wherein none of the substituents are —N(R)$_2$ or —NHC(O)R.

In some embodiments, $L^1$ is optionally substituted methylene. In some embodiments, $L^1$ is —CH$_2$—. In some embodiments, $L^1$ is optionally substituted —CH$_2$CH$_2$—. In some embodiments, $L^1$ is —CH$_2$CH$_2$—. In some embodiments, $L^1$ is —CH(CH$_3$)—. In some embodiments, $L^1$ is —CH(CH$_2$CH$_3$)—. In some embodiments, $L^1$ is —CH(Ph)-. In some embodiments, $L^1$ is —CH(CH$_3$)CH$_2$—. In some embodiments, $L^1$ is —CH(Ph)CH$_2$—.

In some embodiments, $L^1$ is partially unsaturated. In some embodiments, $L^1$ comprises one or more double bonds. In some embodiments, $L^1$ is —CH=CH—. In some embodiments, $L^1$ comprises one or more triple bonds.

In some embodiments, $L^1$ is an optionally substituted bivalent $C_{1-6}$ hydrocarbon chain wherein one or more methylene units are replaced with -Cy-. In some embodiments, $L^1$ is an optionally substituted bivalent $C_{1-2}$ hydrocarbon chain wherein one or more methylene units are replaced with -Cy-. In some embodiments, $L^1$ is an optionally substituted bivalent $C_{1-3}$ hydrocarbon chain wherein one or more methylene units are replaced with -Cy-. In some embodiments, $L^1$ is an optionally substituted bivalent $C_{1-4}$ hydrocarbon chain wherein one or more methylene units are replaced with -Cy-. In some embodiments, $L^1$ is an optionally substituted bivalent $C_{2-3}$ hydrocarbon chain wherein one or more methylene units are replaced with -Cy-. In some embodiments, $L^1$ is an optionally substituted bivalent $C_{2-4}$ hydrocarbon chain wherein one or more methylene units are replaced with -Cy-. In some embodiments, $L^1$ is an optionally substituted bivalent $C_{1-6}$ hydrocarbon chain wherein one methylene unit is replaced with -Cy-. In some embodiments, $L^1$ is an optionally substituted bivalent $C_{1-2}$ hydrocarbon chain wherein one methylene unit is replaced with -Cy-. In some embodiments, $L^1$ is an optionally substituted bivalent $C_{1-3}$ hydrocarbon chain wherein one methylene unit is replaced with -Cy-. In some embodiments, $L^1$ is an optionally substituted bivalent $C_{1-4}$ hydrocarbon chain wherein one methylene unit is replaced with -Cy-. In some embodiments, $L^1$ is an optionally substituted bivalent $C_{2-3}$ hydrocarbon chain wherein one methylene unit is replaced with -Cy-. In some embodiments, $L^1$ is an optionally substituted bivalent $C_{2-4}$ hydrocarbon chain wherein one methylene unit is replaced with -Cy-. In some embodiments, $L^1$ is an optionally substituted bivalent $C_{1-6}$ hydrocarbon chain wherein two or more methylene units are replaced with -Cy-.

As defined generally above, -Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur.

In some embodiments, -Cy- is optionally substituted phenylene. In some embodiments, -Cy- is substituted phenylene. In some embodiments, -Cy- is unsubstituted phenylene.

In some embodiments, -Cy- is optionally substituted 1,2-phenylene

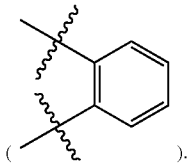 [SMILES: *c1ccccc1*]

In some embodiments, -Cy- is 1,2-phenylene. In some embodiments, $L^1$ is an optionally substituted bivalent $C_{1-6}$ hydrocarbon chain wherein one or more methylene units are replaced with 1,2-phenylene. In some embodiments, $L^1$ is an optionally substituted bivalent $C_{1-6}$ hydrocarbon chain wherein one methylene unit is replaced with 1,2-phenylene. In some embodiments, $L^1$ is an optionally substituted bivalent $C_2$ hydrocarbon chain wherein one methylene unit is replaced with 1,2-phenylene. In some embodiments, $L^1$ is

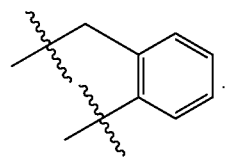 [SMILES: *Cc1ccccc1*]

In some embodiments, -Cy- is optionally substituted 1,3-phenylene or 1,4-phenylene. In some embodiments, -Cy- is optionally substituted 1,3-phenylene

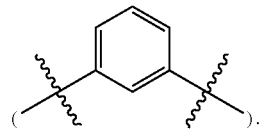 [SMILES: *c1cccc(*)c1]

In some embodiments, -Cy- is 1,3-phenylene. In some embodiments, $L^1$ is an optionally substituted bivalent $C_{1-6}$ hydrocarbon chain wherein one or more methylene units are replaced with 1,3-phenylene. In some embodiments, $L^1$ is an optionally substituted bivalent $C_{1-6}$ hydrocarbon chain wherein one methylene unit is replaced with 1,3-phenylene. In some embodiments, $L^1$ is an optionally substituted bivalent $C_2$ hydrocarbon chain wherein one methylene unit is replaced with 1,3-phenylene. In some embodiments, $L^1$ is

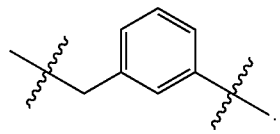 [SMILES: *Cc1cccc(*)c1]

In some embodiments, -Cy- is optionally substituted 1,4-phenylene

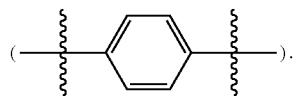

In some embodiments, -Cy- is 1,4-phenylene. In some embodiments, $L^1$ is an optionally substituted bivalent $C_{1-6}$ hydrocarbon chain wherein one or more methylene units are replaced with 1,4-phenylene. In some embodiments, $L^1$ is an optionally substituted bivalent $C_{1-6}$ hydrocarbon chain wherein one methylene unit is replaced with 1,4-phenylene. In some embodiments, $L^1$ is an optionally substituted bivalent $C_2$ hydrocarbon chain wherein one methylene unit is replaced with 1,4-phenylene. In some embodiments, $L^1$ is

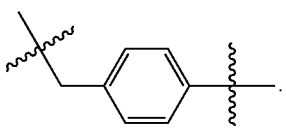 [SMILES: *Cc1ccc(*)cc1]

In some embodiments, $L^1$ is an optionally substituted bivalent $C_3$ hydrocarbon chain wherein one methylene unit is replaced with 1,4-phenylene. In some embodiments, $L^1$ is

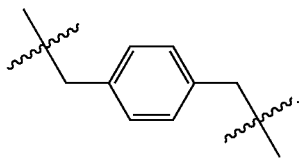 [SMILES: *Cc1ccc(C*)cc1]

In some embodiments, $L^1$ is

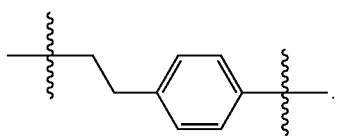 [SMILES: *CCc1ccc(*)cc1]

In certain embodiments, -Cy- is bivalent optionally substituted 3-8 membered saturated carbocyclylene. In certain embodiments, -Cy- is a bivalent optionally substituted 3-6 membered saturated carbocyclylene. In certain embodiments, -Cy- is a bivalent optionally substituted 3 membered saturated carbocyclylene. In certain embodiments, -Cy- is a bivalent optionally substituted 4 membered saturated carbocyclylene. In certain embodiments, -Cy- is a bivalent optionally substituted 5 membered saturated carbocyclylene. In certain embodiments, -Cy- is a bivalent optionally substituted 6 membered saturated carbocyclylene.

In certain embodiments, -Cy- is bivalent optionally substituted 5-membered heteroarylene having 1-4 heteroatoms independently selected from nitrogen, oxygen, or sulfur. In certain embodiments, -Cy- is bivalent optionally substituted 5-membered heteroarylene having 1-2 heteroatoms independently selected from nitrogen, oxygen, or sulfur. In certain embodiments, -Cy- is bivalent optionally substituted 5-membered heteroarylene having one heteroatom independently selected from nitrogen, oxygen, or sulfur.

In some embodiments, -Cy- is optionally substituted

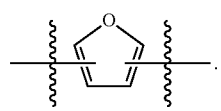

In some embodiments, $L^1$ is an optionally substituted bivalent $C_{1-6}$ hydrocarbon chain wherein one or more methylene units are replaced with

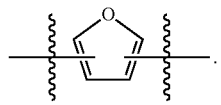

In some embodiments, $L^1$ is an optionally substituted bivalent $C_{1-6}$ hydrocarbon chain wherein one methylene unit is replaced with

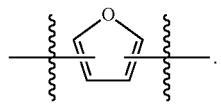

In some embodiments, -Cy- is optionally substituted

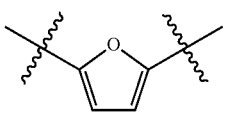

In some embodiments, -Cy- is

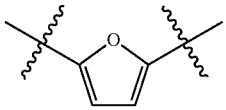

In some embodiments, $L^1$ is an optionally substituted bivalent $C_{1-6}$ hydrocarbon chain wherein one or more methylene units are replaced with

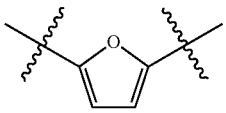

In some embodiments, $L^1$ is an optionally substituted bivalent $C_{1-6}$ hydrocarbon chain wherein one methylene unit is replaced with

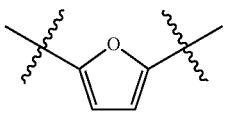

In some embodiments, $L^1$ is an optionally substituted bivalent $C_2$ hydrocarbon chain wherein one methylene unit is replaced with

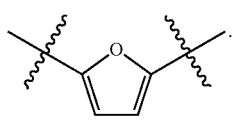 [SMILES: *c1ccc(*)o1]

In some embodiments, $L^1$ is

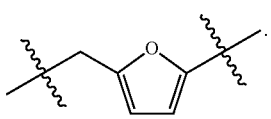 [SMILES: *Cc1ccc(*)o1]

In certain embodiments, -Cy- is bivalent optionally substituted 6-membered heteroarylene having 1-4 heteroatoms independently selected from nitrogen, oxygen, or sulfur. In certain embodiments, -Cy- is bivalent optionally substituted 6-membered heteroarylene having 1-4 nitrogen atoms. In certain embodiments, -Cy- is bivalent optionally substituted 6-membered heteroarylene having one nitrogen atom. In certain embodiments, -Cy- is bivalent optionally substituted 6-membered heteroarylene having 1-2 heteroatoms independently selected from nitrogen, oxygen, or sulfur.

In some embodiments, -Cy- is optionally substituted bivalent pyridinyl ( 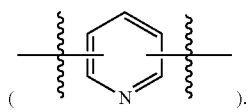 ).

In some embodiments, $L^1$ is an optionally substituted bivalent $C_{1-6}$ hydrocarbon chain wherein one or more methylene units are replaced with

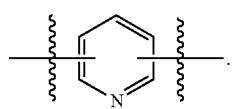

In some embodiments, $L^1$ is an optionally substituted bivalent $C_{1-6}$ hydrocarbon chain wherein one methylene unit is replaced with

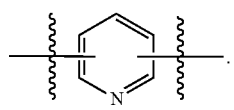

In some embodiments, -Cy- is optionally substituted

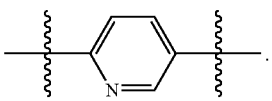

In some embodiments, -Cy- is

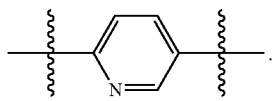

In some embodiments, $L^1$ is an optionally substituted bivalent $C_{1-6}$ hydrocarbon chain wherein one or more methylene units are replaced with

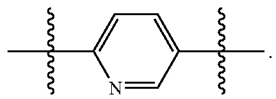

In some embodiments, $L^1$ is an optionally substituted bivalent $C_{1-6}$ hydrocarbon chain wherein one methylene unit is replaced with

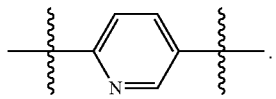

In some embodiments, $L^1$ is an optionally substituted bivalent $C_2$ hydrocarbon chain wherein one methylene unit is replaced with

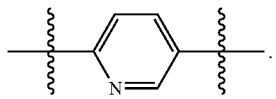 [SMILES: *c1ccc(*)nc1]

In some embodiments, $L^1$ is N

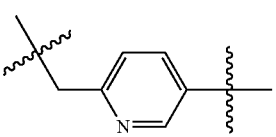

In certain embodiments, -Cy- is bivalent optionally substituted 3-8 membered saturated heterocyclylene having 1-4 heteroatoms independently selected from nitrogen, oxygen, or sulfur. In certain embodiments, -Cy- is a bivalent optionally substituted 3-8 membered saturated heterocyclylene having 1-2 heteroatoms independently selected from nitrogen, oxygen, or sulfur. In certain embodiments, -Cy- is a bivalent optionally substituted 5-6 membered saturated heterocyclylene having 1-4 heteroatoms independently selected from nitrogen, oxygen, or sulfur. In certain embodiments, -Cy- is a bivalent optionally substituted 5-6 membered saturated heterocyclylene having 1-2 heteroatoms independently selected from nitrogen, oxygen, or sulfur. In certain embodiments, -Cy- is a bivalent optionally substituted 5 membered saturated heterocyclylene having 1-2 heteroatoms independently selected from nitrogen, oxygen, or sulfur. In certain embodiments, -Cy- is a bivalent optionally substituted 6 membered saturated heterocyclylene having 1-2 heteroatoms independently selected from nitrogen, oxygen, or sulfur. In certain embodiments, -Cy- is bivalent optionally substituted 3-8 membered saturated heterocyclylene having 1-4 oxygen atoms. In certain embodiments, -Cy- is bivalent optionally substituted 3-8 membered saturated heterocyclylene having 1-4 nitrogen atoms. In certain embodiments, -Cy- is bivalent optionally substituted 3-8 membered saturated heterocyclylene having 1-4 sulfur atoms.

In certain embodiments, -Cy- is bivalent optionally substituted 3-8 membered saturated heterocyclylene having two heteroatoms independently selected from nitrogen, oxygen, or sulfur. In certain embodiments, -Cy- is bivalent optionally substituted 3-8 membered saturated heterocyclylene having two nitrogen atoms. In some embodiments, -Cy- is optionally substituted

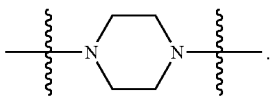 [SMILES: *N1CCN(*)CC1]

In some embodiments, L¹ is an optionally substituted bivalent $C_{1-6}$ hydrocarbon chain wherein one or more methylene units are replaced with

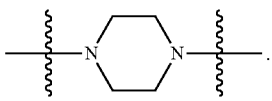

In some embodiments, L¹ is an optionally substituted bivalent $C_{1-6}$ hydrocarbon chain wherein one methylene unit is replaced with

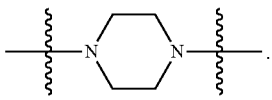 [SMILES: *N1CCN(*)CC1]

In some embodiments, L¹ is an optionally substituted bivalent $C_4$ hydrocarbon chain wherein one methylene unit is replaced with

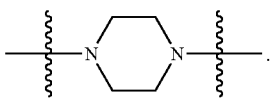

In some embodiments, L¹ is

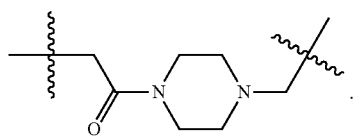 [SMILES: *CC(=O)N1CCN(C*)CC1]

As defined generally above, R¹ is —OR, —SR, —S(O)R, —S(O)₂R, —S(O)₂N(R)₂, —N(R)₂, —C(O)N(R)₂, —C(O)R, —NRC(O)R, —NRC(O)OR, —NRC(O)N(R)₂, —NRS(O)₂R, —NRS(O)₂N(R)₂, —C(O)OH, —C(O)R$^x$, —S(O)₂OH, or —S(O)₂R$^y$, or is selected from:

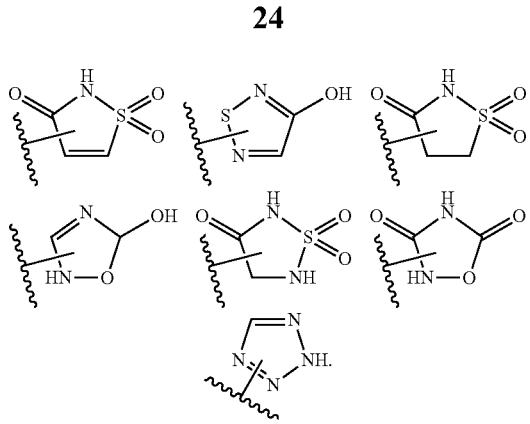

In some embodiments, R¹ is —OR, —SR, —S(O)R, —S(O)₂R, —S(O)₂N(R)₂, —N(R)₂, —C(O)N(R)₂, —C(O)R, —NRC(O)R, —NRC(O)OR, —NRC(O)N(R)₂, —NRS(O)₂R, —NRS(O)₂N(R)₂, —C(O)R$^x$, —S(O)₂OH, or —S(O)₂R$^y$, or is selected from:

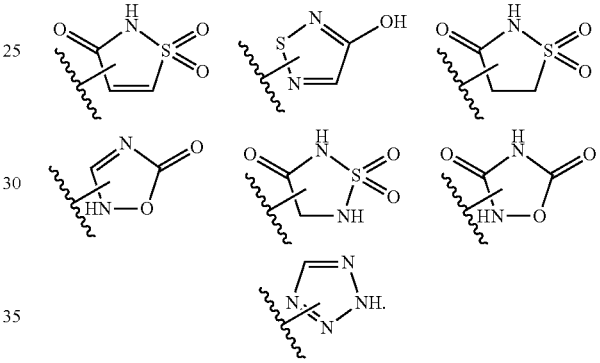

In some embodiments, R¹ is —OR, —SR, —S(O)R, —S(O)₂R, —S(O)₂N(R)₂, —N(R)₂, —C(O)N(R)₂, —C(O)R, —NRC(O)R, —NRC(O)OR, —NRC(O)N(R)₂, —NRS(O)₂R, —NRS(O)₂N(R)₂, —C(O)R$^x$, —S(O)₂OH, or —S(O)₂R$^y$, or is selected from:

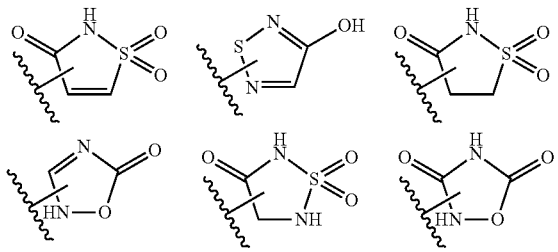

In some embodiments, R¹ is —OR, —SR, —S(O)R, —S(O)₂R, —S(O)₂N(R)₂, —C(O)N(R)₂, —C(O)R, —NRS(O)₂R, —NRS(O)₂N(R)₂, —C(O)OH, —C(O)R$^x$, —S(O)₂OH, or —S(O)₂R$^y$, or is selected from

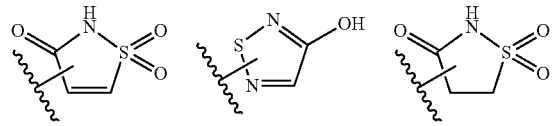

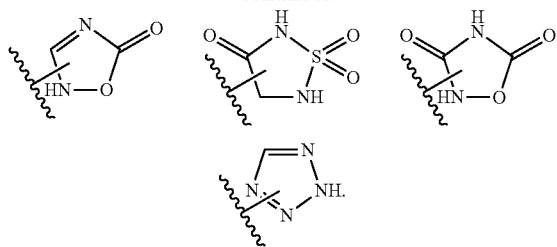

In some embodiments, $R^1$ is —OR, —SR, —S(O)R, —S(O)$_2$R, —S(O)$_2$N(R)$_2$, —C(O)N(R)$_2$, —C(O)R, —NRS(O)$_2$N(R)$_2$, —C(O)$R^x$, —S(O)$_2$OH, or —S(O)$_2R^y$, or is selected from:

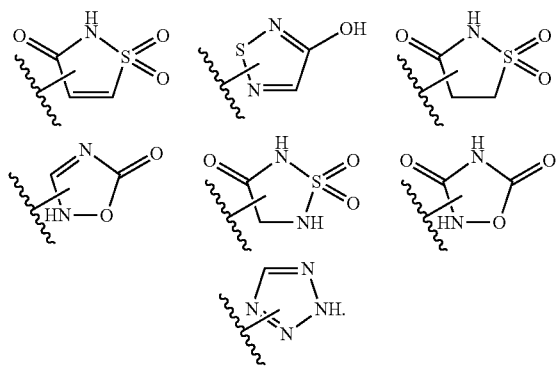

In some embodiments, $R^1$ is —C(O)OH, —C(O)$R^x$, —S(O)$_2$OH, or —S(O)$_2R^y$, or is selected from:

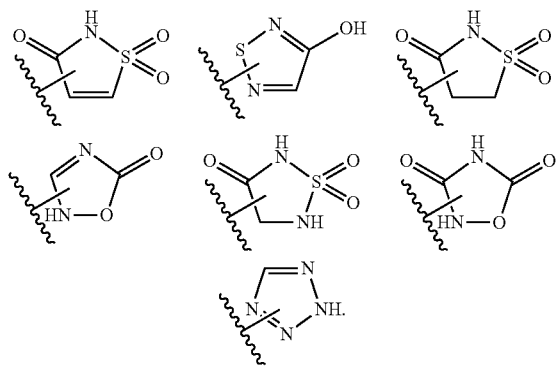

In some embodiments, $R^1$ is —OR. In some embodiments, $R^1$—SR. In some embodiments, $R^1$ is —S(O)R. In some embodiments, $R^1$ is —S(O)$_2$R. In some embodiments, $R^1$ is —S(O)$_2$N(R)$_2$. In some embodiments, $R^1$ is —N(R)$_2$. In some embodiments, $R^1$ is —C(O)N(R)$_2$. In some embodiments, $R^1$ is —C(O)R. In some embodiments, $R^1$ is —NRC(O)R. In some embodiments, $R^1$ is —NRC(O)OR. In some embodiments, $R^1$ is —NRC(O)N(R)$_2$. In some embodiments, $R^1$ is —NRS(O)$_2$R. In some embodiments, $R^1$ is —NRS(O)$_2$N(R)$_2$. In some embodiments, $R^1$ is —C(O)OH. In some embodiments, $R^1$ is —C(O)$R^x$. In some embodiments, $R^1$ is —S(O)$_2$OH. In some embodiments, $R^1$ is —S(O)$_2R^y$. In some embodiments, $R^1$ is selected from:

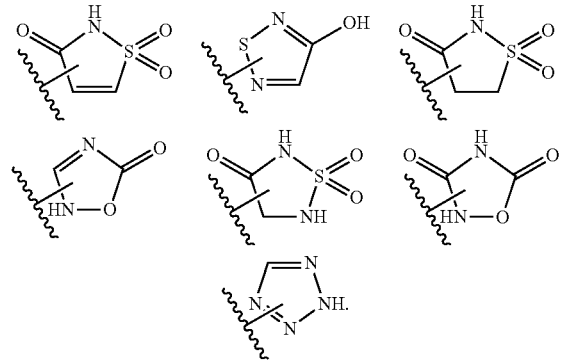

In some embodiments, $R^1$ is —COOH. In some embodiments, $R^1$ is —C(O)NHS(O)$_2$R. In some embodiments, $R^1$ is —C(O)NHS(O)$_2$R, wherein R is optionally substituted $C_{1-6}$ aliphatic. In some embodiments, $R^1$ is —C(O)NHS(O)$_2$Me. In some embodiments, $R^1$ is —C(O)NHS(O)$_2$CH$_2$Ph. In some embodiments, $R^1$ is

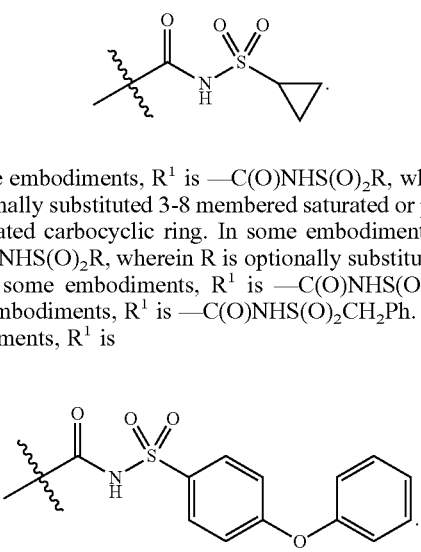

In some embodiments, $R^1$ is —C(O)NHS(O)$_2$R, wherein R is optionally substituted 3-8 membered saturated or partially unsaturated carbocyclic ring. In some embodiments, $R^1$ is —C(O)NHS(O)$_2$R, wherein R is optionally substituted phenyl. In some embodiments, $R^1$ is —C(O)NHS(O)$_2$Ph. In some embodiments, $R^1$ is —C(O)NHS(O)$_2$CH$_2$Ph. In some embodiments, $R^1$ is

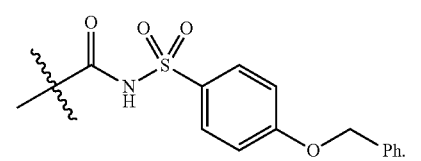 [SMILES: *C(=O)NS(=O)(=O)c1ccc(OCc2ccccc2)cc1]

In some embodiments, $R^1$ is

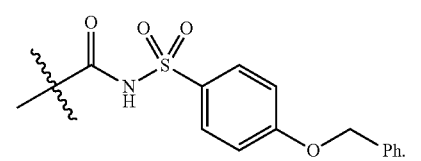 [SMILES: *C(=O)NS(=O)(=O)c1ccc(OCc2ccccc2)cc1]

In some embodiments, $R^1$ is

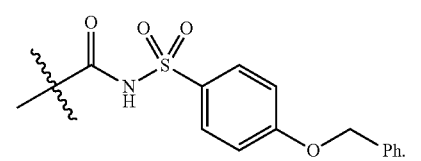 [SMILES: *C(=O)NS(=O)(=O)c1ccc(OCc2ccccc2)cc1]

In some embodiments, R¹ is

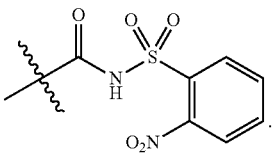 [SMILES: *C(=O)NS(=O)(=O)c1ccccc1[N+](=O)[O-]]

In some embodiments, R¹ is

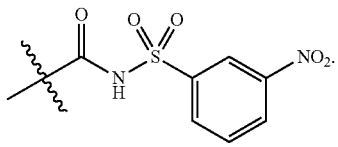 [SMILES: *C(=O)NS(=O)(=O)c1cccc([N+](=O)[O-])c1]

In some embodiments, R¹ is

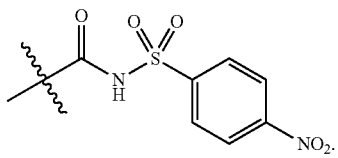 [SMILES: *C(=O)NS(=O)(=O)c1ccc([N+](=O)[O-])cc1]

In some embodiments, R¹ is

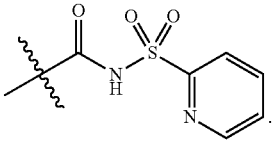 [SMILES: *C(=O)NS(=O)(=O)c1ccccn1]

In some embodiments, R¹ is

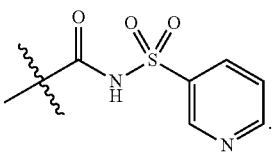 [SMILES: *C(=O)NS(=O)(=O)c1cccnc1]

In some embodiments, R¹ is

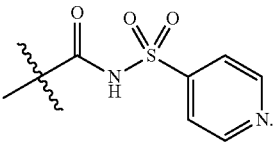 [SMILES: *C(=O)NS(=O)(=O)c1ccncc1]

In some embodiments, R¹ is

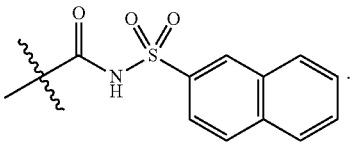 [SMILES: *C(=O)NS(=O)(=O)c1ccc2ccccc2c1]

In some embodiments, R¹ is —S(O)₂OR. In some embodiments, R¹ is —S(O)₂OH. In some embodiments, R¹ is —S(O)₂OR, wherein R is optionally substituted phenyl. In some embodiments, R¹ is —S(O)₂OPh.

As defined generally above, $R^x$ is selected from —C(O)OR, —NRS(O)₂CF₃, —NRC(O)R, —NRC(O)OR, —NRC(O)N(R)₂, or —NRS(O)₂R. In some embodiments, $R^x$ is —C(O)OR. In some embodiments, $R^x$ is —NRS(O)₂CF₃. In some embodiments, $R^x$ is —NRC(O)R. In some embodiments, $R^x$ is —NRC(O)OR. In some embodiments, $R^x$ is —NRC(O)N(R)₂. In some embodiments, $R^x$ is —NRS(O)₂R.

As defined generally above, $R^y$ is selected from —NRC(O)CF₃, —NRC(O)R, or —NRC(O)N(R)₂. In some embodiments, $R^y$ is —NRC(O)CF₃. In some embodiments, $R^y$ is —NRC(O)R. In some embodiments, $R^y$ is NRC(O)N(R)₂.

As defined generally above, R² is selected from R, halo, —NH₂, —CN, —NO₂, and —CF₃. In some embodiments, R² is R. In some embodiments, R² is R, wherein R is optionally substituted $C_{1-6}$ aliphatic. In some embodiments, R² is not optionally substituted $C_{1-6}$ aliphatic connected to the rest of the molecule via —C(O)—. In some embodiments, R² is not —C(O)-(optionally substituted $C_{1-5}$ aliphatic). In some embodiments, R² is not optionally substituted $C_{1-6}$ aliphatic comprising —C(O)—. In some embodiments, R² does not comprise —C(O)—. In some embodiments, R² is not -L¹-R¹. In some embodiments, R² is not optionally substituted $C_{1-6}$ aliphatic comprising —C(O)OH. In some embodiments, R² does not comprise —C(O)OH. In some embodiments, R² is not optionally substituted $C_{1-6}$ aliphatic comprising —C(O)OH or a bioisostere thereof. In some embodiments, R² does not comprise —C(O)OH or a bioisostere thereof. In some embodiments, R² is halo. In some embodiments, R² is —F. In some embodiments, R² is —Cl. In some embodiments, R² is —Br. In some embodiments, R² is —I. In some embodiments, R² is —NH₂. In some embodiments, R² is —CN. In some embodiments, R² is —NO₂.

In some embodiments, R² is —H.

In some embodiments, R² is optionally substituted $C_{1-6}$ aliphatic. In some embodiments, R² is unsubstituted $C_{1-6}$ aliphatic. In some embodiments, R² is $C_{1-6}$ aliphatic substituted with one or more halogen. In some embodiments, R² is $C_{1-6}$ aliphatic substituted with one or more —F. In some embodiments, R² is methyl. In some embodiments, R² is —CF₃.

As defined generally above, each R is independently selected from hydrogen or an optionally substituted group selected from $C_{1-6}$ aliphatic or a ring selected from a 3-8 membered saturated or partially unsaturated carbocyclic ring, phenyl, a 8-10 membered bicyclic aryl ring, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur. In some embodiments, each R is independently selected from hydrogen or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur. In some embodiments, R is substituted. In some embodiments, R is unsubstituted.

In some embodiments, R is hydrogen.

In some embodiments, R is substituted. In some embodiments, R is unsubstituted.

In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is optionally substituted methyl. In some embodiments, R is methyl substituted with one ore more halogen. In some embodiments, R is —$CF_3$. In some embodiments, R is —$CH_2Ph$.

In some embodiments, R is an optionally substituted 3-8 membered saturated or partially unsaturated monocyclic carbocyclic ring. In some embodiments, R is an optionally substituted 3-membered saturated or partially unsaturated monocyclic carbocyclic ring. In some embodiments, R is cyclopropyl. In some embodiments, R is an optionally substituted 4-membered saturated or partially unsaturated monocyclic carbocyclic ring. In some embodiments, R is an optionally substituted 5-membered saturated or partially unsaturated monocyclic carbocyclic ring. In some embodiments, R is an optionally substituted 6-membered saturated or partially unsaturated monocyclic carbocyclic ring. In some embodiments, R is an optionally substituted 7-membered saturated or partially unsaturated monocyclic carbocyclic ring. In some embodiments, R is an optionally substituted 8-membered saturated or partially unsaturated monocyclic carbocyclic ring.

In some embodiments, R is an optionally substituted 3-8 membered saturated monocyclic carbocyclic ring. In some embodiments, R is an optionally substituted cycloheptyl. In some embodiments, R is an optionally substituted cyclohexyl. In some embodiments, R is an optionally substituted cyclopentyl. In some embodiments, R is an optionally substituted cyclobutyl. In some embodiments, R is an optionally substituted cyclopropyl.

In some embodiments, R is an optionally substituted 3-8 membered unsaturated monocyclic carbocyclic ring. In some embodiments, R is an optionally substituted cycloheptenyl. In some embodiments, R is an optionally substituted cyclohexenyl. In some embodiments, R is an optionally substituted cyclopentenyl. In some embodiments, R is an optionally substituted cyclobutenyl. In some embodiments, R is an optionally substituted cyclopropyl.

In some embodiments, R is optionally substituted phenyl. In some embodiments, R is substituted phenyl. In some embodiments, R is unsubstituted phenyl. In some embodiments, R is p-phenoxyphenyl. In some embodiments, R is o-nitrophenyl. In some embodiments, R is m-nitrophenyl. In some embodiments, R is p-nitrophenyl. In some embodiments, R is p-(p-methoxyphenoxy)phenyl. In some embodiments, R is p-(phenylmethoxy)phenyl.

In some embodiments, R is optionally substituted 8-10 membered bicyclic aryl ring. In some embodiments, R is optionally substituted naphthyl. In some embodiments, R is naphthyl. In some embodiments, R is 1-naphthyl. In some embodiments, R is 2-naphthyl. In some embodiments, R is 3-naphthyl.

In some embodiments, R is an optionally substituted 3-8 membered saturated or partially unsaturated heterocyclic ring having 1-2 heteroatoms independently selected from nitrogen, oxygen or sulfur. In some embodiments, R is a substituted 3-8 membered saturated or partially unsaturated heterocyclic ring having 1-2 heteroatoms independently selected from nitrogen, oxygen or sulfur. In some embodiments, R is an unsubstituted 3-8 membered saturated or partially unsaturated heterocyclic ring having 1-2 heteroatoms independently selected from nitrogen, oxygen or sulfur.

In some embodiments, R is a substituted 3-8 membered heterocyclic ring having 1-2 heteroatoms independently selected from nitrogen, oxygen or sulfur. In some embodiments, R is an unsubstituted 3-8 membered heterocyclic ring having 1-2 heteroatoms independently selected from nitrogen, oxygen or sulfur.

In some embodiments, R is an optionally substituted 3-membered heterocyclic ring having one heteroatom selected from nitrogen, oxygen or sulfur. Exemplary R groups include but are not limited to optionally substituted aziridinyl, thiiranyl or oxiranyl. In some embodiments, R is a substituted 3-membered heterocyclic ring having one heteroatom selected from nitrogen, oxygen or sulfur. In some embodiments, R is an unsubstituted 3-membered heterocyclic ring having one heteroatom selected from nitrogen, oxygen or sulfur.

In some embodiments, R is an optionally substituted 4-membered heterocyclic ring having 1-2 heteroatoms independently selected from nitrogen, oxygen, or sulfur. Exemplary R groups include but are not limited to optionally substituted azetidinyl, oxetanyl, thietanyl, oxazetidinyl, thiazetidinyl, or diazetidinyl. In some embodiments, R is a substituted 4-membered heterocyclic ring having 1-2 heteroatoms independently selected from nitrogen, oxygen, or sulfur. In some embodiments, R is an unsubstituted 4-membered heterocyclic ring having 1-2 heteroatoms independently selected from nitrogen, oxygen, or sulfur.

In some embodiments, R is an optionally substituted 5-membered heterocyclic ring having 1-2 heteroatoms independently selected from nitrogen, oxygen, or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, or thiazolidinyl. In some embodiments, R is a substituted 5-membered heterocyclic ring having 1-2 heteroatoms independently selected from nitrogen, oxygen, or sulfur. In some embodiments, R is an unsubstituted 5-membered heterocyclic ring having 1-2 heteroatoms independently selected from nitrogen, oxygen, or sulfur.

In some embodiments, R is an optionally substituted 6-membered heterocyclic ring having 1-2 heteroatoms independently selected from nitrogen, oxygen, or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, and oxathianyl. In some embodiments, R is a substituted 6-membered heterocyclic ring having 1-2 heteroatoms independently selected from nitrogen, oxygen, or sulfur. In some embodiments, R is an unsubstituted 6-membered heterocyclic ring having 1-2 heteroatoms independently selected from nitrogen, oxygen, or sulfur.

In some embodiments, R is optionally substituted 7-membered heterocyclic ring having 1-2 heteroatoms independently selected from nitrogen, oxygen, or sulfur. Exemplary R groups include but are not limited to optionally substituted azepanyl, oxepanyl, thiepanyl, diazepanyl, oxazepanyl, thiazepanyl, dioxepanyl, oxathiepanyl, or dithiepanyl. In some embodiments, R is a substituted 7-membered heterocyclic ring having 1-2 heteroatoms independently selected from nitrogen, oxygen, or sulfur. In some embodiments, R is an unsubstituted 7-membered heterocyclic ring having 1-2 heteroatoms independently selected from nitrogen, oxygen, or sulfur.

In some embodiments, R is optionally substituted 8-membered heterocyclic ring having 1-2 heteroatoms independently selected from nitrogen, oxygen, or sulfur. In some embodiments, R is a substituted 8-membered heterocyclic ring having 1-2 heteroatoms independently selected from nitrogen, oxygen, or sulfur. In some embodiments, R is an unsubstituted 8-membered heterocyclic ring having 1-2 heteroatoms independently selected from nitrogen, oxygen, or sulfur.

In some embodiments, R is an optionally substituted 3-8 membered partially unsaturated heterocyclic ring having 1-2 heteroatoms independently selected from nitrogen, oxygen or sulfur. In certain embodiments, R is an optionally substituted 5-7 membered partially unsaturated ring having 1-2 heteroatoms independently selected from nitrogen, oxygen, or sulfur. In certain embodiments, R is an optionally substituted 5-6 membered partially unsaturated ring having 1-2 heteroatoms independently selected from nitrogen, oxygen, or sulfur. In certain embodiments, R is an optionally substituted 5-membered partially unsaturated ring having 1-2 heteroatoms independently selected from nitrogen, oxygen, or sulfur. Exemplary R groups include but are not limited to optionally substituted dihydroimidazolyl, dihydrothiazolyl, dihydrooxazolyl, or oxazolinyl. In certain embodiments, R is an optionally substituted 6-membered partially unsaturated ring having 1-2 heteroatoms independently selected from nitrogen, oxygen, or sulfur. Exemplary R groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, R is an optionally substituted 7-membered partially unsaturated ring having 1-2 heteroatoms independently selected from nitrogen, oxygen, or sulfur. Exemplary R groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, tetrahydroazepinyl, tetrahydrooxepinyl, tetrahydrothiepinyl, tetrahydrodiazepinyl, tetrahydrooxazepinyl or tetrahydrothiazepinyl. In some embodiments, R is an optionally substituted 8-membered partially unsaturated ring having 1-2 heteroatoms independently selected from nitrogen, oxygen or sulfur.

In some embodiments, R is an optionally substituted 5-6 membered heteroaryl ring having 1-4 heteroatoms independently selected from nitrogen, oxygen, or sulfur. In some embodiments, R is a substituted 5-6 membered heteroaryl ring having 1-4 heteroatoms independently selected from nitrogen, oxygen, or sulfur. In some embodiments, R is an unsubstituted 5-6 membered heteroaryl ring having 1-4 heteroatoms independently selected from nitrogen, oxygen, or sulfur.

In some embodiments, R is an optionally substituted 5-membered heteroaryl ring having 1-4 heteroatoms independently selected from nitrogen, oxygen or sulfur. In some embodiments, R is a substituted 5-membered heteroaryl ring having 1-4 heteroatoms independently selected from nitrogen, oxygen or sulfur. In some embodiments, R is an unsubstituted 5-membered heteroaryl ring having 1-4 heteroatoms independently selected from nitrogen, oxygen or sulfur. In some embodiments, R is an optionally substituted 6-membered heteroaryl ring having 1-4 heteroatoms independently selected from nitrogen, oxygen, or sulfur. In some embodiments, R is a substituted 6-membered heteroaryl ring having 1-4 heteroatoms independently selected from nitrogen, oxygen, or sulfur. In some embodiments, R is an unsubstituted 6-membered heteroaryl ring having 1-4 heteroatoms independently selected from nitrogen, oxygen, or sulfur.

In some embodiments, R is an optionally substituted 5-membered heteroaryl ring having one heteroatom selected from nitrogen, oxygen, or sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, or sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, or sulfur. Exemplary R groups include but are not limited to optionally substituted tetrazolyl, oxatriazolyl and thiatriazolyl.

In some embodiments, R is a 6-membered heteroaryl ring having 1-4 nitrogen atoms. In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl. In some embodiments, R is optionally substituted pyridinyl. In some embodiments, R is pyridinyl. In some embodiments, R is 1-pyridinyl. In some embodiments, R is 2-pyridinyl. In some embodiments, R is 3-pyridinyl.

As defined generally above, $L^2$ is an optionally substituted bivalent $C_{3-6}$ hydrocarbon chain wherein one or two methylene units of $L^2$ are optionally and independently replaced with —O—, —S—, or —NR'—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur. In some embodiments, $L^2$ is an optionally substituted bivalent $C_{3-6}$ hydrocarbon chain wherein one or two methylene units of $L^2$ are optionally and independently replaced with —O—, —S—, or —NR'—. In some embodiments, two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur. In some embodiments, two substituents of $L^2$ are optionally taken together to form optionally substituted bivalent 3-8 membered saturated or partially unsaturated carbocyclylene. In some embodiments, two substituents of $L^2$ are optionally taken together to form optionally substituted bivalent 3-8 membered saturated or partially unsaturated heterocyclylene having 1-4 heteroatoms independently selected from nitrogen, oxygen, or sulfur.

In some embodiments, $L^2$ is a substituted bivalent $C_{3-6}$ hydrocarbon chain wherein one or two methylene units of $L^2$ are optionally and independently replaced with —O—, —S—, or —NR'—. In some embodiments, $L^2$ is an unsubstituted bivalent $C_{3-6}$ hydrocarbon chain wherein one or two methylene units of $L^2$ are optionally and independently replaced with —O—, —S—, or —NR'—. In some embodiments, $L^2$ is a substituted bivalent $C_{3-6}$ hydrocarbon. In some embodiments, $L^2$ is an unsubstituted bivalent $C_{3-6}$ hydrocarbon. In some embodiments, $L^2$ is an optionally substituted bivalent $C_{4-6}$ hydrocarbon chain wherein one or two methylene units of $L^2$ are optionally and independently replaced with —O—, —S—, or —NR'—. In some embodiments, $L^2$ is a substituted bivalent $C_{4-6}$ hydrocarbon chain wherein one or two methylene units of $L^2$ are optionally and independently replaced with —O—, —S—, or —NR'—. In some embodiments, $L^2$ is an unsubstituted bivalent $C_{4-6}$ hydrocarbon chain wherein one or two methylene units of $L^2$ are optionally and independently replaced with —O—, —S—, or —NR'—. In some embodiments, $L^2$ is a substituted bivalent $C_{4-6}$ hydrocarbon. In some embodiments, $L^2$ is an unsubstituted bivalent $C_{4-6}$ hydrocarbon. In some embodiments, $L^2$ is an optionally substituted bivalent $C_{5-6}$ hydrocarbon chain wherein one or two methylene units of $L^2$ are optionally and independently replaced with —O—, —S—, or —NR'—. In some embodiments, $L^2$ is a substituted bivalent $C_{5-6}$ hydrocarbon chain wherein one or two methylene units of $L^2$ are optionally and independently replaced with —O—, —S—, or —NR'—. In some embodiments, $L^2$ is an unsubstituted bivalent $C_{5-6}$ hydrocarbon chain wherein one or two methylene units of $L^2$ are optionally and independently replaced with —O—, —S—, or —NR'—. In some embodiments, one of —O—, —S—, or —NR'— of $L^2$ is directly bonded to $R^3$. In some embodiments, an —O— moiety of $L^2$ is directly bonded to $R^3$. In some embodiments, an —S— moiety of $L^2$ is directly bonded to $R^3$. In some embodiments, an —NR'— moiety of $L^2$ is directly bonded to $R^3$. In some embodiments, $L^2$ is a substituted bivalent $C_{5-6}$ hydrocarbon. In some embodiments, $L^2$ is an unsubstituted bivalent $C_{5-6}$ hydrocarbon.

In some embodiments, $L^2$ is an optionally substituted bivalent $C_3$ hydrocarbon chain wherein one or two methylene units of $L^2$ are optionally and independently replaced with —O—, —S—, or —NR'—. In some embodiments, $L^2$ is a substituted bivalent $C_3$ hydrocarbon chain wherein one or two methylene units of $L^2$ are optionally and independently replaced with —O—, —S—, or —NR'—. In some embodiments, $L^2$ is an unsubstituted bivalent $C_3$ hydrocarbon chain wherein one or two methylene units of $L^2$ are optionally and independently replaced with —O—, —S—, or —NR'—. In some embodiments, $L^2$ is a substituted bivalent $C_3$ hydrocarbon chain. In some embodiments, $L^2$ is an unsubstituted bivalent $C_3$ hydrocarbon chain.

In some embodiments, $L^2$ is an optionally substituted bivalent $C_4$ hydrocarbon chain wherein one or two methylene units of $L^2$ are optionally and independently replaced with —O—, —S—, or —NR'—. In some embodiments, $L^2$ is a substituted bivalent $C_4$ hydrocarbon chain wherein one or two methylene units of $L^2$ are optionally and independently replaced with —O—, —S—, or —NR'—. In some embodiments, $L^2$ is an unsubstituted bivalent $C_4$ hydrocarbon chain wherein one or two methylene units of $L^2$ are optionally and independently replaced with —O—, —S—, or —NR'—. In some embodiments, $L^2$ is a substituted bivalent $C_4$ hydrocarbon chain. In some embodiments, $L^2$ is an unsubstituted bivalent $C_4$ hydrocarbon chain.

In some embodiments, $L^2$ is an optionally substituted bivalent $C_5$ hydrocarbon chain wherein one or two methylene units of $L^2$ are optionally and independently replaced with —O—, —S—, or —NR'—. In some embodiments, $L^2$ is a substituted bivalent $C_5$ hydrocarbon chain wherein one or two methylene units of $L^2$ are optionally and independently replaced with —O—, —S—, or —NR'—. In some embodiments, $L^2$ is an unsubstituted bivalent $C_5$ hydrocarbon chain wherein one or two methylene units of $L^2$ are optionally and independently replaced with —O—, —S—, or —NR'—. In some embodiments, $L^2$ is a substituted bivalent $C_5$ hydrocarbon chain. In some embodiments, $L^2$ is an unsubstituted bivalent $C_5$ hydrocarbon chain.

In some embodiments, $L^2$ is an optionally substituted bivalent $C_6$ hydrocarbon chain wherein one or two methylene units of $L^2$ are optionally and independently replaced with —O—, —S—, or —NR'—. In some embodiments, $L^2$ is a substituted bivalent $C_6$ hydrocarbon chain wherein one or two methylene units of $L^2$ are optionally and independently replaced with —O—, —S—, or —NR'—. In some embodiments, $L^2$ is an unsubstituted bivalent $C_6$ hydrocarbon chain wherein one or two methylene units of $L^2$ are optionally and independently replaced with —O—, —S—, or —NR'—. In some embodiments, $L^2$ is a substituted bivalent $C_6$ hydrocarbon chain. In some embodiments, $L^2$ is an unsubstituted bivalent $C_6$ hydrocarbon chain.

In some embodiments, two substituents of $L^2$ are optionally taken together to form optionally substituted bivalent 3-8 membered saturated or partially unsaturated carbocyclylene. In some embodiments, two substituents of $L^2$ are taken together to form optionally substituted bivalent 3-8 membered saturated or partially unsaturated carbocyclylene. In some embodiments, two substituents of $L^2$ are optionally taken together to form optionally substituted bivalent 3-8 membered saturated carbocyclylene. In some embodiments, two substituents of $L^2$ are taken together to form optionally substituted bivalent 3-8 membered saturated carbocyclylene. In some embodiments, two substituents of $L^2$ are optionally taken together to form optionally substituted bivalent 3-8 membered partially unsaturated carbocyclylene. In some embodiments, two substituents of $L^2$ are taken together to form optionally substituted bivalent 3-8 membered partially unsaturated carbocyclylene.

In some embodiments, two substituents of $L^2$ are taken together to form optionally substituted bivalent 3-membered saturated or partially unsaturated carbocyclylene. In some embodiments, two substituents of $L^2$ are taken together to form optionally substituted bivalent 3-membered saturated carbocyclylene. In some embodiments, two substituents of $L^2$ are taken together to form optionally substituted bivalent 3-membered partially unsaturated carbocyclylene. In some embodiments, two substituents of $L^2$ are taken together to form optionally substituted bivalent 4-membered saturated or partially unsaturated carbocyclylene. In some embodiments, two substituents of $L^2$ are taken together to form optionally substituted bivalent 4-membered saturated carbocyclylene. In some embodiments, two substituents of $L^2$ are taken together to form optionally substituted bivalent 4-membered partially unsaturated carbocyclylene. In some embodiments, two substituents of $L^2$ are taken together to form optionally substituted bivalent 5-membered saturated or partially unsaturated carbocyclylene. In some embodiments, two substituents of $L^2$ are taken together to form optionally substituted bivalent 5-membered saturated carbocyclylene. In some embodiments, two substituents of $L^2$ are taken together to form optionally substituted bivalent 5-membered partially unsaturated carbocyclylene. In some embodiments, two substituents of $L^2$ are taken together to form optionally substituted bivalent 6-membered saturated or partially unsaturated carbocyclylene. In some embodiments, two substituents of $L^2$ are taken together to form optionally substituted bivalent 6-membered saturated carbocyclylene. In some embodiments, two substituents of $L^2$ are taken together to form optionally substituted bivalent 6-membered partially unsaturated carbocyclylene. In some embodiments, two substituents of $L^2$ are taken together to form optionally substituted bivalent 7-membered saturated or partially unsaturated carbocyclylene. In some embodiments, two substituents of $L^2$ are taken together to form optionally substituted bivalent 7-membered saturated carbocyclylene. In some embodiments, two substituents of $L^2$ are taken together to form optionally substituted bivalent 7-membered partially unsaturated carbocyclylene. In some embodiments, two substituents of $L^2$ are taken together to form optionally substituted bivalent 8-membered saturated or partially unsaturated carbocyclylene. In some embodiments, two substituents of $L^2$ are taken together to form optionally substituted bivalent 8-membered saturated carbocyclylene. In some embodiments, two substituents of $L^2$ are taken together to form optionally substituted bivalent 8-membered partially unsaturated carbocyclylene.

In some embodiments, two substituents of $L^2$ are optionally taken together to form optionally substituted bivalent 3-8 membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-8 membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-8 membered saturated heterocyclylene having 1-4 heteroatoms independently selected from nitrogen, oxygen, or sulfur. In some embodiments, two substituents of $L^2$ are taken together to form optionally substituted bivalent 3-8 membered partially unsaturated heterocyclylene having 1-4 heteroatoms independently selected from nitrogen, oxygen, or sulfur.

In some embodiments, two substituents of $L^2$ are taken together to form optionally substituted bivalent 3-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-membered saturated heterocyclylene having 1-4 heteroatoms independently selected from nitrogen, oxygen, or sulfur. In some embodiments, two substituents of $L^2$ are taken together to form optionally substituted bivalent 3-membered partially unsaturated heterocyclylene having 1-4 heteroatoms independently selected from nitrogen, oxygen, or sulfur. In some embodiments, two substituents of $L^2$ are taken together to form optionally substituted bivalent 4-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 4-membered saturated heterocyclylene having 1-4 heteroatoms independently selected from nitrogen, oxygen, or sulfur. In some embodiments, two substituents of $L^2$ are taken together to form optionally substituted bivalent 4-membered partially unsaturated heterocyclylene having 1-4 heteroatoms independently selected from nitrogen, oxygen, or sulfur. In some embodiments, two substituents of $L^2$ are taken together to form optionally substituted bivalent 5-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 5-membered saturated heterocyclylene having 1-4 heteroatoms independently selected from nitrogen, oxygen, or sulfur. In some embodiments, two substituents of $L^2$ are taken together to form optionally substituted bivalent 5-membered partially unsaturated heterocyclylene having 1-4 heteroatoms independently selected from nitrogen, oxygen, or sulfur. In some embodiments, two substituents of $L^2$ are taken together to form optionally substituted bivalent 6-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 6-membered saturated heterocyclylene having 1-4 heteroatoms independently selected from nitrogen, oxygen, or sulfur. In some embodiments, two substituents of $L^2$ are taken together to form optionally substituted bivalent 6-membered partially unsaturated heterocyclylene having 1-4 heteroatoms independently selected from nitrogen, oxygen, or sulfur. In some embodiments, two substituents of $L^2$ are taken together to form optionally substituted bivalent 7-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 7-membered saturated heterocyclylene having 1-4 heteroatoms independently selected from nitrogen, oxygen, or sulfur. In some embodiments, two substituents of $L^2$ are taken together to form optionally substituted bivalent 7-membered partially unsaturated heterocyclylene having 1-4 heteroatoms independently selected from nitrogen, oxygen, or sulfur. In some embodiments, two substituents of $L^2$ are taken together to form optionally substituted bivalent 8-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 8-membered saturated heterocyclylene having 1-4 heteroatoms independently selected from nitrogen, oxygen, or sulfur. In some embodiments, two substituents of $L^2$ are taken together to form optionally substituted bivalent 8-membered partially unsaturated heterocyclylene having 1-4 heteroatoms independently selected from nitrogen, oxygen, or sulfur.

In some embodiments, two substituents of $L^2$ are taken together to form optionally substituted bivalent 3-8 membered saturated or partially unsaturated heterocyclylene having one heteroatom selected from nitrogen, oxygen, or sulfur. In some embodiments, two substituents of $L^2$ are taken together to form optionally substituted bivalent 3-8 membered saturated or partially unsaturated heterocyclylene having two heteroatoms independently selected from nitrogen, oxygen, or sulfur. In some embodiments, two substituents of $L^2$ are taken together to form optionally substituted bivalent 3-8 membered saturated or partially unsaturated heterocyclylene having three heteroatoms independently selected from nitrogen, oxygen, or sulfur. In some embodiments, two substituents of $L^2$ are taken together to form optionally substituted bivalent 3-8 membered saturated or partially unsaturated heterocyclylene having four heteroatoms independently selected from nitrogen, oxygen, or sulfur.

In some embodiments, $L^1$ is an unsubstituted bivalent $C_{1-6}$ hydrocarbon chain, $R^2$ is hydrogen, and $L^2$ is an unsubstituted bivalent $C_{3-6}$ hydrocarbon chain wherein one or two methylene units of $L^2$ are optionally and independently replaced with —O—, —S—, or —NR'—.

In some embodiments, $L^1$ is an unsubstituted bivalent $C_{1-6}$ hydrocarbon chain, $R^2$ is hydrogen, and $L^2$ is an unsubstituted bivalent $C_{3-6}$ hydrocarbon chain.

In some embodiments, one or two methylene units of $L^2$ are replaced with —O—. In some embodiments, one methylene unit of $L^2$ is replaced with —O—. In some embodiments, $L^2$ is an optionally substituted bivalent $C_3$ hydrocarbon chain wherein one methylene unit of $L^2$ is replaced with —O—. In some embodiments, $L^2$ is a substituted bivalent $C_3$ hydrocarbon chain wherein one methylene unit of $L^2$ is replaced with —O—. In some embodiments, $L^2$ is an unsubstituted bivalent $C_3$ hydrocarbon chain wherein one methylene unit of $L^2$ is replaced with —O—. In some embodiments, $L^2$ is an optionally substituted bivalent $C_4$ hydrocarbon chain wherein one methylene unit of $L^2$ is replaced with —O—. In some embodiments, $L^2$ is a substituted bivalent $C_4$ hydrocarbon chain wherein one methylene unit of $L^2$ is replaced with —O—. In some embodiments, $L^2$ is an unsubstituted bivalent $C_4$ hydrocarbon chain wherein one methylene unit of $L^2$ is replaced with —O—. In some embodiments, $L^2$ is an optionally substituted bivalent $C_5$ hydrocarbon chain wherein one methylene unit of $L^2$ is replaced with —O—. In some embodiments, $L^2$ is a substituted bivalent $C_5$ hydrocarbon chain wherein one methylene unit of $L^2$ is replaced with —O—. In some embodiments, $L^2$ is an unsubstituted bivalent $C_5$ hydrocarbon chain wherein one methylene unit of $L^2$ is replaced with —O—. In some embodiments, $L^2$ is an optionally substituted bivalent $C_6$ hydrocarbon chain wherein one methylene unit of $L^2$ is replaced with —O—. In some embodiments, $L^2$ is a substituted bivalent $C_6$ hydrocarbon chain wherein one methylene unit of $L^2$ is replaced with —O—. In some embodiments, $L^2$ is an unsubstituted bivalent $C_6$ hydrocarbon chain wherein one methylene unit of $L^2$ is replaced with —O—.

In some embodiments, one or two methylene units of $L^2$ are replaced with —S—. In some embodiments, one methylene unit of $L^2$ is replaced with —S—. In some embodiments, $L^2$ is an optionally substituted bivalent $C_3$ hydrocarbon chain wherein one methylene unit of $L^2$ is replaced with —S—. In some embodiments, $L^2$ is a substituted bivalent $C_3$ hydrocarbon chain wherein one methylene unit of $L^2$ is replaced with —S—. In some embodiments, $L^2$ is an unsubstituted bivalent $C_3$ hydrocarbon chain wherein one methylene unit of $L^2$ is replaced with —S—. In some embodiments, $L^2$ is an optionally substituted bivalent $C_4$ hydrocarbon chain wherein one methylene unit of $L^2$ is replaced with —S—. In some embodiments, $L^2$ is a substituted bivalent $C_4$ hydrocarbon chain wherein one methylene unit of $L^2$ is replaced with —S—. In some embodiments, $L^2$ is an unsubstituted bivalent $C_4$ hydrocarbon chain wherein one methylene unit of $L^2$ is replaced with —S—. In some embodiments, $L^2$ is an optionally substituted bivalent $C_5$ hydrocarbon chain wherein one methylene unit of $L^2$ is replaced with —S—. In some embodiments, $L^2$ is a substituted bivalent $C_5$ hydrocarbon chain wherein one methylene unit of $L^2$ is replaced with —S—. In some embodiments, $L^2$ is an unsubstituted bivalent $C_5$ hydrocarbon chain wherein one methylene unit of $L^2$ is replaced with —S—. In some embodiments, $L^2$ is an optionally substituted bivalent $C_6$ hydrocarbon chain wherein one methylene unit of $L^2$ is replaced with —S—. In some embodiments, $L^2$ is a substituted bivalent $C_6$ hydrocarbon chain wherein one methylene unit of $L^2$ is replaced with —S—. In some embodiments, $L^2$ is an unsubstituted bivalent $C_6$ hydrocarbon chain wherein one methylene unit of $L^2$ is replaced with —S—.

In some embodiments, one or two methylene units of $L^2$ are replaced with —NR'—. In some embodiments, one methylene unit of $L^2$ is replaced with —NR'—. In some embodiments, $L^2$ is an optionally substituted bivalent $C_3$ hydrocarbon chain wherein one methylene unit of $L^2$ is replaced with —NR'—. In some embodiments, $L^2$ is a substituted bivalent $C_3$ hydrocarbon chain wherein one methylene unit of $L^2$ is replaced with —NR'—. In some embodiments, $L^2$ is an unsubstituted bivalent $C_3$ hydrocarbon chain wherein one methylene unit of $L^2$ is replaced with —NR'—. In some embodiments, $L^2$ is an optionally substituted bivalent $C_4$ hydrocarbon chain wherein one methylene unit of $L^2$ is replaced with —NR'—. In some embodiments, $L^2$ is a substituted bivalent $C_4$ hydrocarbon chain wherein one methylene unit of $L^2$ is replaced with —NR'—. In some embodiments, $L^2$ is an unsubstituted bivalent $C_4$ hydrocarbon chain wherein one methylene unit of $L^2$ is replaced with —NR'—. In some embodiments, $L^2$ is an optionally substituted bivalent $C_5$ hydrocarbon chain wherein one methylene unit of $L^2$ is replaced with —NR'—. In some embodiments, $L^2$ is a substituted bivalent $C_5$ hydrocarbon chain wherein one methylene unit of $L^2$ is replaced with —NR'—. In some embodiments, $L^2$ is an unsubstituted bivalent $C_5$ hydrocarbon chain wherein one methylene unit of $L^2$ is replaced with —NR'—. In some embodiments, $L^2$ is an optionally substituted bivalent $C_6$ hydrocarbon chain wherein one methylene unit of $L^2$ is replaced with —NR'—. In some embodiments, $L^2$ is a substituted bivalent $C_6$ hydrocarbon chain wherein one methylene unit of $L^2$ is replaced with —NR'—. In some embodiments, $L^2$ is an unsubstituted bivalent $C_6$ hydrocarbon chain wherein one methylene unit of $L^2$ is replaced with —NR'—.

In some embodiments, each substituent of $L^2$ is $C_{1-6}$ aliphatic. In some embodiments, each substituent of $L^2$ is $C_{1-6}$ alkyl. In some embodiments, each substituent of $L^2$ is methyl.

In some embodiments, $L^2$ is —CH$_2$CH$_2$O—. In some embodiments, $L^2$ is —CH$_2$CH$_2$CH$_2$O—. In some embodiments, $L^2$ is —CH$_2$CH(CH$_3$)CH$_2$O—.

As defined generally above, each R' is independently hydrogen or optionally substituted $C_{1-4}$ alkyl. In some embodiments, R' is hydrogen. In some embodiments, R' is optionally substituted $C_{1-4}$ alkyl. In some embodiments, R' is substituted $C_{1-4}$ alkyl. In some embodiments, R' is unsubstituted $C_{1-4}$ alkyl. In some embodiments, R' is optionally substituted methyl. In some embodiments, R' is substituted methyl. In some embodiments, R' is methyl. In some embodiments, R' is optionally substituted ethyl. In some embodiments, R' is substituted ethyl. In some embodiments, R' is ethyl. In some embodiments, R' is optionally substituted propyl. In some embodiments, R' is optionally substituted n-propyl. In some embodiments, R' is optionally substituted isopropyl. In some embodiments, R' is substituted propyl. In some embodiments, R' is substituted n-propyl. In some embodiments, R' is substituted isopropyl. In some embodiments, R' is propyl. In some embodiments, R' is n-propyl. In some embodiments, R' is isopropyl. In some embodiments, R' is optionally substituted butyl. In some embodiments, R' is substituted butyl. In some embodiments, R' is butyl. In some embodiments, R' is optionally substituted n-butyl. In some embodiments, R' is substituted n-butyl. In some embodiments, R' is n-butyl. In some embodiments, R' is optionally substituted isobutyl. In some embodiments, R' is substituted isobutyl. In some embodiments, R' is isobutyl. In some embodiments, R' is optionally substituted sec-butyl. In some embodiments, R' is substituted sec-butyl. In some embodiments, R' is sec-butyl. In some embodiments, R' is optionally substituted t-butyl. In some embodiments, R' is substituted t-butyl. In some embodiments, R' is t-butyl.

As defined generally above, $R^3$ is an optionally substituted ring selected from a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur. In some embodiments, $R^3$ is substituted. In some embodiments, $R^3$ is unsubstituted.

In some embodiments, $R^3$ is an optionally substituted 3-8 membered saturated or partially unsaturated monocyclic carbocyclic ring. In some embodiments, $R^3$ is an optionally substituted 3-membered saturated or partially unsaturated monocyclic carbocyclic ring. In some embodiments, $R^3$ is an optionally substituted 4-membered saturated or partially unsaturated monocyclic carbocyclic ring. In some embodiments, $R^3$ is an optionally substituted 5-membered saturated or partially unsaturated monocyclic carbocyclic ring. In some embodiments, $R^3$ is an optionally substituted 6-membered saturated or partially unsaturated monocyclic carbocyclic ring. In some embodiments, $R^3$ is an optionally substituted 7-membered saturated or partially unsaturated monocyclic carbocyclic ring. In some embodiments, $R^3$ is an optionally substituted 8-membered saturated or partially unsaturated monocyclic carbocyclic ring.

In some embodiments, $R^3$ is an optionally substituted 3-8 membered saturated monocyclic carbocyclic ring. In some embodiments, $R^3$ is an optionally substituted cycloheptyl. In some embodiments, $R^3$ is an optionally substituted cyclohexyl. In some embodiments, $R^3$ is an optionally substituted cyclopentyl. In some embodiments, $R^3$ is an optionally substituted cyclobutyl. In some embodiments, $R^3$ is an optionally substituted cyclopropyl.

In some embodiments, $R^3$ is an optionally substituted 3-8 membered unsaturated monocyclic carbocyclic ring. In some embodiments, $R^3$ is an optionally substituted cycloheptenyl. In some embodiments, $R^3$ is an optionally substituted cyclohexenyl. In some embodiments, $R^3$ is an optionally substituted cyclopentenyl. In some embodiments, $R^3$ is an optionally substituted cyclobutenyl. In some embodiments, $R^3$ is an optionally substituted cyclopropyl.

In some embodiments, $R^3$ is optionally substituted phenyl. In some embodiments, $R^3$ is substituted phenyl. In some embodiments, $R^3$ is unsubstituted phenyl. In some embodiments, $R^3$ is 3,5-dimethyl-4-chlorophenyl.

In some embodiments, $R^3$ is an optionally substituted 8-10 membered bicyclic aromatic carbocyclic ring. In some embodiments, $R^3$ is a substituted 8-10 membered bicyclic aromatic carbocyclic ring. In some embodiments, $R^3$ is an unsubstituted 8-10 membered bicyclic aromatic carbocyclic ring. In some embodiments, $R^3$ is an optionally substituted 8-membered bicyclic aromatic carbocyclic ring. In some embodiments, $R^3$ is a substituted 8-membered bicyclic aromatic carbocyclic ring. In some embodiments, $R^3$ is an unsubstituted 8-membered bicyclic aromatic carbocyclic ring. In some embodiments, $R^3$ is an optionally substituted 9-membered bicyclic aromatic carbocyclic ring. In some embodiments, $R^3$ is a substituted 9-membered bicyclic aromatic carbocyclic ring. In some embodiments, $R^3$ is an unsubstituted 9-membered bicyclic aromatic carbocyclic ring. In some embodiments, $R^3$ is an optionally substituted 10-membered bicyclic aromatic carbocyclic ring. In some embodiments, $R^3$ is a substituted 10-membered bicyclic aromatic carbocyclic ring. In some embodiments, $R^3$ is an unsubstituted 10-membered bicyclic aromatic carbocyclic ring. In some embodiments, $R^3$ is optionally substituted naphthyl. In some embodiments, $R^3$ is substituted naphthyl. In some embodiments, $R^3$ is unsubstituted naphthyl. In some embodiments, $R^3$ is optionally substituted 1-naphthyl. In some embodiments, $R^3$ is 1-naphthyl. In some embodiments, $R^3$ is optionally substituted 2-naphthyl. In some embodiments, $R^3$ is 2-naphthyl.

In some embodiments, $R^3$ is an optionally substituted 4-8 membered saturated or partially unsaturated monocyclic heterocyclic ring having 1-2 heteroatoms independently selected from nitrogen, oxygen or sulfur. In some embodiments, $R^3$ is a substituted 4-8 membered saturated or partially unsaturated monocyclic heterocyclic ring having 1-2 heteroatoms independently selected from nitrogen, oxygen or sulfur. In some embodiments, $R^3$ is an unsubstituted 4-8 membered saturated or partially unsaturated monocyclic heterocyclic ring having 1-2 heteroatoms independently selected from nitrogen, oxygen or sulfur.

In some embodiments, $R^3$ is a substituted 4-8 membered heterocyclic ring having 1-2 heteroatoms independently selected from nitrogen, oxygen or sulfur. In some embodiments, $R^3$ is an unsubstituted 4-8 membered heterocyclic ring having 1-2 heteroatoms independently selected from nitrogen, oxygen or sulfur.

In some embodiments, $R^3$ is an optionally substituted 4-membered heterocyclic ring having 1-2 heteroatoms independently selected from nitrogen, oxygen, or sulfur. Exemplary $R^3$ groups include but are not limited to optionally substituted azetidinyl, oxetanyl, thietanyl, oxazetidinyl, thiazetidinyl, or diazetidinyl.

In some embodiments, $R^3$ is an optionally substituted 5-membered heterocyclic ring having 1-2 heteroatoms independently selected from nitrogen, oxygen, or sulfur. Exemplary $R^3$ groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, or thiazolidinyl.

In some embodiments, $R^3$ is an optionally substituted 6-membered heterocyclic ring having 1-2 heteroatoms independently selected from nitrogen, oxygen, or sulfur. Exemplary $R^3$ groups include but are not limited to optionally substituted piperidinyl, tetrahydropyranyl, tetrahydrothiopyranyl, piperazinyl, morpholinyl, thiomorpholinyl, dithianyl, dioxanyl, and oxathianyl.

In some embodiments, $R^3$ is optionally substituted 7-membered heterocyclic ring having 1-2 heteroatoms independently selected from nitrogen, oxygen, or sulfur. Exemplary $R^3$ groups include but are not limited to optionally substituted azepanyl, oxepanyl, thiepanyl, diazepanyl, oxazepanyl, thiazepanyl, dioxepanyl, oxathiepanyl, or dithiepanyl.

In some embodiments, $R^3$ is optionally substituted 8-membered heterocyclic ring having 1-2 heteroatoms independently selected from nitrogen, oxygen, or sulfur.

In some embodiments, $R^3$ is an optionally substituted 4-8 membered partially unsaturated heterocyclic ring having 1-2 heteroatoms independently selected from nitrogen, oxygen or sulfur. In certain embodiments, $R^3$ is an optionally substituted 5-7 membered partially unsaturated ring having 1-2 heteroatoms independently selected from nitrogen, oxygen, or sulfur. In certain embodiments, $R^3$ is an optionally substituted 5-6 membered partially unsaturated ring having 1-2 heteroatoms independently selected from nitrogen, oxygen, or sulfur. In certain embodiments, $R^3$ is an optionally substituted 5-membered partially unsaturated ring having 1-2 heteroatoms independently selected from nitrogen, oxygen, or sulfur. Exemplary $R^3$ groups include but are not limited to optionally substituted dihydroimidazolyl, dihydrothiazolyl, dihydrooxazolyl, or oxazolinyl. In certain embodiments, $R^3$ is an optionally substituted 6-membered partially unsaturated ring having 1-2 heteroatoms independently selected from nitrogen, oxygen, or sulfur. Exemplary $R^3$ groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, $R^3$ is an optionally substituted 7-membered partially unsaturated ring having 1-2 heteroatoms independently selected from nitrogen, oxygen, or sulfur. Exemplary $R^3$ groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, tetrahydroazepinyl, tetrahydrooxepinyl, tetrahydrothiepinyl, tetrahydrodiazepinyl, tetrahydrooxazepinyl or tetrahydrothiazepinyl. In some embodiments, $R^3$ is an optionally substituted 8-membered partially unsaturated ring having 1-2 heteroatoms independently selected from nitrogen, oxygen or sulfur.

In some embodiments, $R^3$ is an optionally substituted 5-6 membered monocyclic heteroaromatic ring having 1-4 heteroatoms independently selected from nitrogen, oxygen, or sulfur. In some embodiments, $R^3$ is a substituted 5-6 membered monocyclic heteroaromatic ring having 1-4 heteroatoms independently selected from nitrogen, oxygen, or sulfur. In some embodiments, $R^3$ is an unsubstituted 5-6 membered monocyclic heteroaromatic ring having 1-4 heteroatoms independently selected from nitrogen, oxygen, or sulfur.

In some embodiments, $R^3$ is an optionally substituted 5-membered monocyclic heteroaromatic ring having 1-4 heteroatoms independently selected from nitrogen, oxygen or sulfur. In some embodiments, $R^3$ is a substituted 5-membered monocyclic heteroaromatic ring having 1-4 heteroatoms independently selected from nitrogen, oxygen or sulfur. In some embodiments, $R^3$ is an unsubstituted 5-membered monocyclic heteroaromatic ring having 1-4 heteroatoms independently selected from nitrogen, oxygen or sulfur. In some embodiments, $R^3$ is an optionally substituted 6-membered monocyclic heteroaromatic ring having 1-4 heteroatoms independently selected from nitrogen, oxygen, or sulfur. In some embodiments, $R^3$ is a substituted 6-membered monocyclic heteroaromatic ring having 1-4 heteroatoms independently selected from nitrogen, oxygen or sulfur. In some embodiments, $R^3$ is an unsubstituted 6-membered monocyclic heteroaromatic ring having 1-4 heteroatoms independently selected from nitrogen, oxygen or sulfur.

In some embodiments, $R^3$ is an optionally substituted 5-membered heteroaryl ring having one heteroatom selected from nitrogen, oxygen, or sulfur. In some embodiments, $R^3$ is selected from optionally substituted pyrrolyl, furanyl, or thienyl.

In some embodiments, $R^3$ is an optionally substituted 5-membered heteroaryl ring having two heteroatoms independently selected from nitrogen, oxygen, or sulfur. In certain embodiments, $R^3$ is an optionally substituted 5-membered heteroaryl ring having one nitrogen atom, and an additional heteroatom selected from sulfur or oxygen. Exemplary $R^3$ groups include but are not limited to optionally substituted pyrazolyl, imidazolyl, thiazolyl, isothiazolyl, oxazolyl or isoxazolyl.

In some embodiments, $R^3$ is an optionally substituted 5-membered heteroaryl ring having three heteroatoms independently selected from nitrogen, oxygen, or sulfur. Exemplary $R^3$ groups include but are not limited to optionally substituted triazolyl, oxadiazolyl or thiadiazolyl.

In some embodiments, $R^3$ is an optionally substituted 5-membered heteroaryl ring having four heteroatoms independently selected from nitrogen, oxygen, or sulfur. Exemplary $R^3$ groups include but are not limited to optionally substituted tetrazolyl, oxatriazolyl and thiatriazolyl.

In some embodiments, $R^3$ is a 6-membered heteroaryl ring having 1-4 nitrogen atoms. In some embodiments, $R^3$ is a 6-membered heteroaryl ring having 1-3 nitrogen atoms. In other embodiments, $R^3$ is an optionally substituted 6-membered heteroaryl ring having 1-2 nitrogen atoms. In some embodiments, $R^3$ is an optionally substituted 6-membered heteroaryl ring having four nitrogen atoms. In some embodiments, $R^3$ is an optionally substituted 6-membered heteroaryl ring having three nitrogen atoms. In some embodiments, $R^3$ is an optionally substituted 6-membered heteroaryl ring having two nitrogen atoms. In certain embodiments, $R^3$ is an optionally substituted 6-membered heteroaryl ring having one nitrogen atom. Exemplary $R^3$ groups include but are not limited to optionally substituted pyridinyl, pyrimidinyl, pyrazinyl, pyridazinyl, triazinyl, or tetrazinyl.

In some embodiments, $R^3$ is an optionally substituted 8-10 membered bicyclic heteroaryl ring having 1-5 heteroatoms independently selected from nitrogen, oxygen, or sulfur. In some embodiments, $R^3$ is a substituted 8-10 membered bicyclic heteroaryl ring having 1-5 heteroatoms independently selected from nitrogen, oxygen, or sulfur. In some embodiments, $R^3$ is an unsubstituted 8-10 membered bicyclic heteroaryl ring having 1-5 heteroatoms independently selected from nitrogen, oxygen, or sulfur. In some embodiments, $R^3$ is an optionally substituted 8-membered bicyclic heteroaryl ring having 1-5 heteroatoms independently selected from nitrogen, oxygen, or sulfur. In some embodiments, $R^3$ is a substituted 8-membered bicyclic heteroaryl ring having 1-5 heteroatoms independently selected from nitrogen, oxygen, or sulfur. In some embodiments, $R^3$ is an unsubstituted 8-membered bicyclic heteroaryl ring having 1-5 heteroatoms independently selected from nitrogen, oxygen, or sulfur. In some embodiments, $R^3$ is an optionally substituted 9-membered bicyclic heteroaryl ring having 1-5 heteroatoms independently selected from nitrogen, oxygen, or sulfur. In some embodiments, $R^3$ is a substituted 9-membered bicyclic heteroaryl ring having 1-5 heteroatoms independently selected from nitrogen, oxygen, or sulfur. In some embodiments, $R^3$ is an unsubstituted 9-membered bicyclic heteroaryl ring having 1-5 heteroatoms independently selected from nitrogen, oxygen, or sulfur. In some embodiments, $R^3$ is an optionally substituted 10-membered bicyclic heteroaryl ring having 1-5 heteroatoms independently selected from nitrogen, oxygen, or sulfur. In some embodiments, $R^3$ is a substituted 10-membered bicyclic heteroaryl ring having 1-5 heteroatoms independently selected from nitrogen, oxygen, or sulfur. In some embodiments, $R^3$ is an unsubstituted 10-membered bicyclic heteroaryl ring having 1-5 heteroatoms independently selected from nitrogen, oxygen, or sulfur.

In some embodiments, $R^3$ is an optionally substituted 5,6-fused heteroaryl ring having 1-5 heteroatoms independently selected from nitrogen, oxygen, or sulfur. In some embodiments, $R^3$ is an optionally substituted 5,6-fused heteroaryl ring having 1-4 heteroatoms independently selected from nitrogen, oxygen, or sulfur. In some embodiments, $R^3$ is an optionally substituted 5,6-fused heteroaryl ring having 1-3 heteroatoms independently selected from nitrogen, oxygen, or sulfur. In some embodiments, $R^3$ is an optionally substituted 5,6-fused heteroaryl ring having two heteroatoms independently selected from nitrogen, oxygen, or sulfur. In some embodiments, $R^3$ is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, $R^3$ is an optionally substituted 5,6-fused heteroaryl ring having three heteroatoms independently selected from nitrogen, oxygen, or sulfur. In some embodiments, $R^3$ is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, $R^3$ is an optionally substituted 5,6-fused heteroaryl ring having four heteroatoms independently selected from nitrogen, oxygen, or sulfur. In some embodiments, $R^3$ is an optionally substituted 5,6-fused heteroaryl ring having five heteroatoms independently selected from nitrogen, oxygen, or sulfur.

In some embodiments, $R^3$ is an optionally substituted 5,6-fused heteroaryl ring having 1-5 heteroatoms independently selected from nitrogen, oxygen, or sulfur. In other embodiments, $R^3$ is an optionally substituted 5,6-fused heteroaryl ring having 1-2 heteroatoms independently selected from nitrogen, oxygen, or sulfur. In certain embodiments, $R^3$ is an optionally substituted 5,6-fused heteroaryl ring having one heteroatom independently selected from nitrogen, oxygen, or sulfur. In some embodiments, $R^3$ is optionally substituted indolyl. In some embodiments, $R^3$ is optionally substituted benzofuranyl. In some embodiments, $R^3$ is optionally substituted benzo[b]thienyl. In certain embodiments, $R^3$ is an optionally substituted 5,6-fused heteroaryl ring having two heteroatoms independently selected from nitrogen, oxygen, or sulfur. In some embodiments, $R^3$ is optionally substituted azaindolyl. In some embodiments, $R^3$ is optionally substituted benzimidazolyl. In some embodiments, $R^3$ is optionally substituted benzothiazolyl. In some embodiments, $R^3$ is optionally substituted benzoxazolyl. In some embodiments, $R^3$ is an optionally substituted indazolyl. In certain embodiments, $R^3$ is an optionally substituted 5,6-fused heteroaryl ring having three heteroatoms independently selected from nitrogen, oxygen, or sulfur. In some embodiments, $R^3$ is optionally substituted oxazolopyridiyl, thiazolopyridinyl or imidazopyridinyl. In certain embodiments, $R^3$ is an optionally substituted 5,6-fused heteroaryl ring having four heteroatoms independently selected from nitrogen, oxygen, or sulfur. In some embodiments, $R^3$ is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, $R^3$ is an optionally substituted 5,6-fused heteroaryl ring having five heteroatoms independently selected from nitrogen, oxygen, or sulfur.

In certain embodiments, $R^3$ is an optionally substituted 6,6-fused heteroaryl ring having 1-5 heteroatoms independently selected from nitrogen, oxygen, or sulfur. In some embodiments, $R^3$ is an optionally substituted 6,6-fused heteroaryl ring having 1-2 heteroatoms independently selected from nitrogen, oxygen, or sulfur. In other embodiments, $R^3$ is an optionally substituted 6,6-fused heteroaryl ring having one heteroatom selected from nitrogen, oxygen, or sulfur. In some embodiments, $R^3$ is optionally substituted quinolinyl. In some embodiments, $R^3$ is optionally substituted isoquinolinyl. In some embodiments, $R^3$ is an optionally substituted 6,6-fused heteroaryl ring having two heteroatoms independently selected from nitrogen, oxygen, or sulfur. In some embodiments, $R^3$ is optionally substituted quinazolinyl, phthalazinyl, quinoxalinyl or naphthyridinyl. In some embodiments, $R^3$ is an optionally substituted 6,6-fused heteroaryl ring having three heteroatoms independently selected from nitrogen, oxygen, or sulfur. In some embodiments, $R^3$ is optionally substituted pyridopyrimidinyl, pyridopyridazinyl, pyridopyrazinyl, or benzotriazinyl. In some embodiments, $R^3$ is an optionally substituted 6,6-fused heteroaryl ring having four heteroatoms independently selected from nitrogen, oxygen, or sulfur. In some embodiments, $R^3$ is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, $R^3$ is an optionally substituted 6,6-fused heteroaryl ring having five heteroatoms independently selected from nitrogen, oxygen, or sulfur.

As defined generally above, $R^4$ is selected from R, halo, —CN, —NO$_2$, —C(O)OR', —OR', —SR', —C(O)N(R')$_2$— N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^4$ is R. In some embodiments, $R^4$ is hydrogen. In some embodiments, $R^4$ is optionally substituted $C_{1-6}$ aliphatic. In some embodiments, $R^4$ is $C_{1-6}$ alkyl. In some embodiments, $R^4$ is methyl.

In some embodiments, $R^4$ is halo. In some embodiments, $R^4$ is —F. In some embodiments, $R^4$ is —Cl. In some embodiments, $R^4$ is —Br. In some embodiments, $R^4$ is —I.

In some embodiments, $R^4$ is —CN. In some embodiments, $R^4$ is —NO$_2$. In some embodiments, $R^4$ is —C(O)OR'. In some embodiments, $R^4$ is —OR'. In some embodiments, $R^4$ is —SR'. In some embodiments, $R^4$ is —C(O)N(R')$_2$. In some embodiments, $R^4$ is —N(R')$_2$. In some embodiments, $R^4$ is —S(O)$_2$N(R)$_2$. In some embodiments, $R^4$ is —N(R')S(O)$_2$CF$_3$. In some embodiments, $R^4$ is —C(O)R'. In some embodiments, $R^4$ is —N(R')C(O)R'. In some embodiments, $R^4$ is —S(O)R'. In some embodiments, $R^4$ is —S(O)$_2$R'. In some embodiments, $R^4$ is —N(R')C(O)OR. In some embodiments, $R^4$ is —N(R')S(O)$_2$R'.

As defined generally above, $R^5$ is selected from R, halo, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^5$ is R. In some embodiments, $R^5$ is hydrogen. In some embodiments, $R^5$ is optionally substituted $C_{1-6}$ aliphatic. In some embodiments, $R^5$ is $C_{1-6}$ alkyl. In some embodiments, $R^5$ is methyl.

In some embodiments, $R^5$ is halo. In some embodiments, $R^5$ is —F. In some embodiments, $R^5$ is —Cl. In some embodiments, $R^5$ is —Br. In some embodiments, $R^5$ is —I.

In some embodiments, $R^5$ is —CN. In some embodiments, $R^5$ is —NO$_2$. In some embodiments, $R^5$ is —C(O)OR'. In some embodiments, $R^5$ is —OR'. In some embodiments, $R^5$ is —SR'. In some embodiments, $R^5$ is —C(O)N(R')$_2$. In some embodiments, $R^5$ is —N(R')$_2$. In some embodiments, $R^5$ is —S(O)$_2$N(R)$_2$. In some embodiments, $R^5$ is —N(R')S(O)$_2$CF$_3$. In some embodiments, $R^5$ is —C(O)R'. In some embodiments, $R^5$ is —N(R')C(O)R'. In some embodiments, $R^5$ is —S(O)R'. In some embodiments, $R^5$ is —S(O)$_2$R'. In some embodiments, $R^5$ is —N(R')C(O)OR. In some embodiments, $R^5$ is —N(R')S(O)$_2$R'.

As defined generally above, $R^6$ is selected from R, halo, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^6$ is R. In some embodiments, $R^6$ is hydrogen. In some embodiments, $R^6$ is optionally substituted $C_{1-6}$ aliphatic. In some embodiments, $R^6$ is optionally substituted $C_{1-6}$ alkyl. In some embodiments, $R^6$ is substituted $C_{1-6}$ alkyl. In some embodiments, $R^6$ is unsubstituted $C_{1-6}$ alkyl. In some embodiments, $R^6$ is methyl. In some embodiments, $R^6$ is $C_{1-6}$ alkyl optionally substituted with one or more halogen. In some embodiments, $R^6$ is $C_{1-6}$ haloalkyl. In some embodiments, $R^6$ is —CF$_3$. In some embodiments, $R^6$ is optionally substituted $C_{3-6}$ cycloalkyl. In some embodiments, $R^6$ is substituted $C_{3-6}$ cycloalkyl. In some embodiments, $R^6$ is unsubstituted $C_{3-6}$ cycloalkyl. In some embodiments, $R^6$ is optionally substituted cyclopropyl. In some embodiments, $R^6$ is substituted cyclopropyl. In some embodiments, $R^6$ is unsubstituted cyclopropyl. In some embodiments, $R^6$ is optionally substituted cyclobutyl. In some embodiments, $R^6$ is substituted cyclobutyl. In some embodiments, $R^6$ is unsubstituted cyclobutyl. In some embodiments, $R^6$ is optionally substituted cyclopentyl. In some embodiments, $R^6$ is substituted cyclopentyl. In some embodiments, $R^6$ is unsubstituted cyclopentyl. In some embodiments, $R^6$ is optionally substituted cyclohexyl. In some embodiments, $R^6$ is substituted cyclohexyl. In some embodiments, $R^6$ is unsubstituted cyclohexyl.

In some embodiments, $R^6$ is halo. In some embodiments, $R^6$ is —F. In some embodiments, $R^6$ is —Cl. In some embodiments, $R^6$ is —Br. In some embodiments, $R^6$ is —I.

In some embodiments, $R^6$ is —CN. In some embodiments, $R^6$ is —NO$_2$. In some embodiments, $R^6$ is —C(O)OR'. In some embodiments, $R^6$ is —OR'. In some embodiments, $R^6$ is —SR'. In some embodiments, $R^6$ is —C(O)N(R')$_2$. In some embodiments, $R^6$ is —N(R')$_2$. In some embodiments, $R^6$ is —S(O)$_2$N(R)$_2$. In some embodiments, $R^6$ is —N(R')S(O)$_2$CF$_3$. In some embodiments, $R^6$ is —C(O)R'. In some embodiments, $R^6$ is —N(R')C(O)R'. In some embodiments, $R^6$ is —S(O)R'. In some embodiments, $R^6$ is —S(O)$_2$R'. In some embodiments, $R^6$ is —N(R')C(O)OR. In some embodiments, $R^6$ is —N(R')S(O)$_2$R'.

As defined generally above, $R^7$ is hydrogen, halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur. In some embodiments, $R^7$ is halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from $C_{1-6}$ alkyl, $C_{1-6}$ alkynyl or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur. In some embodiments, $R^7$ is halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$ R, —NRC(O)OR, or —NRS(O)$_2$R, or an optionally substituted group selected from $C_{1-6}$ alkyl or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is selected from R, halo, —CN, —$NO_2$, —C(O)OR, —$OCF_3$, —OR, —SR, —$S(O)_2$OR, —P(O)(OH)$_2$, —C(O)N(R)$_2$, —N(R)$_2$, —$S(O)_2$N(R)$_2$, —NRS(O)$_2$CF$_3$, —C(O)NRS(O)$_2$R, —$S(O)_2$NRC(O)OR, —$S(O)_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —$S(O)_2$R, —NRC(O)OR, or —NRS(O)$_2$R.

In some embodiments, $R^7$ is an optionally substituted group selected from $C_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

In some embodiments, $R^7$ is R. In some embodiments, $R^7$ is hydrogen.

In some embodiments, $R^7$ is optionally substituted $C_{1-6}$ aliphatic. In some embodiments, $R^7$ is optionally substituted $C_{1-6}$ alkyl. In some embodiments, $R^7$ is substituted $C_{1-6}$ alkyl. In some embodiments, $R^7$ is unsubstituted $C_{1-6}$ alkyl. In some embodiments, $R^7$ is optionally substituted hexyl. In some embodiments, $R^7$ is substituted hexyl. In some embodiments, $R^7$ is unsubstituted hexyl. In some embodiments, $R^7$ is optionally substituted pentyl. In some embodiments, $R^7$ is substituted pentyl. In some embodiments, $R^7$ is unsubstituted pentyl. In some embodiments, $R^7$ is optionally substituted butyl. In some embodiments, $R^7$ is substituted butyl. In some embodiments, $R^7$ is unsubstituted butyl. In some embodiments, $R^7$ is optionally substituted propyl. In some embodiments, $R^7$ is substituted propyl. In some embodiments, $R^7$ is unsubstituted propyl. In some embodiments, $R^7$ is optionally substituted ethyl. In some embodiments, $R^7$ is substituted ethyl. In some embodiments, $R^7$ is unsubstituted ethyl. In some embodiments, $R^7$ is optionally substituted methyl. In some embodiments, $R^7$ is substituted methyl. In some embodiments, $R^7$ is unsubstituted methyl.

In some embodiments, $R^7$ is optionally substituted $C_{3-6}$ carbocyclyl. In some embodiments, $R^7$ is substituted $C_{3-6}$ carbocyclyl. In some embodiments, $R^7$ is unsubstituted $C_{3-6}$ carbocyclyl. In some embodiments, $R^7$ is optionally substituted cyclohexyl. In some embodiments, $R^7$ is substituted cyclohexyl. In some embodiments, $R^7$ is unsubstituted cyclohexyl. In some embodiments, $R^7$ is optionally substituted cyclopentyl. In some embodiments, $R^7$ is substituted cyclopentyl. In some embodiments, $R^7$ is unsubstituted cyclopentyl. In some embodiments, $R^7$ is optionally substituted cyclobutyl. In some embodiments, $R^7$ is substituted cyclobutyl. In some embodiments, $R^7$ is unsubstituted cyclobutyl. In some embodiments, $R^7$ is optionally substituted cyclopropyl. In some embodiments, $R^7$ is substituted cyclopropyl. In some embodiments, $R^7$ is unsubstituted cyclopropyl.

In some embodiments, $R^7$ is halo. In some embodiments, $R^7$ is —F. In some embodiments, $R^7$ is —Cl. In some embodiments, $R^7$ is —Br. In some embodiments, $R^7$ is —I.

In some embodiments, $R^7$ is —CN. In some embodiments, $R^7$ is —$NO_2$. In some embodiments, $R^7$ is —C(O)OR. In some embodiments, $R^7$ is —$OCF_3$. In some embodiments, $R^7$ is —OR. In some embodiments, $R^7$ is —SR. In some embodiments, $R^7$ is —$S(O)_2$OR. In some embodiments, $R^7$ is —P(O)(OH)$_2$. In some embodiments, $R^7$ is —C(O)N(R). In some embodiments, $R^7$ is —N(R)$_2$. In some embodiments, $R^7$ is —$S(O)_2$N(R)$_2$. In some embodiments, $R^7$ is —NRS(O)$_2$CF$_3$. In some embodiments, $R^7$ is —C(O)NRS(O)$_2$R. In some embodiments, $R^7$ is —$S(O)_2$NRC(O)OR. In some embodiments, $R^7$ is —$S(O)_2$NRC(O)N(R)$_2$. In some embodiments, $R^7$ is —C(O)R. In some embodiments, $R^7$ is —C(O)NRS(O)$_2$CF$_3$. In some embodiments, $R^7$ is —NRC(O)R. In some embodiments, $R^7$ is —OC(O)R. In some embodiments, $R^7$ is —OC(O)N(R)$_2$. In some embodiments, $R^7$ is —C(NR)N(R)$_2$. In some embodiments, $R^7$ is —NRC(NR)N(R)$_2$. In some embodiments, $R^7$ is —S(O)R. In some embodiments, $R^7$ is —$S(O)_2$R. In some embodiments, $R^7$ is —NRC(O)OR. In some embodiments, $R^7$ is —NRS(O)$_2$R.

In some embodiments, $R^7$ is an optionally substituted 3-8 membered saturated or partially unsaturated carbocyclic ring. In some embodiments, $R^7$ is an optionally substituted 3-membered saturated or partially unsaturated carbocyclic ring. In some embodiments, $R^7$ is an optionally substituted 4-membered saturated or partially unsaturated carbocyclic ring. In some embodiments, $R^7$ is an optionally substituted 5-membered saturated or partially unsaturated carbocyclic ring. In some embodiments, $R^7$ is an optionally substituted 6-membered saturated or partially unsaturated carbocyclic ring. In some embodiments, $R^7$ is an optionally substituted 7-membered saturated or partially unsaturated carbocyclic ring. In some embodiments, $R^7$ is an optionally substituted 8-membered saturated or partially unsaturated carbocyclic ring.

In some embodiments, $R^7$ is an optionally substituted 3-8 membered saturated monocyclic carbocyclic ring. In some embodiments, $R^7$ is an optionally substituted cycloheptyl. In some embodiments, $R^7$ is an optionally substituted cyclohexyl. In some embodiments, $R^7$ is an optionally substituted cyclopentyl. In some embodiments, $R^7$ is an optionally substituted cyclobutyl. In some embodiments, $R^7$ is an optionally substituted cyclopropyl.

In some embodiments, R⁷ is an optionally substituted 3-8 membered unsaturated carbocyclic ring. In some embodiments, R⁷ is an optionally substituted cycloheptenyl. In some embodiments, R⁷ is an optionally substituted cyclohexenyl. In some embodiments, R⁷ is an optionally substituted cyclopentenyl. In some embodiments, R⁷ is an optionally substituted cyclobutenyl.

In some embodiments, R⁷ is optionally substituted phenyl. In some embodiments, R⁷ is substituted phenyl. In some embodiments, R⁷ is 2-methylphenyl. In some embodiments, R⁷ is phenyl.

In some embodiments, R⁷ is an optionally substituted 3-8 membered saturated or partially unsaturated heterocyclic ring having 1-2 heteroatoms independently selected from nitrogen, oxygen, or sulfur. In some embodiments, R⁷ is an optionally substituted 3-8 membered saturated heterocyclic ring having 1-2 heteroatoms independently selected from nitrogen, oxygen, or sulfur. In some embodiments, R⁷ is an optionally substituted 3-8 membered partially unsaturated heterocyclic ring having 1-2 heteroatoms independently selected from nitrogen, oxygen, or sulfur. Exemplary suitable embodiments for R⁷ include but are not limited to those heterocyclic embodiments described for R.

In some embodiments, R⁷ is an optionally substituted 5-6 membered heteroaryl ring having 1-4 heteroatoms independently selected from nitrogen, oxygen or sulfur. In some embodiments, R⁷ is an optionally substituted 5-membered heteroaryl ring having 1-4 heteroatoms independently selected from nitrogen, oxygen or sulfur. In some embodiments, R⁷ is an optionally substituted 5-membered heteroaryl ring having 1-4 nitrogen atoms. In some embodiments, R⁷ is an optionally substituted 5-membered heteroaryl ring having 1-3 nitrogen atoms. In some embodiments, R⁷ is an optionally substituted 5-membered heteroaryl ring having 1-2 nitrogen atoms. In some embodiments, R⁷ is optionally substituted pyrrolyl. In some embodiments, R⁷ is substituted pyrrolyl. In some embodiments, R⁷ is unsubstituted pyrrolyl.

In some embodiments, R⁷ is optionally substituted pyrazolyl. In some embodiments, R⁷ is pyrazolyl. In some embodiments, R⁷ is

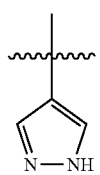

In some embodiments, R⁷ is

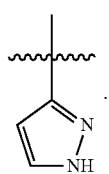

In some embodiments, R⁷ is substituted pyrazolyl. In some embodiments, R⁷ is substituted

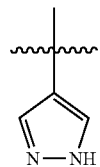

In some embodiments, R⁷ is

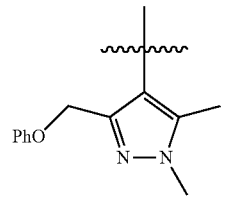

In some embodiments, R⁷ is

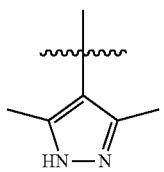

In some embodiments, R⁷ is substituted

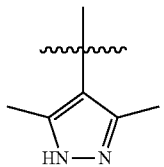

In some embodiments, R⁷ is

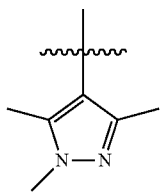

In some embodiments, R⁷ is

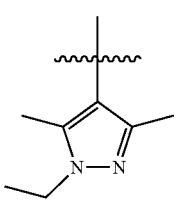

In some embodiments, R⁷ is
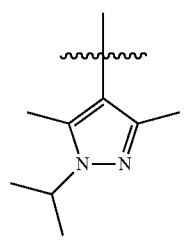
In some embodiments, R⁷ is
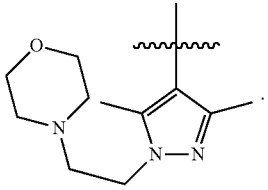 [SMILES: *c1c(C)nn(CCN2CCOCC2)c1C]
In some embodiments, R⁷ is
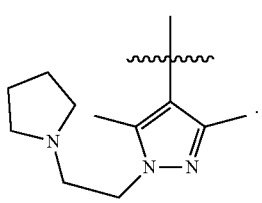 [SMILES: *c1c(C)nn(CCN2CCCC2)c1C]
In some embodiments, R⁷ is
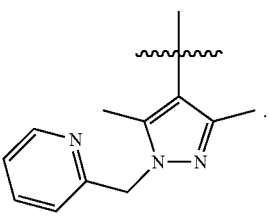 [SMILES: *c1c(C)nn(Cc2ccccn2)c1C]
In some embodiments, R⁷ is
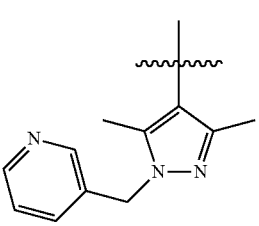
In some embodiments, R⁷ is
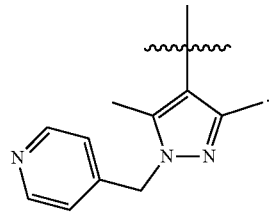 [SMILES: *c1c(C)nn(Cc2ccncc2)c1C]
In some embodiments, R⁷ is
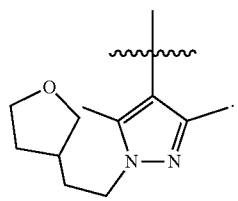 [SMILES: *c1c(C)nn(CCC2CCOC2)c1C]
In some embodiments, R⁷ is
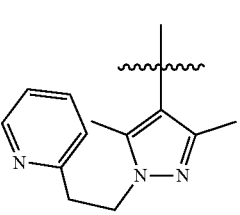
In some embodiments, R⁷ is
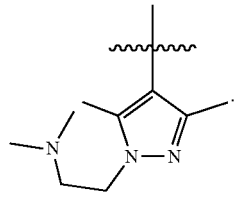
In some embodiments, R⁷ is
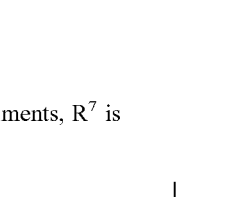
In some embodiments, R⁷ is
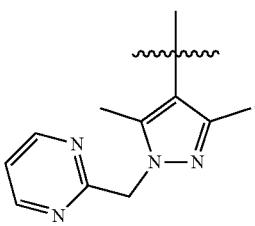

In some embodiments, $R^7$ is substituted

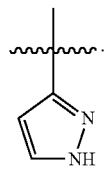

In some embodiments, $R^7$ is

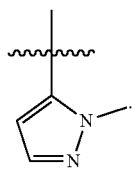 [SMILES: *c1ccnn1C]

In some embodiments, $R^7$ is optionally substituted isoxazolyl. In some embodiments, $R^7$ is substituted isoxazolyl. In some embodiments, $R^7$ is unsubstituted isoxazolyl. In some embodiments, $R^7$ is

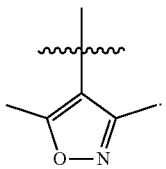

In some embodiments, $R^7$ is optionally substituted isothiazolyl. In some embodiments, $R^7$ is substituted isothiazolyl. In some embodiments, $R^7$ is unsubstituted isothiazolyl. In some embodiments, $R^7$ is optionally substituted thienyl. In some embodiments, $R^7$ is substituted thienyl. In some embodiments, $R^7$ is unsubstituted thienyl. In some embodiments, $R^7$ is optionally substituted furanyl. In some embodiments, $R^7$ is substituted furanyl. In some embodiments, $R^7$ is unsubstituted furanyl. Other exemplary suitable $R^7$ embodiments include but are not limited to those described for R.

In some embodiments, $R^7$ is an optionally substituted 6-membered heteroaryl ring having 1-4 heteroatoms independently selected from nitrogen, oxygen or sulfur. In some embodiments, $R^7$ is an optionally substituted 6-membered heteroaryl ring having 1-4 nitrogen atoms. In some embodiments, $R^7$ is optionally substituted pyridinyl. In some embodiments, $R^7$ is substituted pyridinyl. In some embodiments, $R^7$ is pyridinyl. In some embodiments, $R^7$ is 3-pyridinyl. In some embodiments, $R^7$ is 4-pyridinyl. Other exemplary suitable $R^7$ embodiments include but are not limited to those described for R.

In some embodiments, $R^7$ is an optionally substituted 8-14 membered bicyclic or polycyclic saturated, partially unsaturated or aryl ring. In some embodiments, $R^7$ is an optionally substituted 8-14 membered bicyclic or polycyclic saturated ring. In some embodiments, $R^7$ is an optionally substituted 8-14 membered bicyclic or polycyclic partially saturated ring. In some embodiments, $R^7$ is an optionally substituted 8-14 membered bicyclic or polycyclic aryl ring. In some embodiments, $R^7$ is an optionally substituted 8-10 membered bicyclic saturated, partially unsaturated or aryl ring. In some embodiments, $R^7$ is an optionally substituted 8-10 membered bicyclic saturated ring. In some embodiments, $R^7$ is an optionally substituted 8-10 membered bicyclic partially unsaturated ring. In some embodiments, $R^7$ is an optionally substituted 8-10 membered bicyclic aryl ring. In some embodiments, $R^7$ is optionally substituted naphthyl. In some embodiments, $R^7$ is optionally substituted anthracenyl. In some embodiments, $R^7$ is optionally substituted 9-anthracenyl.

In some embodiments, $R^7$ is an optionally substituted 7-14 membered bicyclic or polycyclic saturated or partially unsaturated heterocyclic ring having 1-5 heteroatoms independently selected from nitrogen, oxygen, or sulfur. In some embodiments, $R^7$ is an optionally substituted 7-10 membered bicyclic saturated or partially unsaturated heterocyclic ring having 1-5 heteroatoms independently selected from nitrogen, oxygen, or sulfur. In some embodiments, $R^7$ is optionally substituted indolinyl. In some embodiments, $R^7$ is optionally substituted isoindolinyl. In some embodiments, $R^7$ is optionally substituted 1, 2, 3, 4-tetrahydroquinolinyl. In some embodiments, $R^7$ is optionally substituted 1, 2, 3, 4-tetrahydroisoquinolinyl. In some embodiments, $R^7$ is an optionally substituted azabicyclo[3.2.1]octanyl.

In some embodiments, $R^7$ is an optionally substituted 8-14 membered bicyclic or polycyclic heteroaryl ring having 1-5 heteroatoms independently selected from nitrogen, oxygen, or sulfur. In some embodiments, $R^7$ is an optionally substituted 8-14 membered bicyclic or tricyclic heteroaryl ring having 1-5 heteroatoms independently selected from nitrogen, oxygen, or sulfur. In some embodiments, $R^7$ is an optionally substituted 8-14 membered bicyclic heteroaryl ring having 1-5 heteroatoms independently selected from nitrogen, oxygen, or sulfur. In some embodiments, $R^7$ is an 8-10 membered bicyclic heteroaryl ring having 1-5 heteroatoms independently selected from nitrogen, oxygen, or sulfur.

In some embodiments, $R^7$ is an optionally substituted 5,6-fused heteroaryl ring having 1-5 heteroatoms independently selected from nitrogen, oxygen, or sulfur. In some embodiments, $R^7$ is an optionally substituted 5,6-fused heteroaryl ring having 1-4 heteroatoms independently selected from nitrogen, oxygen, or sulfur. In some embodiments, $R^7$ is an optionally substituted 5,6-fused heteroaryl ring having 1-3 heteroatoms independently selected from nitrogen, oxygen, or sulfur. In some embodiments, $R^7$ is an optionally substituted 5,6-fused heteroaryl ring having two heteroatoms independently selected from nitrogen, oxygen, or sulfur. In some embodiments, $R^7$ is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, $R^7$ is an optionally substituted 5,6-fused heteroaryl ring having three heteroatoms independently selected from nitrogen, oxygen, or sulfur. In some embodiments, $R^7$ is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, $R^7$ is an optionally substituted 5,6-fused heteroaryl ring having four heteroatoms independently selected from nitrogen, oxygen, or sulfur. In some embodiments, $R^7$ is an optionally substituted 5,6-fused heteroaryl ring having five heteroatoms independently selected from nitrogen, oxygen, or sulfur.

In some embodiments, $R^7$ is an optionally substituted 5,6-fused heteroaryl ring having 1-5 heteroatoms independently selected from nitrogen, oxygen, or sulfur. In other embodiments, $R^7$ is an optionally substituted 5,6-fused heteroaryl ring having 1-2 heteroatoms independently selected from nitrogen, oxygen, or sulfur. In certain embodiments, $R^7$ is an optionally substituted 5,6-fused heteroaryl ring having one heteroatom independently selected from nitrogen, oxygen, or sulfur. In some embodiments, $R^7$ is optionally substituted indolyl. In some embodiments, $R^7$ is optionally substituted benzofuranyl. In some embodiments, $R^7$ is optionally substituted benzo[b]thienyl. In certain embodiments, $R^7$ is an optionally substituted 5,6-fused heteroaryl ring having two heteroatoms independently selected from nitrogen, oxygen, or sulfur. In some embodiments, $R^7$ is optionally substituted azaindolyl. In some embodiments, $R^7$ is optionally substituted benzimidazolyl. In some embodiments, $R^7$ is optionally substituted benzothiazolyl. In some embodiments, $R^7$ is optionally substituted benzoxazolyl. In some embodiments, $R^7$ is an optionally substituted indazolyl. In certain embodiments, $R^7$ is an optionally substituted 5,6-fused heteroaryl ring having three heteroatoms independently selected from nitrogen, oxygen, or sulfur. In some embodiments, $R^7$ is optionally substituted oxazolopyridiyl, thiazolopyridinyl or imidazopyridinyl. In certain embodiments, $R^7$ is an optionally substituted 5,6-fused heteroaryl ring having four heteroatoms independently selected from nitrogen, oxygen, or sulfur. In some embodiments, $R^7$ is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, $R^7$ is an optionally substituted 5,6-fused heteroaryl ring having five heteroatoms independently selected from nitrogen, oxygen, or sulfur.

In certain embodiments, $R^7$ is an optionally substituted 6,6-fused heteroaryl ring having 1-5 heteroatoms independently selected from nitrogen, oxygen, or sulfur. In some embodiments, $R^7$ is an optionally substituted 6,6-fused heteroaryl ring having 1-2 heteroatoms independently selected from nitrogen, oxygen, or sulfur. In other embodiments, $R^7$ is an optionally substituted 6,6-fused heteroaryl ring having one heteroatom selected from nitrogen, oxygen, or sulfur. In some embodiments, $R^7$ is optionally substituted quinolinyl. In some embodiments, $R^7$ is optionally substituted isoquinolinyl. In some embodiments, $R^7$ is an optionally substituted 6,6-fused heteroaryl ring having two heteroatoms independently selected from nitrogen, oxygen, or sulfur. In some embodiments, $R^7$ is optionally substituted quinazolinyl, phthalazinyl, quinoxalinyl or naphthyridinyl. In some embodiments, $R^7$ is an optionally substituted 6,6-fused heteroaryl ring having three heteroatoms independently selected from nitrogen, oxygen, or sulfur. In some embodiments, $R^7$ is optionally substituted pyridopyrimidinyl, pyridopyridazinyl, pyridopyrazinyl, or benzotriazinyl. In some embodiments, $R^7$ is an optionally substituted 6,6-fused heteroaryl ring having four heteroatoms independently selected from nitrogen, oxygen, or sulfur. In some embodiments, $R^7$ is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, $R^7$ is an optionally substituted 6,6-fused heteroaryl ring having five heteroatoms independently selected from nitrogen, oxygen, or sulfur.

In some embodiments, optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted ring selected from 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur. In some embodiments, optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted 3-8 membered saturated or partially unsaturated carbocyclic ring. In some embodiments, optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted phenyl. In some embodiments, optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted 3-8 membered saturated or partially unsaturated heterocyclic ring having 1-2 heteroatoms independently selected from nitrogen, oxygen. In some embodiments, optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted 5-6 membered heteroaryl ring having 1-4 heteroatoms independently selected from nitrogen, oxygen, or sulfur.

In some embodiments, $R^4$ and $R^5$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur. In some embodiments, $R^5$ and $R^6$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur. In some embodiments, $R^6$ and $R^7$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur. In some embodiments, $R^7$ and $L^1$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur. In some embodiments, $R^2$ and $L^1$ are taken together with their intervening atoms to form an optionally substituted ring selected from 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur.
Exemplary compounds are set forth in Table 1, below:
TABLE 1
Exemplary compounds.
| | |
|---|---|
| 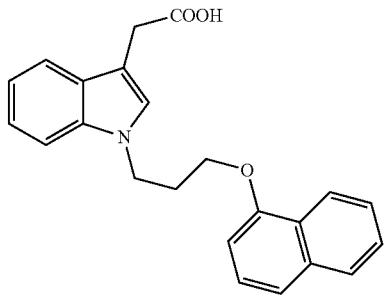 [SMILES: O=C(O)Cc1cn(CCCOc2cccc3ccccc23)c2ccccc12] | 1 |
| 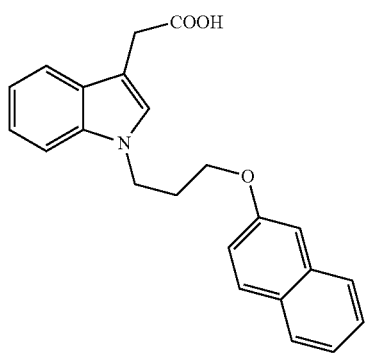 [SMILES: O=C(O)Cc1cn(CCCOc2ccc3ccccc3c2)c2ccccc12] | 2 |
| 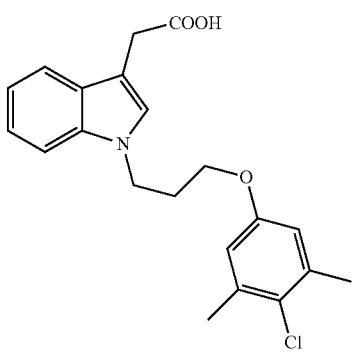 [SMILES: Cc1cc(OCCCn2cc(CC(=O)O)c3ccccc32)cc(C)c1Cl] | 3 |
| 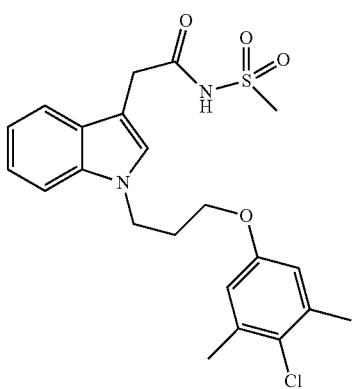 [SMILES: Cc1cc(OCCCn2cc(CC(=O)NS(C)(=O)=O)c3ccccc32)cc(C)c1Cl] | 4 |
TABLE 1-continued
Exemplary compounds.
| | |
|---|---|
| 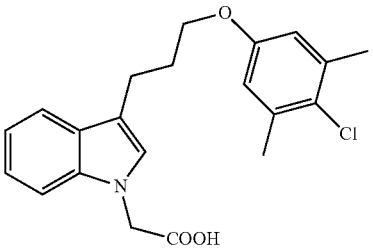 [SMILES: Cc1cc(OCCCc2cn(CC(=O)O)c3ccccc23)cc(C)c1Cl] | 5 |
| 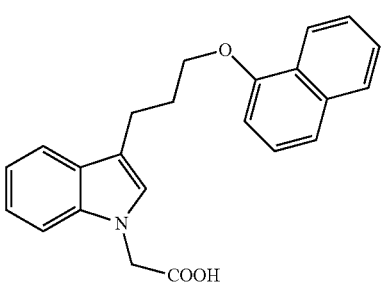 [SMILES: O=C(O)Cn1cc(CCCOc2cccc3ccccc23)c2ccccc21] | 6 |
| 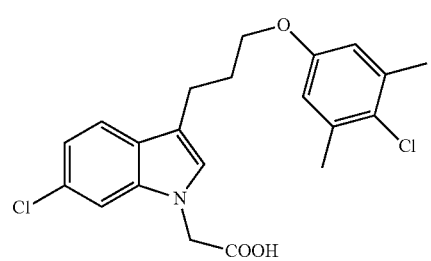 [SMILES: Cc1cc(OCCCc2cn(CC(=O)O)c3cc(Cl)ccc23)cc(C)c1Cl] | 7 |
| 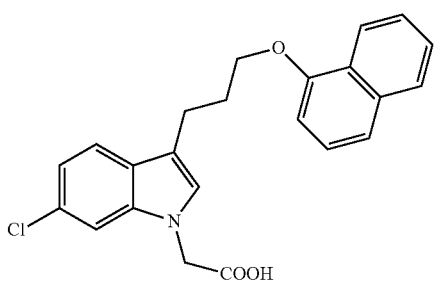 [SMILES: O=C(O)Cn1cc(CCCOc2cccc3ccccc23)c2ccc(Cl)cc21] | 8 |
| 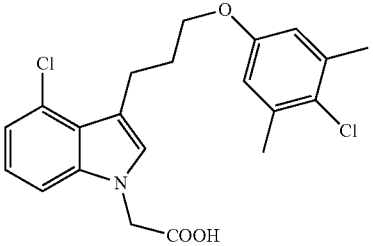 [SMILES: Cc1cc(OCCCc2cn(CC(=O)O)c3cccc(Cl)c23)cc(C)c1Cl] | 9 |

TABLE 1-continued
Exemplary compounds.
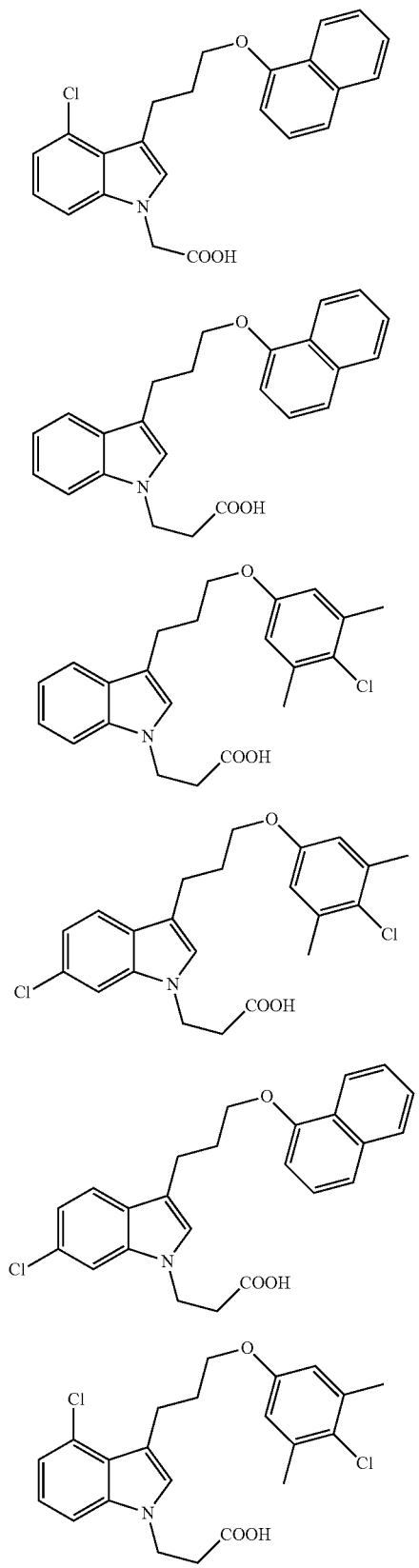
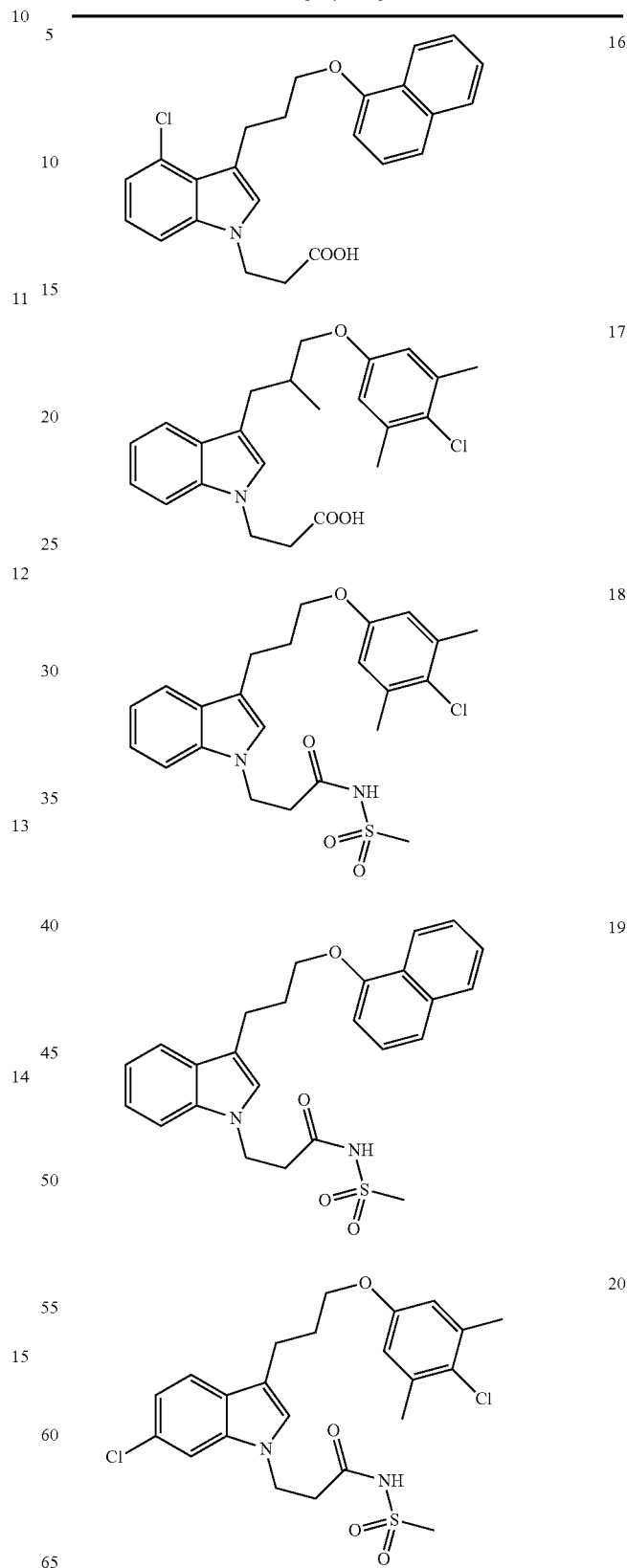

TABLE 1-continued
Exemplary compounds.
21
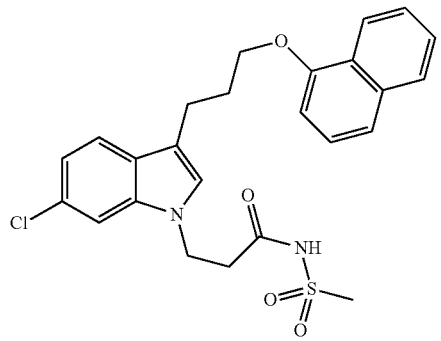 [SMILES: CS(=O)(=O)NC(=O)CCn1cc(CCCOc2cccc3ccccc23)c2ccc(Cl)cc21]
22
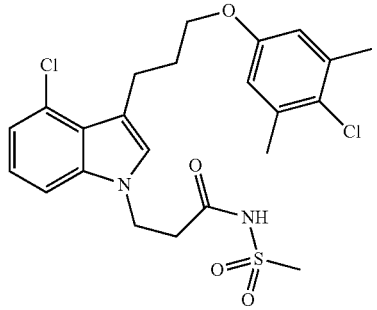 [SMILES: Cc1cc(OCCCc2cn(CCC(=O)NS(C)(=O)=O)c3cccc(Cl)c23)cc(C)c1Cl]
23
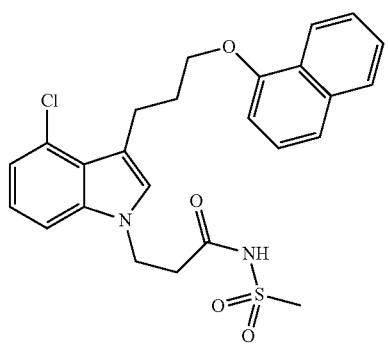 [SMILES: CS(=O)(=O)NC(=O)CCn1cc(CCCOc2cccc3ccccc23)c2c(Cl)cccc21]
24
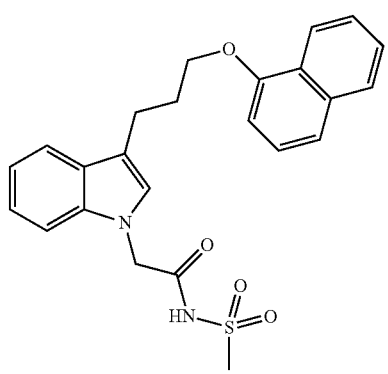 [SMILES: CS(=O)(=O)NC(=O)Cn1cc(CCCOc2cccc3ccccc23)c2ccccc21]
TABLE 1-continued
Exemplary compounds.
25
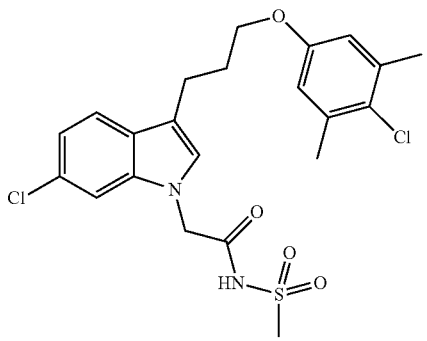 [SMILES: Cc1cc(OCCCc2cn(CC(=O)NS(C)(=O)=O)c3cc(Cl)ccc23)cc(C)c1Cl]
26
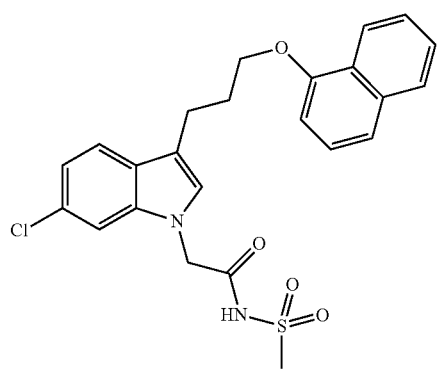 [SMILES: CS(=O)(=O)NC(=O)Cn1cc(CCCOc2cccc3ccccc23)c2ccc(Cl)cc21]
27
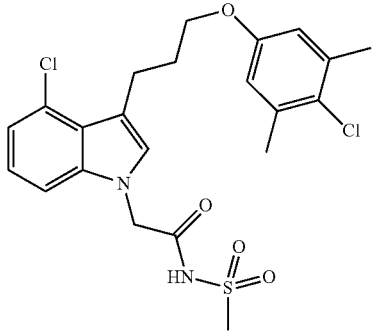 [SMILES: Cc1cc(OCCCc2cn(CC(=O)NS(C)(=O)=O)c3cccc(Cl)c23)cc(C)c1Cl]
28
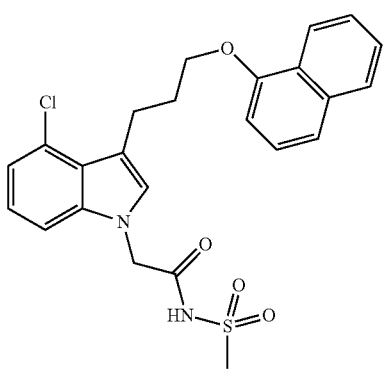 [SMILES: CS(=O)(=O)NC(=O)Cn1cc(CCCOc2cccc3ccccc23)c2c(Cl)cccc21]

TABLE 1-continued
Exemplary compounds.
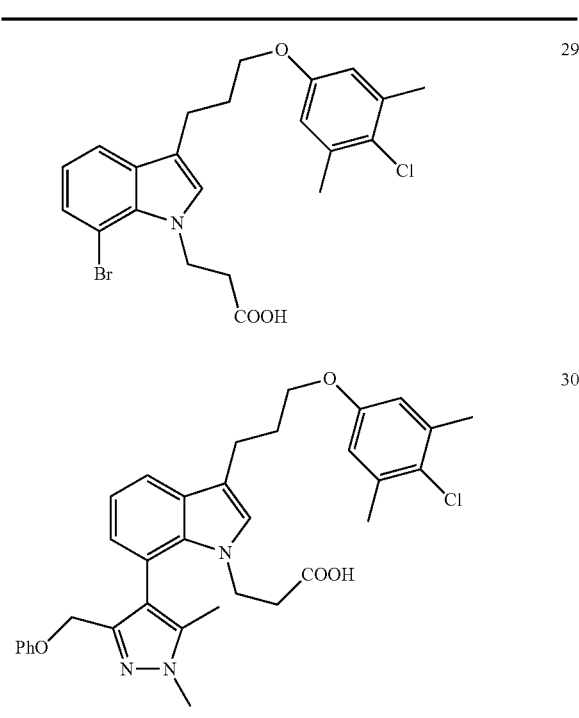
29
30
31
32
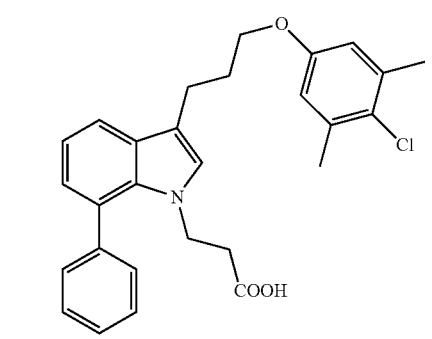
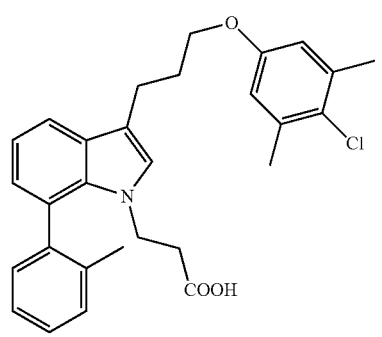 [SMILES: Cc1ccccc1-c1cccc2c(CCCOc3cc(C)c(Cl)c(C)c3)cn(CCC(=O)O)c12]
TABLE 1-continued
Exemplary compounds.
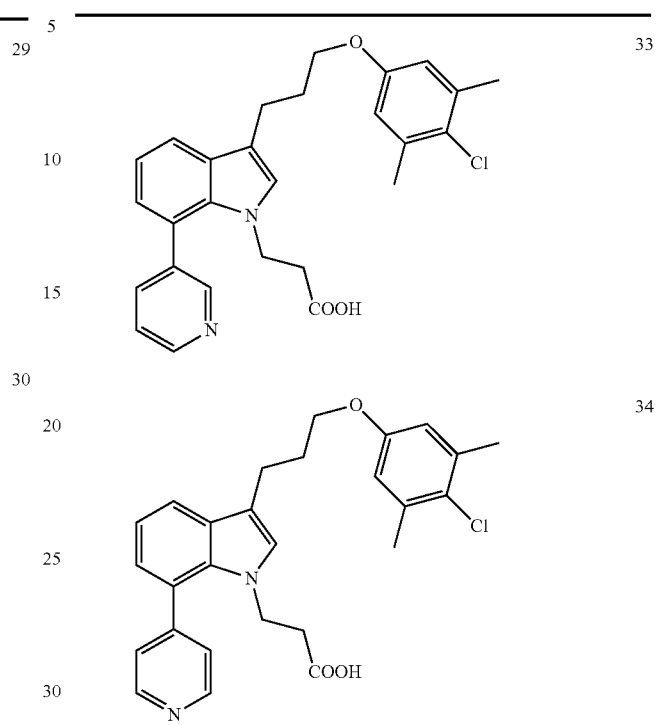
33
34
35
36
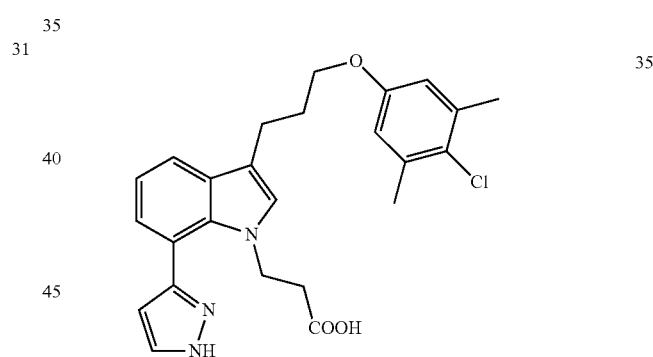
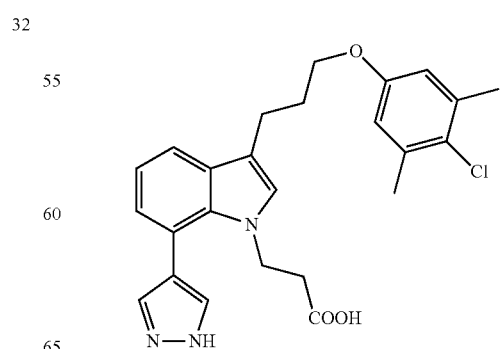

TABLE 1-continued
Exemplary compounds.
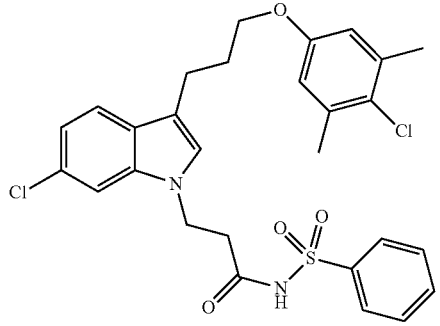 [SMILES: Cc1cc(OCCCc2cn(CCC(=O)NS(=O)(=O)c3ccccc3)c3cc(Cl)ccc23)cc(C)c1Cl] 37
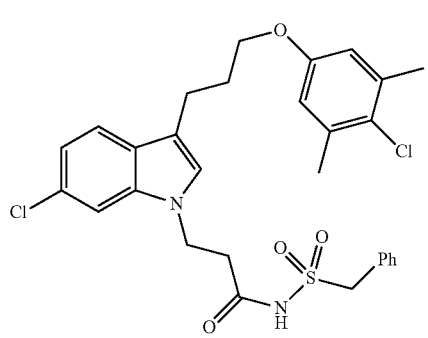 [SMILES: Cc1cc(OCCCc2cn(CCC(=O)NS(=O)(=O)Cc3ccccc3)c3cc(Cl)ccc23)cc(C)c1Cl] 38
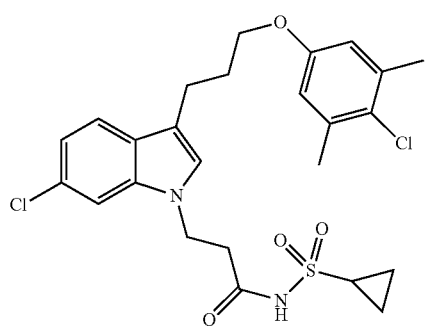 [SMILES: Cc1cc(OCCCc2cn(CCC(=O)NS(=O)(=O)C3CC3)c3cc(Cl)ccc23)cc(C)c1Cl] 39
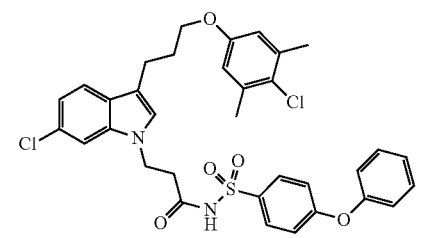 [SMILES: Cc1cc(OCCCc2cn(CCC(=O)NS(=O)(=O)c3ccc(Oc4ccccc4)cc3)c3cc(Cl)ccc23)cc(C)c1Cl] 40
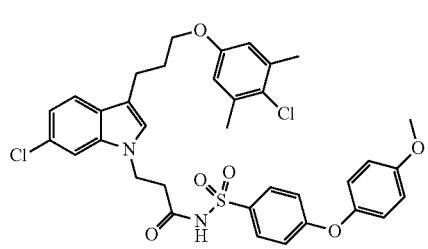 [SMILES: COc1ccc(Oc2ccc(S(=O)(=O)NC(=O)CCn3cc(CCCOc4cc(C)c(Cl)c(C)c4)c4ccc(Cl)cc43)cc2)cc1] 41
TABLE 1-continued
Exemplary compounds.
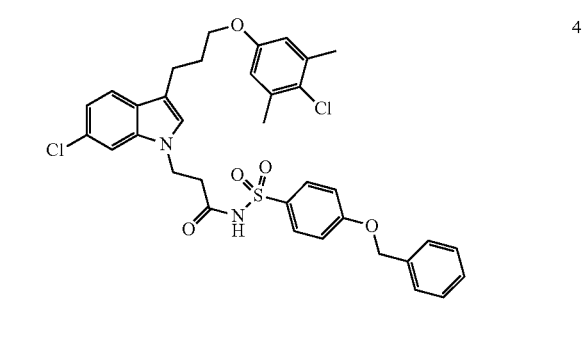 42
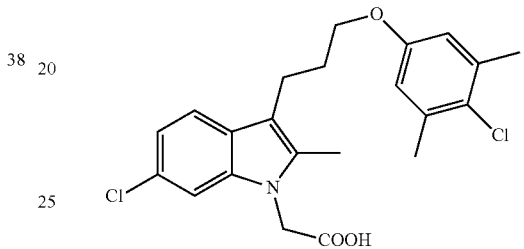 43
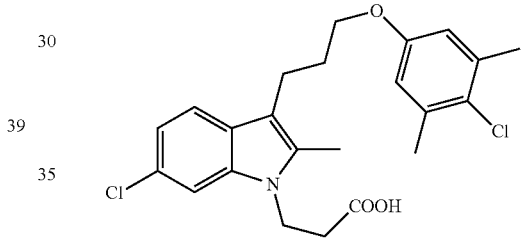 44
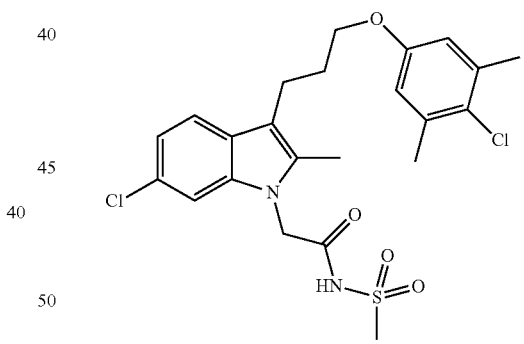 45
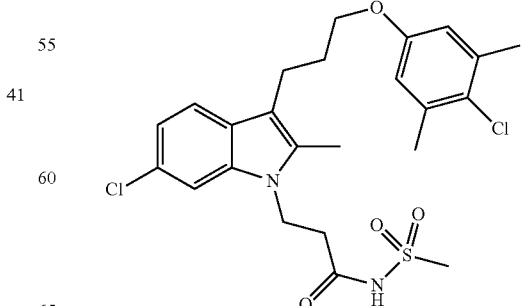 46

TABLE 1-continued
Exemplary compounds.
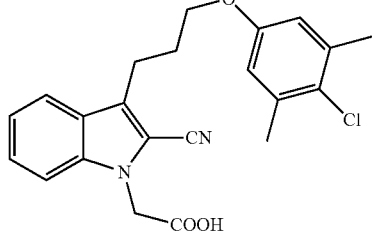 47
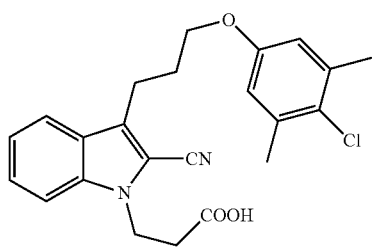 [SMILES: Cc1cc(OCCCc2c(C#N)n(CCC(=O)O)c3ccccc23)cc(C)c1Cl] 48
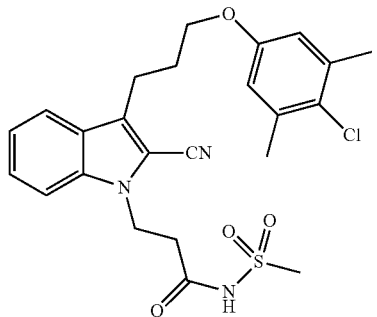 [SMILES: Cc1cc(OCCCc2c(C#N)n(CCC(=O)NS(C)(=O)=O)c3ccccc23)cc(C)c1Cl] 49
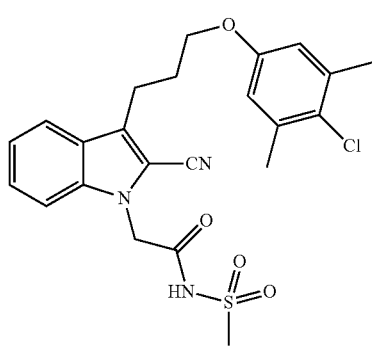 [SMILES: Cc1cc(OCCCc2c(C#N)n(CC(=O)NS(C)(=O)=O)c3ccccc23)cc(C)c1Cl] 50
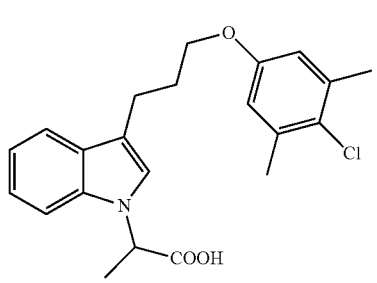 [SMILES: Cc1cc(OCCCc2cn(C(C)C(=O)O)c3ccccc23)cc(C)c1Cl] 51
TABLE 1-continued
Exemplary compounds.
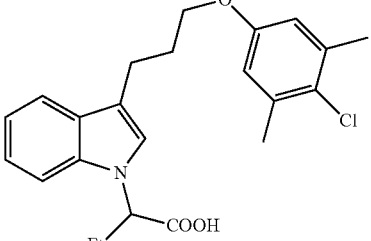 52
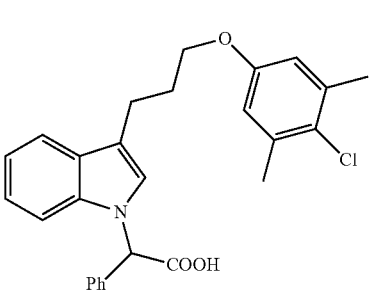 [SMILES: CCC(C(=O)O)n1cc(CCCOc2cc(C)c(Cl)c(C)c2)c2ccccc21] 53
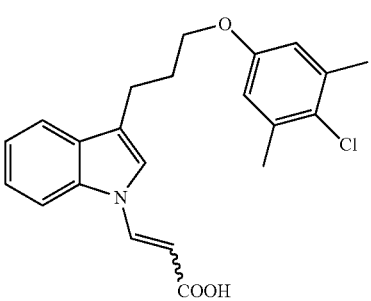 [SMILES: Cc1cc(OCCCc2cn(C=CC(=O)O)c3ccccc23)cc(C)c1Cl] 54
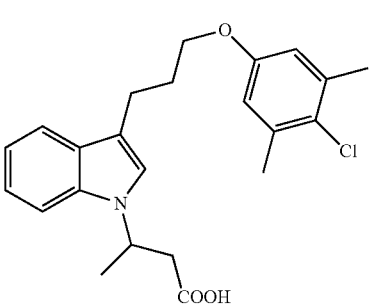 [SMILES: Cc1cc(OCCCc2cn(C(C)CC(=O)O)c3ccccc23)cc(C)c1Cl] 55
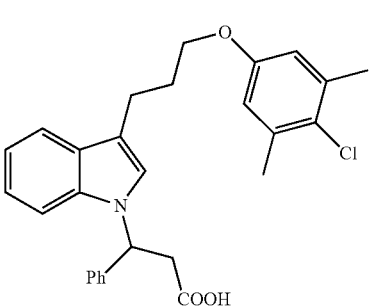 [SMILES: Cc1cc(OCCCc2cn(C(CC(=O)O)c3ccccc3)c3ccccc23)cc(C)c1Cl] 56

TABLE 1-continued
Exemplary compounds.
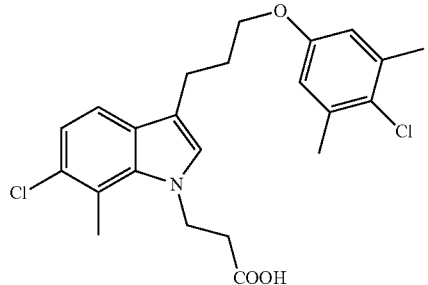 [SMILES: Cc1cc(OCCCc2cn(CCC(=O)O)c3c(C)c(Cl)ccc23)cc(C)c1Cl] 57
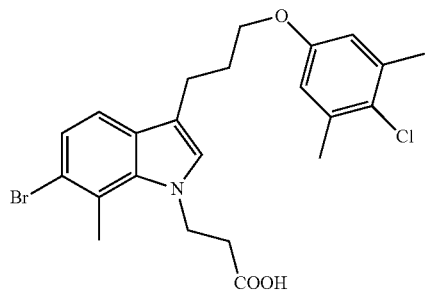 58
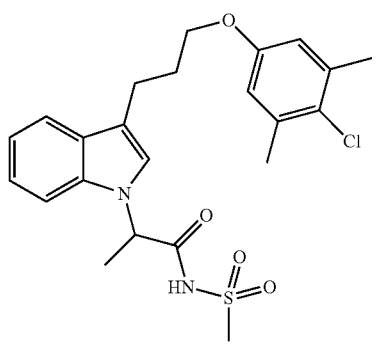 [SMILES: Cc1cc(OCCCc2cn(C(C)C(=O)NS(C)(=O)=O)c3ccccc23)cc(C)c1Cl] 59
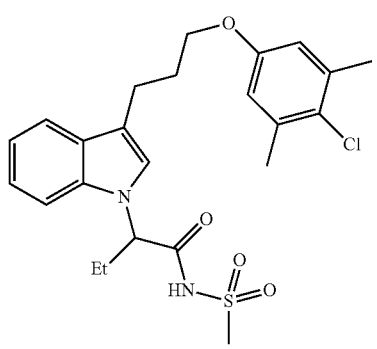 [SMILES: CCC(C(=O)NS(C)(=O)=O)n1cc(CCCOc2cc(C)c(Cl)c(C)c2)c2ccccc21] 60
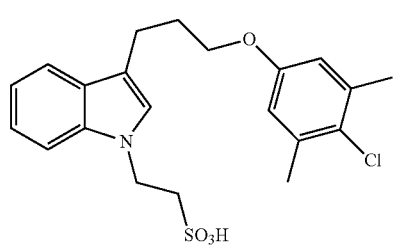 [SMILES: Cc1cc(OCCCc2cn(CCS(=O)(=O)O)c3ccccc23)cc(C)c1Cl] 61
TABLE 1-continued
Exemplary compounds.
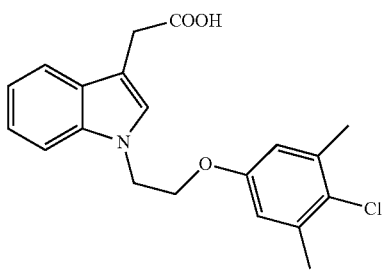 [SMILES: Cc1cc(OCCn2cc(CC(=O)O)c3ccccc32)cc(C)c1Cl] 62
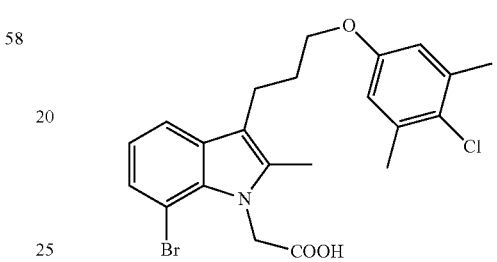 63
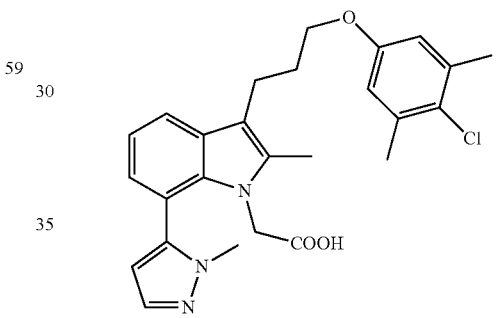 64
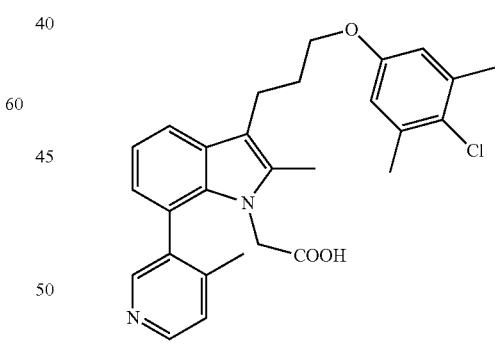 65
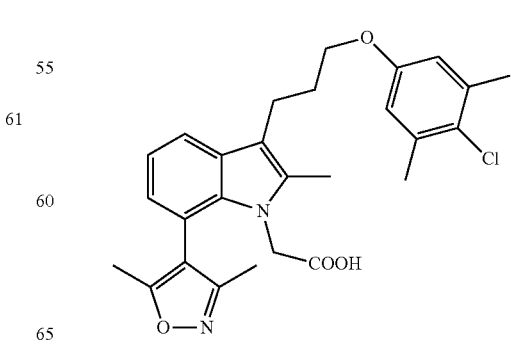 66

TABLE 1-continued
Exemplary compounds.
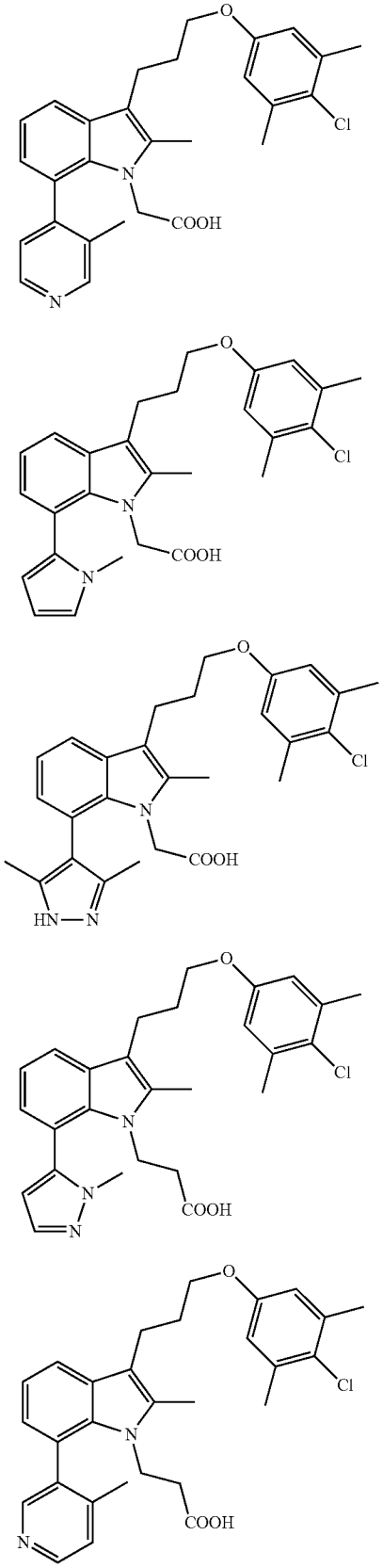
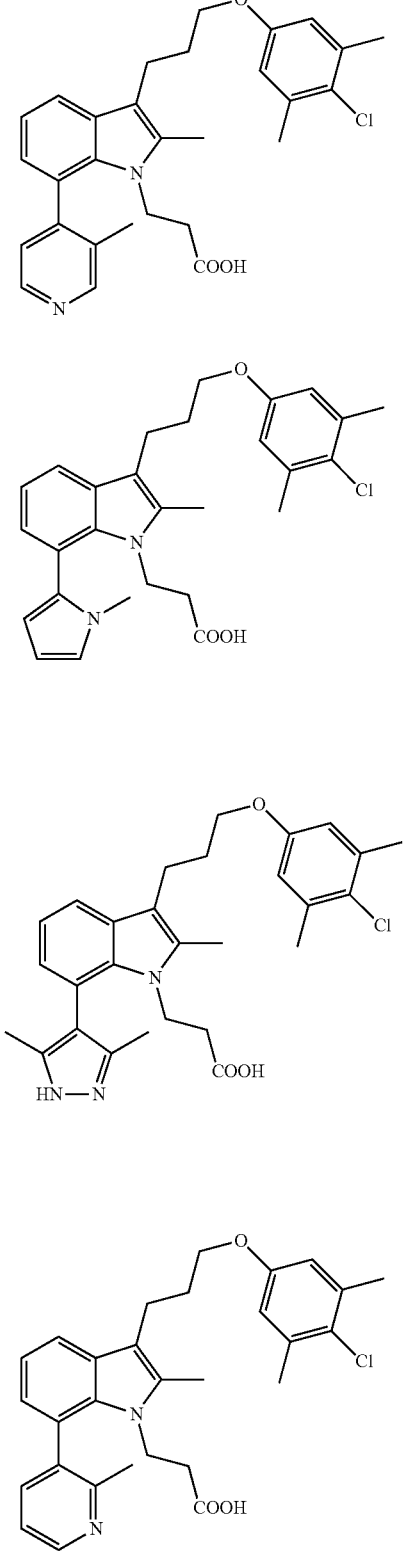

TABLE 1-continued
Exemplary compounds.
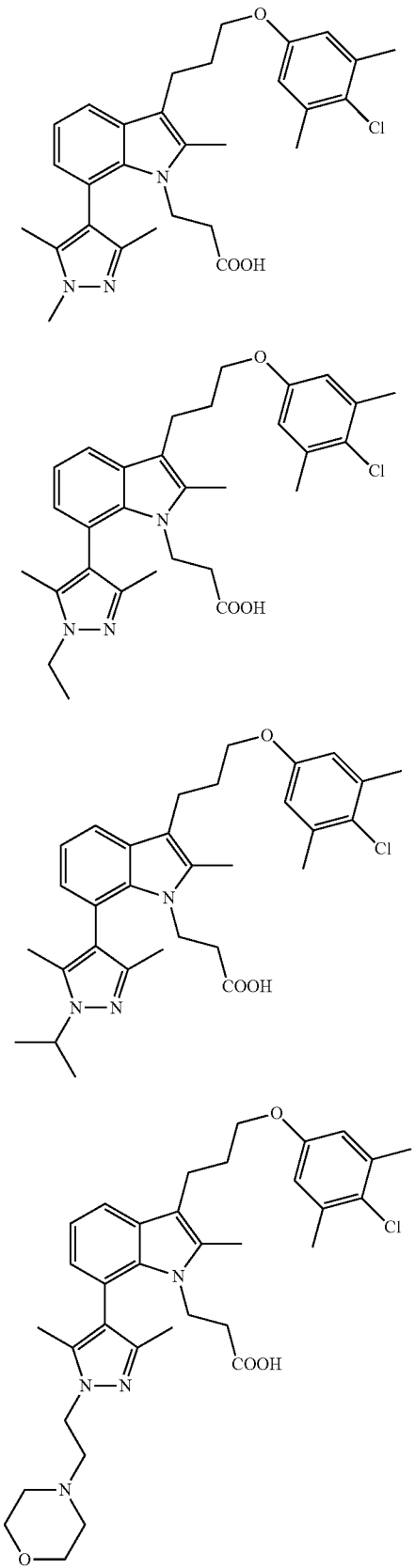
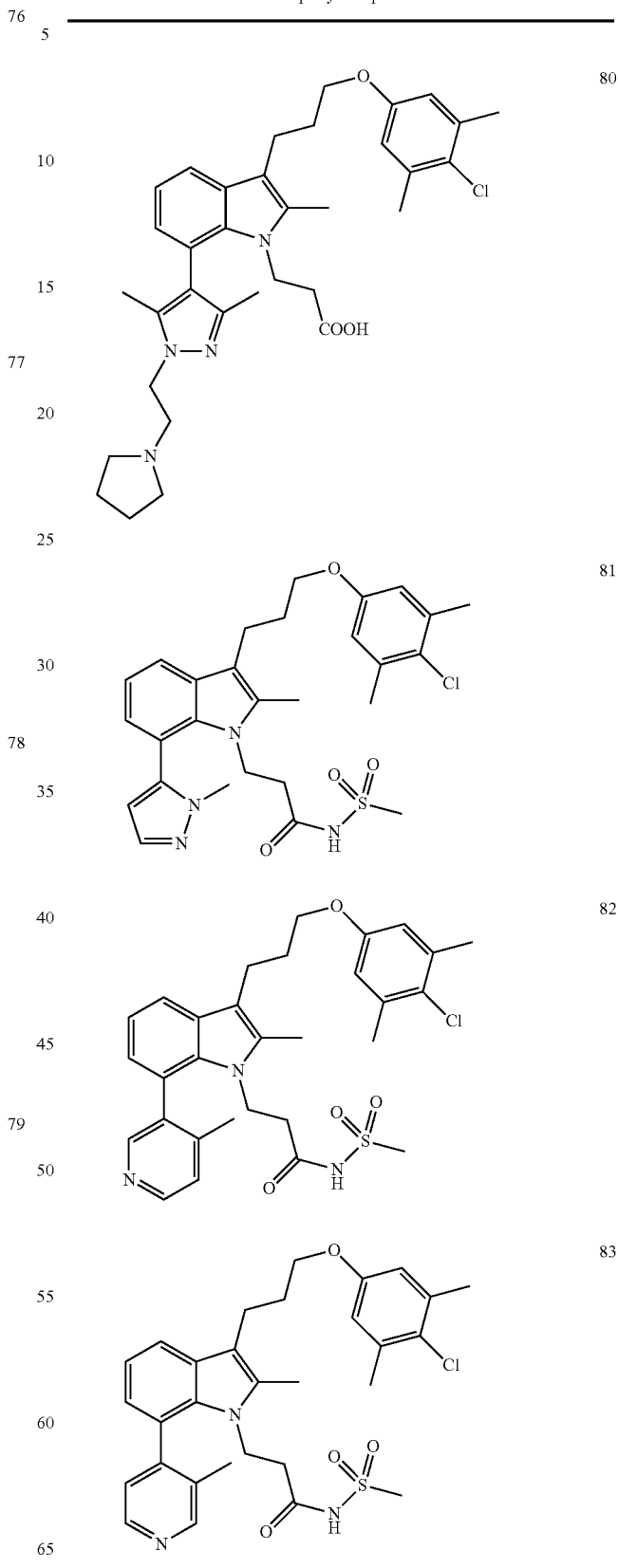

TABLE 1-continued
Exemplary compounds.
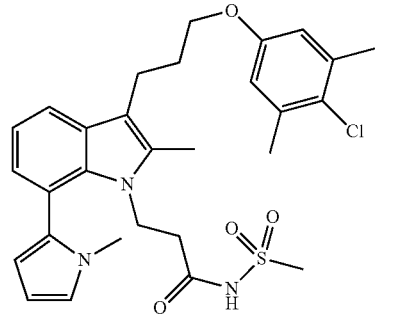 [SMILES: Cc1cc(OCCCc2c(C)n(CCC(=O)NS(C)(=O)=O)c3c(-c4ccnn4C)cccc23)cc(C)c1Cl]
84
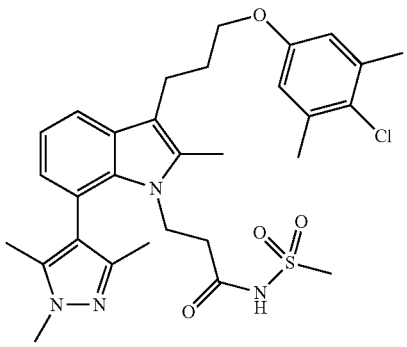
85
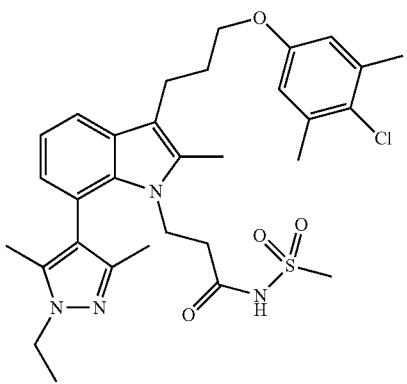
86
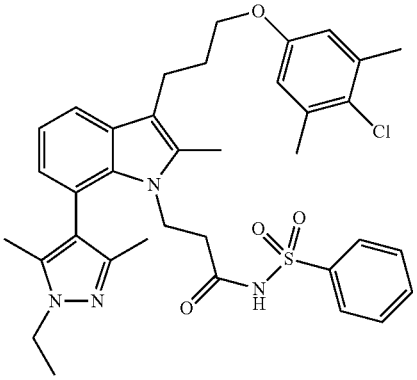 [SMILES: CCn1nc(C)c(-c2cccc3c(CCCOc4cc(C)c(Cl)c(C)c4)c(C)n(CCC(=O)NS(=O)(=O)c4ccccc4)c23)c1C]
87
TABLE 1-continued
Exemplary compounds.
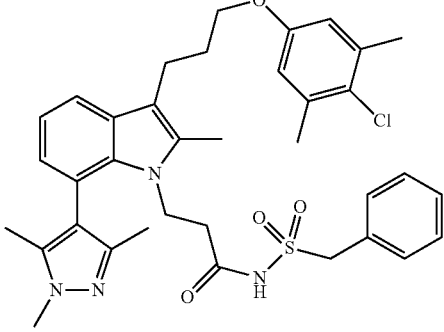
88
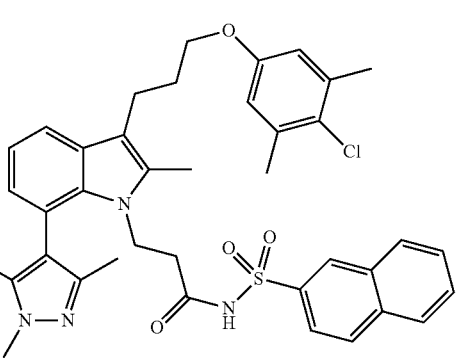
89
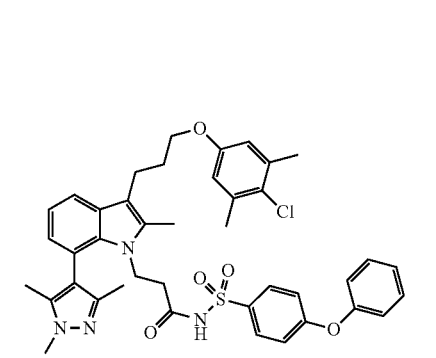 [SMILES: Cc1cc(OCCCc2c(C)n(CCC(=O)NS(=O)(=O)c3ccc(Oc4ccccc4)cc3)c3c(-c4c(C)nn(C)c4C)cccc23)cc(C)c1Cl]
90
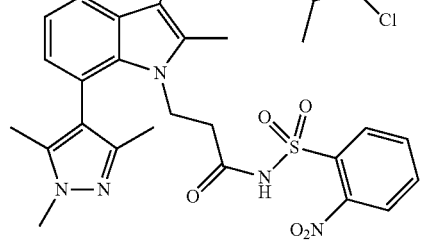
91

TABLE 1-continued
Exemplary compounds.
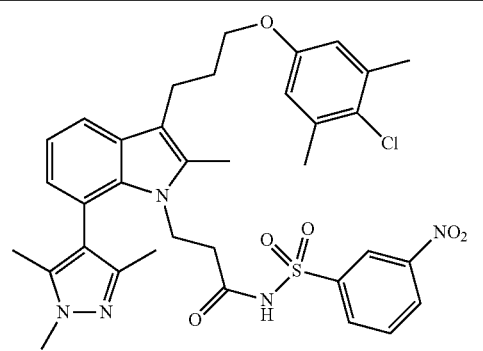
92
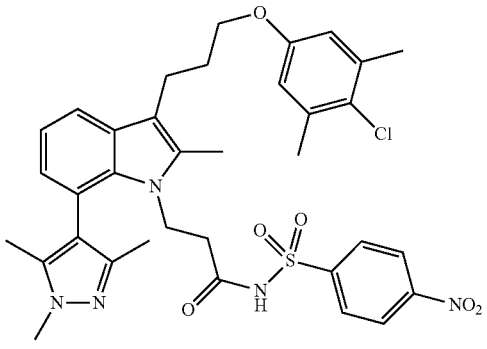 [SMILES: Cc1cc(OCCCc2c(C)n(CCC(=O)NS(=O)(=O)c3ccc([N+](=O)[O-])cc3)c3c(-c4c(C)nn(C)c4C)cccc23)cc(C)c1Cl]
93
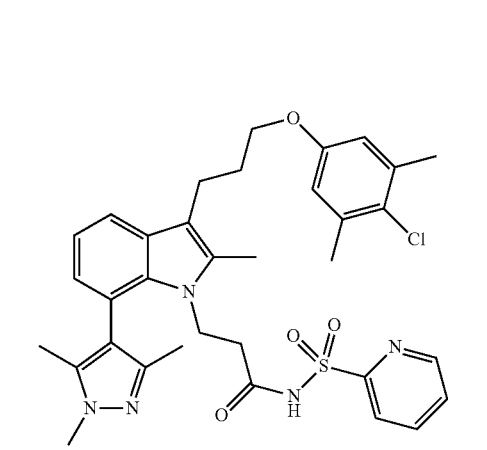 [SMILES: Cc1cc(OCCCc2c(C)n(CCC(=O)NS(=O)(=O)c3ccccn3)c3c(-c4c(C)nn(C)c4C)cccc23)cc(C)c1Cl]
94
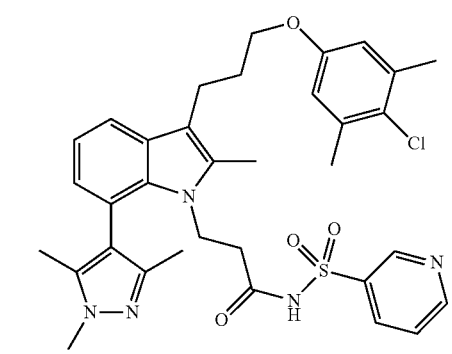 [SMILES: Cc1cc(OCCCc2c(C)n(CCC(=O)NS(=O)(=O)c3cccnc3)c3c(-c4c(C)nn(C)c4C)cccc23)cc(C)c1Cl]
95
TABLE 1-continued
Exemplary compounds.
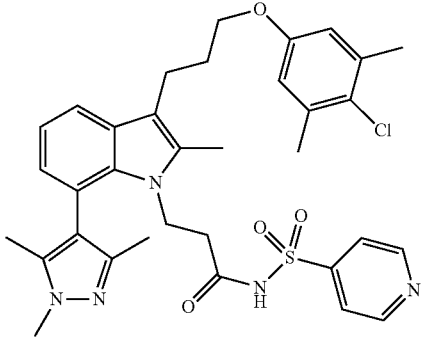 [SMILES: Cc1cc(OCCCc2c(C)n(CCC(=O)NS(=O)(=O)c3ccncc3)c3c(-c4c(C)nn(C)c4C)cccc23)cc(C)c1Cl]
96
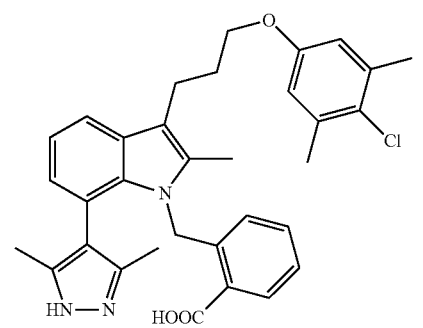
97
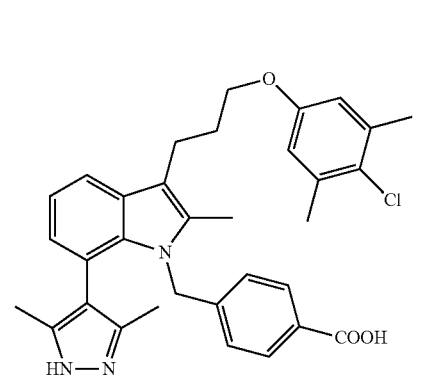
98
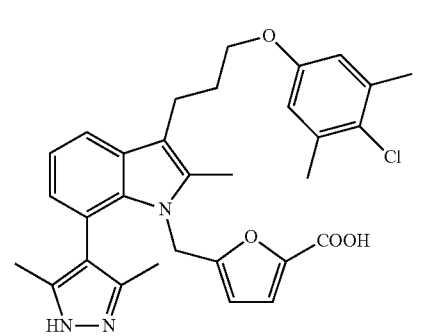
99

TABLE 1-continued
Exemplary compounds.
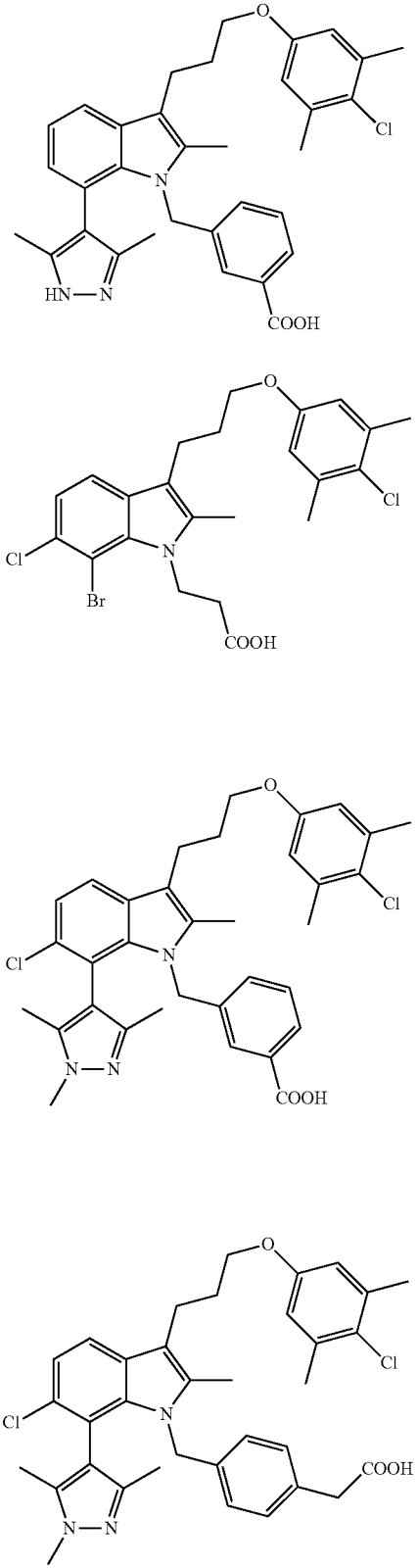
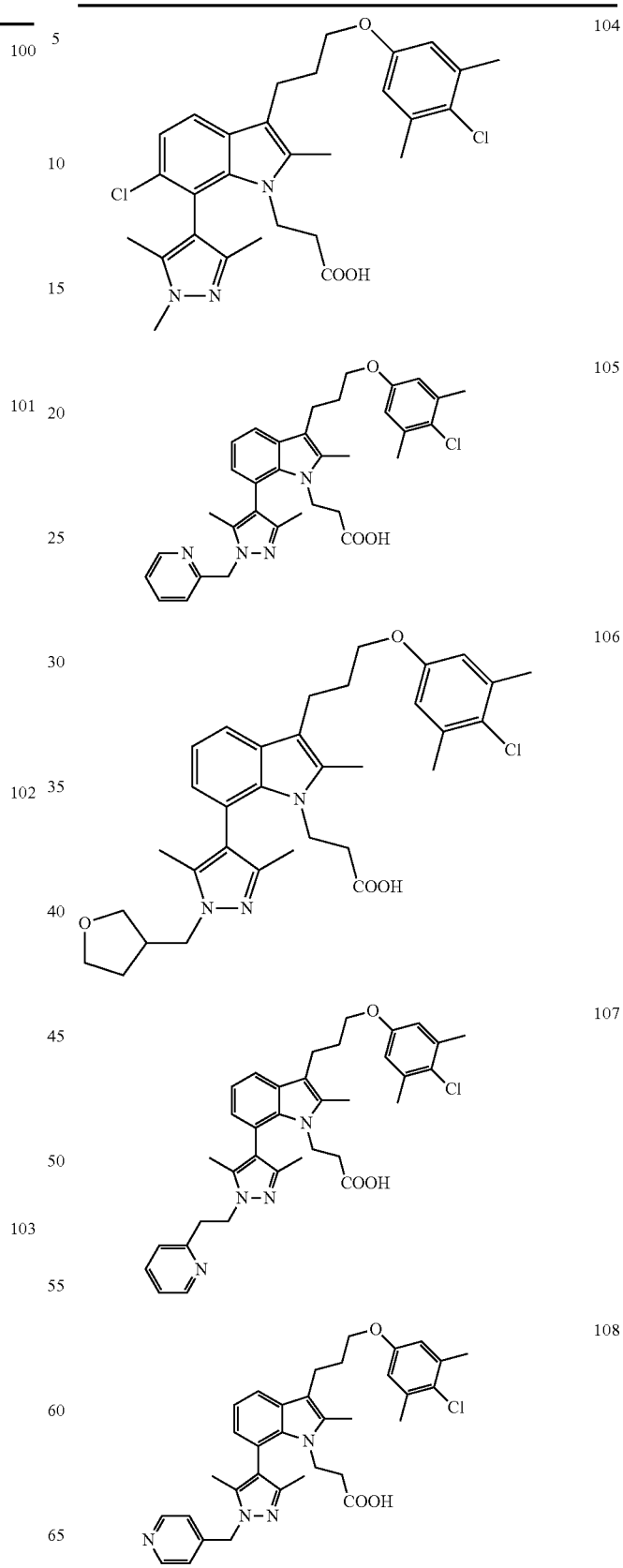

TABLE 1-continued
Exemplary compounds.
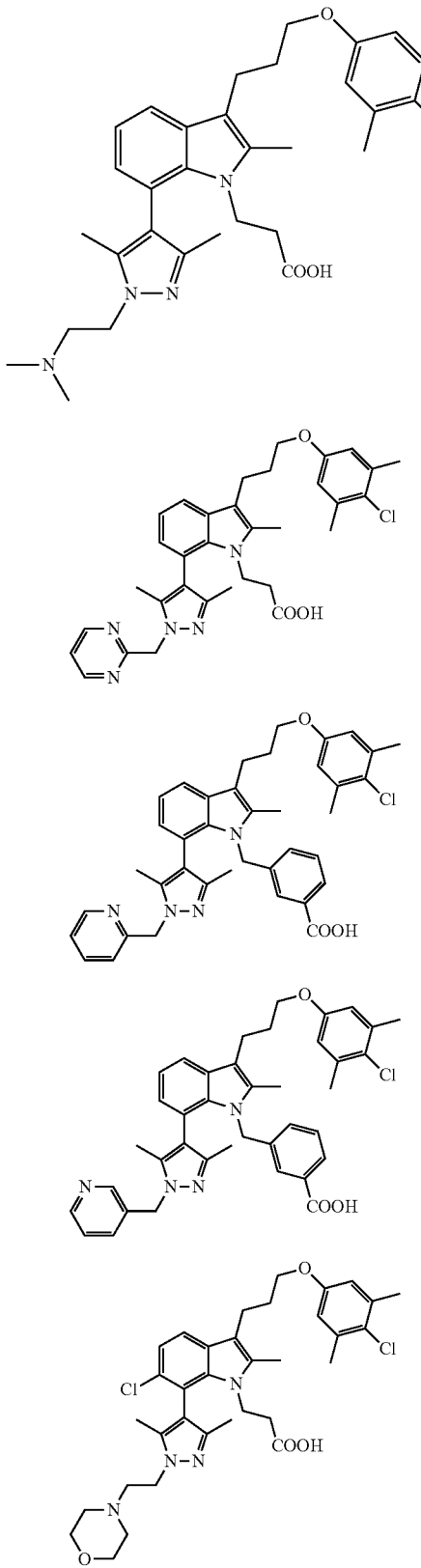
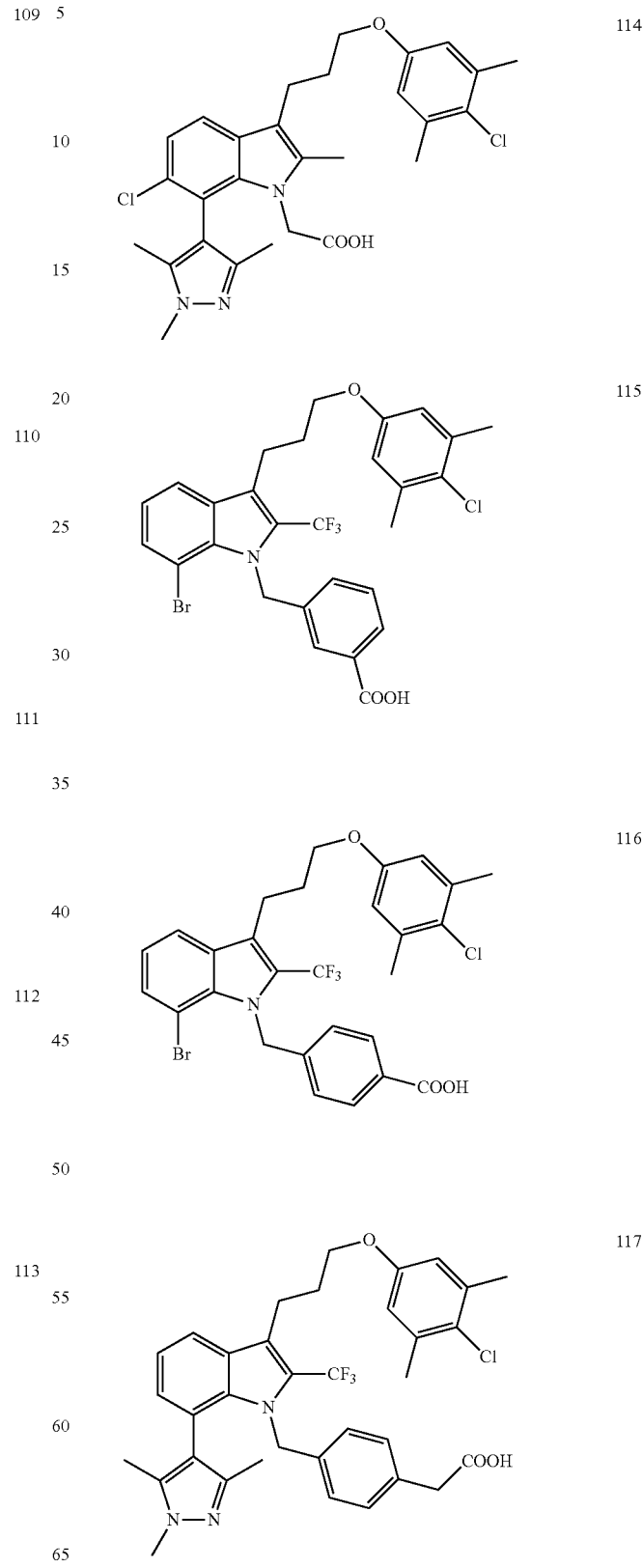

TABLE 1-continued
Exemplary compounds.
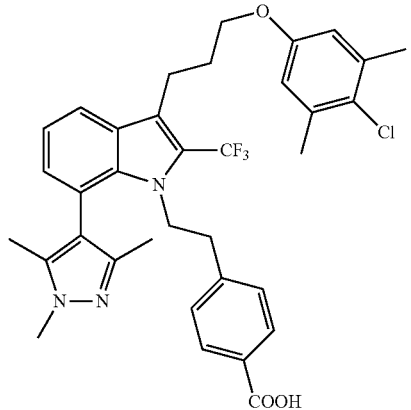 118
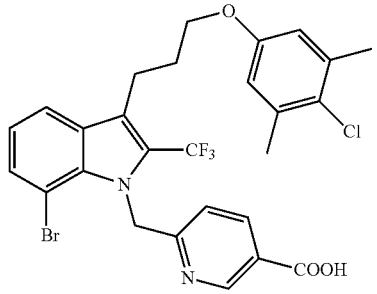 [SMILES: Cc1cc(OCCCc2c(C(F)(F)F)n(Cc3ccc(C(=O)O)cc3)c3c(Br)cccc23)cc(C)c1Cl] 119
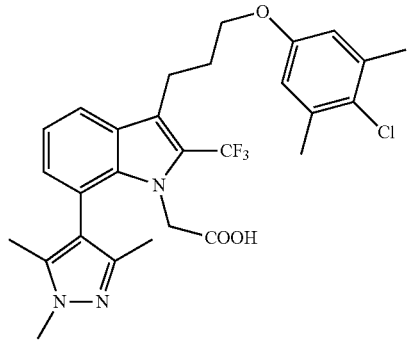 120
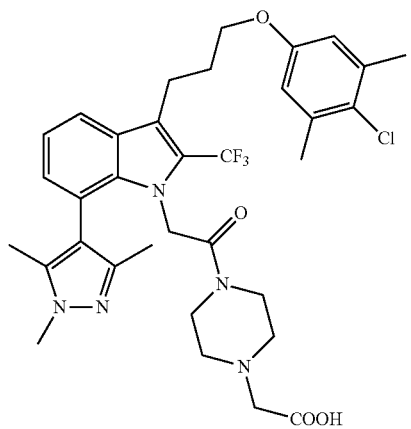 121
TABLE 1-continued
Exemplary compounds.
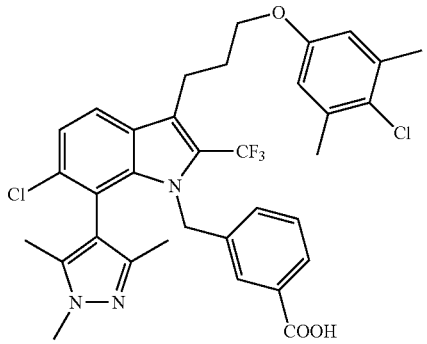 [SMILES: Cc1cc(OCCCc2c(C(F)(F)F)n(Cc3cccc(C(=O)O)c3)c3c(-c4c(C)nn(C)c4C)c(Cl)ccc23)cc(C)c1Cl] 122
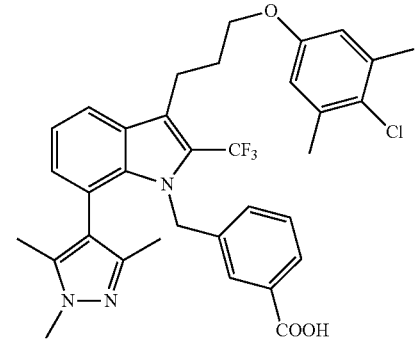 123
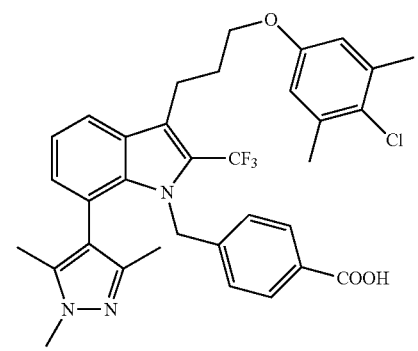 124
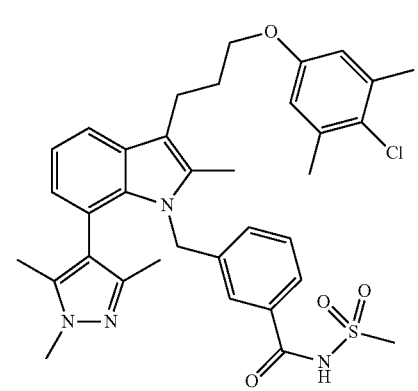 125

TABLE 1-continued
Exemplary compounds.
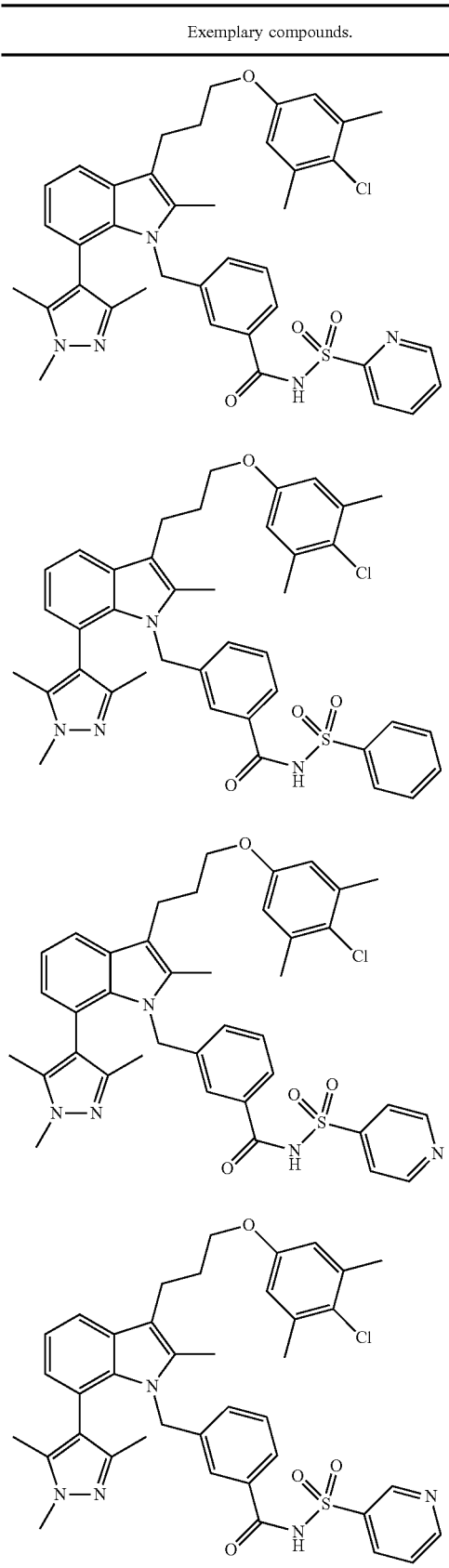
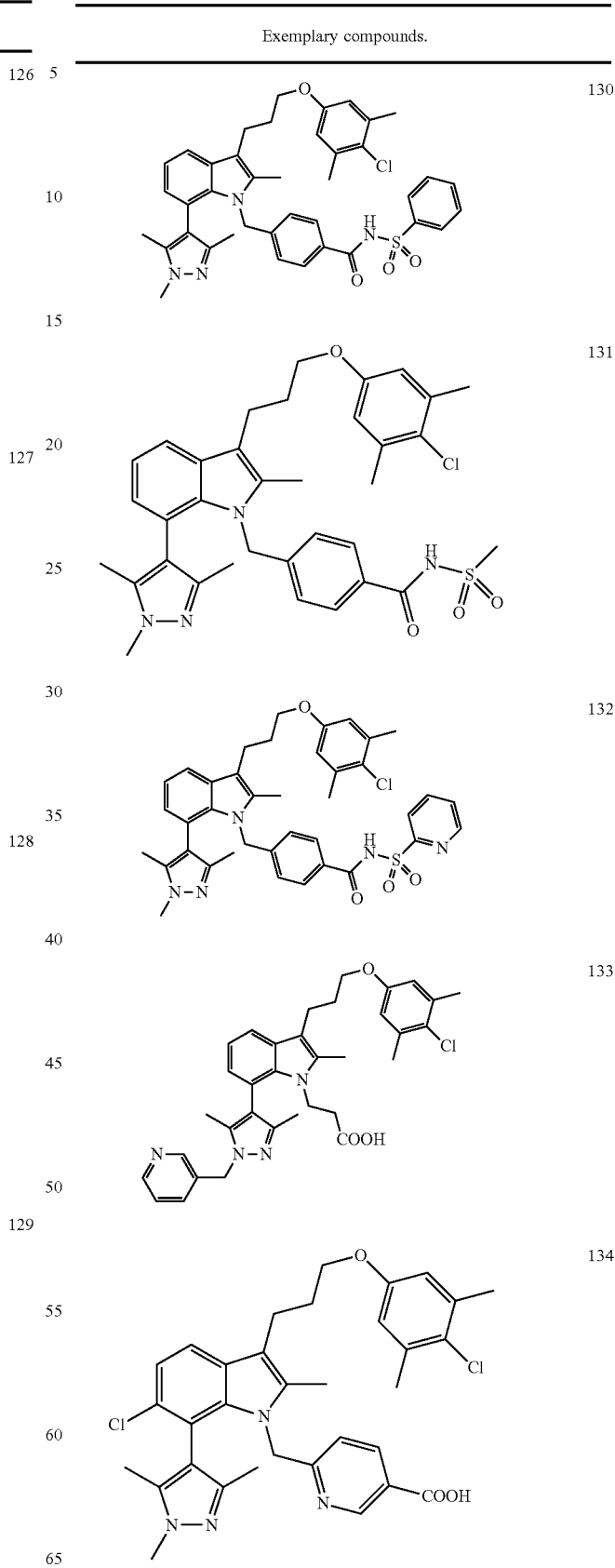

TABLE 1-continued

Exemplary compounds.

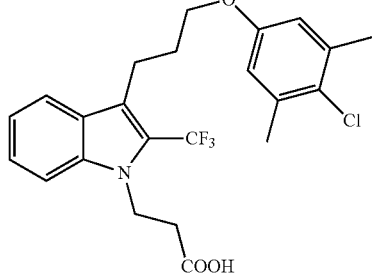
135

In certain embodiments, the present invention provides any compound selected from those depicted in Table 1, above, or a pharmaceutically acceptable salt thereof. In some embodiments, a provided compound is a compound selected from Table 1, or a pharmaceutically acceptable salt thereof.

In some embodiments, $R^1$ is —COOH, and -$L^1$-$R^1$ is other than —CH$_2$COOH. In some embodiments, $R^1$ is —COOH and -$L^1$-$R^1$ is other than —(CH$_2$)3COOH. In some embodiments, $R^1$ is —COOH and -$L^1$-$R^1$ is other than —CH$_2$COOH or —(CH$_2$)3COOH.

In some embodiments, $L^2$ is other than —CH$_2$CH$_2$CH$_2$—. In some embodiments, $L^2$ is other than —C(O)—CH$_2$CH$_2$—. In some embodiments, $L^2$ is other than —OCH$_2$CH$_2$—. In some embodiments, $L^2$ is other than —CH$_2$CH$_2$CH$_2$— and —C(O)—CH$_2$CH$_2$—. In some embodiments, $L^2$ is other than —CH$_2$CH$_2$CH$_2$—, —OCH$_2$CH$_2$—, —C(Me)$_2$CH$_2$C(O)— and —CH$_2$CH(NH$_2$)C(O)—.

In some embodiments, $R^3$ is other than

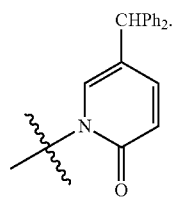

In some embodiments, -$L^2$-$R^3$ is other than

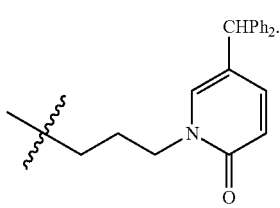

In some embodiments, a compound of formula I is other than

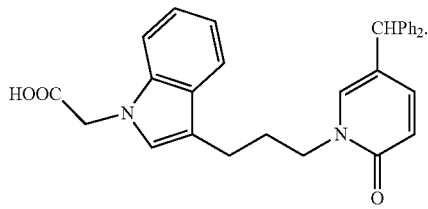

In some embodiments, $R^3$ is other than

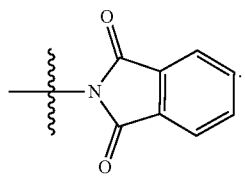 [SMILES: *N1C(=O)c2ccccc2C1=O]

In some embodiments, $R^1$ is —COOH, and a provided compound of formula I is other than

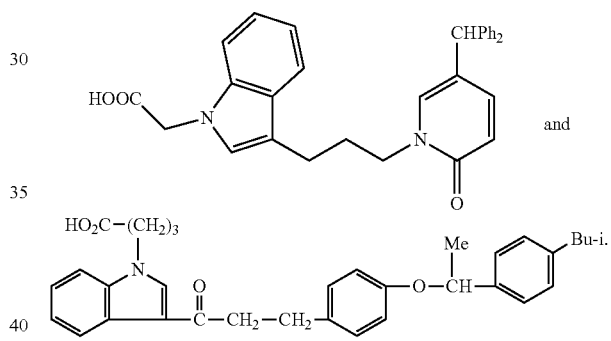
and

In some embodiments, -$L^1$-$R^1$ does not comprise a moiety of formula —CH(N(R)$_2$)—C(O))H or —CH(NH$_2$)—COOR.

In some embodiments, $R^1$ is —N(R)$_2$, wherein at least one R is not hydrogen. In some embodiments, $R^1$ is —NH$_2$.

In some embodiments, $R^1$ is —N(R)$_2$, and a provided compound of formula II is other than:

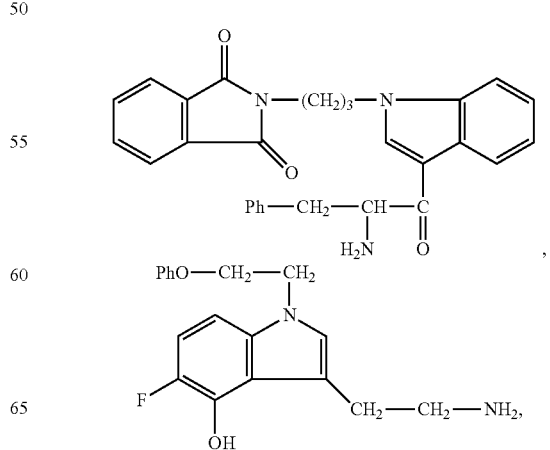

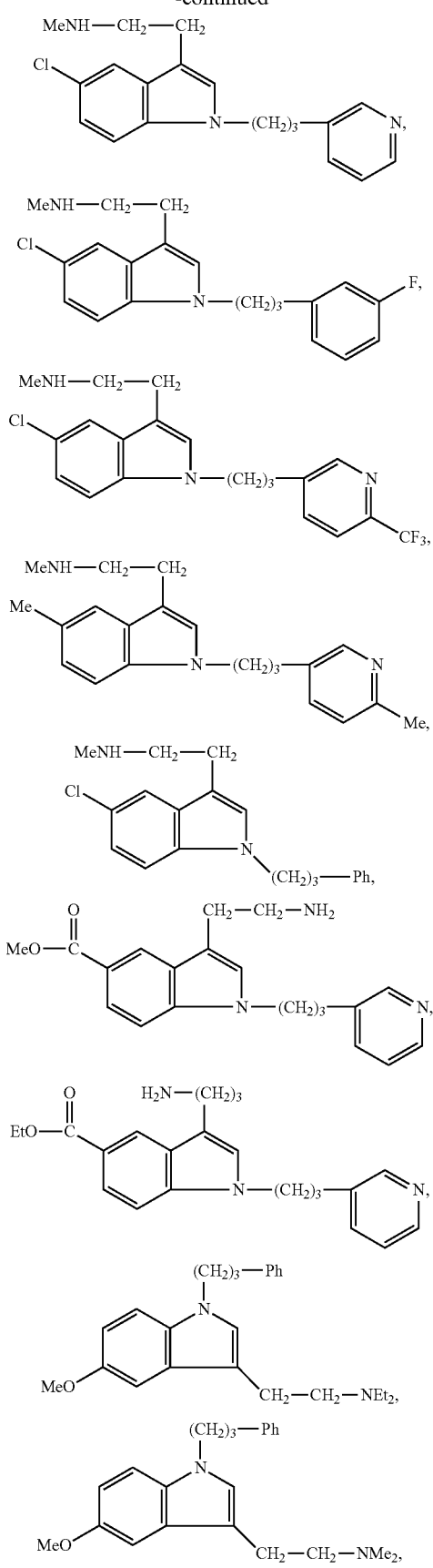
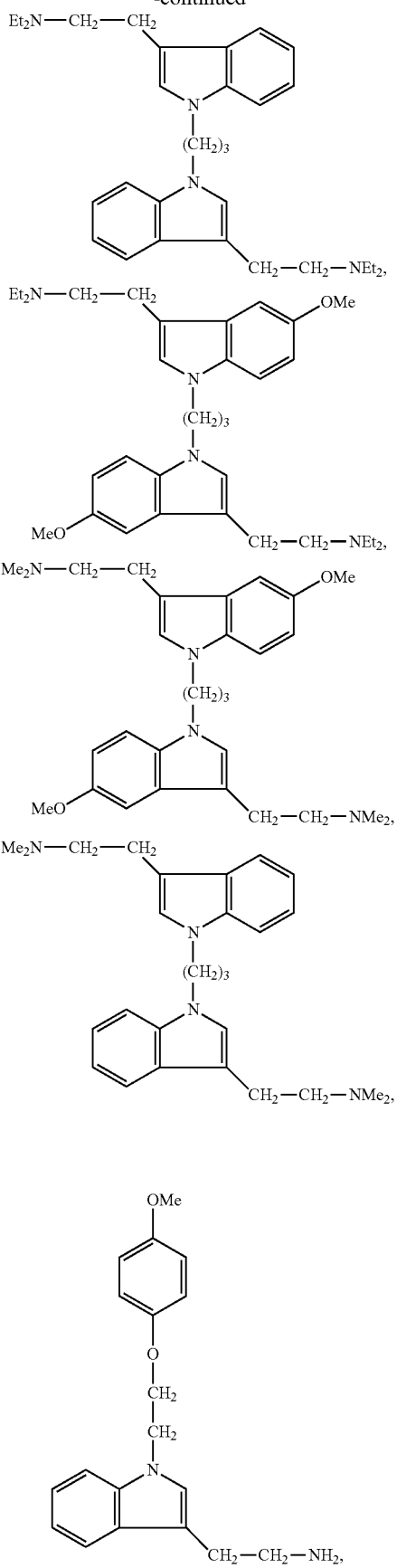

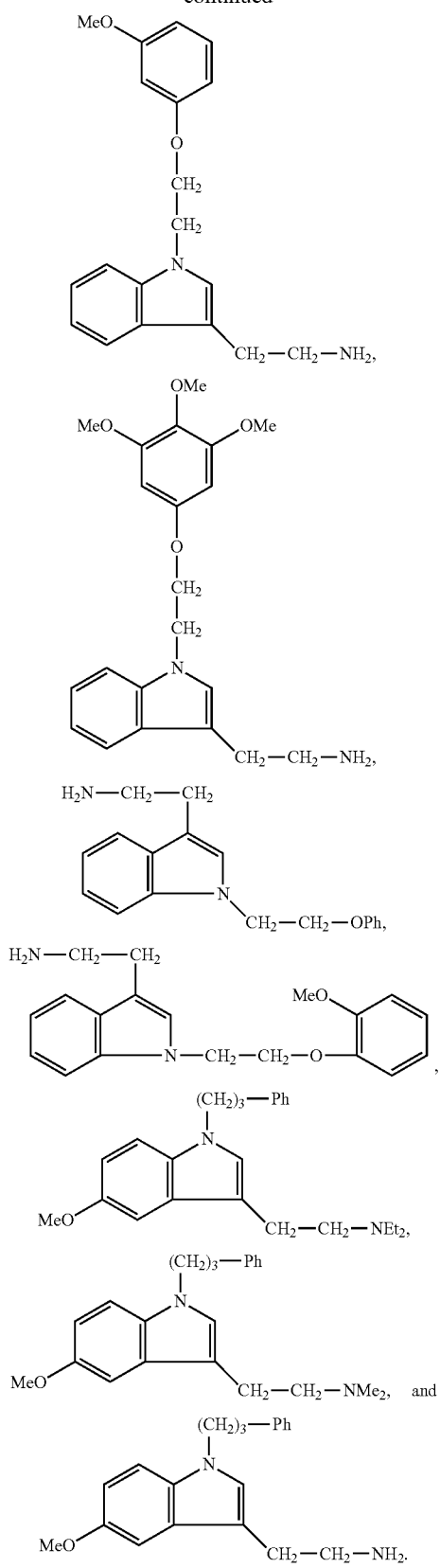
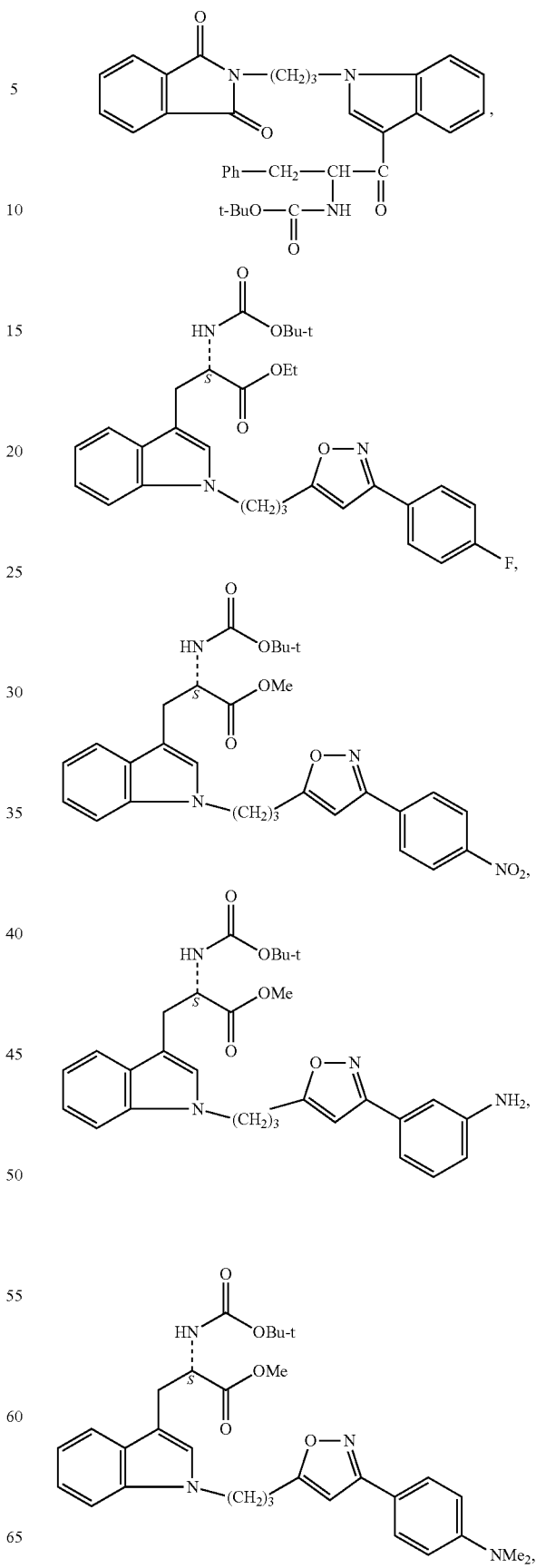
In some embodiments, $R^1$ is —NRC(O)OR, and a provided compound of formula II is other than

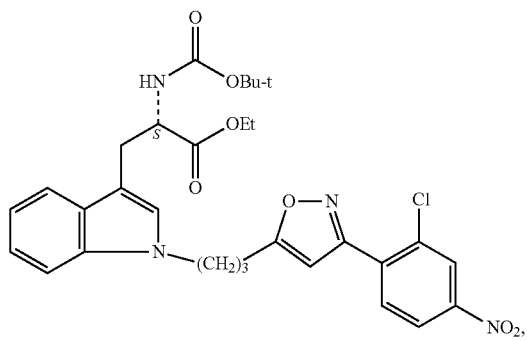
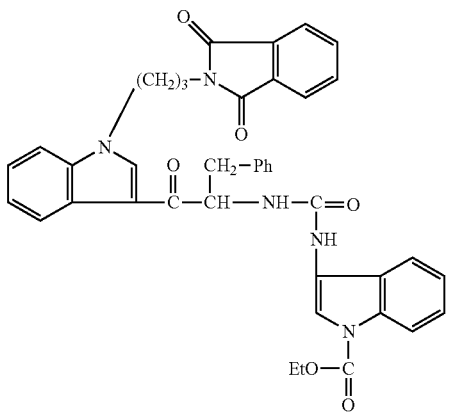
and
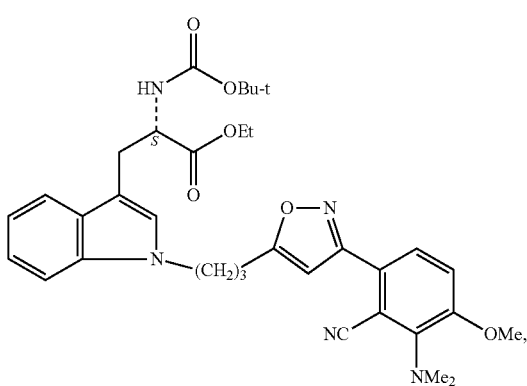
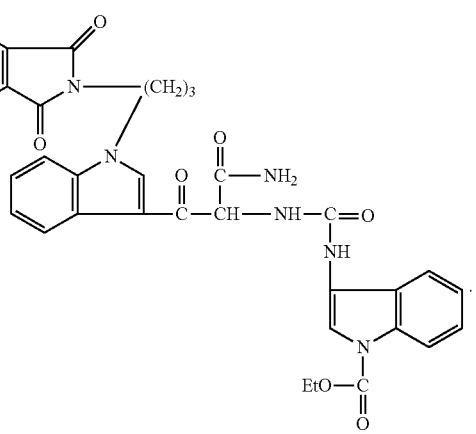
In some embodiments, R¹ is —NRC(O)R, and a provided compound of formula II is other than
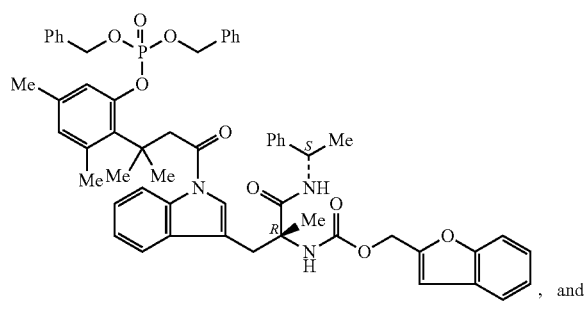
, and
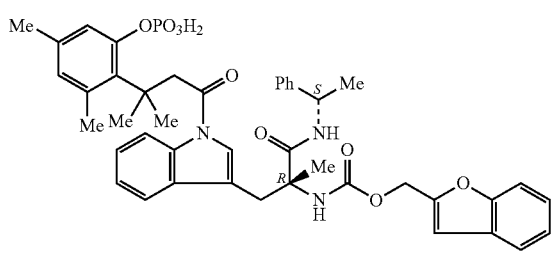
.
In some embodiments, R¹ is —NRC(O)N(R)₂, and a provided compound of formula II is other than
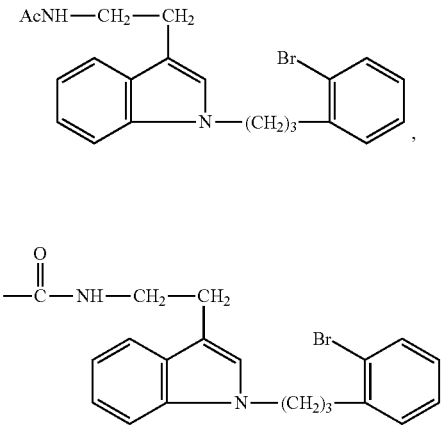

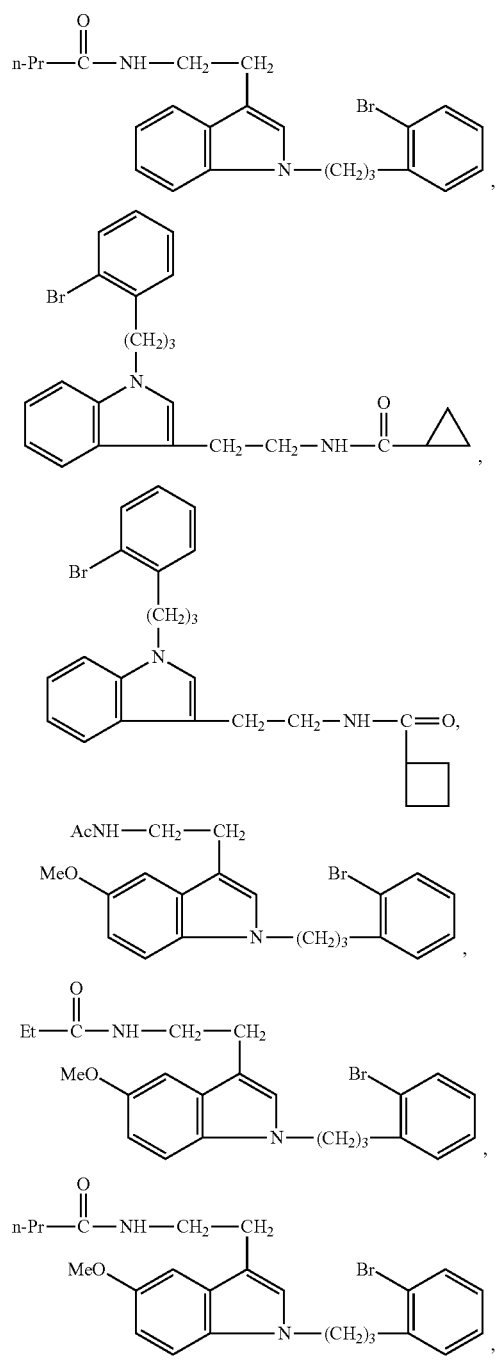
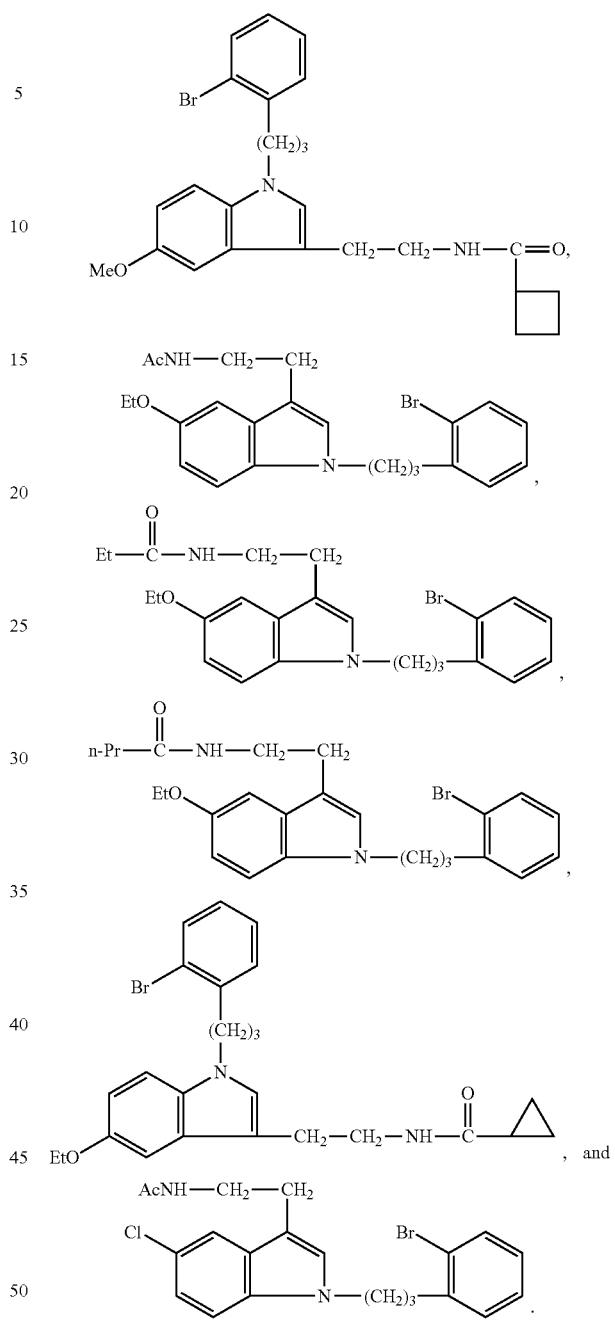
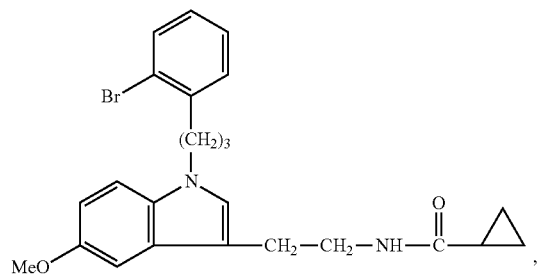
In some embodiments, R[1] is —NRS(O)$_2$R, and a provided compound of formula II is other than
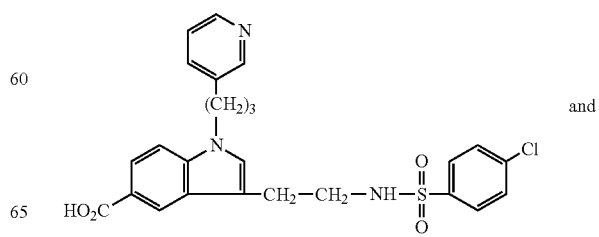

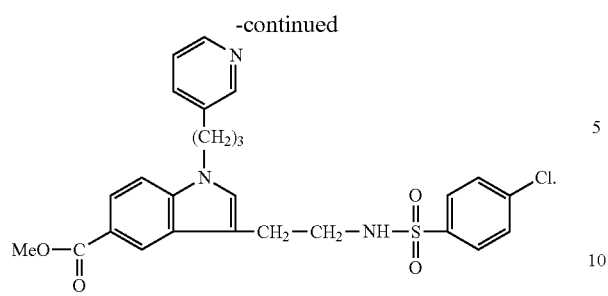
In some embodiments, a provided compound of formula I or II is other than a compound of Table 2, below:
Table 2. List of Certain Compounds.
TABLE 2
List of Certain Compounds.
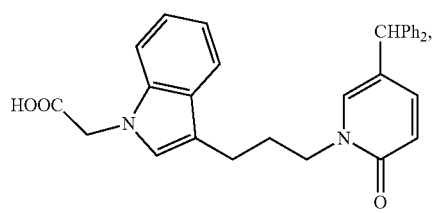
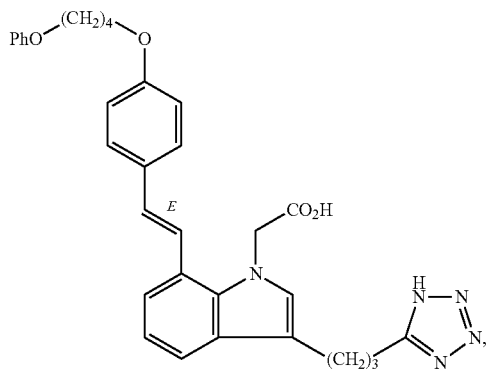
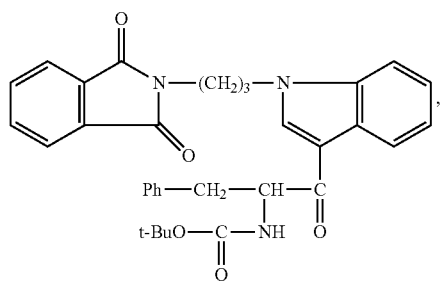
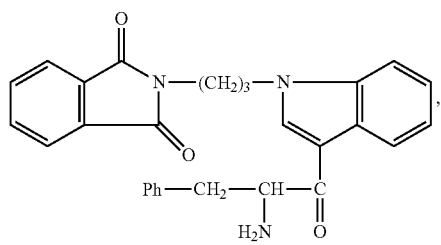

TABLE 2-continued
List of Certain Compounds.
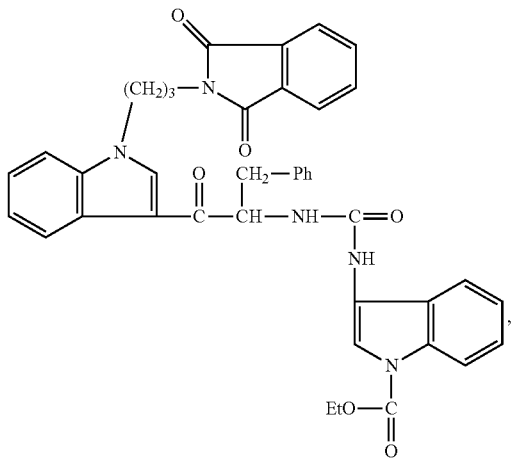
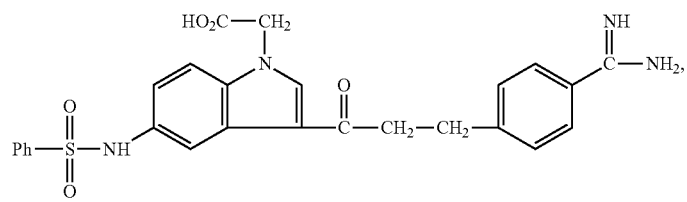 [SMILES: N=C(N)c1ccc(CCC(=O)c2cn(CC(=O)O)c3ccc(NS(=O)(=O)c4ccccc4)cc23)cc1]
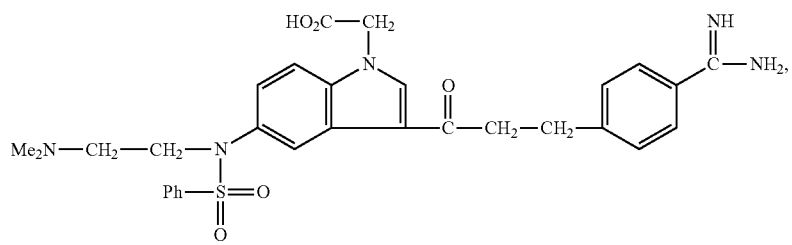 [SMILES: CN(C)CCN(c1ccc2c(c1)c(C(=O)CCc1ccc(C(=N)N)cc1)cn2CC(=O)O)S(=O)(=O)c1ccccc1]
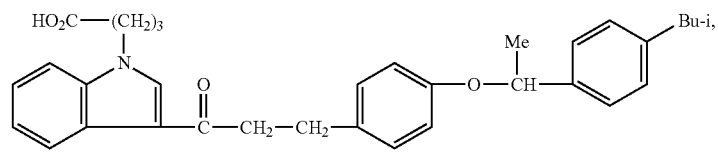
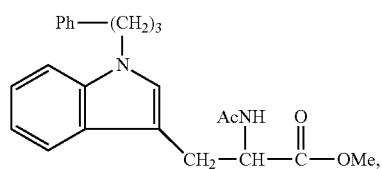
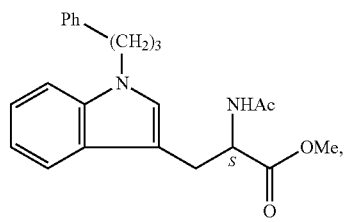

TABLE 2-continued
List of Certain Compounds.
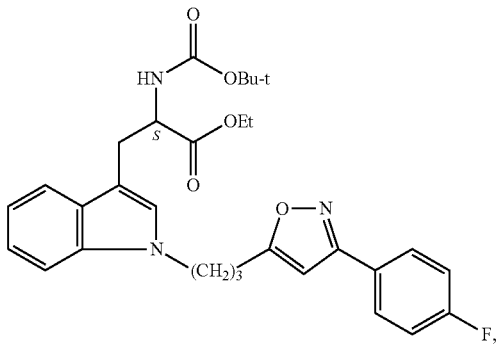
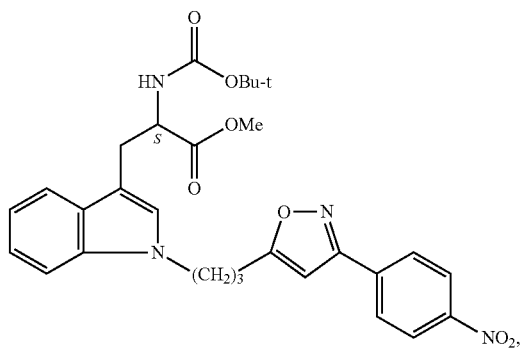
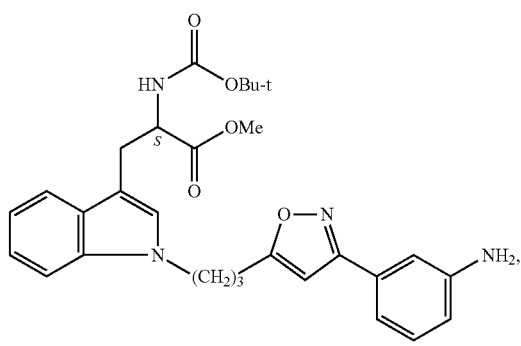
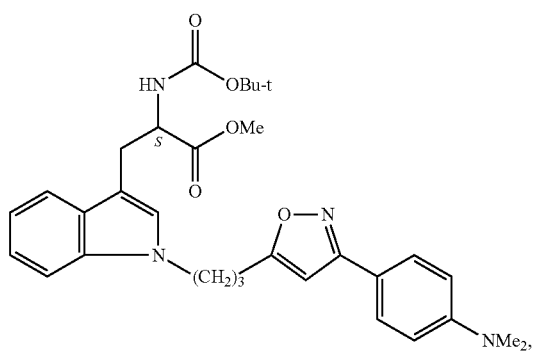

TABLE 2-continued
List of Certain Compounds.
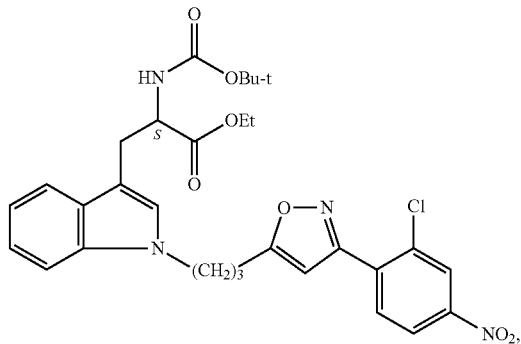
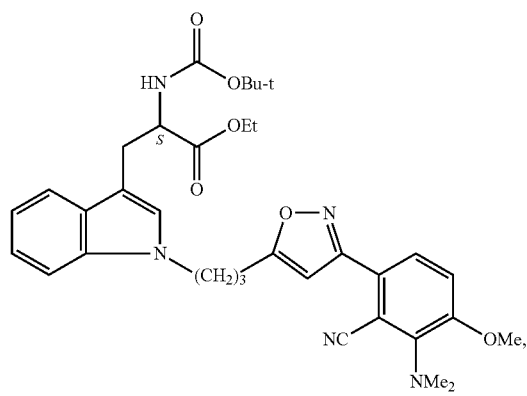
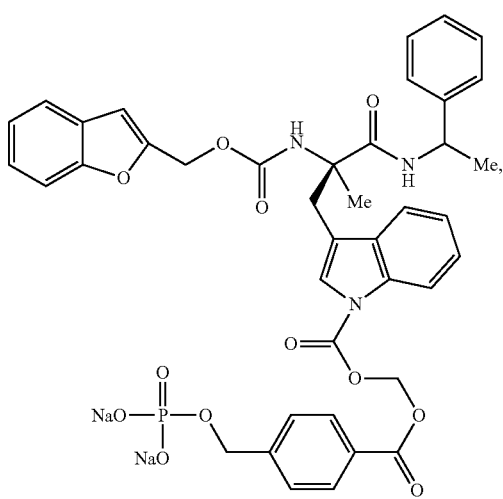

TABLE 2-continued
List of Certain Compounds.
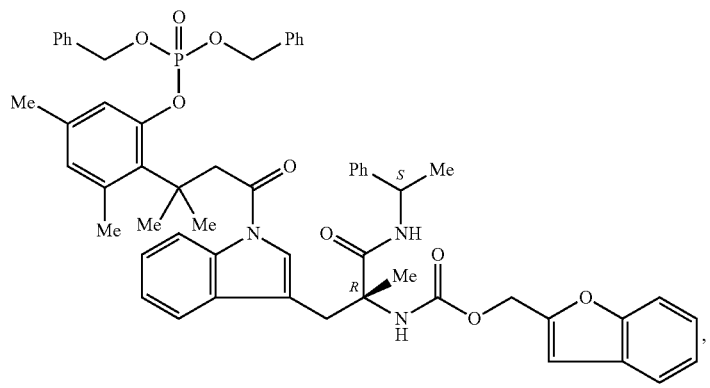
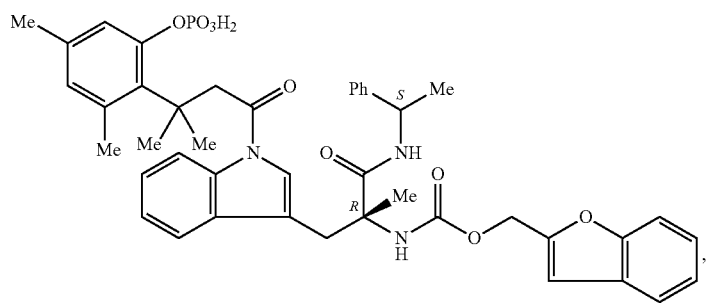
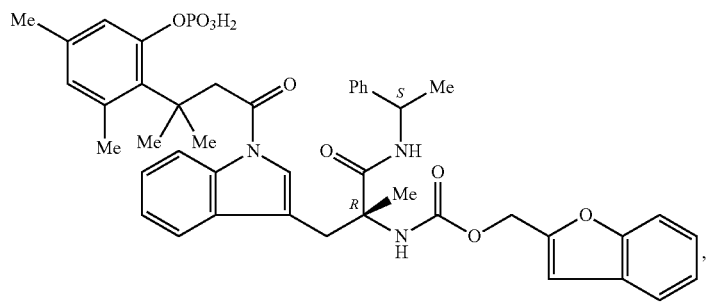
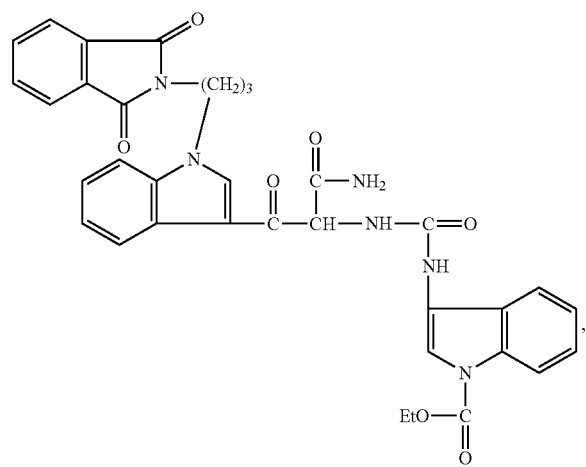

TABLE 2-continued
List of Certain Compounds.
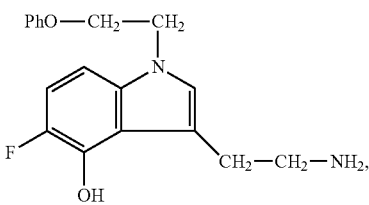 [SMILES: NCCc1cn(CCOc2ccccc2)c2ccc(F)c(O)c12]
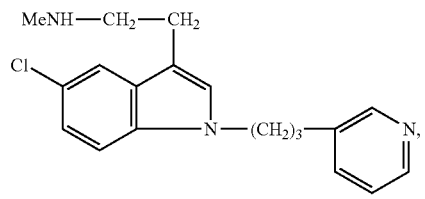
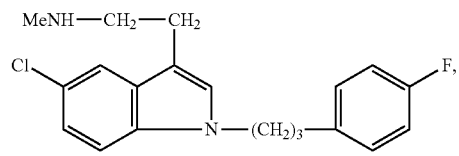
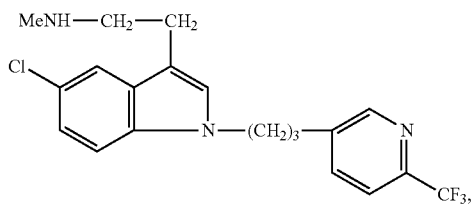
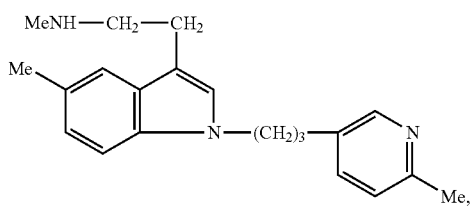
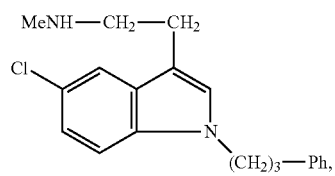
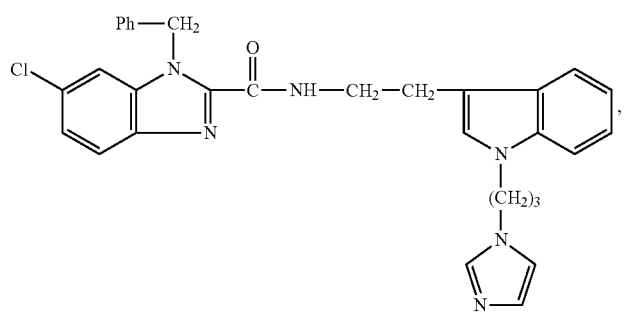

TABLE 2-continued
List of Certain Compounds.
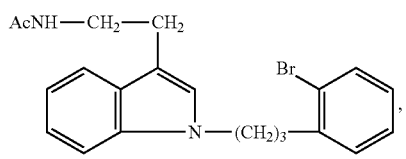,
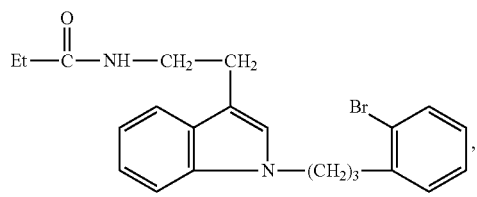,
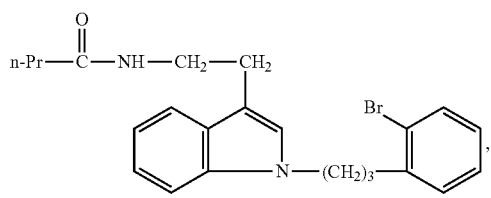,
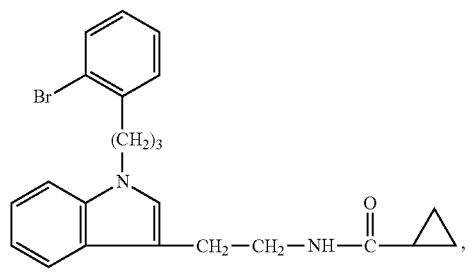,
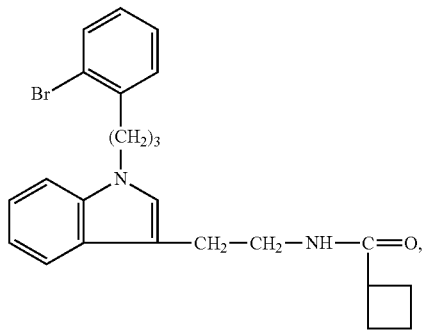,
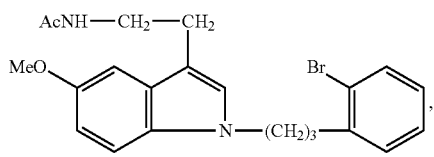,
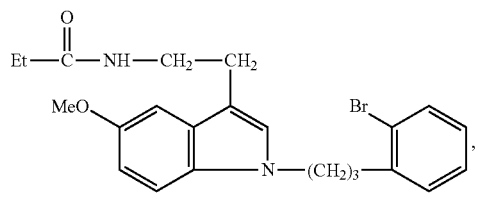, TABLE 2-continued
List of Certain Compounds.
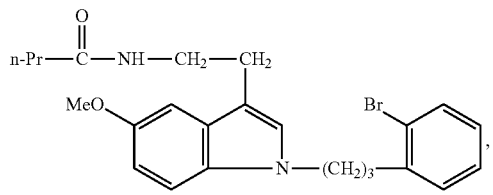
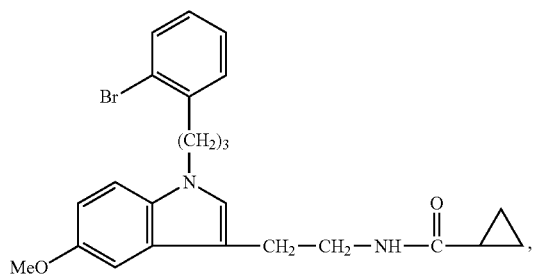
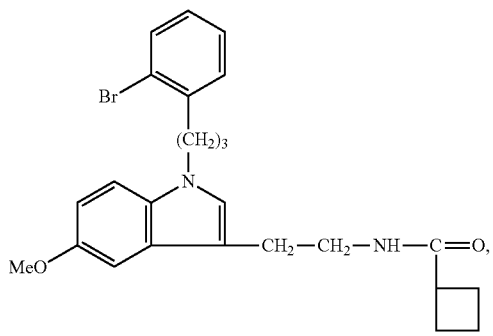
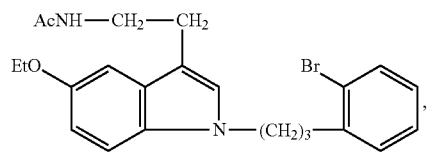
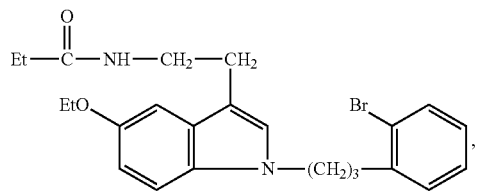
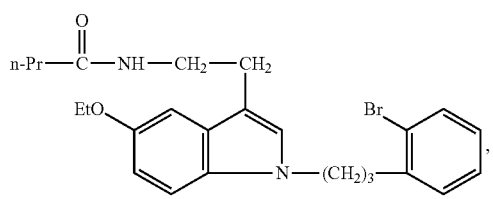

TABLE 2-continued
List of Certain Compounds.
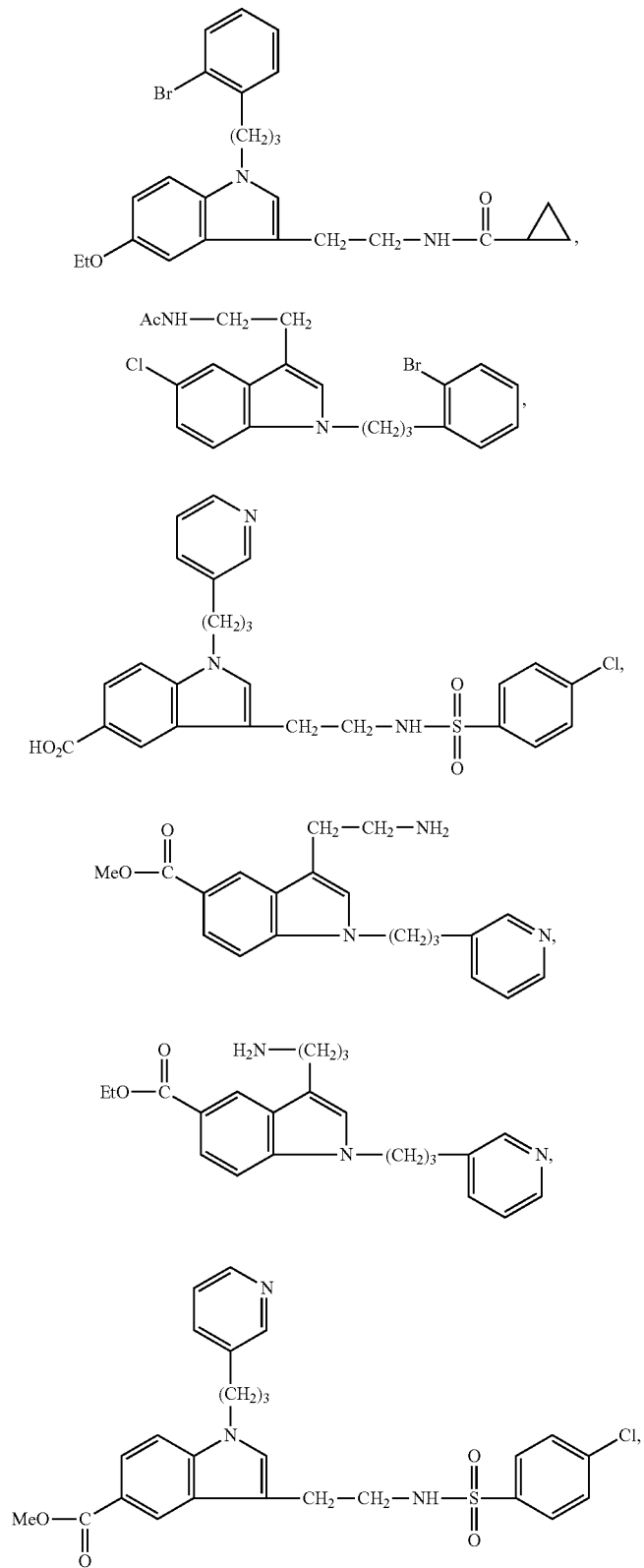

TABLE 2-continued
List of Certain Compounds.
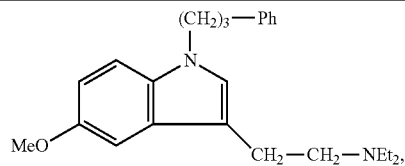
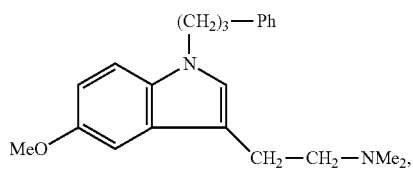
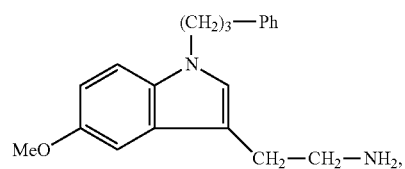
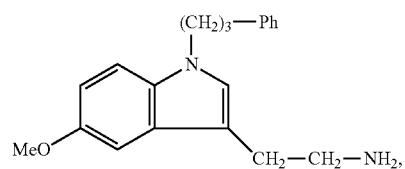
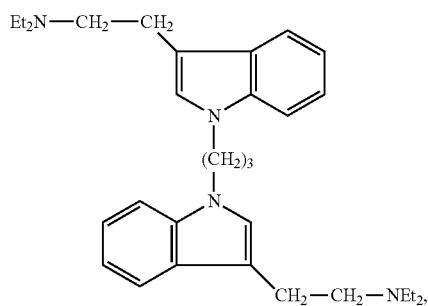
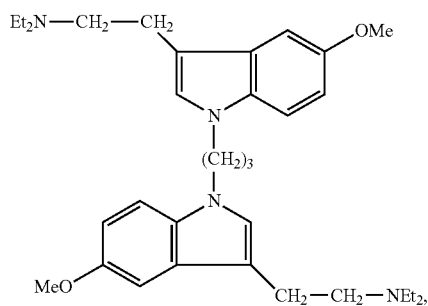
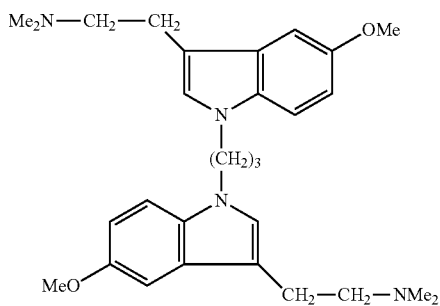

TABLE 2-continued
List of Certain Compounds.
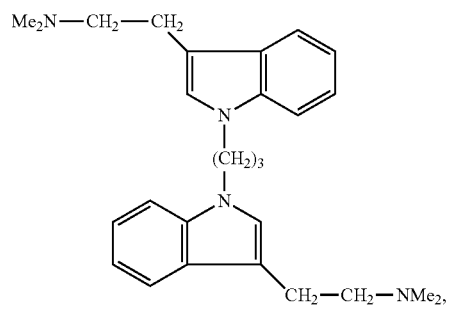
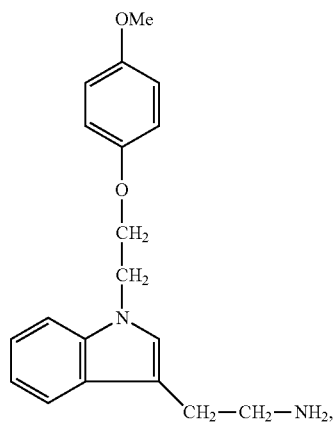 [SMILES: COc1ccc(OCCn2cc(CCN)c3ccccc32)cc1]
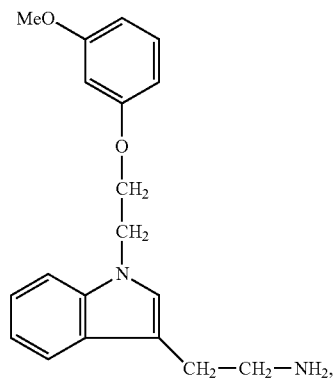 [SMILES: COc1cccc(OCCn2cc(CCN)c3ccccc32)c1]
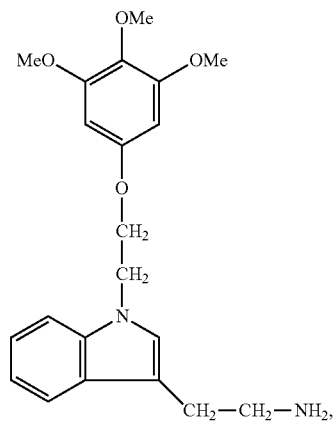 [SMILES: COc1cc(OCCn2cc(CCN)c3ccccc32)cc(OC)c1OC]

TABLE 2-continued

List of Certain Compounds.

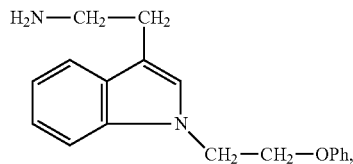

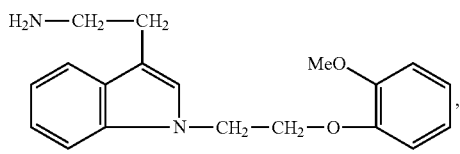

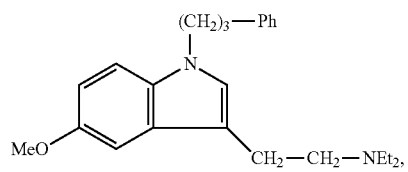

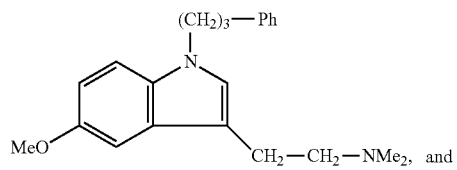

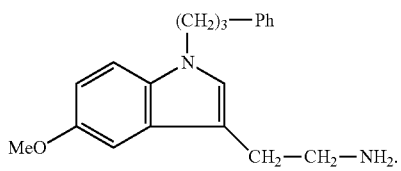

In some embodiments, a provided compound of formula I or II is other than a compound of Table 2, or a pharmaceutically acceptable salt thereof.

4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit Mcl-1, in a biological sample or in a patient. In certain embodiments, the amount of compound in compositions of this invention is such that is effective to measurably inhibit Mcl-1, in a biological sample or in a patient. In certain embodiments, a composition of this invention is formulated for administration to a patient in need of such composition. In some embodiments, a composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Mcl-1, or a mutant thereof, activity in a biological sample is useful for a variety of purposes that are known to one of skill in the art. Examples of such purposes include, but are not limited to, blood transfusion, organ transplantation, biological specimen storage, and biological assays.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In another aspect the present disclosure provides a method of treating a disease or disorder associated with the expression or over-expression of anti-apoptotic Bcl-2 family protein members, and in certain embodiments those diseases characterized by the expression or the over-expression of Mcl-1 proteins, comprising administering to a mammalian patient a therapeutically effective amount of a compound of Formula I or Formula II, or a pharmaceutically acceptable salt or solvate or a pharmaceutically acceptable carrier thereof.

Further, in accordance with the present invention, a method is provided for preventing, modulating, or treating the progression or onset of diseases or disorders associated with the upregulated activity of the Bcl-2 family of proteins, specifically Mcl-1 protein, such as defined above and hereinafter, wherein a therapeutically effective amount of a compound of Formula I or Formula II is administered to a mammalian, i.e., human, patient in need of treatment.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting Mcl-1, or a mutant thereof, activity in a patient comprising the step of administering to said patient a compound of the present invention, or a composition comprising said compound. In other embodiments, the present invention provides a method for treating a disorder mediated by Mcl-1, or a mutant thereof, in a patient in need thereof, comprising the step of administering to said patient a compound according to the present invention or pharmaceutically acceptable composition thereof. Such disorders are described in detail herein.

Compounds of the present invention modulate the activity of the Bcl-2 family of proteins. Preferably, compounds of the present invention inhibit the activity of one type or a subset of anti-apoptotic Bcl-2 family of proteins, for examples of Mcl-1, Bcl-2, Bcl-xL, and Bcl-w proteins. Consequently, the compounds of the present invention may be used in the treatment of multiple diseases or conditions of abnormal cell growth and/or dysregulated apoptosis, such as cancer, autoimmune disease and pro-thrombotic conditions. Examples of diseases or disorders associated with down-regulated apoptosis can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

The compounds of the present invention possess activity as inhibitors of the Bcl-2 family proteins, particularly Mcl-1 protein, and, therefore, may be used in the treatment of diseases associated with anti-apoptotic Bcl-2 family of proteins. Via the inhibitition of the activity of anti-apoptotic Bcl-2 family proteins, the compounds of the present invention may preferably be employed to release pro-apoptotic and promote apoptosis.

Accordingly, the compounds of the present invention can be administered to mammals, preferably humans, for the treatment of a variety of conditions and disorders, including, but not limited to, treating, preventing, or slowing the progression of various hematologic and solid tumor types and related conditions, resistance development associated with chemotherapy. Consequently, it is believed that the compounds of the present invention may be used in preventing, inhibiting, or treating acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that the compounds of the present invention may be used in preventing, inhibiting, or treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like. (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Bf 1. Haematol. 2000 September; 110(3): 584-90; Blood 2000 Feb. 15; 95(4): 1283-92; and New England Journal of Medicine 2004 September; 351(14): 1409-1418).

Involvement of Mcl-1 in acute lymphoblastic leukemia is reported in *Blood* (1998) 91, 991-1000.

Involvement of Mcl-1 in pancreatic carcinoma is reported in *Cancer Chemotherapeutic Pharmacology* (2008) 62, 1055-1064.

Involvement of Mcl-1 in breast cancer is reported in *Anticancer Research* (2004) 24, 473-482.

Involvement of Mcl-1 in breast and non small-cell lung cancer is also reported in *Nature* (2010) 463, 899-905

Involvement of Mcl-1 in non small-cell lung cancer is also reported in *Oncogene* (2011) 30, 1963-1968

Involvement of Mcl-1 in acute myelogenous leukemia is reported in *Blood* (1998) 91, 991-1000.

Involvement of Mcl-1 in cervical cancer is reported in *Cancer Letters* (Shannon, Ireland) (2002) 180, 63-68.

Involvement of Mcl-1 in cervical cancer is also reported in *Medical Oncology* (2011) 3, 673-677.

Involvement of Mcl-1 in chronic lymphocytic leukemia is reported in *Journal of the National Cancer Institute* (2004) 96, 673-682 and *Immunology* (2005) 114, 441-449.

Involvement of Mcl-1 in colorectal cancer, is reported in *Annals of oncology: Official Journal of the European Society for Medical Oncology/ESMO* (2001) 12, 779-785.

Involvement of Mcl-1 in gastric carcinoma, is reported in *Gastric Cancer* (2004) 7, 78-84.

Involvement of Mcl-1 in gestational trophobalstic disease is reported in *Cancer* (2005) 103, 268-276.

Involvement of Mcl-1 in glioblastoma is reported in *Journal of Neurology, Neurosurgery, and Psychiatry* (1999) 67, 763-768.

Involvement of Mcl-1 in head and neck cancer is reported in *Archives of Otolaryngology-Head and Neck Surgery* (1999) 125, 417-422.

Involvement of Mcl-1 in lung cancer is reported in *Pathology Oncology Research: POR* (1999) 5, 179-186.

Involvement of Mcl-1 in lung cancer is also reported in *Cancer Biology and Therapy* (2005) 4, 267-276.

Involvement of Mcl-1 in mesothioloma, is reported in *Clinical Cancer Research* (1999) 5, 3508-3515.

Involvement of Mcl-1 in mesothioloma, is also reported in *Carcinogenesis* (2010) 6, 984-993.

Involvement of Mcl-1 in multiple myeloma is reported in *European Journal of Immunology* (2004) 34, 3156-3164.

Involvement of Mcl-1 in non-Hodgkin's lymphoma is reported in *British Journal of Haematology* (2002) 116, 158-161.

Involvement of Mcl-1 in oligodenroglioma is reported in *Cancer* (1999) 86, 1832-1839.

Involvement of Mcl-1 in ovarian cancer is reported in *Journal of Clinical Oncology. Official Journal of the American Society of Clinical Oncology* (2000) 18, 3775-3781.

Involvement of Mcl-1 in ovarian cancer is also reported in *Molecular Genetics, Gastrointestinal Carcinoma and Ovarian Carcinoma* (2005) 4, 479-486.

Involvement of Mcl-1 in pancreatic cancer is reported in *Oncology* (2002) 62, 354-362.

Involvement of Mcl-1 in peripheral T-cell lymphoma is reported in *Journal of Pathology* (2003) 200, 240-248.

Over-expression of Bcl-2 family protein members is associated with resistance to chemotherapy and is correlated with clinical outcome, disease progression, overall prognosis or a combination thereof in various hematologic and solid tumor types Examples of diseases or disorders associated with the hyperactivity of the Bcl-2 family of proteins, particularly Mcl-1, that can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that compounds having either Formula I or Formula II would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

In one embodiment, a compound of the invention (e.g., compound of Formula I or Formula II), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

In another embodiment, the present invention provides for compositions for treating diseases in a patient during which is expressed or overexpressed an anti-apoptotic Bcl-2 family protein, said compositions comprising an excipient and a therapeutically effective amount of the compound of either Formula I or Formula II and a therapeutically effective amount of one additional therapeutic agent or more than one additional therapeutic agent.

The compounds of the invention can be used alone, in combination with other compounds of the present invention, or in combination with one or more other agent(s). Further, the present invention provides a method for preventing, modulating, or treating the diseases as defined above and hereinafter, wherein a therapeutically effective amount of a combination of a compound of Formula I (or Formula II) and another compound of Formula I (or Formula II) and/or at least one other type of therapeutic agent, is administered to a mammalian, e.g., human, patient in need of treatment.

The present invention includes within its scope pharmaceutical compositions comprising, as an active ingredient, a therapeutically effective amount of at least one of the compounds of Formula I and II, alone or in combination with a pharmaceutical carrier or diluent. Optionally, compounds of the present invention can be used alone, in combination with other compounds of the invention, or in combination with one or more other therapeutic agent(s), e.g., an anticancer agent or other pharmaceutically active material.

Depending upon the particular condition, or disease, to be treated, additional therapeutic agents, which are normally administered to treat that condition, are optionally present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention are also combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents are optionally administered separately from an inventive compound-containing composition, as part of a multiple dosage regimen. Alternatively, those agents are optionally part of a single dosage form, mixed together with a compound of this invention in a single composition. If administered as part of a multiple dosage regime, the two active agents are submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention is administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that is combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, are optionally incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects are prevented or mitigated by pre-coating the device with a pharmaceutically acceptable composition comprising a kinase inhibitor. Implantable devices coated with a compound of this invention are another embodiment of the present invention.

The compounds of the present invention may be employed in in adjunct with other therapies, including conventional surgery, radiotherapy and chemotherapy, for the treatment of cancer.

Such therapies can include one or more of the following categories of anti-cancer agents: alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Examples of suitable alkylating agents include altretamine, AMD-473, AP-5280, apaziquone, bendamustine, brostallicin, busulfan, carboquone, carmustine (BCNU), chlorambucil, Cloretazine™ (VNP 40101 M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Examples of suitable angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Examples of suitable aurora kinase inhibitors include AZD-1152, MLN-8054, VX-680 and the like.

Examples of suitable antimetabolites include ALIMTA® (pemetrexed disodium, L Y231514,MTA), 5 azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflomithine, ElCAR (5-ethynyl-1-~-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-I, tiazofurin, tegafur, TS-1, vidarabine, UFT and the like.

Examples of suitable Bcl protein family member inhibitors include AT-101 ((−)gossypol), GENASENSE® (G3139 or oblimersen (Bcl-2-targeting antisense oglionucleotide)), IPI-194, IPI-565, N-(4-(4-((4'-chloro(1, 1'-biphenyl)-2-yl)methyl)piperazin-1-yl)benzoyl)-4-(((1R)-3-(dimethyl amino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-I-en-1-yl)methyl)piperazin-1-yl)benzoyl)-4-(((1R)-3-(morpholin-4-yl)-I-((phenylsulfanyl)methyl)propyl)amino)-3-((trifluoromethyl)sulfonyl)benzenesulfonamide (ABT-263), N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitro benzenesulfonamide) (ABT-737), ABT-199, GX-070 (obatoclax) and the like.

Examples of suitable Bcr-Abl kinase inhibitors include DASATINIB® (BMS-354825), GLEEVEC® (imatinib) and the like.

Examples of suitable CDK inhibitors include AZD-5438, BMI-I040, BMS-032, BMS-387, CVT-2584, flavopyridol, GPC-286199, MCS-5A, PD0332991, PHA-690509, seliciclib (CYC-202, R-roscovitine), ZK-304709 and the like.

Examples of suitable COX-2 inhibitors include ARCOXIA® (etoricoxib), BEXTRA® (valdecoxib), BMS347070, CELEBREX™ (celecoxib), COX-189 (lumiracoxib), CT-3, DERAMAXX® (deracoxib), 1TE-522, 4-methyl-2-(3,4-dimethylphenyl)-I-(4sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

Examples of suitable EGFR inhibitors include ABX-EGF, anti-EGFr immunoliposomes, EGF-vaccine, EMD-7200, ERBITUX® (cetuximab), HR3, 19A antibodies, IRESSA® (gefitinib), TARCEVA® (erlotinib or OS1-774), TP-38, EGFR fusion protein, TYKERB® (lapatinib) and the like.

Examples of suitable ErbB2 receptor inhibitors include CP-724-714, C1-I033 (canertinib), Herceptin® (trastuzumab), TYKERB® (lapatinib), OMNITARG® (2C4, petuzumab), TAK-165, GW-572016 (ionafamib), GW-282974, EKB-569, P1-166, dHER2 (HER2 vaccine), APC-8024 (HER-2 vaccine), anti-HERl2neu bispecific antibody, B7.her21gG3, AS HER2 trifunctional bispecfic antibodies, mAB AR-209, mAB 2B-1 and the like.

Examples of suitable histone deacetylase inhibitors include depsipeptide, LAQ-824, MS-275, trapoxin, suberoylanilide hydroxamic acid (SAHA), TSA, valproic acid and the like.

Examples of suitable HSP-90 inhibitors include 17-AAG-nab, 17-AAG, CNF-I0l, CNF-I0I0, CNF-2024, 17-DMAG, geldanamycin, 1P1-504, KOS-953, MYCOGRAB®, NCS-683664, PU24FCl, PU3, radicicol, SNX-2112, STA-9090 VER49009 and the like.

Examples of suitable MEK inhibitors include ARRY-142886, ARRY-438162 PD-325901, PD-98059 and the like.

Examples of suitable activators of death receptor pathway include TRAIL, antibodies or other agents that target death receptors (e.g., DR4 and DR5) such as Apomab, conatumumab, ETR2-ST01, GDC0145, lexatumumab, HGS-1029, LBY-135, PRO-1762 and trastuzumab.

Examples of suitable mTOR inhibitors include AP-23573, CC1-779, everolimus, RAD-OO1, rapamycin, temsirolimus and the like.

Examples of suitable non-steroidal anti-inflammatory drugs include AMIGESIC® (salsalate), DOLOB1D® (diflunisal), MOTRIN® (ibuprofen), ORUD1S® (ketoprofen), RELAFEN® (nabumetone), FELDENE® (piroxicam) ibuprofin cream, ALEVE® and NAPROSYN® (naproxen), VOLTAREN® (diclofenac), 1NDOCIN® (indomethacin), CLINORIL® (sulindac), TOLECTIN® (tolmetm), LODINE® (etodolac), TORADOL® (ketorolac), DAYPRO® (oxaprozin) and the like.

Examples of suitable platinum chemotherapeutics include cisplatin, ELOXATIN® (oxaliplatin) eptaplatin, lobaplatin, nedaplatin, PARAPLATIN® (carboplatin), satrap latin and the like.

Examples of suitable polo-like kinase inhibitors include B1-2536 and the like.

Examples of suitable thrombospondin analogs include TSP-1 and the like.

Examples of suitable VEGFR inhibitors include AVASTIN® (bevacizumab), AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), vatalanib (PTK-787, ZK-222584), SUTENT® (sunitinib, SU-11248), VEGF trap, vatalanib, ZACTIMA (vandetanib, ZD-6474) and the like.

Examples of suitable antibiotics include intercalating antibiotics aclarubicin, actinomycin D, amrubicin, annamycin, adriamycin, BLENOXANE® (bleomycin), daunorubicin, CAEL YX® or MYOCET® (doxorubicin), elsamitrucin, epirbucin, glarbuicin, ZA VEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Examples of suitable topoisomerase inhibitors include aclarubicin, 9-aminocamptothecin, amonafide, BN-80915, CAMPTOSAR® (irinotecan hydrochloride). amptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Examples of suitable antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, P ANOREX® (edrecolomab), RENCAREX® (WX G250), RITUXAN® (rituximab), ticilimumab, trastuzimab and and the like.

Examples of suitable hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant),FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Examples of suitable deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Examples of suitable plant alkaloids include, but are not limited to, vincristine, vinblastine, vindesine, vinorelbine and the like.

Examples of suitable PARP inhibitors include olaparib, KU-59436, ABT-888, AZD-2281, AG-014699, BSI-201, BGP-15, INO-IOOI, ONO-2231 and the like.

Examples of suitable proteasome inhibitors include VELCADE® (bortezomib), MG132, NPI-0052, PR-171 and the like.

Examples of suitable immunologicals include interferons and other immune-enhancing agents. Interferons include interferon alpha, interferon alpha-2a, interferon alpha-2b, interferon beta,interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanomavaccine, mitumomab, molgramostim, MYLOTARG™® (gemtuzumab ozogamicin). NEUPOGEN® (filgrastlm), OncoVAC-CL, OvaRex® (oregovomab), pemtumomab(Y-muHMFGl), PROVENGE®, sargaramostim, sizofilan, teceleukin, TheraCys®, ubenimex,VIRULIZIN®, Z-1OO, WF-1O, PROLEUKIN® (aldesleukin), ZADAXIN® (thymalfasin),ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Examples of suitable purine analogs include LANVIS® (thioguanine) and PURI-NETHOL® (mercaptopurine).

Examples of suitable antimitotic agents include batabulin, epothilone D (KOS-862), N-(2-((4- hydroxyphenyl)amino) pyridin-3-yl)-4-methoxybenzenesulfonamide, ixabepilone (BMS 247550), paclitaxel, TAXOTERE® (docetaxel), PNUI00940 (109881), patupilone, XRP-9881(larotaxel), vinflunine, ZK-EPO and the like.

Compounds of the present invention can also be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having either Formula I or Formula II may be combined with other chemotherapeutic agents such as ABRAXANE™ (ABI-007), ADVEXIN®, ALTOCOR® or MEVACOR® (lovastatin), AMPLIGEN® (polyl:poly CI2U, a synthetic RNA), APTOSYN™ (exisulind), AREDIA® (pamidronic acid),arglabin, L-asparaginase, atamestane (1-methyl-3, 17-dione-androsta-1,4-diene), A V AGE® (tazarotne), A VE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C:CYTOXAN® (cyclophosphamide); H: ADRIAMYCIN® (hydroxydoxorubicin); Vincristine (ONCOVIN®); P: prednisone), CyPat™, combrestatin A4P, DAB(389)EGF or TransMID-I07R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f(exatecan mesylate), enzastaurin, EP0906, GARDASIL® (quadrivalent human papillomavirus (Types 6, 11, 16, 18) recombinantvaccine), gastrimmune, genasense, GMK (ganglioside conjugate vaccine), GVAX® (prostate cancer vaccine), halofuginone, histerelin, hydroxycarbamide, ibandronic acid, IGN-101, IL-3-PE38, IL-13-PE38QQR (cintredekin besudotox), IL-13-pseudomonas exotoxin, interferon-a, interferon-y, JUNOVAN™ or MEPACT™ (mifamurtide), lonafarnib, 5,10-25 methylenetetrahydrofolate, miltefosine (hexadecylphosphocholine), NEOVASTAT® (AE-941), NEUTREXIN® (trimetrexate glucuronate), NIPENT® (pentostatin), ONCONASE® (aribonuclease enzyme), ONCOPHAGE® (melanoma vaccine treatment), OncoVAX (IL-2Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEGInterferon A, phenoxodiol, procarbazine, rebimastat, REMOVAB® (catumaxomab),REVLIMID® (lenalidomide), RSR13 (efaproxiral), SOMATULINE® LA (lanreotide), SORIATANE® (acitretin), staurosporine (Streptomyces staurospores), talabostat (PTI00), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio) quinazoline dihydrochloride), TNFerade™ (adenovector: DNA carrier containing the gene for tumornecrosis factor-a), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alpha vbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

The combination therapy can be administered as a simultaneous or sequential regimen. When administered sequentially, the combination can be administered in two or more administrations. The combined administration includes co-administration, using separate formulations or a single pharmaceutical formulation, and consecutive administration in either order, wherein preferably there is a time period while both (or all) active agents simultaneously exert their biological activities.

The above other therapeutic agents, when employed in combination with the compounds of the present invention may be used, for example, in those amounts indicated in the *Physicians' Desk Reference*, as in the patents set out above, or can be lowered due to the combined action (synergy) of the newly identified agent and other chemotherapeutic agents or treatments as determined by one of ordinary skill in the art.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

The compounds of Formula I and II can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating cancers and related diseases, a pharmaceutical composition will be employed containing the compounds of Formula I and/or II, with or without other anticancer agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of Formula I and/or II (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of Formula I and/or IA into a vial, aseptically freeze-drying and sealing. For use, the contents of the vial are mixed with 2 mL of physiological saline, to produce an injectable preparation.

In some embodiments, the present invention provides the following examples:

E1. A compound of formula I or II:

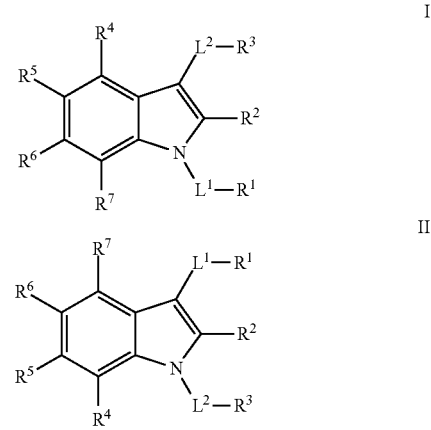

or a pharmaceutically acceptable salt thereof, wherein:

$L^1$ is an optionally substituted bivalent $C_{1-6}$ hydrocarbon chain wherein one or more methylene units are optionally replaced with -Cy-;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^1$ is —OR, —SR, —S(O)R, —S(O)$_2$R, —S(O)$_2$N(R)$_2$, —N(R)$_2$, —C(O)N(R)$_2$, —C(O)R, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

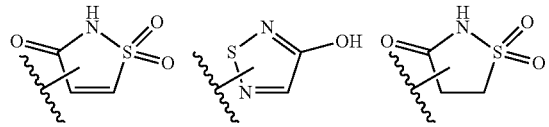

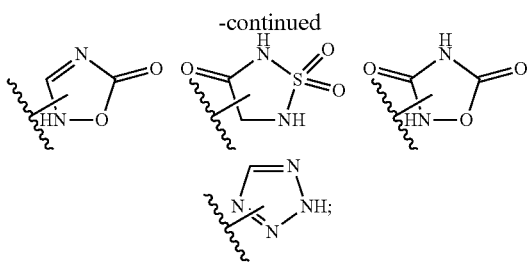

$R^x$ is selected from —C(O)OR, —NRS(O)$_2$CF$_3$, —NRC(O)R, —NRC(O)OR, —NRC(O)N(R)$_2$, or —NRS(O)$_2$R;

$R^y$ is selected from —NRC(O)CF$_3$, —NRC(O)R, or —NRC(O)N(R)$_2$;

$R^2$ is selected from R, halo, —NH$_2$, —CN, —NO$_2$, and —CF$_3$;

each R is independently selected from hydrogen or an optionally substituted group selected from C$_{1-6}$ aliphatic or a ring selected from a 3-8 membered saturated or partially unsaturated carbocyclic ring, phenyl, a 8-10 membered bicyclic aryl ring, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur;

$L^2$ is an optionally substituted bivalent C$_{3-6}$ hydrocarbon chain wherein one or two methylene units of $L^2$ are optionally and independently replaced with —O—, —S—, or —NR'—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted C$_{1-4}$ alkyl;

$R^3$ is an optionally substituted ring selected from a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, or an 8-10 membered bicyclic heteroaromatic ring having 1-5 heteroatoms independently selected from nitrogen, oxygen, and sulfur;

each of $R^4$, $R^5$, and $R^6$ is independently selected from R, halo, —CN, —NO$_2$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R';

$R^7$ is hydrogen, halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur; and optionally one of $R^4$ and $R^5$, $R^5$ and $R^6$, $R^6$ and $R^7$, $R^7$ and $L^1$, or $R^2$ and $L^1$ is taken together with their intervening atoms to form an optionally substituted ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur.

E2. The compound of example E1, wherein the compound is a compound of formula I or a pharmaceutically acceptable salt thereof.

E3. The compound of example E1, wherein the compound is a compound of formula II or a pharmaceutically acceptable salt thereof.

E4. The compound of any one of the preceding examples, wherein the compound is other than a compound of Table 2 or a pharmaceutically acceptable salt thereof.

E5. The compound of any one of the preceding examples, wherein each R is independently selected from hydrogen or an optionally substituted group selected from C$_{1-6}$ aliphatic or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

E6. The compound of any one of the preceding examples, wherein $L^1$ is an optionally substituted bivalent C$_{1-6}$ hydrocarbon chain.

E7. The compound of any one of examples E1-E5, wherein $L^1$ is an optionally substituted bivalent C$_{1-6}$ hydrocarbon chain, wherein one or more methylene units are replaced with -Cy-.

E8. The compound of any one of examples E1-E5 and E7, wherein $L^1$ is an optionally substituted bivalent C$_{1-6}$ hydrocarbon chain, wherein one or more methylene units are replaced with -Cy-, wherein -Cy- is an optionally substituted bivalent ring independently selected from phenylene or 5-6 membered heteroarylene having 1-4 heteroatoms independently selected from nitrogen, oxygen, or sulfur.

E9. The compound of any one of examples E1-E5 and E7-E8, wherein $L^1$ is an optionally substituted bivalent C$_{1-6}$ hydrocarbon chain, wherein one methylene unit is replaced with -Cy-, wherein -Cy- is optionally substituted phenylene.

E10. The compound of any one of examples E1-E5 and E7-E9, wherein $L^1$ is an optionally substituted bivalent C$_{1-6}$ hydrocarbon chain, wherein one methylene unit is replaced with -Cy-, wherein -Cy- is 1,3-phenylene or 1,4-phenylene.

E11. The compound of any one of examples E1-E5 and E7, wherein $L^1$ is an optionally substituted bivalent C$_{1-6}$ hydrocarbon chain, wherein one methylene unit is replaced with -Cy-, wherein -Cy- is optionally substituted 5- membered heteroarylene having 1-4 heteroatoms independently selected from nitrogen, oxygen, or sulfur.

E12. The compound of any one of examples E1-E5, E7 and E11, wherein $L^1$ is an optionally substituted bivalent $C_{1-6}$ hydrocarbon chain, wherein one methylene unit is replaced with -Cy-, wherein -Cy- is

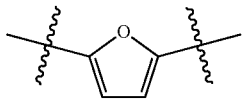

E13. The compound of any one of examples E1-E5 and E7, wherein $L^1$ is an optionally substituted bivalent $C_{1-6}$ hydrocarbon chain, wherein one methylene unit is replaced with -Cy-, wherein -Cy- is optionally substituted 6- membered heteroarylene having 1-4 heteroatoms independently selected from nitrogen, oxygen, or sulfur.

E14. The compound of any one of examples E1-E5, E7 and E13, wherein $L^1$ is an optionally substituted bivalent $C_{1-6}$ hydrocarbon chain, wherein one methylene unit is replaced with -Cy-, wherein -Cy- is N

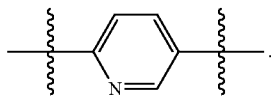 [SMILES: *c1ccc(*)nc1]

E15. The compound of any one of the preceding examples, wherein $L^1$ is unsubstituted.

E16. The compound of any one of the preceding examples, wherein $L^2$ is an optionally substituted bivalent $C_{3-6}$ hydrocarbon chain wherein one or two methylene units of $L^2$ are optionally and independently replaced with —O—, —S—, or —NR'—.

E17. The compound of any one of the preceding examples, wherein $L^2$ is an optionally substituted bivalent $C_{3-6}$ hydrocarbon chain wherein one or two methylene units of $L^2$ are optionally and independently replaced with —O—, —S—, or —NR'—, wherein one of —O—, —S—, or —NR'— of $L^2$ is directly bonded to $R^3$.

E18. The compound of any one of the preceding examples, wherein $L^2$ is an optionally substituted bivalent $C_{3-6}$ hydrocarbon chain wherein one or two methylene units of $L^2$ are independently replaced with —O—.

E19. The compound of any one of the preceding examples, wherein $L^2$ is unsubstituted.

E20. The compound of any one of the preceding examples, wherein $L^2$ is —(CH$_2$)$_3$—O—.

E21. The compound of any one of the preceding examples, wherein each of $L^1$ and $L^2$ is unsubstituted.

E22. The compound of any one of the preceding examples, wherein $R^7$ is selected from R, halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R.

E23. The compound of any one of examples E1-E21, wherein $R^7$ is halo, —CN, —NO$_2$, —C(O)OR, —OCF$_3$, —OR, —SR, —S(O)$_2$OR, —P(O)(OH)$_2$, —C(O)N(R)$_2$, —N(R)$_2$, —S(O)$_2$N(R)$_2$, —NRS(O)$_2$CF$_3$, —C(O)NRS(O)$_2$R, —S(O)$_2$NRC(O)OR, —S(O)$_2$NRC(O)N(R)$_2$, —C(O)R, —C(O)NRS(O)$_2$CF$_3$, —NRC(O)R, —OC(O)R, —OC(O)N(R)$_2$, —C(NR)N(R)$_2$, —NRC(NR)N(R)$_2$, —S(O)R, —S(O)$_2$R, —NRC(O)OR, or —NRS(O)$_2$R, or an optionally substituted group selected from $C_{1-6}$ alkyl, $C_{1-6}$ alkynyl or a ring selected from a 3-8 membered saturated or partially unsaturated carbocyclic ring, phenyl, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, an 8-14 membered bicyclic or polycyclic saturated, partially unsaturated or aryl ring, a 7-14 membered bicyclic or polycyclic saturated or partially unsaturated heterocyclic ring having 1-5 heteroatoms independently selected from nitrogen, oxygen, or sulfur, or an 8-14 membered bicyclic or polycyclic heteroaryl ring having 1-5 heteroatoms independently selected from nitrogen, oxygen, or sulfur.

E24. The compound of any one of the preceding examples, wherein $R^7$ is an optionally substituted 5-6 membered heteroaryl ring having 1-4 heteroatoms independently selected from nitrogen, oxygen, or sulfur.

E25. The compound of any one of the preceding examples, wherein $R^7$ is an optionally substituted 5-membered heteroaryl ring having 1-4 heteroatoms independently selected from nitrogen, oxygen, or sulfur.

E26. The compound of any one of the preceding examples, wherein $R^7$ is optionally substituted

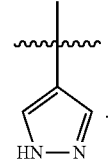

E27. The compound of any one of examples E1-E25, wherein $R^7$ is optionally substituted

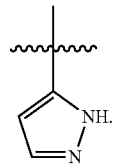

E28. The compound of any one of examples E1-E25, wherein R' is optionally substituted

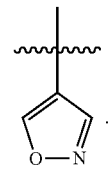

E29. The compound of any one of examples E1-E24, wherein $R^7$ is an optionally substituted 6-membered heteroaryl ring having 1-4 heteroatoms independently selected from nitrogen, oxygen, or sulfur.

E30. The compound of any one of examples E1-E24 and E29, wherein $R^7$ is optionally substituted pyridinyl.

E31. The compound of any one of the preceding examples, wherein $R^2$ does not comprise —C(O)—.

E32. The compound of any one of the preceding examples, wherein $R^2$ is hydrogen.

E33. The compound of any one of examples E1-E31, wherein $R^2$ is optionally substituted $C_{1-6}$ aliphatic.

E34. The compound of any one of examples E1-E31 and E33, wherein $R^2$ is unsubstituted $C_{1-6}$ aliphatic.

E35. The compound of any one of examples E1-E31 and E33-E34, wherein $R^2$ is methyl.

E36. The compound of any one of examples E1-E31 and E33, wherein $R^2$ is $C_{1-6}$ aliphatic optionally substituted with halogen.

E37. The compound of any one of examples E1-E31, E33 and E36, wherein $R^2$ is $C_{1-6}$ aliphatic substituted with halogen.

E38. The compound of any one of examples E1-E31, E33 and E36-E37, wherein $R^2$ is $C_{1-6}$ aliphatic substituted with —F.

E39. The compound of any one of examples E1-E31, E33 and E36-E38, wherein $R^2$ is —$CF_3$.

E40. The compound of any one of the preceding examples, wherein $R^1$ is —C(O)$R^x$, —S(O)$_2$OH, or —S(O)$_2$R, or is selected from:

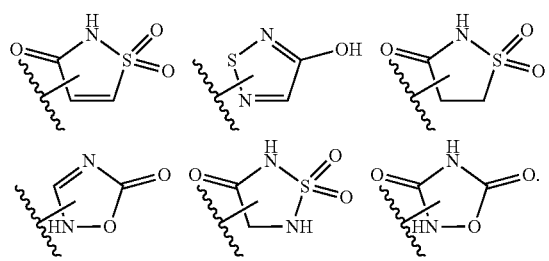

E41. The compound of any one of examples E1-E39, wherein $R^1$ is —C(O)OH.

E42. The compound of any one of examples E1-E39, wherein $R^1$ is —OR, —SR, —S(O)R, —S(O)$_2$R, —S(O)$_2$N(R)$_2$, —N(R)$_2$, —C(O)N(R)$_2$, —C(O)R, —NRC(O)R, —NRC(O)OR, —NRC(O)N(R)$_2$, —NRS(O)$_2$R, —NRS(O)$_2$N(R)$_2$, —C(O)$R^x$, —S(O)$_2$OH, or —S(O)$_2$$R^y$, or is selected from:

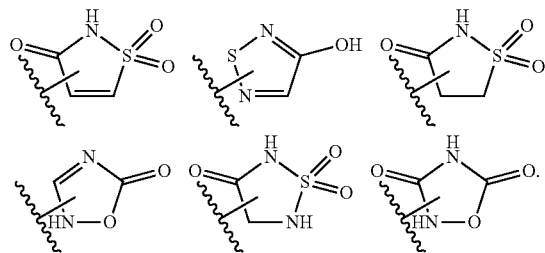

E43. The compound of any one of examples E1-E39, wherein $R^1$ is —OR, —SR, —S(O)R, —S(O)$_2$R, —S(O)$_2$N(R)$_2$, —C(O)N(R)$_2$, —C(O)R, —NRS(O)$_2$N(R)$_2$, —C(O)$R^x$, —S(O)$_2$OH, or —S(O)$_2$$R^y$, or is selected from:

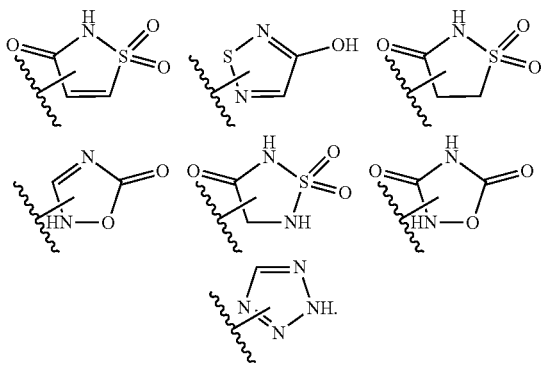

E44. The compound of any one of examples E1-E39, wherein $R^1$ is —C(O)NHS(O)$_2$R, wherein R is optionally substituted $C_{1-6}$ aliphatic or phenyl.

E45. The compound of any one of the preceding examples, wherein -$L^2$-$R^3$ is —(CH$_2$)$_3$—O—$R^3$.

E46. The compound of any one of the preceding examples, wherein the compound is selected from Table 1, or a pharmaceutically acceptable salt thereof.

E47. A pharmaceutical composition comprised of a therapeutically effective amount of a compound of any one of the preceding examples, and, optionally, a pharmaceutically acceptable carrier.

E48. The pharmaceutical composition of example E47 further comprising one or more other therapeutically active agents.

E49. A method of modulating the activity of the Bcl-2 family of proteins comprising administering to a mammalian patient in need thereof a therapeutically effective amount of at least one compound of any one of examples E1-E46, and, optionally, an additional therapeutic agent.

E50. A method for treating diseases or disorders associated with the expression or over-expression of Mcl-1, comprising administering to a subject in need thereof, a therapeutically effective amount of a compound of any one of examples E1-E46, wherein:

the diseases or disorders are selected from the group consisting of acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor, embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

E51. A method for preventing, inhibiting, or treating the progression or onset of diseases or disorders associated with the expression or over-expression of anti-apoptotic Bcl-2 family protein members, particularly Mcl-1 protein, comprising administering to a mammalian patient in need of prevention, inhibition, or treatment a therapeutically effective amount of at least one compound of any one of examples E1-E46, and, optionally, an additional therapeutic agent wherein:

(a) the diseases or disorders are selected from the group consisting of acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeloegeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor, embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer; and (b) the additional therapeutic agent is selected from the group of anti-cancer agents consisting of alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (lAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Exemplary methods include, but are not limited to, those described below.

The novel compounds of the invention may be prepared using the reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of the invention falling into a given class may be compatible with some of the reaction conditions required in some of the methods described. Such restrictions to the substituents, which are compatible with the reaction conditions, will be readily apparent to one skilled in the art and alternate methods must be used.

Scheme 1

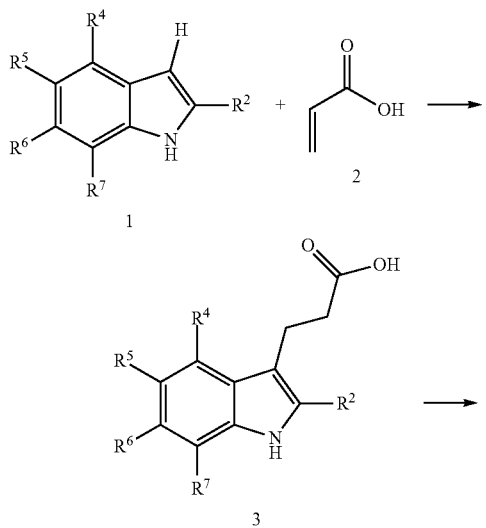

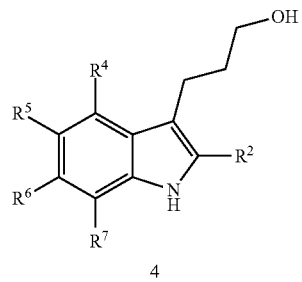

Compounds of Formula 4 may be prepared by procedures depicted in Scheme 1. Indoles of Formula 1 can be reacted with acrylic acid (Formula 2). The conjugated addition may be accomplished under acidic condition, for example, using acetic anhydride in a suitable solvent such as acetic acid, DMF, THF, DME, CH$_3$CN, 1,4-dioxane, water or the like, to afford compounds of Formula 3. Compounds of Formula 4 can be produced by reduction of compounds 3 with BH$_3$ or LiAlH$_4$ at a number of conditions that are routine for those skilled in the art of organic synthesis.

Scheme 2

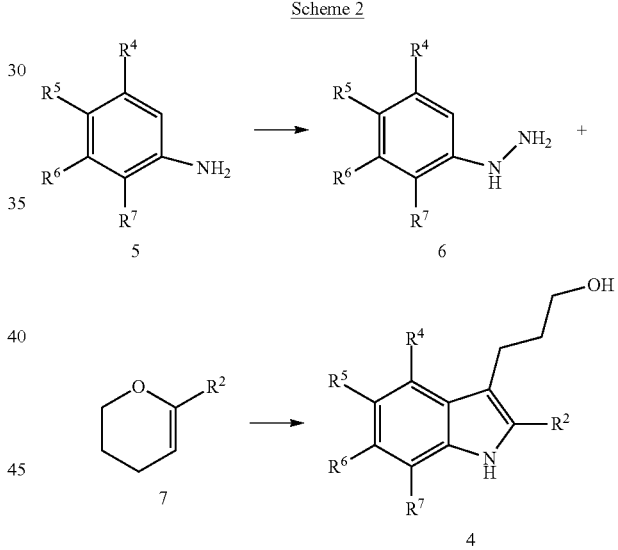

Alternatively, compounds of Formula 4 may be prepared as shown in Scheme 2. Preparation of an aryl hydrazine 6 can be accomplished, for example, by treatment of a corresponding substituted aniline 5 with NaNO$_2$ followed by reduction of the N-nitroso intermediate with SnCl$_2$ in conc. HCl. Assembly of the core indole intermediate 4 is accomplished by Fischer indole cyclization of the aryl hydrazine 6 and a suitably substituted 3,4-dihydro-2H-pyran 7 by methods described by, but not limited to, R. J. Sundberg, "Indoles, Best Synthetic Methods" (1996), Academic Press, San Diego, Calif. For example, treatment of the aryl hydrazine 6 as the free base or the corresponding mineral acid salt with the 3,4-dihydro-2H-pyran 7 (R$^2$=H, Me, Et, etc) in an alcoholic solvent, DMF, DMAc, THF, DME, 1,4-dioxane, water, or the like, in the presence of mineral acid affords the indoles 4.

Scheme 3

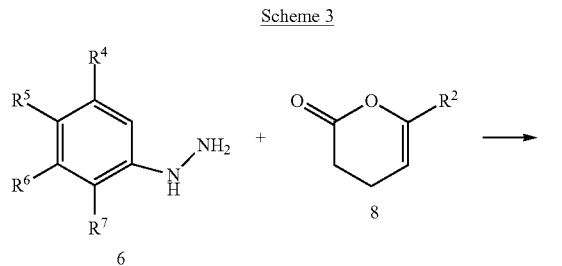

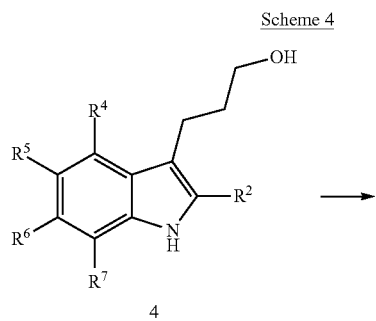

Scheme 3 illustrates another method for constructing the indole intermediate 3. Fischer indole cyclization of the aryl hydrazine 6 and a substituted 3,4-dihydro-2H-pyran-2-one 8 by methods described by Scheme 3 affords the indoles 3. They can be used for subsequent reduction to produce compounds of formula 4 as described in Scheme 1.

Scheme 4

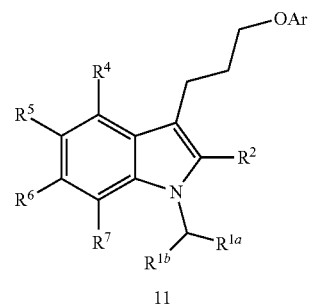

Compounds of Formula 11 of this invention may be prepared as shown in Scheme 4. The OH containing indole 4 can be condensed with substituted phenols or hydroxy-heterocycles via Mitsunobu reaction to give indole ethers 9 using, but not limited to, DEAD, Di-PrAD or Dt-BuAD. Compounds of Formular 9 can be reacted with compounds of formular 10, wherein X is defined as Cl, Br, I, OMs, or OTs with a base such as NaH, $K_2CO_3$, $Cs_2CO_3$, $Et_3N$, or DIPEA in a suitable solvent such as DMF, THF, ether, DME, or the like, to give compounds of Formula 11.

Scheme 5

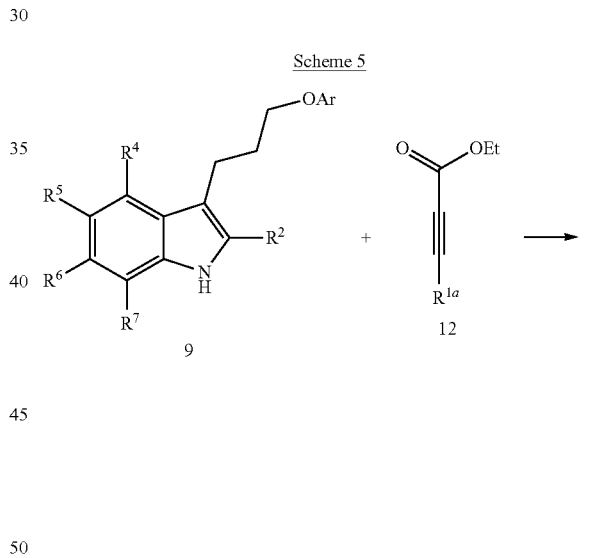

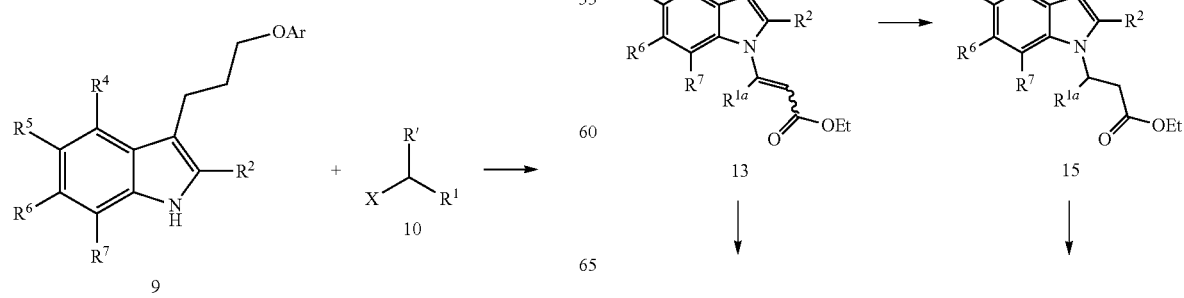

149

-continued

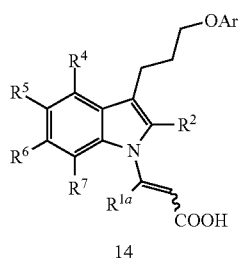

14

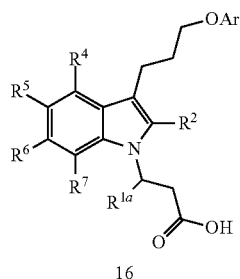

16

Scheme 5 depicts utility of the indole intermediate 9 in conjugated addition reactions. Compounds 9 can be reacted with substituted ethyl propiolates of Formula 12 with TBAF or a base such as NaHMDS or LiHMDS in a suitable solvent such as THF, ether, DME, or the like, to give compounds of Formula 13. Compounds of Formula 14 can be produced by saphonification of compounds 13 with appropriate bases, such as $Cs_2CO_3$, $K_2CO_3$, LiOH or NaOH, at a number of conditions that are routine for those skilled in the art of organic synthesis to give the carboxylic acids 14. The intermediates 13 can also be hydrogenated to produce compounds of Formula 15 using Pd, or Pt as a catalyst. Applying same saponification protocol as described above, compounds of Formular 16 can be generated.

150

Compounds of Formula 21 containing Ar substituents as $R^7$ group may be synthesized by procedures illustrated in Scheme 6. Compounds of Formula 17, wherein X=Cl, Br or I, can be prepared as previously described in Scheme 1-4, and NH of 17 can be substituted as described in Scheme 4. Boronic acids or borates 20, which are commercially available or can be prepared, can be coupled with intermediates 18 via Suzuki coupling protocol to give compounds of formula 21. For a review and leading references of palladium catalyzed cross coupling reactions (Miyaura, N., Suzuki, A., *Chem. Rev.* (1995), 2457). One such procedure entails treatment of the aryl bromide or iodide 18 with a aryl boronic acids in the presence of a catalytic Pd(O) species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd(O) catalyst, and a base such as $Na_2CO_3$, $K_2CO_3$, $Ba(OH)_2$ or $Et_3N$. Alternatively, the reaction sequence can be reversed by conducting Suzuki coupling to produce intermediate 19 followed by NH alkylation as shown above.

Scheme 7

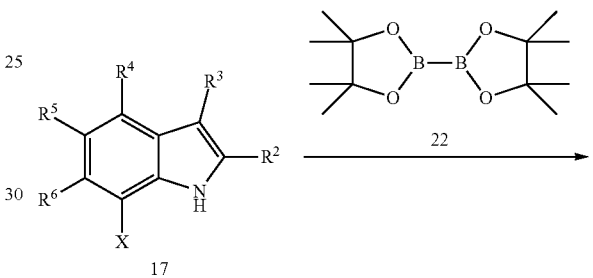

Scheme 6

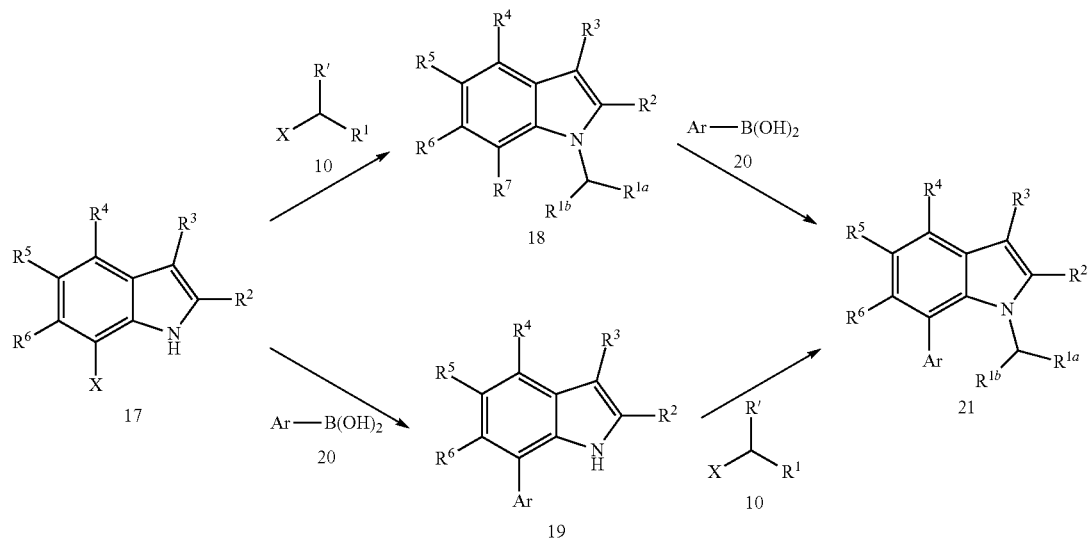

151
-continued

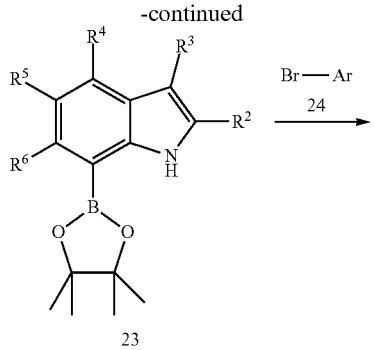
23

Scheme 9

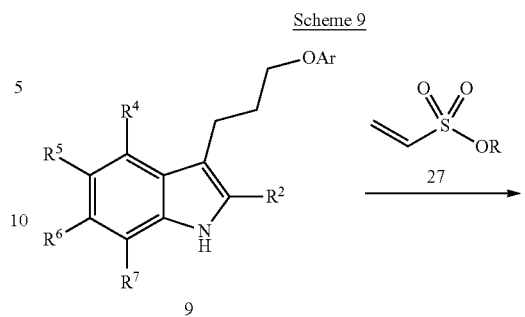
9

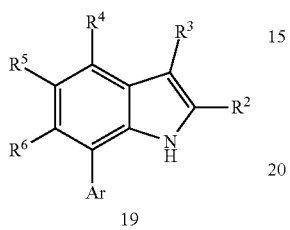
19

Additional methods of preparing intermediates 19 containing Ar substituents as $R^7$ group are shown in Scheme 7 and proceeds from bromo- or iodo- derivatives 17. Treatment of compounds 17 with bis(pinacolato)diboron 22 in the presence of a catalytic Pd(O) species, such as Pd(dppf)Cl$_2$, Pd(PPh$_3$)$_4$, Pd(PPh$_3$)$_2$Cl$_2$, Pd(OAc)$_2$, or Pd$_2$(dba)$_3$, and a base such as potassium acetate or sodium acetate in a suitable solvent such as DMF, THF, ether, DME, or the like, to give compounds of Formula 23. Aryl-Br or Heteroaryl-Br can be coupled to the borates 23 via Suzuki coupling protocol described above.

Scheme 8

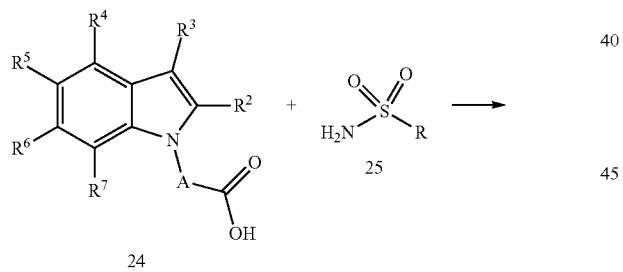
24

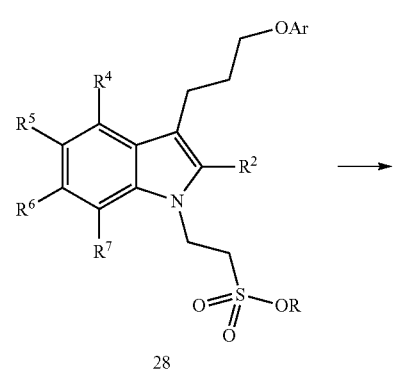
28

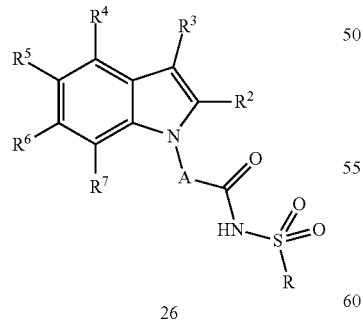
26

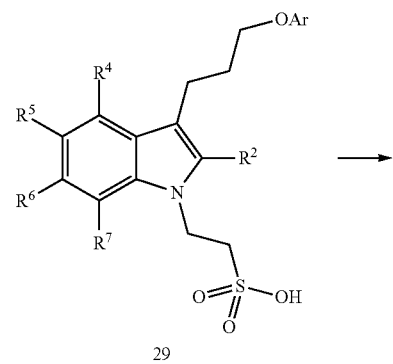
29

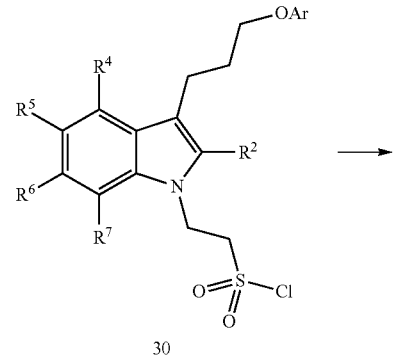
30

Compounds of Formula 24 can be produced by coupling of compounds 24 with suitable sulfonamides using coupling reagents, but not limited to, PyBOP, DCC, EDC, HBTU, or TBTU at a number of conditions that are routine for those skilled in the art of organic synthesis.

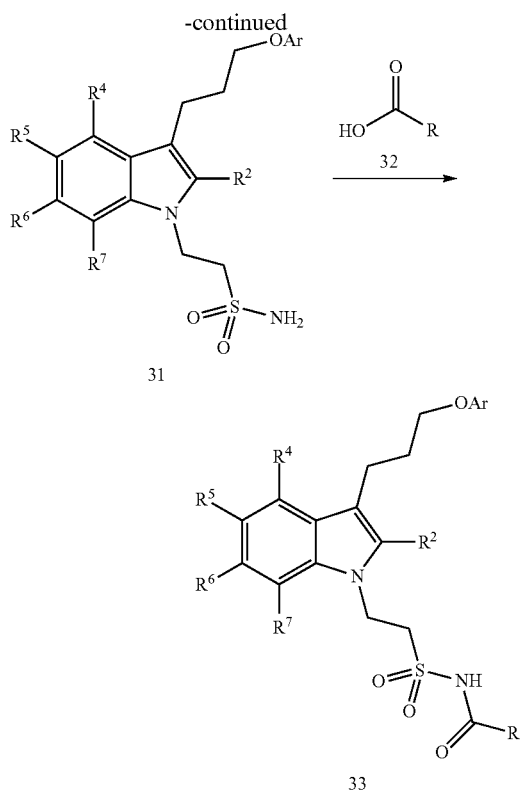

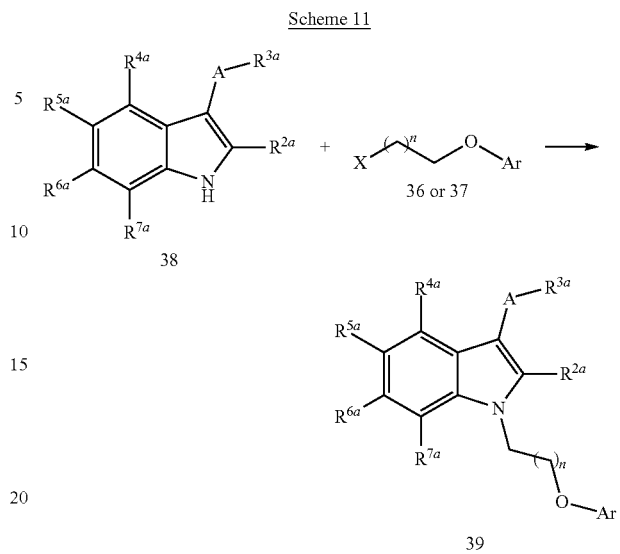

Compounds of Formula 39 may be prepared by procedures outlined in Scheme 11. Suitably substituted indoles of Formular 38 can be reacted with compounds of formular 36 or 37, wherein X is defined as Br or I with a base such as NaH, $K_2CO_3$, $Cs_2CO_3$, $Et_3N$, or DIPEA in a suitable solvent such as DMF, THF, ether, DME, or the like, to give compounds of Formula 39.

The following abbreviations are employed:
DEAD=diethyl azodicarboxylate
Di-PrAD=di-i-propyl azodicarboxylate
Dt-BuAD=di-tert-butyl azodicarboxylate
DBU=1,8-Diazabicycloundec-7-ene
DMF=dimethylformamide
DMAc=dimethylacetamide
DMSO=dimethylsulfoxide
THF=tetrahydrofuran
$K_2CO_3$=potassiumm carbonate
$Cs_2CO_3$=cesium carbonate
DME=1,2-dimethoxyethane
t-BuONa=sodium tert-butoxide
$LiAlH_4$=lithium aluminum hydride
$SOCl_2$=thionyl chloride
$POCl_3$=phosphoryl chloride
$PCl_5$=phosphorus pentachloride
LDA=lithium di-isopropylamide
NaHMDS=sodium hexamethyldisilazide
LiHMDS=lithium hexamethyldisilazide
n-BuLi=n-butyl lithium
ether=diethyl ether
NaOH=sodium hydroxide
KOH=potassium hydroxide
EtOAc=ethyl acetate
$Na_2CO_3$=sodium carbonate
$Na_2SO_4$=sodium sulfate
$MgSO_4$=magnesium sulfate
$SiO_2$=silicon dioxide
$CH_2Cl_2$=methylene chloride
MeOH=methanol
EtOH=ethanol
Hex=hexanes
HCl=hydrochloric acid
$Pd(PPh_3)_4$=tetrakis(triphenylphosphine)palladium(0)

Acylsulfonamide derivatives of Formula 33 of may be prepared as shown in Scheme 9. Indole ethers 5 can be reacted with alkyl or aryl ethenesulfonates 27 to give conjugated adducts 28 using TBAF or a base such as NaHMDS or LiHMDS in a suitable solvent such as DMF, THF, ether, DME, or the like. Compounds of Formula 28 can be hydrolyzed to produce sulfonic acids 29 with appropriate bases, such as $Cs_2CO_3$, $K_2CO_3$, LiOH or NaOH, at a number of conditions that are routine for those skilled in the art of organic synthesis. Compounds of Formula 30 can be prepared by treating sulfonic acids 29 with $POCl_3$, $PCl_5$, $SOCl_2$, oxalyl chloride, or the like. Sulfonyl chlorides 30 can be converted to sulfonamides 31 by treating with $NH_3$ in alcoholic solvent such as MeOH. Suitable carboxylic acid 32 may be coupled to sulfonamide 31 as described in Scheme 8 to give acylsulsonamides 33.

Scheme 10

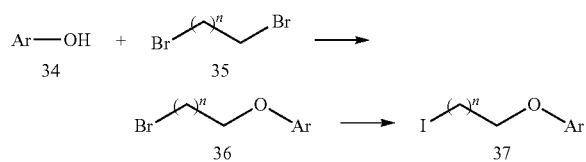

Reagents of Formula 36 and 37 can be prepared by methods illustrated in Scheme 10. Phenol derivatives of Formula 34 can be alkylated with dibromoalkane 35 using an inorganic base such as NaOH or KOH in water to produce compounds of Formula 36. The reactivity of reagents of Formula 36 can be improved further by generating Iodo containing reagents 37 via Finkelstine protocol with NaI or KI in acetone as a solvent.

Pd(dppf)Cl$_2$=[1,1'-bis(diphenylphosphino)ferrocene]dichloropalladium (II)
Pd$_2$(dba)$_3$=tris(dibenzylideneacetone)dipalladium (0)
TFA=trifluoroacetic acid
Fu Catalyst=Bis(tri-tert-butylphosphine)palladium(0)
Et$_3$N=triethylamine
DIPEA=N,N-diisopropylethylamine
SnCl$_2$=tin(II) chloride
min=minute(s)
h or hr=hour(s)
mL or ml=milliliter
g=gram(s)
mg=milligram(s)
mmol=millimole(s)
LRMS=low resolution mass spectrometry
NMR=nuclear magnetic resonance

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

Example 1

Preparation of 2-(1-(3-(naphthalen-1-yloxy)propyl)-1H-indol-3-yl)acetic acid

Step A. Preparation of methyl 2-(1-(3-(naphthalen-1-yloxy)propyl)-1H-indol-3-yl)acetate: To a solution of methyl 2-(1H-indol-3-yl)acetate (95 mg, 0.5 mmol) and 1-(3-bromopropoxy)naphthalene (265 mg, 1.0 mmol) in DMF (3.0 mL) was added Cs$_2$CO$_3$ (489 mg, 1.5 mmol). The reaction mixture was heated at 60° C. for 15 h then at 80° C. for 6 h. The reaction was quenched by addition of H$_2$O, extracted with EtOAc, dried over MgSO$_4$, filtered and concentrated in vacuo. The crude product was purified by flash chromatography (Combi-flash Rf, hex/EtOAc 0-40% gradient) to give the title compound which was used for the next step directly. MS (ES) 374.2 (M+H).

Step B: To a solution of methyl 2-(1-(3-(naphthalen-1-yloxy)propyl)-1H-indol-3-yl)acetate in THF (1.0 mL) and MeOH (1.0 mL) was added KOH (140 mg, 2.5 mmol). The reaction mixture was heated at 50° C. for 15 h then quenched by addition of TFA until the solution became acidic. The quenched reaction mixture was concentrated then purified by reverse phase prep. HPLC (Phenomenex Gemini C18, H$_2$O/CH$_3$CN gradient to 95% CH$_3$CN 0.1% TFA) the title compound (46 mg, 0.13 mmol) as a white solid. MS (ES) 360.2 (M+H).

Example 2

Preparation of 2-(1-(3-(naphthalen-2-yloxy)propyl)-1H-indol-3-yl)acetic acid

Step A. Preparation of methyl 2-(1-(3-(naphthalen-2-yloxy)propyl)-1H-indol-3-yl)acetate: Title compound was prepared according to procedures described in Example 1 Step A by using methyl 2-(1H-indol-3-yl)acetate (95 mg, 0.5 mmol) and substituting 1-(3-bromopropoxy)naphthalene with 2-(3-bromopropoxy)naphthalene. MS (ES) 374.2 (M+H).

Step B: Title compound (51 mg, 0.14 mmol) was prepared according to procedures described in Example 1 Step B by using methyl 2-(1-(3-(naphthalen-2-yloxy)propyl)-1H-indol-3-yl)acetate. MS (ES) 360.2 (M+H).

Example 3

Preparation of 2-(1-(3-(4-chloro-3,5-dimethylphenoxy)propyl)-1H-indol-3-yl)acetic acid Step A. Preparation of methyl 2-(1-(3-(4-chloro-3,5-dimethylphenoxy)propyl)-1H-indol-3-yl)acetate: Title compound was prepared according to procedures described in Example 1 Step A by using methyl 2-(1H-indol-3-yl)acetate (95 mg, 0.5 mmol) and substituting 1-(3-bromopropoxy)naphthalene with 5-(3-bromopropoxy)-2-chloro-1,3-dimethylbenzene (278 mg, 1.0 mmol). MS (ES) 386.1 (M+H).

Step B: Title compound (57 mg, 0.15 mmol) was prepared according to procedures described in Example 1 Step B by using methyl 2-(1-(3-(4-chloro-3,5-dimethylphenoxy)propyl)-1H-indol-3-yl)acetate. MS (ES) 372.1 (M+H).

Example 4

Preparation of 2-(1-(3-(4-chloro-3,5-dimethylphenoxy)propyl)-1H-indol-3-yl)-N-(methylsulfonyl)acetamide To a solution of 2-(1-(3-(4-chloro-3,5-dimethylphenoxy)propyl)-1H-indol-3-yl)acetic acid (57 mg, 0.15 mmol) and mathanesulfonamide (17 mg, 0.18 mmol) in CH$_2$Cl$_2$ (1.0 mL) was added PyBOP (94 mg, 0.18) followed by DIPEA (58 mg, 0.45 mmol) at 20° C. The reaction mixture was stirred for 15h at 20° C. then concentrated in vacuo. The residue was purified by reverse phase prep. HPLC (Phenomenex Gemini C18, H$_2$O/CH$_3$CN gradient to 95% CH$_3$CN 0.1% TFA) to give the title compound (42 mg, 0.094 mmol) as a white solid. MS (ES) 449.1.

Example 5

Preparation of 2-(3-(3-(4-chloro-3,5-dimethylphenoxy)propyl)-1H-indol-1-yl)acetic acid Step A. Preparation of 3-(1H-indol-3-yl)propan-1-ol: To a solution of 3-(1H-indol-3-yl)propanoic acid (1.6 g, 8.5 mmol) in THF (15 mL) was added BH$_3$ in THF (1M, 17 mL, 17 mmol) dropwise at 0° C. The reaction mixture was stirred for 20 min at 0° C. then warmed to 20° C. and stirred for 2h. The reaction was quenched by slow addition of MeOH (20 mL). The reaction mixture was stirred for additional 30 min at 20° C. The reaction mixture was concentrated and purified by flash chromatography (Combi-flash Rf, hex/EtOAc 0-40% gradient) to give the title compound (1.34 g, 7.65 mmol) as a light yellow oil. MS (ES) 176.2 (M+H).

Step B. Preparation of 3-(3-(4-chloro-3,5-dimethylphenoxy)propyl)-1H-indole To a solution of 3-(1H-indol-3-yl)propan-1-ol (250 mg, 1.43 mmol), PPh$_3$ (560 mg, 2.14 mmol), and 4-chloro-3,5-dimethylphenol (358 mg, 2.28 mmol) in THF (14 mL) was added Dt-BuAD (493 mg, 2.14 mmol) at 20° C. The reaction mixture was stirred for 2h at 20° C. then concentrated in vacuo. The residue was purified by flash chromatography (Combi-flash Rf, Hexane/EtOAc gradient 0-10%) to give the title compound (340 mg, 1.08 mmol) as a colorless oil. MS (ES) 314.2 (M+H).

Step C: To a solution of 3-(3-(4-chloro-3,5-dimethylphenoxy)propyl)-1H-indole (25 mg, 0.079 mmol) in DMF (0.3 mL) was added NaH (60%, 6 mg, 0.15 mmol) at 0° C. The reaction mixture was stirred for 10 min at 0° C. then methyl bromoacetate (25 µL, 0.25 mmol) was added in one portion. The reaction mixture was warmed to 20° C. and stirred for 2h. The reaction was quenched by addition of MeOH (1.0 mL) followed by 10% aqueous LiOH solution (0.2 mL). The reaction mixture was stirred for additional 30 min at 20° C. The reaction mixture was filtered and directly purified by reverse phase prep. HPLC (Phenomenex Gemini C18, $H_2O$/$CH_3CN$ gradient to 95% $CH_3CN$ 0.1% TFA) the title compound (26 mg, 0.071 mmol) as a white solid. MS (ES) 372.2 (M+H).

Example 6

Preparation of 2-(3-(3-(naphthalen-1-yloxy)propyl)-1H-indol-1-yl)acetic acid

Step A. Preparation of 3-(3-(naphthalen-1-yloxy)propyl)-1H-indole: Title compound was prepared (313 mg, 1.04 mmol) as a white solid according to procedures described in Example 5 Step B by substituting 4-chloro-3,5-dimethylphenol with 1-naphthol (330 mg, 0.28 mmol). MS (ES) 302.2 (M+H).

Step B: Title compound was prepared (24 mg, 0.067 mmol) as a white solid according to procedures described in Example 5 Step C using 3-(3-(naphthalen-1-yloxy)propyl)-1H-indole (25 mg, 0.083 mmol). MS (ES) 360.1 (M+H).

Example 7

Preparation of 2-(6-chloro-3-(3-(4-chloro-3,5-dimethylphenoxy)propyl)-1H-indol-1-yl)acetic acid Step A. Preparation of 3-(6-chloro-1H-indol-3-yl)propanoic acid: To a solution of 6-Cl-indole (1.5 g, 10 mmol) and acrylic acid (2.0 mL) in acetic acid (10 mL) was added acetic anhydride (1.9 mL). The reaction mixture was heated at 90° C. for 5 days. The reaction was monitored by LCMS. The reaction mixture was concentrated in vacuo, and the residue was purified by flash chromatography (Combi-flash Rf, Hex/EtOAc 0-70% gradient) to give the title compound (1.9 g, 8.5 mmol). MS (ES) 224.0 (M+H).

Step B. Preparation of 3-(6-chloro-1H-indol-3-yl)propan-1-ol: Title compound was prepared (1.1 g, 5.26 mmol) as a light red oil according to procedures described in Example 5 Step A by using 3-(6-chloro-1H-indol-3-yl)propanoic acid (1.9 g, 8.5 mmol) and $BH_3$ in THF (1M, 17 mL, 17 mmol). MS (ES) 210.1 (M+H).

Step C. Preparation of 6-chloro-3-(3-(4-chloro-3,5-dimethylphenoxy)propyl)-1H-indole: Title compound was prepared (170 mg, 0.49 mmol) as a white solid according to procedures described in Example 5 Step B by using 3-(6-chloro-1H-indol-3-yl)propan-1-ol (105 mg, 0.50 mmol), $PPh_3$ (197 mg, 1.5 mmol), 4-chloro-3,5-dimethylphenol (125 mg, 1.6 mmol), and Dt-BuAD (173 mg, 1.5 mmol). MS (ES) 348.1 (M+H).

Step D: Title compound was prepared (15 mg, 0.037 mmol) as a white solid according to procedures described in Example 5 Step C using 6-chloro-3-(3-(4-chloro-3,5-dimethylphenoxy)propyl)-1H-indole (17.4 mg, 0.05 mmol). MS (ES) 406.1 (M+H).

Example 8

Preparation of 2-(6-chloro-3-(3-(naphthalen-1-yloxy)propyl)-1H-indol-1-yl)acetic acid Step A. Preparation of 6-chloro-3-(3-(naphthalen-1-yloxy)propyl)-1H-indole: Title compound was prepared (130 mg, 0.39 mmol) as a white solid according to procedures described in Example 5 Step B by using 3-(6-chloro-1H-indol-3-yl)propan-1-ol (105 mg, 0.50 mmol), $PPh_3$ (197 mg, 1.5 mmol), 1-naphthol (115 mg, 1.6 mmol), and Dt-BuAD (173 mg, 1.5 mmol). MS (ES) 336.1 (M+H).

Step B: Title compound was prepared (14 mg, 0.042 mmol) as a white solid according to procedures described in Example 5 Step C using 6-chloro-3-(3-(naphthalen-1-yloxy)propyl)-1H-indole (17 mg, 0.05 mmol). MS (ES) 394.1 (M+H).

Example 9

Preparation of 2-(4-chloro-3-(3-(4-chloro-3,5-dimethylphenoxy)propyl)-1H-indol-1-yl)acetic acid Step A. Preparation of 3-(4-chloro-1H-indol-3-yl)propanoic acid: Title compound was prepared (70 mg, 0.21 mmol) as a glassy oil according to procedures described in Example 7 Step A by using 4-Cl-indole (150 mg, 1.0 mmol) and acrylic acid (0.2 mL) in acetic acid (1.0 mL) was added acetic anhydride (0.19 mL). MS (ES) 224.1 (M+H).

Step B. Preparation of 3-(4-chloro-1H-indol-3-yl)propan-1-ol: Title compound was prepared (50 mg, 0.23 mmol) as a glassy solid according to procedures described in Example 5 Step A by using 3-(4-chloro-1H-indol-3-yl)propanoic acid (65 mg, 0.29 mmol) and $BH_3$ in THF (1M, 0.6 mL, 0.6 mmol). MS (ES) 210.1 (M+H).

Step C. Preparation of 4-chloro-3-(3-(4-chloro-3,5-dimethylphenoxy)propyl)-1H-indole: Title compound was prepared (80 mg, 0.23 mmol) as a white solid according to procedures described in Example 5 Step B by using 3-(4-chloro-1H-indol-3-yl)propan-1-ol (80 mg, 0.38 mmol), $PPh_3$ (150 mg, 0.57 mmol), 4-chloro-3,5-dimethylphenol (95 mg, 0.61 mmol), and Dt-BuAD (131 mg, 0.57 mmol). MS (ES) 348.1 (M+H).

Step D: Title compound was prepared (14 mg, 0.034 mmol) as a white solid according to procedures described in Example 5 Step C using 4-chloro-3-(3-(4-chloro-3,5-dimethylphenoxy)propyl)-1H-indole (17.4 mg, 0.05 mmol). MS (ES) 406.1 (M+H).

Example 10

Preparation of 2-(4-chloro-3-(3-(naphthalen-1-yloxy)propyl)-1H-indol-1-yl)acetic acid Step A. Preparation of 4-chloro-3-(3-(naphthalen-1-yloxy)propyl)-1H-indole: Title compound was prepared (71 mg, 0.20 mmol) as a white solid according to procedures described in Example 5 Step B by using 3-(4-chloro-1H-indol-3-yl)propan-1-ol (80 mg, 0.38 mmol), $PPh_3$ (150 mg, 0.57 mmol), 4-chloro-3,5-dimethylphenol (95 mg, 0.61 mmol), and Dt-BuAD (131 mg, 0.57 mmol). MS (ES) 336.1 (M+H).

Step B: Title compound was prepared (15 mg, 0.034 mmol) as a white solid according to procedures described in Example 5 Step C using 4-chloro-3-(3-(naphthalen-1-yloxy)propyl)-1H-indole (17.4 mg, 0.05 mmol). MS (ES) 394.1 (M+H).

Example 11

Preparation of 3-(3-(3-(naphthalen-1-yloxy)propyl)-1H-indol-1-yl)propanoic acid

To a solution of 3-(3-(naphthalen-1-yloxy)propyl)-1H-indole (25 mg, 0.083 mmol) in DMF (0.3 mL) was added NaH (60%, 16 mg, 0.40 mmol) at 0° C. The reaction mixture was stirred for 20 min at 0° C. then ethyl bromopropionate (32 µL, 0.25 mmol) was added in one portion. The reaction mixture was warmed to 20° C. and stirred for 2h. The reaction was quenched by addition of MeOH (1.0 mL) and 10% aqueous LiOH solution (0.2 mL) was added. The reaction mixture was stirred for additional 30 min at 20° C. The reaction mixture was filtered and directly purified by reverse phase prep. HPLC (Phenomenex Gemini C18, $H_2O$/$CH_3CN$ gradient to 95% $CH_3CN$ 0.1% TFA) the title compound (22 mg, 0.059 mmol) as a white solid. MS (ES) 374.2 (M+H).

Example 12

Preparation of 3-(3-(3-(4-chloro-3,5-dimethylphenoxy)propyl)-1H-indol-1-yl)propanoic acid Title compound was prepared (16 mg, 0.041 mmol) as a white solid according to procedures described in Example 11 using 3-(3-(4-chloro-3,5-dimethylphenoxy)propyl)-1H-indole (16 mg, 0.05 mmol). MS (ES) 386.1 (M+H).

Example 13

Preparation of 3-(6-chloro-3-(3-(4-chloro-3,5-dimethylphenoxy)propyl)-1H-indol-1-yl)propanoic acid Title compound was prepared (16 mg, 0.038 mmol) as a white solid according to procedures described in Example 11 using 6-chloro-3-(3-(4-chloro-3,5-dimethylphenoxy)propyl)-1H-indole (17.4 mg, 0.05 mmol). MS (ES) 420.1 (M+H).

Example 14

Preparation of 3-(6-chloro-3-(3-(naphthalen-1-yloxy)propyl)-1H-indol-1-yl)propanoic acid Title compound was prepared (15 mg, 0.037 mmol) as a white solid according to procedures described in Example 11 using 6-chloro-3-(3-(naphthalen-1-yloxy)propyl)-1H-indole (17 mg, 0.05 mmol). MS (ES) 408.1 (M+H).

Example 15

Preparation of 3-(4-chloro-3-(3-(4-chloro-3,5-dimethylphenoxy)propyl)-1H-indol-1-yl)propanoic acid Title compound was prepared (14 mg, 0.034 mmol) as a white solid according to procedures described in Example 11 using 4-chloro-3-(3-(4-chloro-3,5-dimethylphenoxy)propyl)-1H-indole (17.4 mg, 0.05 mmol). MS (ES) 420.1 (M+H).

Example 16

Preparation of 3-(4-chloro-3-(3-(naphthalen-1-yloxy)propyl)-1H-indol-1-yl)propanoic acid Title compound was prepared (15 mg, 0.037 mmol) as a white solid according to procedures described in Example 11 using 4-chloro-3-(3-(naphthalen-1-yloxy)propyl)-1H-indole (17 mg, 0.05 mmol). MS (ES) 408.1 (M+H).

Example 17

Preparation of 3-(3-(3-(4-chloro-3,5-dimethylphenoxy)-2-methylpropyl)-1H-indol-1-yl)propanoic acid Step A. Preparation of methyl 3-(1H-indol-3-yl)propanoate: To a solution of 3-(1H-indol-3-yl)propanoic acid (2 g) in methanol (50 ml) at 0° C. was added sulfuric acid (5 ml). The mixture was then warmed to rt. After 15h, the mixture was poured into ice water, basified with 30% $NH_4OH$, extracted with $CH_2Cl_2$, dried $Na_2SO_4$, filtered and concentrated in vacuo to give the title compound. It was used without further purification. MS (ES) 204.3 (M+H).

Step B. Preparation of tert-butyl 3-(3-methoxy-3-oxopropyl)-1H-indole-1-carboxylate: To a solution of methyl 3-(1H-indol-3-yl)propanoate (2.13 g) in THF (52.4 ml) at rt was added $Boc_2O$ (3.65 ml) and DMAP (0.128 g). After 3 h, the mixture was concentrated in vacuo. The residue was purified by flash column chromatography (Combi-flash Rf, Hex/EtOAc 0-10% gradient) to give the title compound product. MS (ES) 248.2 (M-t-Bu+H).

Step C. Preparation of tert-butyl 3-(3-methoxy-2-methyl-3-oxopropyl)-1H-indole-1-carboxylate: To a solution of tert-butyl 3-(3-methoxy-3-oxopropyl)-1H-indole-1-carboxylate (1 g) in THF (16.48 ml) at −78° C. was added 1M LiHMDS (3.46 ml). After 30 min, methyl iodide (0.412 ml) was added to the mixture. The mixture was then warmed to rt. After 25h, the mixture was acidified with 1M HCl, extracted with EtOAc, dried $MgSO_4$, filtered and concentrated in vacuo. The residue was purified by flash column chromatography (Combi-flash Rf, Hex/EtOAc 0-10% gradient) to give the title compound. MS (ES) 262.2 (M-t-Bu+H), 218.2 (M-Boc+H).

Step D. Preparation of methyl 3-(1H-indol-3-yl)-2-methylpropanoate: A mixture of tert-butyl 3-(3-methoxy-2-methyl-3-oxopropyl)-1H-indole-1-carboxylate (0.26 g) in $CH_2Cl_2$ (7.45 ml) and TFA (0.75 ml) was stirred at rt. After 3h, the mixture was concentrated in vacuo to give the title compound. MS (ES) 218.2 (M+H).

Step E. Preparation of 3-(1H-indol-3-yl)-2-methylpropan-1-ol: To a solution of methyl 3-(1H-indol-3-yl)-2-methylpropanoate (0.178 g) in THF (3.56 ml) at rt was added 1M borane THF complex (3.36 ml). After 15h, MeOH was added to the mixture and concentrated in vacuo. The crude residue was purified by reverse phase prep. HPLC (Phenomenex Gemini C18, $H_2O$/$CH_3CN$ gradient to 95% $CH_3CN$ 0.1% TFA) the title compound. MS (ES) 190.3 (M+H).

Step. F. Preparation of 3-(3-(4-chloro-3,5-dimethylphenoxy)-2-methylpropyl)-1H-indole: Title compound was prepared as a white solid according to procedures described in Example 5 Step B by using 3-(1H-indol-3-yl)-2-methylpropan-1-ol (30 mg, 0.16 mmol), $PPh_3$ (50 mg, 0.24 mmol), 4-chloro-3,5-dimethylphenol (30 mg, 0.26 mmol), and Dt-BuAD (44 mg, 0.24 mmol). MS (ES) 328.2 (M+H).

Step G: To a solution of 3-(3-(4-chloro-3,5-dimethylphenoxy)-2-methylpropyl)-1H-indole (9 mg) in DMF (183 µl) at rt was added ethyl 3-bromopropanoate (7.00 µl) and cesium carbonate (22.36 mg). The mixture was then warmed to 75° C. After 20h, the mixture was concentrated in vacuo. To the crude ester (MS (ES) 428.2 (M+H)) was added THF (183 µl), EtOH (183 µl) and 5M KOH (82 µl). The mixture was then warmed to 60° C. After 15 h, the mixture was acidified with 1N HCl and concentrated in vacuo. The crude residue was purified by reverse phase prep. HPLC (Phenomenex Gemini C18, $H_2O/CH_3CN$ gradient to 95% $CH_3CN$ 0.1% TFA) to give the title compound. MS (ES) 400.2.

Example 18

Preparation of 3-(3-(3-(4-chloro-3,5-dimethylphenoxy)propyl)-1H-indol-1-yl)-N-(methylsulfonyl)propanamide To a solution of 3-(3-(3-(4-chloro-3,5-dimethylphenoxy)propyl)-1H-indol-1-yl)propanoic acid (9.0 mg, 0.023 mmol) and Me-sulfonamide (3.3 mg, 0.035 mmol) in $CH_2Cl_2$ (0.3 mL) was added EDC.HCl (7.1 mg, 0.046) followed by DMAP (7.0 mg, 0.058 mmol) at 20° C. The reaction mixture was stirred for 15h at 20° C. then quenched by addition of $NH_4Cl$ aq. Solution. The reaction mixture was extracted with $CH_2Cl_2$ and concentrated in vacuo. The residue was purified by reverse phase prep. HPLC (Phenomenex Gemini C18, $H_2O/CH_3CN$ gradient to 95% $CH_3CN$ 0.1% TFA) to give the title compound (9.0 mg, 0.02 mmol) as a white solid. MS (ES) 463.1.

Example 19

Preparation of 3-(3-(3-(naphthalen-1-yloxy)propyl)-1H-indol-1-yl)-N-(methylsulfonyl)propanamide Title compound was prepared (10 mg, 0.022 mmol) as a white solid according to procedures described in Example 18 by using 3-(3-(3-(naphthalen-1-yloxy)propyl)-1H-indol-1-yl)propanoic acid (10 mg, 0.026 mmol). MS (ES) 451.2 (M+H).

Example 20

Preparation of 3-(6-chloro-3-(3-(4-chloro-3,5-dimethylphenoxy)propyl)-1H-indol-1-yl)-N-(methylsulfonyl)propanamide Title compound was prepared (13 mg, 0.024 mmol) as a white solid according to procedures described in Example 18 by using 3-(6-chloro-3-(3-(4-chloro-3,5-dimethylphenoxy)propyl)-1H-indol-1-yl)propanoic acid (12 mg, 0.028 mmol). MS (ES) 497.1 (M+H).

Example 21

Preparation of 3-(6-chloro-3-(3-(naphthalen-1-yloxy)propyl)-1H-indol-1-yl)-N-(methylsulfonyl)propanamide Title compound was prepared (12 mg, 0.025 mmol) as a white solid according to procedures described in Example 18 by using 3-(6-chloro-3-(naphthalen-1-yloxy)propyl)-1H-indol-1-yl)propanoic acid (12 mg, 0.029 mmol). MS (ES) 485.1 (M+H).

Example 22

Preparation of 3-(4-chloro-3-(3-(4-chloro-3,5-dimethylphenoxy)propyl)-1H-indol-1-yl)-N-(methylsulfonyl)propanamide Title compound was prepared (13 mg, 0.024 mmol) as a white solid according to procedures described in Example 18 by using 3-(4-chloro-3-(3-(4-chloro-3,5-dimethylphenoxy)propyl)-1H-indol-1-yl)propanoic acid (13 mg, 0.031 mmol). MS (ES) 497.1 (M+H).

Example 23

Preparation of 3-(4-chloro-3-(3-(naphthalen-1-yloxy)propyl)-1H-indol-1-yl)-N-(methylsulfonyl)propanamide Title compound was prepared (11 mg, 0.023 mmol) as a white solid according to procedures described in Example 18 by using 3-(4-chloro-3-(naphthalen-1-yloxy)propyl)-1H-indol-1-yl)propanoic acid (11 mg, 0.027 mmol). MS (ES) 485.1 (M+H).

Example 24

Preparation of N-(methylsulfonyl)-2-(3-(3-(naphthalen-1-yloxy)propyl)-1H-indol-1-yl)acetamide Title compound was prepared (9.0 mg, 0.021 mmol) as a white solid according to procedures described in Example 18 by using 2-(3-(3-(naphthalen-1-yloxy)propyl)-1H-indol-1-yl)acetic acid (9.0 mg, 0.025 mmol). MS (ES) 437.1 (M+H).

Example 25

Preparation of 2-(6-chloro-3-(3-(4-chloro-3,5-dimethylphenoxy)propyl)-1H-indol-1-yl)-N-(methylsulfonyl)acetamide Title compound was prepared (7.0 mg, 0.014 mmol) as a white solid according to procedures described in Example 18 by using 2-(6-chloro-3-(3-(4-chloro-3,5-dimethylphenoxy)propyl)-1H-indol-1-yl)acetic acid (9.0 mg, 0.025 mmol). MS (ES) 483.1 (M+H).

Example 26

Preparation of 2-(6-chloro-3-(3-(naphthalen-1-yloxy)propyl)-1H-indol-1-yl)-N-(methylsulfonyl)acetamide Title compound was prepared (8.9 mg, 0.019 mmol) as a white solid according to procedures described in Example 18 by using 2-(6-chloro-3-(3-(naphthalen-1-yloxy)propyl)-1H-indol-1-yl)acetic acid (8.5 mg, 0.021 mmol). MS (ES) 471.1 (M+H).

Example 27

Preparation of 2-(4-chloro-3-(3-(4-chloro-3,5-dimethylphenoxy)propyl)-1H-indol-1-yl)-N-(methylsulfonyl)acetamide Title compound was prepared (7.0 mg, 0.014 mmol) as a white solid according to procedures described in Example 18 by using 2-(6-chloro-3-(3-(4-chloro-3,5-dimethylphenoxy)propyl)-1H-indol-1-yl)acetic acid (7.5 mg, 0.018 mmol). MS (ES) 483.1 (M+H).

Example 28

Preparation of 2-(4-chloro-3-(3-(naphthalen-1-yloxy)propyl)-1H-indol-1-yl)-N-(methylsulfonyl)acetamide Title compound was prepared (9.1 mg, 0.019 mmol) as a white solid according to procedures described in Example 18 by using 2-(6-chloro-3-(3-(naphthalen-1-yloxy)propyl)-1H-indol-1-yl)acetic acid (9.0 mg, 0.023 mmol). MS (ES) 471.1 (M+H).

Example 29

Preparation of 3-(7-bromo-3-(3-(4-chloro-3,5-dimethylphenoxy)propyl)-1H-indol-1-yl)propanoic acid Step A. Preparation of 3-(7-bromo-1H-indol-3-yl)propan-1-ol: To a solution of (2-bromophenyl)hydrazine hydrochloride (5 g, 22.4 mmol) in dioxane (22.37 ml) and water (5.59 ml) at rt was added 3,4-dihydro-2H-pyran (2.14 ml, 23.4 mmol). The mixture was then warmed to 90° C. After 20h, the mixture was concentrated in vacuo. The residue was diluted with water, extracted with EtOAc, dried MgSO$_4$, filtered and concentrated in vacuo. The residue was purified by flash column chromatography (Combi-flash Rf, Hex/EtOAc 0-40% gradient) to give the title compound. MS (ES) 254.1 (M+H).

Step B. Preparation of 7-bromo-3-(3-(4-chloro-3,5-dimethylphenoxy)propyl)-1H-indole: To a solution of 3-(7-bromo-1H-indol-3-yl)propan-1-ol (2.7 g) in THF (35.4 ml) at rt was added 4-chloro-3,5-dimethylphenol (2.0 g), triphenylphosphine (3.34 g) and Dt-BuAD (2.94 g). The mixture then stirred at rt. After 25h, the mixture was concentrated in vacuo. The residue was taken up in 10% TFA/DCM (40.9 ml, 53.1 mmol). After 1 h, the mixture was concentrated in vacuo. The residue was taken up in hexanes, filtered to remove all solids, and the hexane washes concentrated in vacuo. The residue was purified by flash column chromatography (Combi-flash Rf, Hex/EtOAc 0-10% gradient) to give the title compound. MS (ES) 392.1 (M+H).

Step C. Preparation of ethyl 3-(7-bromo-3-(3-(4-chloro-3,5-dimethylphenoxy)propyl)-1H-indol-1-yl)propanoate: To a solution of 7-bromo-3-(3-(4-chloro-3,5-dimethylphenoxy)propyl)-1H-indole (247 mg, 0.63 mmol) in DMF (1.3 mL) at rt was added ethyl 3-bromopropanoate (162 µL, 1.26 mmol) and cesium carbonate (519 mg). The mixture was then warmed to 82° C. After 15h, the reaction mixture was diluted with EtOAc. The combined organics were washed with water, sat NaCl, dried MgSO$_4$, filtered and concentrated in vacuo. The residue was purified by flash chromatography (Combi-flash Rf, Hex/EtOAc 0-30% gradient) to give the title compound (216 mg, 0.44 mmol). MS (ES) 492.1 (M+H).

Step D: To a solution of ethyl 3-(7-bromo-3-(3-(4-chloro-3,5-dimethylphenoxy)propyl)-1H-indol-1-yl)propanoate ethyl 3-(3-(3-(4-chloro-3,5-dimethylphenoxy)propyl)-1H-indol-1-yl)propanoate (23 mg) in THF (0.1 mL), EtOH (0.1 mL) and water (60 µL) at rt was added LiOH (11 mg). After 3h, the mixture was acidified with 1M HCl and concentrated in vacuo. The crude residue was purified by reverse phase prep. HPLC (Phenomenex Gemini C18, H$_2$O/CH$_3$CN gradient to 95% CH$_3$CN 0.1% TFA) to give the title compound. MS (ES) 464.0 (M+H).

Example 30

Preparation of 3-(3-(3-(4-chloro-3,5-dimethylphenoxy)propyl)-7-(1,5-dimethyl-3-(phenoxymethyl)-1H-pyrazol-4-yl)-1H-indol-1-yl)propanoic acid Step A. 3-(3-(4-chloro-3,5-dimethylphenoxy)propyl)-7-(4,4,5,5-tetramethyl-1,3,2-dioxaborolan-2-yl)-1H-indole: To a solution of 7-bromo-3-(3-(4-chloro-3,5-dimethylphenoxy)propyl)-1H-indole (100 mg) in DMF (1.27 mL) at rt was added bis(pinacolato)diboron (78 mg), potassium acetate (115 mg) and Pd(dppf)Cl$_2$ CH$_2$Cl$_2$ complex (9.3 mg). The mixture was then warmed to 60° C. After 15h, the mixture was concentrated in vacuo. The residue was taken up in CH$_2$Cl$_2$, washed with water, filtered and concentrated in vacuo. The residue was purified by flash column chromatography (Combi-flash Rf, Hex/EtOAc 0-10% gradient) to give the title compound. MS (ES) 440.2 (M+H).

Step B. (4-(3-(3-(4-chloro-3,5-dimethylphenoxy)propyl)-1H-indol-7-yl)-1,5-dimethyl-1H-pyrazol-3-yl)methanol: To a solution of 3-(3-(4-chloro-3,5-dimethylphenoxy)propyl)-7-(4,4,5,5-tetramethyl-1,3,2-dioxaborolan-2-yl)-1H-indole (0.078 g) in DME (0.66 mL) and methanol (0.33 mL) at rt was added (4-bromo-1,5-dimethyl-1H-pyrazol-3-yl)methanol (40 mg), Pd(PPh$_3$)$_4$(10.3 mg) and cesium fluoride (81 mg). The mixture was then heated to 120° C. in Biotage Initiator for 20 min. After 20 min, the mixture was concentrated in vacuo. The residue was purified by flash column chromatography (Combi-flash Rf, MeOH/CH$_2$Cl$_2$ 0-10% gradient) to give the title compound. MS (ES) 438.3 (M+H).

Step C. 3-(3-(4-chloro-3,5-dimethylphenoxy)propyl)-7-(1,5-dimethyl-3-(phenoxymethyl)-1H-pyrazol-4-yl)-1H-indole: To a solution of (4-(3-(3-(4-chloro-3,5-dimethylphenoxy)propyl)-1H-indol-7-yl)-1,5-dimethyl-1H-pyrazol-3-yl)methanol (40 mg) in THF (0.9 ml) at rt was added phenol (10.3 mg), triphenylphosphine (30 mg) and Dt-BuAD (25 mg). The mixture then stirred at rt. After 2h, the mixture was concentrated in vacuo. The crude residue was purified by reverse phase prep. HPLC (Phenomenex Gemini C18, H$_2$O/CH$_3$CN gradient to 95% CH$_3$CN 0.1% TFA) to give title compound. MS (ES) 514.2 (M+H).

Step D: To a solution of 3-(3-(4-chloro-3,5-dimethylphenoxy)propyl)-7-(1,5-dimethyl-3-(phenoxymethyl)-1H-pyrazol-4-yl)-1H-indole (16 mg) in DMF (0.21 mL) at rt was added ethyl 3-bromopropanoate (7.9 µl) and cesium carbonate (25 mg). The mixture was then warmed to 60° C. After 2 days, the mixture was concentrated in vacuo. To the crude ester in THF (0.21 mL) and EtOH (0.21 mL) at rt was added 2M LiOH (0.23 mL). The mixture was then warmed to 40° C. After 2h, the mixture was concentrated in vacuo. The crude residue was purified by reverse phase prep. HPLC (Phenomenex Gemini C18, H$_2$O/CH$_3$CN gradient to 95% CH$_3$CN 0.1% TFA) to give the title compound. MS (ES) 586.2 (M+H).

Example 31

Preparation of 3-(3-(3-(4-chloro-3,5-dimethylphenoxy)propyl)-7-phenyl-1H-indol-1-yl)propanoic acid A mixture of ethyl 3-(7-bromo-3-(3-(4-chloro-3,5-dimethylphenoxy)propyl)-1H-indol-1-yl)propanoate (15 mg, 0.030 mmol), phenylboronic acid (18 mg, 0.15 mmol) and Pd(PPh$_3$)2Cl$_2$ (2.5 mg, 0.003 mmol) in 2M Na$_2$CO$_3$ (0.2 mL) and 7:2:3 DME/EtOH/H$_2$O (1.2 mL) was irradiated under microwave for 30 min at 150° C. The reaction was quenched by addition of 1M HCl (0.3 mL) then extracted with EtOAc. The crude product was purified by reserve phase HPLC (Phenomenex Gemini C18, $H_2O/CH_3CN$ gradient to 95% $CH_3CN$ 0.1% TFA) to give the title compound (13 mg, 0.028 mmol). MS (ES) 462.2 (M+H).

Example 32

Preparation of 3-(3-(3-(4-chloro-3,5-dimethylphenoxy)propyl)-7-(o-tolyl)-1H-indol-1-yl)propanoic acid Title compound was prepared (14 mg, 0.029 mmol) as a white solid according to procedures described in Example 31 by using ethyl 3-(7-bromo-3-(3-(4-chloro-3,5-dimethylphenoxy)propyl)-1H-indol-1-yl)propanoate (15 mg, 0.030 mmol) and o-tolylboronic acid (20 mg, 0.15 mmol). MS (ES) 476.2 (M+H).

Example 33

Preparation of 3-(3-(3-(4-chloro-3,5-dimethylphenoxy)propyl)-7-(pyridin-3-yl)-1H-indol-1-yl)propanoic acid Title compound was prepared (15 mg, 0.027 mmol, TFA salt) as a tan solid according to procedures described in Example 31 by using ethyl 3-(7-bromo-3-(3-(4-chloro-3,5-dimethylphenoxy)propyl)-1H-indol-1-yl)propanoate (15 mg, 0.030 mmol) and 3-pyridylboronic acid (18 mg, 0.15 mmol). MS (ES) 463.2 (M+H).

Example 34

Preparation of 3-(3-(3-(4-chloro-3,5-dimethylphenoxy)propyl)-7-(pyridin-4-yl)-1H-indol-1-yl)propanoic acid Title compound was prepared (16 mg, 0.029 mmol, TFA salt) as a tan solid according to procedures described in Example 31 by using ethyl 3-(7-bromo-3-(3-(4-chloro-3,5-dimethylphenoxy)propyl)-1H-indol-1-yl)propanoate (15 mg, 0.030 mmol) and 4-pyridylboronic acid (18 mg, 0.15 mmol). MS (ES) 463.2 (M+H).

Example 35

Preparation of 3-(3-(3-(4-chloro-3,5-dimethylphenoxy)propyl)-7-(1H-pyrazol-3-yl)-1H-indol-1-yl)propanoic acid Title compound was prepared (5 mg, 0.011 mmol) as a tan solid according to procedures described in Example 31 by using ethyl 3-(7-bromo-3-(3-(4-chloro-3,5-dimethylphenoxy)propyl)-1H-indol-1-yl)propanoate (15 mg, 0.030 mmol) and 1H-Pyrazol-3-ylboronic acid hydrate (17 mg, 0.15 mmol). MS (ES) 452.2 (M+H).

Example 36

Preparation of 3-(3-(3-(4-chloro-3,5-dimethylphenoxy)propyl)-7-(1H-pyrazol-4-yl)-1H-indol-1-yl)propanoic acid Title compound was prepared (11 mg, 0.024 mmol) as a white solid according to procedures described in Example 31 by using ethyl 3-(7-bromo-3-(3-(4-chloro-3,5-dimethylphenoxy)propyl)-1H-indol-1-yl)propanoate (15 mg, 0.030 mmol) and 4-Pyrazoleboronic acid pinacol ester (29 mg, 0.15 mmol). MS (ES) 452.2 (M+H).

Example 37

Preparation of 3-(6-chloro-3-(3-(4-chloro-3,5-dimethylphenoxy)propyl)-1H-indol-1-yl)-N-(phenylsulfonyl)propanamide Title compound was prepared (12 mg, 0.021 mmol) as a white solid according to procedures described in Example 18 by using 2-(6-chloro-3-(3-(4-chloro-3,5-dimethylphenoxy)propyl)-1H-indol-1-yl)acetic acid (10 mg, 0.023 mmol) and benzenesulfonamide (4.1 mg, 0.026 mmol). MS (ES) 559.1 (M+H).

Example 38

Preparation of N-(benzylsulfonyl)-3-(6-chloro-3-(3-(4-chloro-3,5-dimethylphenoxy)propyl)-1H-indol-1-yl)propanamide Title compound was prepared (12 mg, 0.021 mmol) as a white solid according to procedures described in Example 18 by using 2-(6-chloro-3-(3-(4-chloro-3,5-dimethylphenoxy)propyl)-1H-indol-1-yl)acetic acid (10 mg, 0.023 mmol) and phenylmethanesulfonamide (4.5 mg, 0.026 mmol). MS (ES) 573.1 (M+H).

Example 39

Preparation of 3-(6-chloro-3-(3-(4-chloro-3,5-dimethylphenoxy)propyl)-1H-indol-1-yl)-N-(cyclopropylsulfonyl)propanamide Title compound was prepared (10 mg, 0.019 mmol) as a white solid according to procedures described in Example 18 by using 2-(6-chloro-3-(3-(4-chloro-3,5-dimethylphenoxy)propyl)-1H-indol-1-yl)acetic acid (10 mg, 0.023 mmol) and cyclopropanesulfonamide (3.2 mg, 0.026 mmol). MS (ES) 523.1 (M+H).

Example 40

Preparation of 3-(6-chloro-3-(3-(4-chloro-3,5-dimethylphenoxy)propyl)-1H-indol-1-yl)-N-((4-phenoxyphenyl)sulfonyl)propanamide Title compound was prepared (13 mg, 0.020 mmol) as a white solid according to procedures described in Example 18 by using 2-(6-chloro-3-(3-(4-chloro-3,5-dimethylphenoxy)propyl)-1H-indol-1-yl)acetic acid (10 mg, 0.023 mmol) and 4-phenoxybenzenesulfonamide (6.5 mg, 0.026 mmol). MS (ES) 651.1 (M+H).

Example 41

Preparation of 3-(6-chloro-3-(3-(4-chloro-3,5-dimethylphenoxy)propyl)-1H-indol-1-yl)-N-((4-(4-methoxyphenoxy)phenyl)sulfonyl)propanamide Title compound was prepared (13 mg, 0.019 mmol) as a white solid according to procedures described in Example 18 by using 2-(6-chloro-3-(3-(4-chloro-3,5-dimethylphenoxy)propyl)-1H-indol-1-yl)acetic acid (10 mg, 0.023 mmol) and 4-(4-methoxyphenoxy)benzenesulfonamide (7.3 mg, 0.026 mmol). MS (ES) 681.1 (M+H).

Example 42

Preparation of N-((4-(benzyloxy)phenyl)sulfonyl)-3-(6-chloro-3-(3-(4-chloro-3,5-dimethylphenoxy)propyl)-1H-indol-1-yl)propanamide Title compound was prepared (12 mg, 0.018 mmol) as a white solid according to procedures described in Example 18 by using 2-(6-chloro-3-(3-(4-chloro-3,5-dimethylphenoxy)propyl)-1H-indol-1-yl)acetic acid (10 mg, 0.023 mmol) and 4-(benzyloxy)benzenesulfonamide (6.8 mg, 0.026 mmol). MS (ES) 665.2 (M+H).

Example 43

Preparation of 2-(6-chloro-3-(3-(4-chloro-3,5-dimethylphenoxy)propyl)-2-methyl-1H-indol-1-yl)acetic acid Step A. Preparation of 5-(2-(3-chlorophenyl)hydrazono)-6-ethoxy-6-oxohexanoic acid: To a stirring mixture of 3-chloroaniline (2.1 mL, 20 mmol) in 1M HCl (25 mL) and water (5 mL) at 0° C. was added $NaNO_2$ (1.38 g, 20 mmol) in water (20 mL), $NaCH_3COOH$ (9.23 g, 112 mmol) in water (25 mL) and ethyl 2-oxocyclopentane carboxylate (3.0 mL, 20 mmol) in sequence. The reaction mixture was stirred for 15 min at 0° C. then warmed to 20° C. over 2h and extracted with $CH_2Cl_2$, dried over $MgSO_4$, filtered and concentrated in vacuo to give the title compound as a red oil in 5.9 g (95% crude).

Step B. Preparation of ethyl 6-chloro-3-(3-ethoxy-3-oxopropyl)-1H-indole-2-carboxylate: To a solution of 5-(2-(3-chlorophenyl)hydrazono)-6-ethoxy-6-oxohexanoic acid (5.9 g, 19 mmol) in EtOH (30 mL) was added conc. $H_2SO_4$ (7.5 mL), slowly. The reaction mixture was refluxed for 1.5 h. The reaction was quenched by pouring into ice then extracted with $CH_2Cl_2$. The combined organic layer was washed with sat. $NaHCO_3$, water, brine, dried over $MgSO_4$, filtered and concentrated in vacuo. The reaction yielded 2:1 mixture of diastereomers and the title compound (2.9 g, 9.0 mmol) was isolated by flash chromatography (Combi-flash Rf Hex/EtOAc 15% gradient) as a white needle shape solid. MS (ES) 324.1 (M+H).

Step C. Preparation of 3-(6-chloro-2-methyl-1H-indol-3-yl)propan-1-ol: To a solution of ethyl 6-chloro-3-(3-ethoxy-3-oxopropyl)-1H-indole-2-carboxylate (1.9 g, 6.0 mmol) in THF (25 mmol) was added $BH_3$ in THF (25 mL, 20 mmol) at 20° C. The reaction mixture was stirred for 30h at 20° C. and quenched by addition of MeOH then concentrated in vacuo. The residue was purified by flash chromatography (Combi-flash Rf Hexane/EtOAc gradient 0-50%) to give the title compound (340 mg, 1.5 mmol) as a off-white solid as a byproduct along with the major product ethyl 6-chloro-3-(3-hydroxypropyl)-1H-indole-2-carboxylate (1.2 g, 4.3 mmol). MS (ES) 224.1 (M+H).

Step D. Preparation of 6-chloro-3-(3-(4-chloro-3,5-dimethylphenoxy)propyl)-2-methyl-1H-indole: Title compound was prepared (181 mg, 0.5 mmol) as a off-white solid according to procedures described in Example 5 Step B by using 3-(6-chloro-2-methyl-1H-indol-3-yl)propan-1-ol (157 mg, 0.7 mmol). MS (ES) 362.1 (M+H).

Step E: Title compound was prepared (10 mg, 0.024 mmol) as a white solid according to procedures described in Example 5 Step C using 6-chloro-3-(3-(4-chloro-3,5-dimethylphenoxy)propyl)-2-methyl-1H-indole (50.0 mg, 0.14 mmol). MS (ES) 420.1 (M+H).

Example 44

Preparation of 3-(6-chloro-3-(3-(4-chloro-3,5-dimethylphenoxy)propyl)-2-methyl-1H-indol-1-yl)propanoic acid Title compound was prepared (25 mg, 0.058 mmol) as a white solid according to procedures described in Example 11 using 6-chloro-3-(3-(4-chloro-3,5-dimethylphenoxy)propyl)-2-methyl-1H-indole (50.0 mg, 0.14 mmol). MS (ES) 434.1 (M+H).

Example 45

Preparation of 2-(6-chloro-3-(3-(4-chloro-3,5-dimethylphenoxy)propyl)-2-methyl-1H-indol-1-yl)-N-(methylsulfonyl)acetamide Title compound was prepared (11 mg, 0.022 mmol) as a white solid according to procedures described in Example 18 by using 2-(6-chloro-3-(3-(4-chloro-3,5-dimethylphenoxy)propyl)-2-methyl-1H-indol-1-yl)acetic acid (10.4 mg, 0.024 mmol). MS (ES) 437.1 (M+H).

Example 46

Preparation of 3-(6-chloro-3-(3-(4-chloro-3,5-dimethylphenoxy)propyl)-2-methyl-1H-indol-1-yl)-N-(methylsulfonyl)propanamide Title compound was prepared (6.0 mg, 0.012 mmol) as a white solid according to procedures described in Example 18 by using 3-(6-chloro-3-(3-(4-chloro-3,5-dimethylphenoxy)propyl)-2-methyl-1H-indol-1-yl)propanoic acid (6.0 mg, 0.014 mmol). MS (ES) 511.1 (M+H).

Example 47

Preparation of 2-(3-(3-(4-chloro-3,5-dimethylphenoxy)propyl)-2-cyano-1H-indol-1-yl)acetic acid Step A. Preparation of N-(tert-butyl)-6-chloro-3-(3-(4-chloro-3,5-dimethylphenoxy)propyl)-1H-indole-2-carboxamide: To a solution of 3-(3-(4-chloro-3,5-dimethylphenoxy)propyl)-1H-indole (115 mg, 0.36 mmol) and t-Bu-isocyanate (65 μL, 0.55 mmol) in $CH_2Cl_2$ (0.6 mL) was added $BF_3$—$OEt_2$ (90 μL, 0.73 mmol) at 20° C. The reaction mixture was stirred for 15h 20° C. Additional amount of t-Bu-isocyanate (65 μL, 0.55 mmol) and $BF_3$—$OEt_2$ $BF_3$—$OEt_2$ (90 μL, 0.73 mmol) were added. The reaction mixture was warmed to 35° C. and stirred additional 15 h. The reaction was quenched by addition of NaOAc aqueous solution. Organic layer was separated and concentrated. The residue was dissolved in $CH_2Cl_2$ (1.8 mL) and TFA (0.2 mL) was added at rt. The reaction mixture was stirred for 15h then concentrated. The residue was directly purified by flash chromatography (Combi-flash Rf Hexane/EtOAc gradient 0-10%) to give the title compound (110 mg, 0.27 mmol) as a yellow solid. MS (ES) 413.2 (M+H).

Step B. Preparation of 3-(3-(4-chloro-3,5-dimethylphenoxy)propyl)-1H-indole-2-carbonitrile: A mixture of N-(tert-butyl)-6-chloro-3-(3-(4-chloro-3,5-dimethylphenoxy)propyl)-1H-indole-2-carboxamide (413 mg, 1.0 mmol) and $POCl_3$ (0.56 mL, 6.0 mmol) in benzene (3.0 mL)

was heated at 80° C. for 3h then cooled. The reaction was quenched by addition of sat. NaHCO$_3$ aq. solution then extracted with CH$_2$Cl$_2$. Organic layer was separated, concentrated and the residue was purified by reserve phase HPLC (Phenomenex Gemini C18, H$_2$O/CH$_3$CN gradient to 95% CH$_3$CN 0.1% TFA) to give the title product (254 mg, 0.75 mmol) as a white solid. MS (ES) 339.1 (M+H).

Step C: Title compound was prepared (20 mg, 0.050 mmol) as a white solid according to procedures described in Example 5 Step C using 3-(3-(4-chloro-3,5-dimethylphenoxy)propyl)-1H-indole-2-carbonitrile (27 mg, 0.079 mmol). MS (ES) 397.1 (M+H).

Example 48

Preparation of 3-(3-(3-(4-chloro-3,5-dimethylphenoxy)propyl)-2-cyano-1H-indol-1-yl)propanoic acid Title compound was prepared (95 mg, 0.23 mmol) as an off-white solid according to procedures described in Example 11 by using 3-(3-(4-chloro-3,5-dimethylphenoxy)propyl)-1H-indole-2-carbonitrile (104 mg, 0.30 mmol). MS (ES) 411.1 (M+H).

Example 49

Preparation of 3-(3-(3-(4-chloro-3,5-dimethylphenoxy)propyl)-2-cyano-1H-indol-1-yl)-N-(methylsulfonyl)propanamide Title compound was prepared (11 mg, 0.020 mmol) as a white solid according to procedures described in Example 18 by using 3-(3-(3-(4-chloro-3,5-dimethylphenoxy)propyl)-2-cyano-1H-indol-1-yl)propanoic acid (10 mg, 0.024 mmol). MS (ES) 488.1 (M+H).

Example 50

Preparation of 2-(3-(3-(4-chloro-3,5-dimethylphenoxy)propyl)-2-cyano-1H-indol-1-yl)-N-(methylsulfonyl)acetamide Title compound was prepared (11 mg, 0.021 mmol) as a white solid according to procedures described in Example 18 by using 2-(3-(3-(4-chloro-3,5-dimethylphenoxy)propyl)-2-cyano-1H-indol-1-yl)acetic acid (10 mg, 0.025 mmol). MS (ES) 474.1 (M+H).

Example 51

Preparation of (±)-2-(3-(3-(4-chloro-3,5-dimethylphenoxy)propyl)-1H-indol-1-yl)propanoic acid To a solution of 3-(3-(4-chloro-3,5-dimethylphenoxy)propyl)-1H-indole (100 mg, 0.31 mmol) in DMF (1.5 mL) was added NaH (60%, 64 mg, 1.6 mmol) at 0° C. in several portions. The reaction mixture was stirred for 10 min at 0° C. then ethyl 2-bromopropanoate (124 µL, 0.95 mmol) was added in one portion. The reaction mixture was warmed to 20° C. and stirred for 2h. The reaction was quenched by addition of MeOH (6.0 mL) followed by 10% aqueous LiOH solution (1.5 mL). The reaction mixture was stirred for additional 30 min at 20° C. The reaction mixture was filtered and concentrated in vacuo. The crude product was purified by reverse phase prep. HPLC (Phenomenex Gemini C18, H$_2$O/CH$_3$CN gradient to 95% CH$_3$CN 0.1% TFA) to give the title compound (95 mg, 0.25 mmol) as a white solid. MS (ES) 386.2 (M+H).

Example 52

Preparation of (±)-2-(3-(3-(4-chloro-3,5-dimethylphenoxy)propyl)-1H-indol-1-yl)butanoic acid Title compound was prepared (80 mg, 0.2 mmol) as a white solid according to procedures described in Example 18 by using 3-(3-(4-chloro-3,5-dimethylphenoxy)propyl)-1H-indole (100 mg, 0.31 mmol) and ethyl 2-bromobutanoate (140 µL, 0.95 mmol). MS (ES) 400.2 (M+H).

Example 53

Preparation of (±)-2-(3-(3-(4-chloro-3,5-dimethylphenoxy)propyl)-1H-indol-1-yl)-2-phenylacetic acid Title compound was prepared (84 mg, 0.19 mmol) as a white solid according to procedures described in Example 18 by using 3-(3-(4-chloro-3,5-dimethylphenoxy)propyl)-1H-indole (100 mg, 0.31 mmol) and ethyl 2-bromo-2-phenylacetate (166 µL, 0.95 mmol). MS (ES) 448.2 (M+H).

Example 54

Preparation of (E/Z)-3-(3-(3-(4-chloro-3,5-dimethylphenoxy)propyl)-1H-indol-1-yl)acrylic acid A solution of TBAF (1 M in THF, 76 µL, 0.076 mmol) was added dropwise to a solution of 3-(3-(4-chloro-3,5-dimethylphenoxy)propyl)-1H-indole (24 mg, 0.076 mmol) and methyl propynoate (7 µL, 0.076 mmol) in THF (0.46 m). The reaction mixture was stirred at 20° C. for 15 h then concentrated in vacuo. The residue was dissolved in MeOH (0.5 mL) and 10% aqueous LiOH solution (150 µL) was added. The reaction mixture was stirred for additional 30 min at 20° C. The reaction mixture was concentrated in vacuo and purified by reverse phase prep. HPLC (Phenomenex Gemini C18, H$_2$O/CH$_3$CN gradient to 95% CH$_3$CN 0.1% TFA) to give the title compound (5 mg, 0.013 mmol) as an off-white solid. MS (ES) 384.1 (M+H).

Example 55

Preparation of (±)-3-(3-(3-(4-chloro-3,5-dimethylphenoxy)propyl)-1H-indol-1-yl)butanoic acid Step A. Preparation of (E/Z)-ethyl 3-(3-(3-(4-chloro-3,5-dimethylphenoxy)propyl)-1H-indol-1-yl)but-2-enoate: To a solution of solution of 3-(3-(4-chloro-3,5-dimethylphenoxy)propyl)-1H-indole (100 mg, 0.31 mmol) and ethyl but-2-ynoate (41 µL, 0.36 mmol) in THF (1.8 mL) was added TBAF (1M in THF 350 µL, 0.35 mmol) at 20° C. The reaction mixture was stirred for 15h at 20° C. then checked by LCMS (~30% conversion). Additional amount of ethyl but-2-ynoate (82 µL, 0.72 mmol) and TBAF (1M in THF 700 µL, 0.70 mmol) were added and stirred for additional 24h. The reaction mixture was concentrated in vacuo then the residue was purified by flash chromatography (Combiflash Rf Hexane/EtOAc gradient 0-10%) to give the title compound (64 mg, 0.15 mmol) as a colorless viscous oil. MS (ES) 426.2 (M+H).

Step B: To a solution of (E/Z)-ethyl 3-(3-(3-(4-chloro-3,5-dimethylphenoxy)propyl)-1H-indol-1-yl)but-2-enoate (20 mg, 0.047 mmol) in MeOH (2.0 mL) was added Pd/C (5% 5.0 mg) at 20° C. The reaction mixture was stirred for 5h at 20° C. under $H_2$ atmosphere then filtered. To a filtrate was added 10% aqueous LiOH solution (500 μL) and stirred for 2h at 20° C. The reaction mixture was acidified with 1N HCl and directly purified by reverse phase prep. HPLC (Phenomenex Gemini C18, $H_2O/CH_3CN$ gradient to 95% $CH_3CN$ 0.1% TFA) to give the title compound (14 mg, 0.035 mmol) as an off-white solid. MS (ES) 400.2 (M+H).

Example 56

Preparation of (±)-3-(3-(3-(4-chloro-3,5-dimethylphenoxy)propyl)-1H-indol-1-yl)-3-phenylpropanoic acid Step A. Preparation of (E/Z)-ethyl 3-(3-(3-(4-chloro-3,5-dimethylphenoxy)propyl)-1H-indol-1-yl)-3-phenylacrylate: Title compound was prepared (97 mg, 0.20 mmol) as a pale yellow oil according to procedures described in Example 55 Step A by using 3-(3-(4-chloro-3,5-dimethylphenoxy)propyl)-1H-indole (100 mg, 0.31 mmol) and ethyl 3-phenylpropiolate (174 μL, 1.05 mmol). MS (ES) 488.2 (M+H).

Step B: Title compound was prepared (11 mg, 0.024 mmol) as a white solid according to procedures described in Example 55 Step B by using (E/Z)-ethyl 3-(3-(3-(4-chloro-3,5-dimethylphenoxy)propyl)-1H-indol-1-yl)-3-phenylacrylate (20 mg, 0.040 mmol) and ethyl 3-phenylpropiolate (174 μL, 1.05 mmol). MS (ES) 462.2 (M+H).

Example 57

Preparation of 3-(6-chloro-3-(3-(4-chloro-3,5-dimethylphenoxy)propyl)-7-methyl-1H-indol-1-yl)propanoic acid Step A. preparation of 3-(6-chloro-7-methyl-1H-indol-3-yl)propan-1-ol: To a solution of (3-chloro-2-methylphenyl)hydrazine hydrochloride (1.171 g, 6.0 mmol) in dioxane (6.1 mL) and water (1.5 mL) at rt was added 3,4-dihydro-2H-pyran (0.58 mL). The mixture was then warmed to 90° C. After 20h, the mixture was concentrated in vacuo. The residue was diluted with water, extracted with EtOAc, dried $MgSO_4$, filtered and concentrated in vacuo. The residue was purified by flash chromatography (Combi-flash Rf Hexane/EtOAc gradient 0-40%) to give the title compound (1.1 g, 4.9 mmol). MS (ES) 224.2 (M+H).

Step B. Preparation of 6-chloro-3-(3-(4-chloro-3,5-dimethylphenoxy)propyl)-7-methyl-1H-indole: Title compound was prepared (130 mg, 0.39 mmol) as a white solid according to procedures described in Example 5 Step B by using 3-(6-chloro-7-methyl-1H-indol-3-yl)propan-1-ol (470 mg, 2.1 mmol), $PPh_3$ (661 mg), 4-chloro-3,5-dimethylphenol (395 mg), and Dt-BuAD (581 mg, 1.5 mmol). MS (ES) 362.2 (M+H).

Step C: To a solution of 6-chloro-3-(3-(4-chloro-3,5-dimethylphenoxy)propyl)-7-methyl-1H-indole (50 mg) in DMF (0.92 mL) at rt was added ethyl 3-bromopropanoate (35 μL) and cesium carbonate (112 mg). The mixture was then warmed to 80° C. After 55h, the mixture was concentrated in vacuo. To the crude ester (MS (ES) 462.1 (M+H)) was added THF (0.92 mL), EtOH (0.92 mL) and 5M KOH (1.04 mL). The mixture was then warmed to 60° C. After 15h, the mixture was acidified with 1N HCl and concentrated in vacuo. The crude residue was purified by by reverse phase prep. HPLC (Phenomenex Gemini C18, $H_2O/CH_3CN$ gradient to 95% $CH_3CN$ 0.1% TFA) to give the title compound (45 mg, 0.10 mmol). MS (ES) 434.2 (M+H).

Example 58

Preparation of 3-(6-bromo-3-(3-(4-chloro-3,5-dimethylphenoxy)propyl)-7-methyl-1H-indol-1-yl)propanoic acid Step A. Preparation of 3-(6-bromo-7-methyl-1H-indol-3-yl)propan-1-ol: Title compound was prepared according to procedures described in Example 57 Step A by substituting (3-bromo-2-methylphenyl)hydrazine hydrochloride for (3-chloro-2-methylphenyl)hydrazine hydrochloride. MS (ES) 268.2 (M+H).

Step B. Preparation of 6-bromo-3-(3-(4-chloro-3,5-dimethylphenoxy)propyl)-7-methyl-1H-indole: Title compound was prepared according to procedures described in Example 57 Step B by substituting 3-(6-bromo-7-methyl-1H-indol-3-yl)propan-1-ol for 3-(6-chloro-7-methyl-1H-indol-3-yl)propan-1-ol. MS (ES) 406.0 (M+H).

Step C: Title compound was prepared according to procedures described in Example 57 Step C by substituting 6-bromo-3-(3-(4-chloro-3,5-dimethylphenoxy)propyl)-7-methyl-1H-indole for 6-chloro-3-(3-(4-chloro-3,5-dimethylphenoxy)propyl)-7-methyl-1H-indole. MS (ES) 478.1 (M+H).

Example 59

Preparation of (±)-2-(3-(3-(4-chloro-3,5-dimethylphenoxy)propyl)-1H-indol-1-yl)-N-(methylsulfonyl)propanamide Title compound was prepared (11 mg, 0.024 mmol) as a white solid according to procedures described in Example 18 by using (+)-2-(3-(3-(4-chloro-3,5-dimethylphenoxy)propyl)-1H-indol-1-yl)propanoic acid (11 mg, 0.028 mmol). MS (ES) 463.1 (M+H).

Example 60

Preparation of (±)-2-(3-(3-(4-chloro-3,5-dimethylphenoxy)propyl)-1H-indol-1-yl)-N-(methylsulfonyl)butanamide Title compound was prepared (12 mg, 0.025 mmol) as a white solid according to procedures described in Example 18 by using (+)-2-(3-(3-(4-chloro-3,5-dimethylphenoxy)propyl)-1H-indol-1-yl)propanoic acid (11 mg, 0.027 mmol). MS (ES) 477.2 (M+H).

Example 61

Preparation of 2-(3-(3-(4-chloro-3,5-dimethylphenoxy)propyl)-1H-indol-1-yl)ethanesulfonic acid Step A. Preparation of phenyl 2-(3-(3-(4-chloro-3,5-dimethylphenoxy)propyl)-1H-indol-1-yl)ethanesulfonate: To a solution of 3-(3-(4-chloro-3,5-dimethylphenoxy)propyl)-1H-indole (100 mg, 0.31 mmol) and Phenyl vinylsulfonate (65 mg, 0.35 mmol) in DMF was added LiHMDS (1.0M in THF 0.35 mL, 0.35 mmol) at 0° C. The reaction mixture was stirred for 20 min at 0° C. then warmed to 20° C. and stirred for additional 15h. The reaction was quenched by addition of $H_2O$, extracted with EtOAc, dried over $MgSO_4$, filtered and concentrated in vacuo. The crude product was purified by flash chromatography (Combi-flash Rf Hexane/EtOAc gradient 0-50%) to give the title compound (75 mg, 0.15 mmol) as a yellow oil. MS (ES) 498.1 (M+H).

Step B: To a solution of phenyl 2-(3-(3-(4-chloro-3,5-dimethylphenoxy)propyl)-1H-indol-1-yl)ethanesulfonate (10 mg, 0.02 mmol) in EtOH (2.0 mL) was added NaOH (50% aq. 75 L) and stirred for 3h at 50° C. The reaction was quenched by addition of 1N HCl and concentrated in vacuo. The residue was purified by reserve phase HPLC (Phenomenex Gemini C18, $H_2O$/$CH_3CN$ gradient to 95% $CH_3CN$ 0.1% TFA) to give the title compound product (5 mg, 0.12 mmol) as a white solid. MS (ES) 422.1 (M+H).

Example 62

Preparation of 2-(1-(2-(4-chloro-3,5-dimethylphenoxy)ethyl)-1H-indol-3-yl)acetic acid Step A. Preparation of methyl 2-(1-(2-(4-chloro-3,5-dimethylphenoxy)ethyl)-1H-indol-3-yl)acetate: Title compound was prepared according to procedures described in Example 1 Step A by using methyl 2-(1H-indol-3-yl)acetate (95 mg, 0.5 mmol) and 5-(2-bromoethoxy)-2-chloro-1,3-dimethylbenzene (264 mg, 1.0 mmol). MS (ES) 372.1 (M+H).

Step B: Title compound (58 mg, 0.16 mmol) was prepared according to procedures described in Example 1 Step B by using methyl methyl 2-(1-(2-(4-chloro-3,5-dimethylphenoxy)ethyl)-1H-indol-3-yl)acetate. MS (ES) 358.1 (M+H).

Example 63

Preparation of 2-(7-bromo-3-(3-(4-chloro-3,5-dimethylphenoxy)propyl)-2-methyl-1H-indol-1-yl)acetic acid Step A. Preparation of ethyl 3-(7-bromo-2-methyl-1H-indol-3-yl)propanoate: To a solution of 2-bromopehenyl hydrazine hydrochloride (13.0 g, 58.2 mmol) in EtOH (90 mL) was added 6-methyl-3,4-dihydro-2H-pyran-2-one (5.99 mL, 62.5 mmol), followed by adding concentrated sulfuric acid (6 mL). The reaction mixture was heated for 36 h under reflux condition then solvent was removed in vacuo. The residue was purified by column chromatography using Hex/EtOAc (Combi-flash Rf, 0 to 30% EtOAc gradient) to afford the title compound as a yellow oil (12.4 g, 69%). $^1$H NMR ($CDCl_3$, 400 MHz) δ (ppm) 7.96 (s, 1H), 7.45 (dd, J=8.0, 3.6 Hz, 1H), 7.27 (d, J=8.0 Hz, 1H), 6.98 (t, J=8.0 Hz, 1H), 4.13 (q, J=7.2 Hz, 2H), 3.03 (t, J=8.8 Hz, 2H), 2.64 (q, J=7.6 Hz, 2H), 2.45 (s, 3H), 1.24 (t, J=7.2 Hz, 3H); LCMS (ESI) tR: 1.161 min (>99%, ELSD), m/z: 311.1 (M+H).

Step B. Preparation of 3-(7-bromo-2-methyl-1H-indol-3-yl)propan-1-ol: To a solution of ethyl 3-(7-bromo-2-methyl-1H-indol-3-yl)propanoate (12.4 g, 39.9 mmol) in THF (133 mL) was added $BH_3$.THF (79.8 mL, 1M solution in THF) at 0° C. The reaction mixture was stirred for overnight at room temperature then quenched with methanol (100 mL). The solvent was removed in vacuo and residue was purified by column chromatography using Hex/EtOAc (Combi-flash Rf, 0 to 60% EtOAc gradient) to afford the title compound (9.52 g, 89%). $^1$H NMR ($CDCl_3$, 400 MHz) δ (ppm) 7.94 (s, 1H), 7.46 (d, J=8.0 Hz, 1H), 7.27 (d, J=8.0 Hz, 1H), 6.97 (t, J=8.0 Hz, 1H), 3.68 (t, J=6.0 Hz, 2H), 2.80 (t, J=7.2 Hz, 2H), 2.44 (s, 3H), 1.90 (qt, J=7.2 Hz, 2H); LCMS (ESI) tR: 0.955 min (>99%, ELSD), m/z: 270.1 (M+H).

Step C. Preparation of 7-bromo-3-(3-(4-chloro-3,5-dimethylphenoxy)propyl)-2-methyl-1H-indole: To a solution of di-tert-butyl diazocarboxylate (8.96 g, 38.9 mmol) in THF (120 mL) was added triphenyl phosphine (10.2 g, 38.9 mmol) followed by addition of 3-(7-bromo-2-methyl-1H-indol-3-yl)propan-1-ol (8.02 g, 29.92 mmol) in THF (20 mL). The reaction mixture was stirred at 0° C. for 15 min. 4-chloro-3,5dimethylphenol (6.05 g, 38.9 mmol) in anhydrous tetrahydrofurane (20 mL) was added to the reaction mixture at 0° C. The reaction mixture was allowed to worm up to room temperature and stirred additionally for 5 h. The solvent was removed in vacuo and the residue was purified by column chromatography using Hex/EtOAc (Combi-flash Rf, 0 to 15% EtOAc gradient) to afford the title compound (9.66 g, 80%). $^1$H NMR ($CDCl_3$, 400 MHz) δ (ppm) 7.89 (s, 1H), 7.42 (d, J=8.0 Hz, 1H), 7.25 (d, J=8.0 Hz, 1H), 6.93 (t, J=8.0 Hz, 1H), 6.60 (s, 2H), 3.84 (t, J=6.0 Hz, 2H), 2.87 (t, J=7.2 Hz, 2H), 2.36 (s, 3H), 2.32 (s, 6H), 2.07 (qt, J=6.0 Hz, 2H); LCMS (ESI) tR: 1.700 min (>99%, ELSD), m/z: 408.1 (M+H).

Step D. Preparation of ethyl-2-(7-bromo-3-(3-(4-chloro-3,5-dimethylphenoxy)propyl)-2-methyl-1H-indol-1-yl)acetate: To a solution of 7-bromo-3-(3-(4-chloro-3,5-dimethylphenoxy)propyl)-2-methyl-1H-indole (3.0 g, 7.38 mmol) in acetonitrile (15 mL) was added cesium carbonate (4.33 g, 13.3 mmol) and ethyl 2-bromoacetate (1.22 mL, 11.1 mmol). The reaction mixture was heated at 125° C. for 2 h under microwave condition. The residual cesium carbonate was removed by filtration and solvent was concentrated in vacuo. The residue was purified by column chromatography using Hex/EtOAc (Combi-flash Rf, 0 to 20% EtOAc gradient) to afford the title compound (2.95 g, 81%). $^1$H NMR ($CDCl_3$, 400 MHz) δ (ppm) 7.43 (d, J=8.0 Hz, 1H), 7.25 (d, J=8.0 Hz, 1H), 6.90 (t, J=8.0 Hz, 1H), 6.60 (s, 2H), 4.22 (q, J=6.8 Hz, 2H), 3.84 (t, J=6.0 Hz, 2H), 2.90 (t, J=7.2 Hz, 2H), 2.32 (s, 6H), 2.22 (s, 3H), 2.03 (qt, J=6.0 Hz, 2H), 1.26 (t, J=6.8 Hz, 3H); LCMS (ESI) tR: 1.750 min (>99%, ELSD), m/z: 494.1 (M+H).

Step E. To a solution of ethyl-2-(7-bromo-3-(3-(4-chloro-3,5-dimethylphenoxy)propyl)-2-methyl-1H-indol-1-yl)acetate (0.99 g, 2.01 mmol) in mixture of methanol and dioxane (10 mL/5 mL) was added 2M sodium hydroxide (2 mL). The reaction mixture was stirred for 3h at room temperature, acidified with 1 N HCl (2 mL), concentrated in vacuo, and recrystallized from hot methanol to afford the title compound (0.88 g, 94%). LCMS (ESI) tR: 1.544 min (>99%, ELSD), m/z: 464.1 (M+H).

Example 64

Preparation of 2-(3-(3-(4-chloro-3,5-dimethylphenoxy)propyl)-2-methyl-7-(1-methyl-1H-pyrazol-5-yl)-1H-indol-1-yl)acetic acid To a solution of 2-(7-bromo-3-(3-(4-chloro-3,5-dimethylphenoxy)propyl)-2-methyl-1H-indol-1-yl)acetic acid (50 mg, 0.108 mmol) in MeOH/DME (½ mL) was added cesium fluoride (49 mg, 0.324 mmol), Pd(PPh$_3$)$_4$(7 mg, cat.), and (1-methyl-1H-pyrazol-5-yl)boronic acid (15 mg, 0.118 mmol) under Ar at room temperature. The reaction mixture was heated at 120° C. for 20 min under microwave condition and solvent was concentrated in vacuo. The residue was purified by column chromatography using dichloromethane/MeOH (Combi-flash Rf, 0 to 30% MeOH gradient) to afford the title compound. $^1$H NMR (MeOD, 400 MHz) δ (ppm) 7.61 (d, J=7.2 Hz, 1H), 7.58 (d, J=2.0 Hz, 1H), 7.08 (t, J=7.6 Hz, 1H), 6.90 (d, J=6.8 Hz, 1H), 6.69 (s, 2H), 6.36 (d, J=2.0 Hz, 1H), 4.47 (d, J=18.8 Hz, 1H), 4.17 (d, J=18.8 Hz, 1H), 3.91 (t, J=6.0 Hz, 2H), 3.58 (s, 3H), 2.98 (t, J=6.8 Hz, 2H), 2.32 (s, 6H), 2.23 (s, 3H), 2.08 (qt, J=6.4 Hz, 2H); LCMS (ESI) tR: 1.324 min (>99%, ELSD), m/z: 466.1 (M+H).

Example 65

Preparation of 2-(3-(3-(4-chloro-3,5-dimethylphenoxy)propyl)-2-methyl-7-(4-methylpyridin-3-yl)-1H-indol-1-yl)acetic acid Title compound was synthesized as a white solid according to procedures described in Example 64 using 2-(7-bromo-3-(3-(4-chloro-3,5-dimethylphenoxy)propyl)-2-methyl-1H-indol-1-yl)acetic acid and methyl (4-methylpyridin-3-yl)boronic acid. LCMS (ESI) tR: 1.155 min (>99%, ELSD), m/z: 477.1 (M+H).

Example 66

Preparation of 2-(3-(3-(4-chloro-3,5-dimethylphenoxy)propyl)-7-(3,5-dimethylisoxazol-4-yl)-2-methyl-1H-indol-1-yl)acetic acid Title compound was synthesized as a white solid according to procedures described in Example 64 using 2-(7-bromo-3-(3-(4-chloro-3,5-dimethylphenoxy)propyl)-2-methyl-1H-indol-1-yl)acetic acid and (3,5-dimethylisoxazol-4-yl)boronic acid. LCMS (ESI) tR: 1.376 min (>99%, ELSD), m/z: 481.1 (M+H).

Example 67

Preparation of 2-(1-(2-(4-chloro-3,5-dimethylphenoxy)ethyl)-1H-indol-3-yl)acetic acid Title compound was synthesized as a white solid according to procedures described in Example 64 using 2-(7-bromo-3-(3-(4-chloro-3,5-dimethylphenoxy)propyl)-2-methyl-1H-indol-1-yl)acetic acid and (3-methylpyridin-4-yl)boronic acid. LCMS (ESI) tR: 1.201 min (>99%, ELSD), m/z: 477.1 (M+H).

Example 68

Preparation of 2-(3-(3-(4-chloro-3,5-dimethylphenoxy)propyl)-2-methyl-7-(1-methyl-1H-pyrrol-2-yl)-1H-indol-1-yl)acetic acid Title compound was synthesized as a white solid according to procedures described in Example 64 using 2-(7-bromo-3-(3-(4-chloro-3,5-dimethylphenoxy)propyl)-2-methyl-1H-indol-1-yl)acetic acid and 1-methyl-2-(4,4,5,5-tetramethyl-1,3,2-dioxaborolan-2-yl)-1H-pyrrole. LCMS (ESI) tR: 1.429 min (>99%, ELSD), m/z: 465.1 (M+H).

Example 69

Preparation of 2-(1-(2-(4-chloro-3,5-dimethylphenoxy)ethyl)-1H-indol-3-yl)acetic acid Title compound was synthesized as a white solid according to procedures described in Example 64 using 2-(7-bromo-3-(3-(4-chloro-3,5-dimethylphenoxy)propyl)-2-methyl-1H-indol-1-yl)acetic acid and 3,5-dimethyl-4-(4,4,5,5-tetramethyl-1,3,2-dioxaborolan-2-yl)-1H-pyrazole. $^1$H NMR (DMSO, 400 MHz) δ (ppm) 7.42 (d, J=8.0 Hz, 1H), 6.97 (t, J=8.0 Hz, 1H), 6.75 (s, 2H), 6.65 (d, J=8.0 Hz, 1H), 4.43 (s, 2H), 3.91 (t, J=6.4 Hz, 2H), 2.82 (t, J=7.2 Hz, 2H), 2.25 (s, 6H), 2.13 (s, 3H), 1.95 (qt, J=6.4 Hz, 2H), 1.89 (s, 6H); LCMS (ESI) tR: 1.201 min (>99%, ELSD), m/z: 480.2 (M+H).

Example 70

Preparation of 3-(3-(3-(4-chloro-3,5-dimethylphenoxy)propyl)-2-methyl-7-(1-methyl-1H-pyrazol-5-yl)-1H-indol-1-yl)propanoic acid Step A. Preparation of methyl 3-(7-bromo-3-(3-(4-chloro-3,5-dimethylphenoxy)propyl)-2-methyl-1H-indol-1-yl) propanoate: To a solution of 7-bromo-3-(3-(4-chloro-3,5-dimethylphenoxy)propyl)-2-methyl-1H-indole (3.0 g, 7.38 mmol) in acetonitrile (37 mL) was added methyl acrylate (8 mL) and DBU (4.41 mL, 29.52 mmol). The reaction mixture was heated for 2 h under reflux condition and solvent was removed in vacuo. The residue was diluted in EtOAc (30 mL), washed with water (50 mL) and dried over MgSO$_4$. The residue was purified by column chromatography using Hex/EtOAc (Combi-flash Rf, 0 to 20% EtOAc gradient) to afford the title compound (3.28 g, 77%). LCMS (ESI) tR: 1.768 min (>99%, ELSD), m/z: 494.1 (M+H).

Step B. To a solution of methyl 3-(7-bromo-3-(3-(4-chloro-3,5-dimethylphenoxy)propyl)-2-methyl-1H-indol-1-yl) propanoate (50 mg, 0.10 mmol) in 2.4 mL of DME/EtOH/H$_2$O (7:2:3) was added sodium carbonate (0.6 mL, 1M solution), Pd(PPh$_3$)$_2$Cl$_2$ (7 mg, cat.), and (1-methyl-1H-pyrazol-5-yl)boronic acid (38 mg, 0.30 mmol) at room temperature. The reaction mixture was heated at 150° C. for 30 min under microwave condition and solvent was concentrated in vacuo. The residue was purified by column chromatography using dichloromethane/MeOH (Combi-flash Rf, 0 to 30% MeOH gradient) to afford the title compound. LCMS (ESI) tR: 1.348 min (>99%, ELSD), m/z: 480.1 (M+H).

Example 71

Preparation of 3-(3-(3-(4-chloro-3,5-dimethylphenoxy)propyl)-2-methyl-7-(4-methylpyridin-3-yl)-1H-indol-1-yl)propanoic acid The title compound was synthesized according to the procedure described in Example 70 Step B using methyl 3-(7-bromo-3-(3-(4-chloro-3,5-dimethylphenoxy)propyl)-2-methyl-1H-indol-1-yl) propanoate and methyl (4-methylpyridin-3-yl)boronic acid. LCMS (ESI) tR: 1.208 min (>99%, ELSD), m/z: 491.1 (M+H).

Example 72

Preparation of 3-(3-(3-(4-chloro-3,5-dimethylphenoxy)propyl)-2-methyl-7-(3-methylpyridin-4-yl)-1H-indol-1-yl)propanoic acid The title compound was synthesized according to the procedure described in Example 70 Step B using methyl 3-(7-bromo-3-(3-(4-chloro-3,5-dimethylphenoxy)propyl)-2-methyl-1H-indol-1-yl) propanoate and (3-methylpyridin-4-yl)boronic acid. LCMS (ESI) tR: 1.213 min (>99%, ELSD), m/z: 491.1 (M+H).

Example 73

Preparation of 3-(3-(3-(4-chloro-3,5-dimethylphenoxy)propyl)-2-methyl-7-(1-methyl-1H-pyrrol-2-yl)-1H-indol-1-yl)propanoic acid The title compound was synthesized according to the procedure described in Example 70 Step B using methyl 3-(7-bromo-3-(3-(4-chloro-3,5-dimethylphenoxy)propyl)-2-methyl-1H-indol-1-yl) propanoate and 1-methyl-2-(4,4,5,5-tetramethyl-1,3,2-dioxaborolan-2-yl)-1H-pyrrole. LCMS (ESI) tR: 1.469 min (>99%, ELSD), m/z: 479.2 (M+H).

Example 74

Preparation of 3-(3-(3-(4-chloro-3,5-dimethylphenoxy)propyl)-7-(3,5-dimethyl-1H-pyrazol-4-yl)-2-methyl-1H-indol-1-yl)propanoic acid The title compound was synthesized according to the procedure described in Example 70 Step B using methyl 3-(7-bromo-3-(3-(4-chloro-3,5-dimethylphenoxy)propyl)-2-methyl-1H-indol-1-yl) propanoate and 3,5-dimethyl-4-(4,4,5,5-tetramethyl-1,3,2-dioxaborolan-2-yl)-1H-pyrazole. $^1$H NMR (MeOD, 400 MHz) δ (ppm) 7.45 (d, J=6.8 Hz, 1H), 7.01 (t, J=6.8 Hz, 1H), 6.74 (d, J=6.8 Hz, 1H), 6.65 (s, 2H), 4.01 (t, J=8.0 Hz, 2H), 3.88 (t, J=6.0 Hz, 2H), 2.92 (t, J=7.2 Hz, 2H), 2.28 (s, 9H), 2.08 (s, 6H), 2.10-2.01 (m, 4H); LCMS (ESI) tR: 1.262 min (>99%, ELSD), m/z: 494.1 (M+H).

Example 75

Preparation of 3-(3-(3-(4-chloro-3,5-dimethylphenoxy)propyl)-2-methyl-7-(2-methylpyridin-3-yl)-1H-indol-1-yl)propanoic acid The title compound was synthesized according to the procedure described in Example 70 Step B using methyl 3-(7-bromo-3-(3-(4-chloro-3,5-dimethylphenoxy)propyl)-2-methyl-1H-indol-1-yl) propanoate and (2-methylpyridin-3-yl)boronic acid. LCMS (ESI) tR: 1.213 min (>99%, ELSD), m/z: 491.1 (M+H).

Example 76

Preparation of 3-(3-(3-(4-chloro-3,5-dimethylphenoxy)propyl)-2-methyl-7-(1,3,5-trimethyl-1H-pyrazol-4-yl)-1H-indol-1-yl)propanoic acid To a solution of 3-(3-(3-(4-chloro-3,5-dimethylphenoxy)propyl)-7-(3,5-dimethyl-1H-pyrazol-4-yl)-2-methyl-1H-indol-1-yl)propanoic acid (35 mg, 0.07 mmol) in DMF (1.5 mL) was added sodium hydride (6 mg, 60% in mineral oil) at 0° C. After stirring 30 min at 0° C., methyl iodide (13 μL, 0.21 mmol) was added to reaction mixture. The reaction mixture was stirred for 5 h at room temperature, quenched with water, extracted with EtOAc and dried over MgSO$_4$. The residual ester compound was dissolved in MeOH (2 mL), treated with NaOH (0.1 mL, 2M solution), stirred for 2 h, and acidified with 1N HCl (1 mL). The residue was extracted with EtOAc, dried over MgSO$_4$, and purified by column chromatography using dichloromethane/MeOH (Combi-flash Rf, 0 to 30% MeOH gradient) to afford the title compound. LCMS (ESI) tR: 1.285 min (>99%, ELSD), m/z: 508.2 (M+H).

Example 77

Preparation of 3-(3-(3-(4-chloro-3,5-dimethylphenoxy)propyl)-7-(1-ethyl-3,5-dimethyl-1H-pyrazol-4-yl)-2-methyl-1H-indol-1-yl)propanoic acid The title compound was synthesized according to the procedure described in Example 76 using 3-(3-(3-(4-chloro-3,5-dimethylphenoxy)propyl)-7-(3,5-dimethyl-1H-pyrazol-4-yl)-2-methyl-1H-indol-1-yl)propanoic acid and ethyl iodide. LCMS (ESI) tR: 1.308 min (>99%, ELSD), m/z: 522.1 (M+H).

Example 78

Preparation of 3-(3-(3-(4-chloro-3,5-dimethylphenoxy)propyl)-7-(1-isopropyl-3,5-dimethyl-1H-pyrazol-4-yl)-2-methyl-1H-indol-1-yl)propanoic acid The title compound was synthesized according to the procedure described in Example 76 using 3-(3-(3-(4-chloro-3,5-dimethylphenoxy)propyl)-7-(3,5-dimethyl-1H-pyrazol-4-yl)-2-methyl-1H-indol-1-yl)propanoic acid and 2-bromopropane. LCMS (ESI) tR: 1.326 min (>99%, ELSD), m/z: 536.2 (M+H).

Example 79

Preparation of 3-(3-(3-(4-chloro-3,5-dimethylphenoxy)propyl)-7-(3,5-dimethyl-1-(2-morpholinoethyl)-1H-pyrazol-4-yl)-2-methyl-1H-indol-1-yl)propanoic acid The title compound was synthesized according to the procedure described in Example 76 using 3-(3-(3-(4-chloro-3,5-dimethylphenoxy)propyl)-7-(3,5-dimethyl-1H-pyrazol-4-yl)-2-methyl-1H-indol-1-yl)propanoic acid and 4-(2-chloroethyl)morpholine. LCMS (ESI) tR: 1.224 min (>99%, ELSD), m/z: 607.3 (M+H).

Example 80

Preparation of 3-(3-(3-(4-chloro-3,5-dimethylphenoxy)propyl)-7-(3,5-dimethyl-1-(2-(pyrrolidin-1-yl)ethyl)-1H-pyrazol-4-yl)-2-methyl-1H-indol-1-yl)propanoic acid The title compound was synthesized according to the procedure described in Example 76 using 3-(3-(3-(4-chloro-3,5-dimethylphenoxy)propyl)-7-(3,5-dimethyl-1H-pyrazol-4-yl)-2-methyl-1H-indol-1-yl)propanoic acid and 1-(2-chloroethyl)pyrrolidine. LCMS (ESI) tR: 1.224 min (>99%, ELSD), m/z: 591.3 (M+H).

Example 81

Preparation of 3-(3-(3-(4-chloro-3,5-dimethylphenoxy)propyl)-2-methyl-7-(1-methyl-1H-pyrazol-5-yl)-1H-indol-1-yl)-N-(methylsulfonyl)propanamide To a solution of 3-(3-(3-(4-chloro-3,5-dimethylphenoxy)propyl)-2-methyl-7-(1-methyl-1H-pyrazol-5-yl)-1H-indol-1-yl)propanoic acid (16 mg, 0.033 mmol) in dichloromethane (1.5 mL) was added methanesulfonamide (5 mg, 0.05 mmol), EDCI (13 mg, 0.66 mmol) and catalytic amount of DMAP. The reaction mixture was stirred for 5 h at room temperature and solvent was removed in vacuo. The residue was purified by column chromatography using dichloromethane/MeOH (Combi-flash Rf, 0 to 15% MeOH gradient) to afford the title compound as a white solid. LCMS (ESI) tR: 1.299 min (>99%, ELSD), m/z: 557.1 (M+H).

Example 82

Preparation of 3-(3-(3-(4-chloro-3,5-dimethylphenoxy)propyl)-2-methyl-7-(4-methylpyridin-3-yl)-1H-indol-1-yl)-N-(methylsulfonyl)propanamide The title compound was synthesized according to the procedure described in Example 81 using methanesulfonamide and 3-(3-(3-(4-chloro-3,5-dimethylphenoxy)propyl)-2-methyl-7-(4-methylpyridin-3-yl)-1H-indol-1-yl)propanoic acid. LCMS (ESI) tR: 1.165 min (>99%, ELSD), m/z: 568.2 (M+H).

Example 83

Preparation of 3-(3-(3-(4-chloro-3,5-dimethylphenoxy)propyl)-2-methyl-7-(3-methylpyridin-4-yl)-1H-indol-1-yl)-N-(methylsulfonyl)propanamide The title compound was synthesized according to the procedure described in Example 81 using methanesulfonamide and 3-(3-(3-(4-chloro-3,5-dimethylphenoxy)propyl)-2-methyl-7-(3-methylpyridin-4-yl)-1H-indol-1-yl)propanoic acid. LCMS (ESI) tR: 1.166 min (>99%, ELSD), m/z: 568.1 (M+H).

Example 84

Preparation of 3-(3-(3-(4-chloro-3,5-dimethylphenoxy)propyl)-2-methyl-7-(1-methyl-1H-pyrrol-2-yl)-1H-indol-1-yl)-N-(methylsulfonyl)propanamide The title compound was synthesized according to the procedure described in Example 81 using methanesulfonamide and 3-(3-(3-(4-chloro-3,5-dimethylphenoxy)propyl)-2-methyl-7-(1-methyl-1H-pyrrol-2-yl)-1H-indol-1-yl)propanoic acid. LCMS (ESI) tR: 1.398 min (>99%, ELSD), m/z: 556.1 (M+H).

Example 85

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-(methylsulfonyl)propanamide The title compound was synthesized according to the procedure described in Example 81 using methanesulfonamide and 3-(3-(3-(4-chloro-3,5-dimethylphenoxy)propyl)-2-methyl-7-(1,3,5-trimethyl-1H-pyrazol-4-yl)-1H-indol-1-yl)propanoic acid. $^1$H NMR (MeOD, 400 MHz) δ (ppm) 7.47 (d, J=8.0 Hz, 1H), 7.04 (t, J=7.6 Hz, 1H), 6.77 (d, J=7.6 Hz, 1H), 6.70 (s, 2H), 4.08 (t, J=7.6 Hz, 2H), 3.92 (t, J=6.0 Hz, 2H), 3.23 (s, 3H), 3.15 (s, 3H), 2.94 (t, J=7.2 Hz, 2H), 2.32 (s, 6H), 2.25-2.08 (m, 4H), 2.15 (s, 3H), 2.07 (s, 6H), 2.01 (s, 3H); LCMS (ESI) tR: 1.257 min (>99%, ELSD), m/z: 585.2 (M+H).

Example 86

Preparation of 3-(3-(3-(4-chloro-3,5-dimethylphenoxy)propyl)-7-(1-ethyl-3,5-dimethyl-1H-pyrazol-4-yl)-2-methyl-1H-indol-1-yl)-N-(methylsulfonyl)propanamide The title compound was synthesized according to the procedure described in Example 81 using methanesulfonamide and 3-(3-(3-(4-chloro-3,5-dimethylphenoxy)propyl)-7-(1-ethyl-3,5-dimethyl-1H-pyrazol-4-yl)-2-methyl-1H-indol-1-yl)propanoic acid. LCMS (ESI) tR: 1.288 min (>99%, ELSD), m/z: 599.2 (M+H).

Example 87

Preparation of 3-(3-(3-(4-chloro-3,5-dimethylphenoxy)propyl)-7-(1-ethyl-3,5-dimethyl-1H-pyrazol-4-yl)-2-methyl-1H-indol-1-yl)-N-(phenylsulfonyl)propanamide The title compound was synthesized according to the procedure described in Example 81 using benzenesulfonamide and 3-(3-(3-(4-chloro-3,5-dimethylphenoxy)propyl)-7-(1-ethyl-3,5-dimethyl-1H-pyrazol-4-yl)-2-methyl-1H-indol-1-yl)propanoic acid. LCMS (ESI) tR: 1.366 min (>99%, ELSD), m/z: 661.2 (M+H).

Example 88

Preparation of N-(benzylsulfonyl)-3-(3-(3-(4-chloro-3,5-dimethylphenoxy)propyl)-2-methyl-7-(1,3,5-trimethyl-1H-pyrazol-4-yl)-1H-indol-1-yl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and phenylmathanesulfonamide. LCMS (ESI) tR: 1.352 min (>99%, ELSD), m/z: 661.2 (M+H).

Example 89

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-(naphthalen-2-ylsulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and naphthalene-2-sulfonamide. LCMS (ESI) tR: 1.385 min (>99%, ELSD), m/z: 697.2 (M+H).

Example 90

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-((4-phenoxyphenyl)sulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and 4-phenoxybenzenesulfonamide. LCMS (ESI) tR: 1.435 min (>99%, ELSD), m/z: 739.2 (M+H).

Example 91

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-((2-nitrophenyl)sulfonyl)propanamide The title compound was synthesized according to the procedure described in Example 81 using 3-(3-(3-(4-chloro- 3,5-dimethylphenoxy)propyl)-2-methyl-7-(1,3,5-trimethyl-1H-pyrazol-4-yl)-1H-indol-1-yl)propanoic acid and 2-nitrobenzenesulfonamide. LCMS (ESI) tR: 1.334 min (>99%, ELSD), m/z: 692.1 (M+H).

Example 92

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-((3-nitrophenyl)sulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and 3-nitrobenzenesulfonamide. LCMS (ESI) tR: 1.343 min (>99%, ELSD), m/z: 692.1 (M+H).

Example 93

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-((4-nitrophenyl)sulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and 4-nitrobenzenesulfonamide. LCMS (ESI) tR: 1.343 min (>99%, ELSD), m/z: 692.2 (M+H).

Example 94

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-(pyridin-2-ylsulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and pyridine-2-sulfonamide. LCMS (ESI) tR: 1.282 min (>99%, ELSD), m/z: 648.2 (M+H).

Example 95

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-(pyridin-3-ylsulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and pyridine-3-sulfonamide. LCMS (ESI) tR: 1.282 min (>99%, ELSD), m/z: 648.2 (M+H).

Example 96

Preparation of 3-(3-(3-(4-chloro-3,5-dimethylphenoxy)propyl)-2-methyl-7-(1,3,5-trimethyl-1H-pyrazol-4-yl)-1H-indol-1-yl)-N-(pyridin-4-ylsulfonyl)propanamide The title compound was synthesized according to the procedure described in Example 81 using 3-(3-(3-(4-chloro-3,5-dimethylphenoxy)propyl)-2-methyl-7-(1,3,5-trimethyl-1H-pyrazol-4-yl)-1H-indol-1-yl)propanoic acid and pyridine-4-sulfonamide. LCMS (ESI) tR: 1.282 min (>99%, ELSD), m/z: 648.2 (M+H).

Example 97

Preparation of 2-((3-(3-(4-chloro-3,5-dimethylphenoxy)propyl)-7-(3,5-dimethyl-1H-pyrazol-4-yl)-2-methyl-1H-indol-1-yl)methyl)benzoic acid Step A. Preparation of methyl 2-((7-bromo-3-(3-(4-chloro-3,5-dimethylphenoxy)propyl)-2-methyl-1H-indol-1-yl) methyl)benzoate: To a solution of 7-bromo-3-(4-(4-chloro-3,5-dimethylphenyl)butyl)-2-methyl-1H-indole (0.35 g, 0.86 mmol) in acetonitrile (15 mL) was added cesium carbonate (0.48 g, 1.46 mmol) and methyl 2-(bromomethyl)benzoate (0.26 g, 1.12 mmol). The reaction mixture was heated at 120° C. for 40 min under microwave condition. The residual cesium carbonate was removed by filtration and solvent was concentrated in vacuo. The residue was purified by column chromatography using Hex/EtOAc (Combi-flash Rf, 0 to 50% EtOAc gradient) to afford the title compound. LCMS (ESI) tR: 1.557 min (>99%, ELSD), m/z: 554.0 (M+H).

Step B: To a solution of methyl 2-((7-bromo-3-(3-(4-chloro-3,5-dimethylphenoxy)propyl)-2-methyl-1H-indol-1-yl) methyl)benzoate (50 mg, 0.10 mmol) in 2.7 mL of dioxane/water (3:1) was added potassium carbonate (37 mg, 0.27 mmol), Pd(PPh$_3$)$_4$ (10 mg, cat.), and 3,5-dimethyl-4-(4,4,5,5-tetramethyl-1,3,2-dioxaborolan-2-yl)-1H-pyrazole (26 mg, 0.12 mmol) at room temperature. The reaction mixture was heated at 160° C. for 15 min under microwave condition and solvent was concentrated in vacuo. The residue was dissolved in dioxane (1 mL), treated with NaOH (50 μL, 2M solution), stirred for 2 h, and acidified with 1N HCl (1 mL). The residue was extracted with EtOAc, dried over MgSO$_4$, and purified by reverse phase prep. HPLC (Phenomenex Gemini C18, H$_2$O/CH$_3$CN gradient to 95% CH$_3$CN 0.1% TFA) to afford the title compound. LCMS (ESI) 556.2 (M+H).

Example 98

Preparation of 4-((3-(3-(4-chloro-3,5-dimethylphenoxy)propyl)-7-(3,5-dimethyl-1H-pyrazol-4-yl)-2-methyl-1H-indol-1-yl)methyl)benzoic acid Step A. Preparation of methyl 4-((7-bromo-3-(3-(4-chloro-3,5-dimethylphenoxy)propyl)-2-methyl-1H-indol-1-yl) methyl)benzoate: The title compound was synthesized according to the procedure described in Example 97 Step A using 7-bromo-3-(3-(4-chloro-3,5-dimethylphenoxy)propyl)-2-methyl-1H-indole and 4-(bromomethyl)benzoate. $^1$H NMR (CDCl$_3$, 400 MHz) δ (ppm) 7.91 (d, J=8.0 Hz, 2H), 7.50 (d, J=8.0 Hz, 1H), 7.27 (d, J=7.6 Hz, 1H), 6.95-6.88 (m, 3H), 6.65 (s, 2H), 5.85 (s, 2H), 3.88 (s, 3H), 3.84 (t, J=6.0 Hz, 2H), 2.94 (t, J=7.2 Hz, 2H), 2.31 (s, 6H), 2.19 (s, 3H), 2.07 (t, J=6.4 Hz, 2H); LCMS (ESI) tR: 1.538 min (>99%, ELSD), m/z: 554.2 (M+H).

Step B: The title compound was synthesized according to the procedure described in Example 97 Step B using 4-((7-bromo-3-(3-(4-chloro-3,5-dimethylphenoxy)propyl)-2-methyl-1H-indol-1-yl) methyl)benzoate. LCMS (ESI) tR: 1.183 min (>99%, ELSD), m/z: 556.2 [M+1]+

Example 99

Preparation of 5-((3-(3-(4-chloro-3,5-dimethylphenoxy)propyl)-7-(3,5-dimethyl-1H-pyrazol-4-yl)-2-methyl-1H-indol-1-yl)methyl)furan-2-carboxylic acid Step A. Preparation of methyl 5-((7-bromo-3-(3-(4-chloro-3,5-dimethylphenoxy)propyl)-2-methyl-1H-indol-1-yl)methyl)furan-2-carboxylate: The title compound was synthesized according to the procedure described in Example 97 Step A using 7-bromo-3-(4-(4-chloro-3,5-dimethylphenyl)butyl)-2-methyl-1H-indole and methyl 5-(chloromethyl)furan-2-carboxylate. $^1$H NMR (CDCl$_3$, 400 MHz) δ (ppm) 7.48 (d, J=7.6 Hz, 2H), 7.30 (d, J=7.6, 1H), 7.03 (d, J=7.6, 1H), 6.94 (t, J=7.6, 1H), 6.62 (s, 2H), 5.83 (s, 1H), 5.82 (s, 2H), 3.90 (s, 3H), 3.87 (t, J=6.0 Hz, 2H), 2.94 (t, J=7.2 Hz, 2H), 2.34 (s, 6H), 2.33 (s, 3H), 2.07 (qt, J=6.0 Hz, 2H); LCMS (ESI) tR: 1.533 min (>99%, ELSD), m/z: 544.1 [M+1]+

Step B: The title compound was synthesized according to the procedure described in Example 97 Step B using methyl 5-((7-bromo-3-(3-(4-chloro-3,5-dimethylphenoxy)propyl)-2-methyl-1H-indol-1-yl)methyl)furan-2-carboxylate. LCMS (ESI) tR: 1.223 min (>99%, ELSD), m/z: 546.1 (M+H).

Example 100

Preparation of 3-((3-(3-(4-chloro-3,5-dimethylphenoxy)propyl)-7-(3,5-dimethyl-1H-pyrazol-4-yl)-2-methyl-1H-indol-1-yl)methyl)benzoic acid Step A. Preparation of methyl 3-((7-bromo-3-(3-(4-chloro-3,5-dimethylphenoxy)propyl)-2-methyl-1H-indol-1-yl) methyl)benzoate: The title compound was synthesized according to the procedure described in Example 97 Step A using 7-bromo-3-(3-(4-chloro-3,5-dimethylphenoxy)propyl)-2-methyl-1H-indole and 3-(bromomethyl)benzoate. $^1$H NMR (CDCl$_3$, 400 MHz) δ (ppm) 7.93 (d, J=8.0 Hz, 2H), 7.74 (s, 1H), 7.54 (dd, J=8.0, 1.2 Hz, 1H), 7.34-7.28 (m, 2H), 6.98-6.92 (m, 2H), 6.63 (s, 2H), 5.88 (s, 2H), 3.91 (s, 3H), 3.89 (t, J=6.0 Hz, 2H), 2.98 (t, J=7.2 Hz, 2H), 2.34 (s, 6H), 2.23 (s, 3H), 2.11 (t, J=6.0 Hz, 2H); LCMS (ESI) tR: 1.607 min (>99%, ELSD), m/z: 554.1 (M+H).

Step B: The title compound was synthesized according to the procedure described in Example 97 Step B using 3-((7-bromo-3-(3-(4-chloro-3,5-dimethylphenoxy)propyl)-2-methyl-1H-indol-1-yl) methyl)benzoate. LCMS (ESI) tR: 1.240 min (>99%, ELSD), m/z: 556.2 [(M+H).

Example 101

Preparation of 3-(7-bromo-6-chloro-3-(3-(4-chloro-3,5-dimethylphenoxy)propyl)-1H-indol-1-yl)propanoic acid Step A. Preparation of ethyl 3-(7-bromo-6-chloro-2-methyl-1H-indol-3-yl)propanoate: The title compound was synthesized according to the procedure described in Example 63 Step A using 2-bromo-3-chlorophenyl hydrazine hydrochloride and 6-methyl-3,4-dihydro-2H-pyran-2-one. LCMS (ESI) tR: 1.161 min (>99%, ELSD), m/z: 344.0 (M+H).

Step B. Preparation of 3-(7-bromo-6-chloro-2-methyl-1H-indol-3-yl)propan-1-ol: The title compound was synthesized according to the procedure described in Example 63 Step B using ethyl 3-(7-bromo-6-chloro-2-methyl-1H-indol-3-yl)propanoate and BH$_3$-THF. LCMS (ESI) tR: 0.955 min (>99%, ELSD), m/z: 302.0 (M+H).

Step C. Preparation of 7-bromo-6-chloro-3-(3-(4-chloro-3,5-dimethylphenoxy)propyl)-2-methyl-1H-indole: The title compound was synthesized according to the procedure described in Example 63 Step C using 3-(7-bromo-6-chloro-2-methyl-1H-indol-3-yl)propan-1-ol. LCMS (ESI) tR: 1.700 min (>99%, ELSD), m/z: 440.0 (M+H).

Step D: To a solution of 7-bromo-6-chloro-3-(3-(4-chloro-3,5-dimethylphenoxy)propyl)-2-methyl-1H-indole (140 mg, 0.317 mmol) in acetonitrile (4 mL) was added methyl acrylate (0.6 mL) and DBU (190 µL, 1.27 mmol). The reaction mixture was heated for 3 h under reflux condition and solvent was removed in vacuo. The residual ester compound was dissolved in dioxane (1.5 mL), treated with NaOH (0.3 mL, 2M solution), stirred for 2 h, and acidified with 1N HCl (1 mL). The residue was extracted with EtOAc, dried over MgSO$_4$, and purified by column chromatography using dichloromethane/MeOH (Combiflash Rf, 0 to 10% MeOH gradient) to afford the title compound (78 mg, 48%). $^1$H NMR (CDCl$_3$, 400 MHz) δ (ppm) 7.39 (d, J=8.0 Hz, 2H), 7.12 (d, J=8.0, 1H), 6.64 (s, 2H), 4.83-4.77 (m, 2H), 3.85 (t, J=6.0 Hz, 2H), 2.89 (t, J=7.2 Hz, 2H), 2.68 (t, J=8.0 Hz, 2H), 2.35 (s, 3H), 2.30 (s, 6H), 2.01 (qt, J=6.0 Hz, 2H); LCMS (ESI) tR: 1.650 min (>99%, ELSD), m/z: 512.0 (M+H).

Example 102

Preparation of 3-((6-chloro-3-(3-(4-chloro-3,5-dimethylphenoxy)propyl)-2-methyl-7-(1,3,5-trimethyl-1H-pyrazol-4-yl)-1H-indol-1-yl)methyl)benzoic acid Step A. preparation of 6-chloro-3-(3-(4-chloro-3,5-dimethylphenoxy)propyl)-2-methyl-7-(1,3,5-trimethyl-1H-pyrazol-4-yl)-1H-indole: To a solution of 7-bromo-6-chloro-3-(3-(4-chloro-3,5-dimethylphenoxy)propyl)-2-methyl-1H-indole (25 mg, 0.057 mmol) in 2.0 mL of dioxane/water (3:1) was added potassium carbonate (24 mg, 0.17 mmol), Pd(PPh$_3$)$_4$(7 mg, cat.), and 1,3,5-trimethyl-4-(4,4,5,5-tetramethyl-1,3,2-dioxaborolan-2-yl)-1H-pyrazole (20 mg, 0.085 mmol) at room temperature. The reaction mixture was heated at 150° C. for 20 min under microwave condition and solvent was concentrated in vacuo. The residue was purified by column chromatography using dichloromethane/MeOH (Combi-flash Rf, 0 to 10% MeOH gradient) to afford the title compound (17 mg, 71%). LCMS (ESI) 470.2 [M+1]+

Step B: To a solution of 6-chloro-3-(3-(4-chloro-3,5-dimethylphenoxy)propyl)-2-methyl-7-(1,3,5-trimethyl-1H-pyrazol-4-yl)-1H-indole (17 mg, 0.036 mmol) in acetonitrile (2 mL) was added cesium carbonate (21 mg, 0.065 mmol) and methyl 3-(bromomethyl)benzoate (12 mg, 0.054 mmol). The reaction mixture was heated at 120° C. for 30 min under microwave condition. The residual cesium carbonate was removed by filtration and solvent was concentrated in vacuo. The residual ester compound was dissolved in dioxane (1 mL), treated with NaOH (50 µL, 2M solution), stirred for 2 h, and acidified with 1N HCl (1 mL). The residue was extracted with EtOAc, dried over MgSO$_4$, and purified by reverse phase prep. HPLC (Phenomenex Gemini C18, H$_2$O/CH$_3$CN gradient to 95% CH$_3$CN 0.1% TFA) to afford the title compound. LCMS (ESI) tR: 0.956 min (>99%, ELSD), m/z: 604.2 (M+H).

Example 103

Preparation of 2-(4-((6-chloro-3-(3-(4-chloro-3,5-dimethylphenoxy)propyl)-2-methyl-7-(1,3,5-trimethyl-1H-pyrazol-4-yl)-1H-indol-1-yl)methyl)phenyl)acetic acid The title compound was synthesized according to the procedure described in Example 102 Step B using 6-chloro-3-(3-(4-chloro-3,5-dimethylphenoxy)propyl)-2-methyl-7-(1,3,5-trimethyl-1H-pyrazol-4-yl)-1H-indole and methyl 2-(4-(bromomethyl)phenyl)acetate. LCMS (ESI) tR: 0.745 min (>99%, ELSD), m/z: 618.2 (M+H).

Example 104

Preparation of 3-(6-chloro-3-(3-(4-chloro-3,5-dimethylphenoxy)propyl)-2-methyl-7-(1,3,5-trimethyl-1H-pyrazol-4-yl)-1H-indol-1-yl)propanoic acid The title compound was synthesized according to the procedure described in Example 101 Step D using 6-chloro-3-(3-(4-chloro-3,5-dimethylphenoxy)propyl)-2-methyl-7-(1,3,5-trimethyl-1H-pyrazol-4-yl)-1H-indole and methyl acrylate. LCMS (ESI) tR: 0.924 min (>99%, ELSD), m/z: 542.2 (M+H).

Example 105

Preparation of 3-(3-(3-(4-chloro-3,5-dimethylphenoxy)propyl)-7-(3,5-dimethyl-1-(pyridin-2-ylmethyl)-1H-pyrazol-4-yl)-2-methyl-1H-indol-1-yl)propanoic acid To a solution of 3-(3-(3-(4-chloro-3,5-dimethylphenoxy)propyl)-7-(3,5-dimethyl-1H-pyrazol-4-yl)-2-methyl-1H-indol-1-yl)propanoic acid (25.0 mg, 0.05 mmol) in DMF (0.5 mL) at rt was added cesium carbonate (82.4 mg, 0.25 mmol) and 2-(bromomethyl)pyridine hydrobromide (38.0 mg, 0.15 mmol). The mixture was heated at 90° C. for 24 h. The mixture was quenched with water and the aqueous layer was extracted with ethyl acetate. The combined organic layer was dried over and. MgSO₄ and concentrated in vacuo. The crude residue was purified by reverse phase prep. HPLC (Phenomenex Gemini C18, H₂O/CH₃CN gradient to 95% CH₃CN 0.1% TFA) to give the title compound (9.0 mg, 0.015 mmol). MS (ES) 585.2 (M+H), tR: 1.368 min.

Example 106

Preparation of 3-(3-(3-(4-chloro-3,5-dimethylphenoxy)propyl)-7-(3,5-dimethyl-1-((tetrahydrofuran-3-yl)methyl)-1H-pyrazol-4-yl)-2-methyl-1H-indol-1-yl)propanoic acid Title compound was prepared (5.0 mg, 0.008 mmol) according to procedures described in Example 105 by using 3-(3-(3-(4-chloro-3,5-dimethylphenoxy)propyl)-7-(3,5-dimethyl-1H-pyrazol-4-yl)-2-methyl-1H-indol-1-yl)propanoic acid (25 mg, 0.05 mmol), cesium carbonate (82.4 mg, 0.25 mmol) and 3-(bromomethyl)tetrahydrofuran (16 µL, 0.15 mmol). MS (ES) 578.2 (M+H), tR: 1.480 min.

Example 107

Preparation of 3-(3-(3-(4-chloro-3,5-dimethylphenoxy)propyl)-7-(3,5-dimethyl-1-(2-(pyridin-2-yl)ethyl)-1H-pyrazol-4-yl)-2-methyl-1H-indol-1-yl)propanoic acid Title compound was prepared (6.0 mg, 0.01 mmol) according to procedures described in Example 105 by using 3-(3-(3-(4-chloro-3,5-dimethylphenoxy)propyl)-7-(3,5-dimethyl-1H-pyrazol-4-yl)-2-methyl-1H-indol-1-yl)propanoic acid (25.0 mg, 0.05 mmol), cesium carbonate (82.4 mg, 0.25 mmol) and 2-(2-bromoethyl)pyridine hydrobromide (40.0 mg, 0.15 mmol). MS (ES) 599.3 (M+H). tR: 1.175 min.

Example 108

Preparation of 3-(3-(3-(4-chloro-3,5-dimethylphenoxy)propyl)-7-(3,5-dimethyl-1-(pyridin-4-ylmethyl)-1H-pyrazol-4-yl)-2-methyl-1H-indol-1-yl)propanoic acid Title compound was prepared (7.0 mg, 0.011 mmol) according to procedures described in Example 105 by using 3-(3-(3-(4-chloro-3,5-dimethylphenoxy)propyl)-7-(3,5-dimethyl-1H-pyrazol-4-yl)-2-methyl-1H-indol-1-yl)propanoic acid (29.0 mg, 0.058 mmol), cesium carbonate (95.6 mg, 0.29 mmol) and 4-(bromomethyl)pyridine hydrobromide (44.0 mg, 0.17 mmol). MS (ES) 585.3 (M+H). tR: 1.239 min.

Example 109

Preparation of 3-(3-(3-(4-chloro-3,5-dimethylphenoxy)propyl)-7-(1-(2-(dimethylamino)ethyl)-3,5-dimethyl-1H-pyrazol-4-yl)-2-methyl-1H-indol-1-yl)propanoic acid Title compound was prepared (10.0 mg, 0.017 mmol) according to procedures described in Example 105 by using 3-(3-(3-(4-chloro-3,5-dimethylphenoxy)propyl)-7-(3,5-dimethyl-1H-pyrazol-4-yl)-2-methyl-1H-indol-1-yl)propanoic acid (30.0 mg, 0.06 mmol), cesium carbonate (99 mg, 0.3 mmol) and 2-bromo-N,N-dimethylethan-1-amine hydrobromide (42.0 mg, 0.18 mmol). MS (ES) 565.3 (M+H), tR: 1.236 min.

Example 110

Preparation of 3-(3-(3-(4-chloro-3,5-dimethylphenoxy)propyl)-7-(3,5-dimethyl-1-(pyrimidin-2-ylmethyl)-1H-pyrazol-4-yl)-2-methyl-1H-indol-1-yl)propanoic acid Title compound was prepared (7.0 mg, 0.011 mmol) according to procedures described in Example 105 by using 3-(3-(3-(4-chloro-3,5-dimethylphenoxy)propyl)-7-(3,5-dimethyl-1H-pyrazol-4-yl)-2-methyl-1H-indol-1-yl)propanoic acid (20.0 mg, 0.04 mmol), cesium carbonate (66.0 mg, 0.2 mmol) and 2-(bromomethyl)pyrimidine (16.0 mg, 0.12 mmol). MS (ES) 586.3 (M+H), tR: 1.564 min.

Example 111

Preparation of 3-((3-(3-(4-chloro-3,5-dimethylphenoxy)propyl)-7-(3,5-dimethyl-1-(pyridin-2-ylmethyl)-1H-pyrazol-4-yl)-2-methyl-1H-indol-1-yl)methyl)benzoic acid To a solution of 3-((3-(3-(4-chloro-3,5-dimethylphenoxy)propyl)-7-(3,5-dimethyl-1H-pyrazol-4-yl)-2-methyl-1H-indol-1-yl)methyl)bezoic acid (25 mg, 0.044 mmol) in DMF (0.5 mL) at rt was added cesium carbonate (73.2 mg, 0.23 mmol) and 2-(bromomethyl)pyridine hydrobromide (33.5 mg, 0.13 mmol). The mixture was heated at 90° C. for 24 h. The mixture was quenched with water and the aqueous layer was extracted with ethyl acetate. The combined organic layer was dried over and. $MgSO_4$ and concentrated in vacuo. The crude residue was purified by reverse phase prep. HPLC (Phenomenex Gemini C18, $H_2O/CH_3CN$ gradient to 95% $CH_3CN$ 0.1% TFA) to give the title compound (9.0 mg, 0.013 mmol). MS (ES) 647.3 (M+H), tR: 1.435 min.

Example 112

Preparation of 3-((3-(3-(4-chloro-3,5-dimethylphenoxy)propyl)-7-(3,5-dimethyl-1-(pyridin-3-ylmethyl)-1H-pyrazol-4-yl)-2-methyl-1H-indol-1-yl)methyl)benzoic acid Title compound was prepared (8.0 mg, 0.012 mmol) according to procedures described in Example 111 by using 3-((3-(3-(4-chloro-3,5-dimethylphenoxy)propyl)-7-(3,5-dimethyl-1H-pyrazol-4-yl)-2-methyl-1H-indol-1-yl)methyl)bezoic acid (23.0 mg, 0.041 mmol), cesium carbonate (66.7 mg, 0.2 mmol) and 3-(bromomethyl)pyridine hydrobromide (31.1 mg, 0.12 mmol). MS (ES) 647.2 (M+H), tR: 1.290 min.

Example 113

Preparation of 3-(6-chloro-3-(3-(4-chloro-3,5-dimethylphenoxy)propyl)-7-(3,5-dimethyl-1-(2-morpholinoethyl)-1H-pyrazol-4-yl)-2-methyl-1H-indol-1-yl)propanoic acid Step A. Preparation of 4-(2-(3,5-dimethyl-4-(4,4,5,5-tetramethyl-1,3,2-dioxaborolan-2-yl)-1H-pyrazol-1-yl)ethyl)morpholine: To a solution of 3,5-dimethyl-4-(4,4,5,5-tetramethyl-1,3,2-dioxaborolan-2-yl)-1H-pyrazole (200.0 mg, 0.9 mmol) in DMF (2.0 mL) at rt was added cesium carbonate (879.8 mg, 2.7 mmol) and 4-(2-chloroethyl)morpholine hydrochloride (333.0 mg, 1.8 mmol). The mixture was heated at 160° C. for 2.5 h in Biotage Initiator. The mixture was quenched with water and the aqueous layer was extracted with ethyl acetate. The combined organic layer was dried over and. $MgSO_4$ and concentrated in vacuo. The crude (150.0 mg) residue was used for the next step. MS (ES) 336.2 (M+H), tR: 0.809 min.

Step B. Preparation of 4-(2-(4-(6-chloro-3-(3-(4-chloro-3,5-dimethylphenoxy)propyl)-2-methyl-1H-indol-7-yl)-3,5-dimethyl-1H-pyrazol-1-yl)ethyl)morpholine: To a solution of 7-bromo-6-chloro-3-(3-(4-chloro-3,5-dimethylphenoxy)propyl)-2-methyl-1H-indole (151.3 mg, 0.34 mmol) in 1,4-dioxane (3.0 mL) and $H_2O$ (1.0 mL) at rt was added 4-(2-(3,5-dimethyl-4-(4,4,5,5-tetramethyl-1,3,2-dioxaborolan-2-yl)-1H-pyrazol-1-yl)ethyl)morpholine (150 mg, 0.44 mmol), $Pd(PPh_3)_4$ (40.0 mg, 0.034 mmol) and $K_2CO_3$ (140.9 mg, 1.02 mmol). The mixture was then heated to 150° C. in Biotage Initiator for 45 min. The mixture was concentrated in vacuo. The residue was purified by flash column chromatography (Combi-flash Rf, hexane/ethyl acetate 0-100% gradient then $CH_2Cl_2$/MeOH 0-10% gradient) to give the title compound (80.0 mg, 41%). MS (ES) 569.1 (M+H), tR: 1.382 min.

Step C. Preparation of methyl 3-(6-chloro-3-(3-(4-chloro-3,5-dimethylphenoxy)propyl)-7-(3,5-dimethyl-1-(2-morpholinoethyl)-1H-pyrazol-4-yl)-2-methyl-1H-indol-1-yl)propanoate: To a solution of 4-(2-(4-(6-chloro-3-(3-(4-chloro-3,5-dimethylphenoxy)propyl)-2-methyl-1H-indol-7-yl)-3,5-dimethyl-1H-pyrazol-1-yl)ethyl)morpholine (80.0 mg, 0.14 mmol) in $CH_3CN$ (2.0 mL) were added DBU (0.083 mL, 0.56 mmol) and methyl acrylate (0.15 mL, 1.68 mmol). The mixture was heated to 150° C. in Biotage Initiator for 45 min. The solvent was removed in vacuo. The residue was purified by flash column chromatography (Combi-flash Rf, hexane/ethyl acetate 0-100% gradient then $CH_2Cl_2$/MeOH 0-20% gradient) to give the title compound (40.0 mg, 43%). MS (ES) 655.0 (M+H), tR: 1.398 min.

Step D: To a solution of methyl 3-(6-chloro-3-(3-(4-chloro-3,5-dimethylphenoxy)propyl)-7-(3,5-dimethyl- -(2-morpholinoethyl)-1H-pyrazol-4-yl)-2-methyl-1H-indol-1-yl)propanoate (25.0 mg, 0.03 mmol) in 0.5 mL of 1,4-dioxane was added aq. 1.0 M NaOH (0.3 mL, 0.3 mmol). The mixture was heated at 45° C. for 2 h. The reaction was quenched with aq. 1.0 M HCl and the aqueous layer was extracted with ethyl acetate. The combined organic layer was dried ($MgSO_4$), filtered and concentrated. The crude was purified by reverse phase prep. HPLC (Phenomenex Gemini C18, $H_2O/CH_3CN$ gradient to 95% $CH_3CN$ 0.1% TFA) to give the title compound (13.0 mg, 54%). MS (ES) 641.3 (M+H), tR: 1.286 min.

Example 114

Preparation of 2-(6-chloro-3-(3-(4-chloro-3,5-dimethylphenoxy)propyl)-2-methyl-7-(1,3,5-trimethyl-1H-pyrazol-4-yl)-1H-indol-1-yl)acetic acid Step A. Preparation of 6-chloro-3-(3-(4-chloro-3,5-dimethylphenoxy)propyl)-2-methyl-7-(1,3,5-trimethyl-1H-pyrazol-4-yl)-1H-indole: To a solution of 7-bromo-6-chloro-3-(3-(4-chloro-3,5-dimethylphenoxy)propyl)-2-methyl-1H-indole (1.0 g, 2.26 mmol) in 1,4-dioxane (9.0 mL) and $H_2O$ (3.0 mL) at rt was added 1,3,5-trimethyl-4-(4,4,5,5-tetramethyl-1,3,2-dioxaborolan-2-yl)-1H-pyrazole (802.7 mg, 3.39 mmol), $Pd(PPh_3)_4$ (261.1 mg, 0.226 mmol) and $K_2CO_3$ (936.9 mg, 6.78 mmol). The mixture was then heated to 150° C. in Biotage Initiator for 20 min. The mixture was concentrated in vacuo. The residue was purified by flash column chromatography (Combi-flash Rf, hexane/ethyl acetate 0-100% gradient) to give the title compound (910.0 mg, 85%). MS (ES) 470.4 (M+H).

Step B. Preparation of ethyl 2-(6-chloro-3-(3-(4-chloro-3,5-dimethylphenoxy)propyl)-2-methyl-7-(1,3,5-trimethyl-1H-pyrazol-4-yl)-1H-indol-1-yl)acetate: To a solution of 6-chloro-3-(3-(4-chloro-3,5-dimethylphenoxy)propyl)-2-methyl-7-(1,3,5-trimethyl-1H-pyrazol-4-yl)-1H-indole (100.0 mg, 0.21 mmol) in DMF (2.0 mL) were added $Cs_2CO_3$ (205.2 mg, 0.63 mmol) and ethyl iodoacetate (0.12 mL, 1.05 mmol). The mixture was then heated to 120° C. under in Biotage Initiator for 20 min. The mixture was concentrated in vacuo. The residue was purified by flash column chromatography (Combi-flash Rf, $CH_2Cl_2$/MeOH 0-10% gradient) to give the title compound (75.0 mg, 63%). MS (ES) 556.5 (M+H), tR: 1.527 min.

Step C: To a solution of ethyl 2-(6-chloro-3-(3-(4-chloro-3,5-dimethylphenoxy)propyl)-2-methyl-7-(1,3,5-trimethyl-1H-pyrazol-4-yl)-1H-indol-1-yl)acetate (97.0 mg, 0.174 mmol) in 1,4-dioxane (1.0 mL) was added 1.0 M NaOH (0.87 mL, 0.87 mmol). The mixture was stirred at rt for 3 h. The reaction was quenched with aq. 1.0 M HCl and the aqueous layer was extracted with ethyl acetate. The combined organic layer was dried (MgSO$_4$), filtered and concentrated. The crude was purified by flash column chromatography (Combi-flash Rf, CH$_2$Cl$_2$/MeOH 0-20% gradient) to give the title compound (64.0 mg, 70%). MS (ES) 528.1 (M+H), tR: 1.33 min.

Example 115

Preparation of 3-((7-bromo-3-(3-(4-chloro-3,5-dimethylphenoxy)propyl)-2-(trifluoromethyl)-1H-indol-1-yl)methyl)benzoic acid Step A. Preparation of ethyl 3-(7-bromo-2-(trifluoromethyl)-1H-indol-3-yl)propanoate: To a flame dried round bottom flask equipped with condenser and magnetic stir bar was added 2-bromopehenyl hydrazine hydrochloride (2.3 g, 10 mmol), methyl 6,6,6-trifluoro-5-oxohexanoate (2.20 g, 12 mmol), anhydrous ethanol (50 mL) and concentrated sulfuric acid (1 mL) and the solution was heated to 90° C. for 2 h under nitrogen atmosphere. The solvent was evaporated and the residue was dissolved in ethyl acetate and washed with saturated NaHCO$_3$, water and brine. The organic layer was dried with over MgSO$_4$ and concentrated in vacuo. The residue was dissolved in anhydrous toluene (70 mL), and p-toluene sulfonic acid (1.9 g, 10 mmols) was added. The solution was heated to 130-140° C. for 3 h under nitrogen atmosphere then cooled to rt. The reaction mixture was filtered, and the filtrate was concentrated. The crude product was purified by flash chromatography (Combi-flash Rf, Hex/EtOAc 0-10% gradient) to give the title compound as a white solid (2.3 g, 62%). $^1$H-NMR (CDCl$_3$) δ 8.38 (broad s, 1H), 7.68 (d, 1H, J=8 Hz), 7.52 (d, 1H, J=8 Hz), 7.11 (t, 1H, J=8 Hz), 4.15 (q, 2H, J=8 Hz), 3.23 (t, 2H, J=8 Hz), 2.66 (t, 2H, J=8 Hz), 1.24 (t, 2H, J=8 Hz); $^{19}$F-NMR (CDCl$_3$) δ −58.4.

Step B. Preparation of 3-(7-bromo-2-(trifluoromethyl)-1H-indol-3-yl)propan-1-ol: To a flame dried round bottom flask equipped with magnetic stir bar was added ethyl 3-(7-bromo-2-(trifluoromethyl)-1H-indol-3-yl)propanoate (1.5 g, 4.1 mmol) followed by anhydrous THF (25 mL). The reaction mixture was stirred at 0° C. for 15 min. BH$_3$ THF complex in THF (1M, 8.2 mL, 8.2 mmol) was added dropwise, and the reaction mixture was warmed up to rt then stirred additional 2 h. The mixture was cooled down to 0° C. and quenched by careful addition of methanol. The quenched reaction mixture was concentrated in vacuo, and the residue was purified by flash chromatography (Combi-flash Rf, Hex/EtOAc 0-60% gradient) to give the title compound (1.15 g, 86%). $^1$H-NMR (CDCl$_3$) δ 8.37 (broad s, 1H), 7.68 (d, 1H, J=8 Hz), 7.50 (d, 1H, J=8 Hz), 7.10 (t, 1H, J=8 Hz), 3.71 (t, 2H, J=8 Hz), 3.02 (t, 2H, J=8 Hz), 1.96 (q, 2H, J=8 Hz); $^{19}$F-NMR (CDCl$_3$) δ −58.9.

Step C. Preparation of 7-bromo-3-(3-(4-chloro-3,5-dimethylphenoxy)propyl)-2-(trifluoromethyl)-1H-indole: To a flame dried round bottom flask equipped with magnetic stir bar was added Dt-BuAD (1.36 g, 5.9 mmols) followed by anhydrous THF (25 mL). The reaction mixture was stirred at 0° C. for 15 min. PPh$_3$ (1.54 g, 5.9 mmols) was added, followed by a solution of 3-(7-bromo-2-(trifluoromethyl)-1H-indol-3-yl)propan-1-ol and 4-chloro-3,5-dimethylphenol in anhydrous THF (10 mL). The reaction mixture was warmed up to rt and stirred additional 3 h. The reaction mixture was concentrated, and the residue was purified by flash chromatography (Combi-flash Rf, Hex/EtOAc 0-10% gradient) to give the title compound (1.3 g, 62%). $^1$H-NMR (CDCl$_3$) δ 8.37 (broad s, 1H), 7.63 (d, 1H, J=8 Hz), 7.50 (d, 1H, J=8 Hz), 7.06 (t, 1H, J=8 Hz), 6.63 (s, 2H), 3.94 (t, 2H, J=8 Hz), 3.08 (t, 2H, J=8 Hz), 2.35 (s, 6H), 2.14 (q, 2H, J=8 Hz); $^{19}$F-NMR (CDCl$_3$) δ −58.5.

Step D. Preparation of methyl 3-((7-bromo-3-(3-(4-chloro-3,5-dimethylphenoxy)propyl)-2-(trifluoromethyl)-1H-indol-1-yl)methyl)benzoate: In a microwave vial were sequentially added compound 7-bromo-3-(3-(4-chloro-3,5-dimethylphenoxy)propyl)-2-(trifluoromethyl)-1H-indole (40 mg, 0.086 mmol), methyl 3-(bromomethyl)benzoate (26 mg, 0.11 mmols), solid Cs$_2$CO$_3$ (100 mg, 0.31 mmol) and anhydrous acetonitrile (4 mL). The reaction mixture was irradiated under microwave for 20 min at 120° C. in Biotage Initiator. The reaction mixture was concentrated, and the residue purified by flash chromatography (Combi-flash Rf, Hex/EtOAc 0-20% gradient) to give the title compound (46 mg, 86%). $^1$H-NMR (CDCl$_3$) δ 7.90 (d, 1H, J=8 Hz), 7.70 (d, 1H, J=8 Hz) 7.67 (s, 1H), 7.49 (d, 1H, J=8 Hz), 7.30 (tr, 1H, J=8 Hz), 7.04 (t, 1H, J=8 Hz), 6.88 (d, 1H, J=8 Hz), 6.63 (s, 2H), 6.00 (broad s, 2H), 3.96 (t, 2H, J=8 Hz), 3.88 (s, 3H), 3.16 (t, 2H, J=8 Hz), 2.13 (s, 6H), 2.14 (q, 2H, J=8 Hz); $^{19}$F-NMR (CDCl$_3$) δ −55.6.

Step E: 3-((7-bromo-3-(3-(4-chloro-3,5-dimethylphenoxy)propyl)-2-(trifluoromethyl)-1H-indol-1-yl)methyl)benzoate (20 mg, 0.033 mmol) was dissolved in a 1:1 mixture of 1,4-dioxane and MeOH (2 mL) and aq. NaOH (2M, 300 μL)solution. The reaction mixture was stirred at rt for 2 h then acidified with 1N HCl (1 mL). The crude product was purified by reverse phase prep. HPLC (Phenomenex Gemini C18, H$_2$O/CH$_3$CN gradient from 60% to 95% CH$_3$CN, 0.1% TFA) to yield the title compound (46 mg, 86%). $^1$H-NMR (MeOH-d$_4$) δ 7.88 (d, 1H, J=8 Hz), 7.78 (d, 1H, J=8 Hz), 7.51 (d, 1H, J=8 Hz), 7.45 (s, 1H), 7.35 (t, 1H, J=8 Hz), 7.05 (d, 1H, J=8 Hz), 7.02 (t, 1H, J=8 Hz), 6.66 (s, 2H), 3.96 (t, 2H, J=8 Hz), 3.16 (t, 2H, J=8 Hz), 2.03 (s, 6H), 2.13 (q, 2H, J=8 Hz); $^{19}$F-NMR (MeOH-d$_4$) δ −55.6.

Example 116

Preparation of 4-((7-bromo-3-(3-(4-chloro-3,5-dimethylphenoxy)propyl)-2-(trifluoromethyl)-1H-indol-1-yl)methyl)benzoic acid Step A. Preparation of methyl 4-((7-bromo-3-(3-(4-chloro-3,5-dimethylphenoxy)propyl)-2-(trifluoromethyl)-1H-indol-1-yl)methyl)benzoate: The title compound was prepared (48 mg, 90%) according to the procedure described in Example 115 Step D by using 7-bromo-3-(3-(4-chloro-3,5-dimethylphenoxy)propyl)-2-(trifluoromethyl)-1H-indole (40 mg, 0.086 mmol) and methyl 4-(bromomethyl)benzoate. $^1$H-NMR (CDCl$_3$) δ 7.94 (d, 2H, J=8 Hz), 7.69 (d, 1H, J=8 Hz) 7.48 (d, 1H, J=8 Hz), 7.03 (t, 1H, J=8 Hz), 6.90 (d, 2H, J=8 Hz), 6.63 (s, 2H), 6.10 (broad s, 2H), 3.96 (t, 2H, J=8 Hz), 3.90 (s, 3H), 3.16 (t, 2H, J=8 Hz), 2.15 (s, 6H), 2.14 (q, 2H, J=8 Hz); $^{19}$F-NMR (CDCl$_3$) δ −55.6.

Step B: The title compound was prepared according to the procedure described in Example 115 Step E by using methyl 4-((7-bromo-3-(3-(4-chloro-3,5-dimethylphenoxy)propyl)-2-(trifluoromethyl)-1H-indol-1-yl)methyl)benzoate. $^1$H-NMR (MeOH-d$_6$) δ 7.91 (d, 2H, J=8 Hz), 7.79 (d, 1H, J=8 Hz) 7.52 (d, 1H, J=8 Hz), 7.05 (t, 1H, J=8 Hz), 6.88 (d, 1H, J=8 Hz), 6.64 (s, 2H), 3.96 (t, 2H, J=8 Hz), 3.21 (t, 2H, J=8 Hz), 2.31 (s, 6H), 2.12 (q, 2H, J=8 Hz); $^{19}$F-NMR (MeOH-d$_6$) δ −55.6.

Example 117

Preparation of 2-(4-((3-(3-(4-chloro-3,5-dimethylphenoxy)propyl)-2-(trifluoromethyl)-7-(1,3,5-trimethyl-1H-pyrazol-4-yl)-1H-indol-1-yl)methyl)phenyl)acetic acid Step A. Preparation of 3-(3-(4-chloro-3,5-dimethylphenoxy)propyl)-2-(trifluoromethyl)-7-(1,3,5-trimethyl-1H-pyrazol-4-yl)-1H-indole: In a microwave vial were sequentially added compound 7-bromo-3-(3-(4-chloro-3,5-dimethylphenoxy)propyl)-2-(trifluoromethyl)-1H-indole (40 mg, 0.086 mmol), Pd(PPh$_3$)$_4$(5 mg, 0.004 mmol), K$_2$CO$_3$ (36 mg, 0.26 mmol), 1,3,5-trimethyl-4-(4,4,5,5-tetramethyl-1,3,2-dioxaborolan-2-yl)-1H-pyrazole (31 mg, 0.13 mmol), 1,4-dioxane (3 mL) and water (1 mL). The reaction mixture was irradiated under microwave for 20 min at 150° C. in Biotage Initiator. The reaction mixture was concentrated, and the residue was purified by flash chromatography (Combi-flash Rf, Hex/EtOAc 0-50% gradient) to give the title compound (20 mg, 48%). $^1$H-NMR (CDCl$_3$) δ 7.98 (broad s, 1H), 7.67 (d, 1H, J=8 Hz), 7.25 (t, 1H, J=8 Hz), 7.13 (d, 1H, J=8 Hz), 6.66 (s, 2H), 3.99 (t, 2H, J=8 Hz), 3.86 (s, 3H), 3.11 (t, 2H, J=8 Hz), 2.35 (s, 6H), 2.16 (s, 6H), 2.14 (q, 2H, J=8 Hz); $^{19}$F-NMR (CDCl$_3$) δ −58.2; MS (ES) 490.3 (M+H).

Step B. Preparation of ethyl 2-(4-((3-(3-(4-chloro-3,5-dimethylphenoxy)propyl)-2-(trifluoromethyl)-7-(1,3,5-trimethyl-1H-pyrazol-4-yl)-1H-indol-1-yl)methyl)phenyl)acetate: The title compound was prepared (40 mg, 74%) according to the procedure described in Example 115 Step D by using 3-(3-(4-chloro-3,5-dimethylphenoxy)propyl)-2-(trifluoromethyl)-7-(1,3,5-trimethyl-1H-pyrazol-4-yl)-1H-indole and ethyl 2-(4-(bromomethyl)phenyl)acetate. $^1$H-NMR (CDCl$_3$) δ 7.69 (d, 1H, J=8 Hz), 7.49 (d, 1H, J=8 Hz) 7.18 (d, 1H, J=8 Hz), 7.03 (t, 1H, J=8 Hz), 6.78 (d, 2H, J=8 Hz), 6.63 (s, 2H), 5.96 (broad s, 2H), 3.96 (t, 2H, J=8 Hz), 3.69 (s, 3H), 3.58 (s, 2H), 3.11 (t, 1H, J=8 Hz), 2.35 (s, 6H), 2.12 (q, 2H, J=8 Hz); $^{19}$F-NMR (CDCl$_3$) δ −55.6.

Step C: The title compound was prepared (16 mg, 82%) according to the procedure described in Example 115 Step E by using ethyl 2-(4-((3-(3-(4-chloro-3,5-dimethylphenoxy)propyl)-2-(trifluoromethyl)-7-(1,3,5-trimethyl-1H-pyrazol-4-yl)-1H-indol-1-yl)methyl)phenyl)acetate:
$^1$H-NMR (MeOH-d$_4$) δ 7.69 (d, 1H, J=8 Hz), 7.49 (d, 1H, J=8 Hz) 7.18 (d, 1H, J=8 Hz), 7.03 (t, 1H, J=8 Hz), 6.78 (d, 2H, J=8 Hz), 6.63 (s, 2H), 5.96 (broad s, 2H), 3.96 (t, 2H, J=8 Hz), 3.69 (s, 3H), 3.58 (s, 2H), 3.11 (t, 1H, J=8 Hz), 2.35 (s, 6H), 2.12 (q, 2H, J=8 Hz); $^{19}$F-NMR (MeOH-d$_4$) δ −55.9; MS (ES) 638.1 (M+H).

Example 118

Preparation of 4-(2-(3-(3-(4-chloro-3,5-dimethylphenoxy)propyl)-2-(trifluoromethyl)-7-(1,3,5-trimethyl-1H-pyrazol-4-yl)-1H-indol-1-yl)ethyl)benzoic acid Step A. Preparation of methyl 4-(2-(3-(3-(4-chloro-3,5-dimethylphenoxy)propyl)-2-(trifluoromethyl)-7-(1,3,5-trimethyl-1H-pyrazol-4-yl)-1H-indol-1-yl)ethyl)benzoate: The title compound was prepared (16 mg, 30%) according to the procedure described in Example 115 Step D by using 3-(3-(4-chloro-3,5-dimethylphenoxy)propyl)-2-(trifluoromethyl)-7-(1,3,5-trimethyl-1H-pyrazol-4-yl)-1H-indole and methyl 4-(2-bromoethyl)benzoate (10 eq). $^1$H-NMR (CDCl$_3$) δ 8.03 (d, 2H, J=8 Hz), 7.67 (d, 1H, J=8 Hz) 7.58 (d, 1H, J=8 Hz), 7.37 (d, 2H, J=8 Hz), 7.03 (t, 1H, J=8 Hz), 6.64 (s, 2H), 4.84 (broad s, 2H), 4.00 (m, 5H), 3.15 (m, 4H), 2.35 (s, 6H), 2.14 (q, 2H, J=8 Hz); $^{19}$F-NMR (CDCl$_3$) δ −55.9.

Step B: The title compound was prepared (12 mg, 75%) according to the procedure described in Example 115 Step E by using methyl 4-(2-(3-(3-(4-chloro-3,5-dimethylphenoxy)propyl)-2-(trifluoromethyl)-7-(1,3,5-trimethyl-1H-pyrazol-4-yl)-1H-indol-1-yl)ethyl)benzoate. $^1$H-NMR (MeOH-d$_4$) δ 7.83 (d, 1H, J=8 Hz), 7.22 (t, 1H, J=8 Hz), 7.09 (d, 1H, J=8 Hz) 6.86 (d, 1H, J=8 Hz), 6.67 (s, 2H), 6.39 (d, 2H, J=8 Hz), 5.18 (q, 2H, J=16 Hz), 4.04 (t, 2H, J=8 Hz), 3.81 (s, 2H), 3.22 (m, 2H), 2.35 (s, 6H), 2.22 (s, 6H), 2.02 (m, 2H); $^{19}$F-NMR (MeOH-d$_4$) δ −55.9; MS (ES) 638.2 (M+H).

Example 119

Preparation of 6-((7-bromo-3-(3-(4-chloro-3,5-dimethylphenoxy)propyl)-2-(trifluoromethyl)-1H-indol-1-yl)methyl)nicotinic acid Step A. Preparation of methyl 6-((7-bromo-3-(3-(4-chloro-3,5-dimethylphenoxy)propyl)-2-(trifluoromethyl)-1H-indol-1-yl)methyl)nicotinate: The title compound was prepared (20 mg, 26%) according to the procedure described in Example 115 Step D by using 7-bromo-3-(3-(4-chloro-3,5-dimethylphenoxy)propyl)-2-(trifluoromethyl)-1H-indole (40 mg, 0.086 mmol) and methyl 6-(bromomethyl)nicotinate. $^1$H-NMR (CDCl$_3$) δ 9.19 (d, 1H, J=2 Hz), 8.15 (dd, 1H, J=4 Hz, J$_2$=8 Hz) 7.72 (d, 1H, J=8 Hz), 7.50 (d, 1H, J=8 Hz), 7.06 (t, 1H, J=8 Hz), 6.63 (s, 2H), 6.10 (broad s, 2H), 3.94 (m, 5H), 3.16 (t, 2H, J=8 Hz), 2.35 (s, 6H), 2.13 (q, 2H, J=8 Hz); $^{19}$F-NMR (CDCl$_3$) δ −55.9; MS (ES) 609.1 (M+H).

Step B: The title compound (13 mg, 76%) was prepared according to the procedure described in Example 115 Step E by using methyl 6-((7-bromo-3-(3-(4-chloro-3,5-dimethylphenoxy)propyl)-2-(trifluoromethyl)-1H-indol-1-yl)methyl)nicotinate. $^1$H-NMR (MeOH-d$_4$) δ 9.06 (d, 1H, J=2 Hz), 8.21 (dd, 1H, J$_1$=4 Hz, J$_2$=8 Hz), 7.81 (d, 1H, J=8 Hz), 7.54 (d, 1H, J=8 Hz), 7.06 (t, 1H, J=8 Hz), 6.69 (d, 1H, J=8 Hz), 6.65 (s, 2H), 3.97 (t, 3H, J=8 Hz), 3.16 (m, 2H), 2.31 (s, 6H), 2.13 (q, 2H, J=8 Hz); $^{19}$F-NMR (MeOH-d$_4$) δ −55.2; MS (ES) 595.1 (M+H).

Example 120

Preparation of 2-(3-(3-(4-chloro-3,5-dimethylphenoxy)propyl)-2-(trifluoromethyl)-7-(1,3,5-trimethyl-1H-pyrazol-4-yl)-1H-indol-1-yl)acetic acid The title compound was prepared (36 mg, 94%) according to the procedure described in Example 115 Step D by using 3-(3-(4-chloro-3,5-dimethylphenoxy)propyl)-2-(trifluoromethyl)-7-(1,3,5-trimethyl-1H-pyrazol-4-yl)-1H-indole and ethyl bromoacetate followed by saponification described in Example 115 Step E. $^1$H-NMR (MeOH-d$_4$) 7.75 (d, 1H, J=8 Hz), 7.18 (t, 1H, J=8 Hz), 7.02 (d, 1H, J=8 Hz), 6.72 (s, 2H), 3.99 (t, 2H, J=8 Hz), 4.69 (s, 3H), 3.86 (s, 2H), 3.18 (t, 2H, J=8 Hz), 2.16 (s, 6H), 2.12 (q, 2H, J=8 Hz), 2.02 (s, 3H), 1.98 (s, 3H); $^{19}$F-NMR (MeOH-d$_4$) δ −58.8; MS (ES) 548.2 (M+H).

Example 121

Preparation of 2-(4-(2-(3-(3-(4-chloro-3,5-dimethylphenoxy)propyl)-2-(trifluoromethyl)-7-(1,3,5-trimethyl-1H-pyrazol-4-yl)-1H-indol-1-yl)acetyl)piperazin-1-yl)acetic acid To a solution of 2-(3-(3-(4-chloro-3,5-dimethylphenoxy)propyl)-2-(trifluoromethyl)-7-(1,3,5-trimethyl-1H-pyrazol-4-yl)-1H-indol-1-yl)acetic acid (30 mg, 0.055 mmol) in $CH_2Cl_2$ (2 mL) were added EDCI (21 mg, 0.1 mmol), DMAP (cat. Amount), DIPEA (45 µL, 0.27 mmol) and methyl 2-(piperazin-1-yl)acetate (20 mg, 0.083 mmol). The reaction mixture was stirred at rt for overnight. The reaction was diluted with water and extracted with $CH_2Cl_2$. The organic layers were dried over $MgSO_4$ then concentrated. The residue was dissolved in a 1:1 mixture of 1,4-dioxane and MeOH (2 mL) and aq. NaOH (2M, 300 µL) solution. The reaction mixture was stirred at rt for 2 h then acidified with 1N HCl (1 mL). The crude product was purified by reverse phase prep. HPLC (Phenomenex Gemini C18, $H_2O$/$CH_3CN$ gradient from 50% to 95% $CH_3CN$, 0.1% TFA) to yield the title compound (2 mg, 11%). MS (ES) 674.3 (M+H).

Example 122

Preparation of 3-((6-chloro-3-(3-(4-chloro-3,5-dimethylphenoxy)propyl)-2-(trifluoromethyl)-7-(1,3,5-trimethyl-1H-pyrazol-4-yl)-1H-indol-1-yl)methyl)benzoic acid Step A. Preparation of ethyl 3-(7-bromo-6-chloro-2-(trifluoromethyl)-1H-indol-3-yl)propanoate: The title compound was prepared (45%) according to the procedure described in Example 115 Step A by using 2-bromo-3-chlorophenyl hydrazine and methyl 6,6,6-trifluoro-5-oxohexanoate. $^1$H-NMR ($CDCl_3$) δ 8.41 (broad s, 1H), 7.60 (d, 1H, J=8 Hz), 7.29 (d, 1H, J=8 Hz), 4.13 (q, 2H, J=8 Hz), 3.21 (t, 2H, J=8 Hz), 2.65 (t, 2H, J=8 Hz), 1.26 (t, 2H, J=8 Hz); $^{19}$F-NMR ($CDCl_3$) δ −58.7.

Step B. Preparation of 3-(7-bromo-6-chloro-2-(trifluoromethyl)-1H-indol-3-yl)propan-1-ol: The title compound was prepared (80%) according to the procedure described in Example 115 Step B. $^1$H-NMR ($CDCl_3$) δ 8.36 (broad s, 1H), 7.60 (d, 1H, J=8 Hz), 7.27 (d, 1H, J=8 Hz), 3.71 (t, 2H, J=8 Hz), 3.00 (t, 2H, J=8 Hz), 1.94 (q, 2H, J=8 Hz); $^{19}$F-NMR ($CDCl_3$) δ −58.4.

Step C. Preparation of 7-bromo-6-chloro-3-(3-(4-chloro-3,5-dimethylphenoxy)propyl)-2-(trifluoromethyl)-1H-indole: The title compound (55%) was prepared according to the procedure described in Example 115 Step C. $^1$H-NMR ($CDCl_3$) δ 8.28 (broad s, 1H), 7.45 (d, 1H, J=8 Hz), 7.14 (d, 1H, J=8 Hz), 6.52 (s, 2H), 3.83 (t, 2H, J=8 Hz), 2.97 (t, 2H, J=8 Hz), 2.26 (s, 6H), 2.03 (q, 2H, J=8 Hz); $^{19}$F-NMR ($CDCl_3$) δ −58.6.

Step D. Preparation of 3-(6-chloro-3-(4-chloro-3,5-dimethylphenoxy)propyl)-2-(trifluoromethyl)-7-(1,3,5-trimethyl-1H-pyrazol-4-yl)-1H-indole: The title compound (32%) was prepared according to the procedure described in Example 117 Step A using 7-bromo-6-chloro-3-(3-(4-chloro-3,5-dimethylphenoxy)propyl)-2-(trifluoromethyl)-1H-indole and 1,3,5-trimethyl-4-(4,4,5,5-tetramethyl-1,3,2-dioxaborolan-2-yl)-1H-pyrazole. $^1$H-NMR ($CDCl_3$) δ 7.93 (broad s, 1H), 7.58 (d, 1H, J=8 Hz), 7.26 (d, 1H, J=8 Hz), 6.65 (s, 2H), 3.98 (t, 2H, J=8 Hz), 3.87 (s, 3H), 3.09 (t, 2H, J=8 Hz), 2.14 (q, 2H, J=8 Hz), 2.18 (s, 6H), 2.10 (s, 6H); $^{19}$F-NMR ($CDCl_3$) δ −58.2.; MS (ES) 524.2 (M+H).

Step E: The title compound was prepared according to the procedure described in Example 115 Step D and E using 3-(6-chloro-3-(4-chloro-3,5-dimethylphenoxy)propyl)-2-(trifluoromethyl)-7-(1,3,5-trimethyl-1H-pyrazol-4-yl)-1H-indole and methyl 3-(bromomethyl)benzoate. $^1$H-NMR (MeOH-$d_4$) δ 7.82 (m, 1H), 7.77 (d, 1H, J=8 Hz), 7.27 (m, 2H), 6.99 (s, 1H), 6.53 (s, 2H), 6.52 (d, 1H, J=8 Hz), 5.21 (q, 2H, J=16 Hz), 3.97 (t, 2H, J=8 Hz), 3.67 (s, 3H), 2.28 (s, 6H), 2.19 (q, 2H, J=8 Hz); $^{19}$F-NMR (MeOH-$d_4$) δ −55.6; MS (ES) 658.2 (M+H).

Example 123

Preparation of 3-((3-(3-(4-chloro-3,5-dimethylphenoxy)propyl)-2-(trifluoromethyl)-7-(1,3,5-trimethyl-1H-pyrazol-4-yl)-1H-indol-1-yl)methyl)benzoic acid The title compound (19 mg, 90%) was prepared according to the procedure described in Example 117 Step A using methyl 3-((7-bromo-3-(3-(4-chloro-3,5-dimethylphenoxy)propyl)-2-(trifluoromethyl)-1H-indol-1-yl)methyl)benzoate and 1,3,5-trimethyl-4-(4,4,5,5-tetramethyl-1,3,2-dioxaborolan-2-yl)-1H-pyrazole Under the reaction condition, the methyl ester was also hydrolyzed to give the title compound. $^1$H-NMR (MeOH-$d_4$) δ 7.82 (m, 1H), 7.23 (t, 1H, J=8 Hz) 7.17 (t, 1H, J=8 Hz), 7.01 (s, 1H), 6.92 (d, 1H, J=8 Hz), 6.70 (s, 2H), 6.50 (d, 1H, J=8 Hz), 5.21 (q, 2H, J=16 Hz), 4.01 (t, 2H, J=8 Hz), 3.67 (s, 3H), 3.16 (t, 2H, J=8 Hz), 2.25 (s, 6H), 2.19 (q, 2H, J=8 Hz); $^{19}$F-NMR (MeOH-$d_4$) δ −55.6; MS (ES) 624.2 (M+H).

Example 124

Preparation of 4-((3-(3-(4-chloro-3,5-dimethylphenoxy)propyl)-2-(trifluoromethyl)-7-(1,3,5-trimethyl-1H-pyrazol-4-yl)-1H-indol-1-yl)methyl)benzoic acid The title compound (18 mg, 86%) was prepared according to the procedure described in Example 117 Step A using methyl 4-((7-bromo-3-(3-(4-chloro-3,5-dimethylphenoxy)propyl)-2-(trifluoromethyl)-1H-indol-1-yl)methyl)benzoate and 1,3,5-trimethyl-4-(4,4,5,5-tetramethyl-1,3,2-dioxaborolan-2-yl)-1H-pyrazole Under the reaction condition, the methyl ester was also hydrolyzed to give the title compound. $^1$H-NMR (MeOH-$d_4$) δ 7.70 (d, 2H, J=8 Hz), 7.65 (d, 1H, J=8 Hz) 7.08 (t, 1H, J=8 Hz), 6.83 (d, 1H, J=8 Hz), 6.57 (s, 2H), 6.25 (d, 2H, J=8 Hz), 5.14 (q, 2H, J=16 Hz), 3.91 (t, 2H, J=8 Hz), 3.52 (s, 3H), 3.16 (t, 2H, J=8 Hz), 2.20 (s, 6H), 2.06 (q, 2H, J=8 Hz); $^{19}$F-NMR (MeOH-$d_4$ δ −55.6; MS (ES) 624.2 (M+H).

Example 125

Preparation of 3-((3-(3-(4-chloro-3,5-dimethylphenoxy)propyl)-2-methyl-7-(1,3,5-trimethyl-1H-pyrazol-4-yl)-1H-indol-1-yl)methyl)-N-(methylsulfonyl)benzamide To a solution of 3-((3-(3-(4-chloro-3,5-dimethylphenoxy)propyl)-7-(3,5-dimethyl-1H-pyrazol-4-yl)-2-methyl-1H-indol-1-yl)methyl)benzoic acid (30 mg, 0.05 mmol) in $CH_2Cl_2$ was added EDCI (20 mg, 0.1 mmol), DMAP (10 mg, 0.09 mmol) and methanesulfonamide (10 mg, 0.078 mmol). The reaction mixture was stirred for 12 h at rt then concentrated in vacuo. The residue was purified by reverse phase prep. HPLC (Phenomenex Gemini C18, H₂O/CH₃CN gradient from 60% to 95% CH₃CN, 0.1% TFA) to yield the title compound (16 mg, 50%). $^1$HNMR: (400 MHz) CDCl₃ δ: 1.25 (s, 3H), 1.67 (s, 3H), 2.16 (t, 2H, J=11 Hz), 2.31 (s, 9H), 3.00 (t, 2H, J=14 Hz), 3.40 (s, 3H), 3.87 (s, 3H), 3.91 (t, 2H, J=12 Hz), 4.93 (s, 2H), 6.41 (d, 1H, J=7.7 Hz), 6.62 (s, 2H), 6.68 (d, 1H, J=6.9 Hz), 7.03 (s, 1H) 7.10 (t, 1H, J=15 Hz), 7.18 (t, 1H, J=15 Hz), 7.61 (d, 1H, J=7.8 Hz), 7.75 (d, 1H, J=7.8 Hz); MS (ES) 647.2 (M+H).

Example 126

Preparation of 3-((3-(3-(4-chloro-3,5-dimethylphenoxy)propyl)-2-methyl-7-(1,3,5-trimethyl-1H-pyrazol-4-yl)-1H-indol-1-yl)methyl)-N-(pyridin-2-ylsulfonyl)benzamide The title compound was prepared according to the procedure described in Example 126 using 3-((3-(3-(4-chloro-3,5-dimethylphenoxy)propyl)-7-(3,5-dimethyl-1H-pyrazol-4-yl)-2-methyl-1H-indol-1-yl)methyl)benzoic acid and pyridine-2-sulfonamide. MS (ES) 710.2 (M+H), tR: 1.497 min.

Example 127

Preparation of 3-((3-(3-(4-chloro-3,5-dimethylphenoxy)propyl)-2-methyl-7-(1,3,5-trimethyl-1H-pyrazol-4-yl)-1H-indol-1-yl)methyl)-N-(phenylsulfonyl)benzamide The title compound was prepared according to the procedure described in Example 126 using 3-((3-(3-(4-chloro-3,5-dimethylphenoxy)propyl)-7-(3,5-dimethyl-1H-pyrazol-4-yl)-2-methyl-1H-indol-1-yl)methyl)benzoic acid and benzenesulfonamide. MS (ES) 709.2 (M+H), tR: 1.602 min.

Example 128

Preparation of 3-((3-(3-(4-chloro-3,5-dimethylphenoxy)propyl)-2-methyl-7-(1,3,5-trimethyl-1H-pyrazol-4-yl)-1H-indol-1-yl)methyl)-N-(pyridin-4-ylsulfonyl)benzamide The title compound was prepared according to the procedure described in Example 126 using 3-((3-(3-(4-chloro-3,5-dimethylphenoxy)propyl)-7-(3,5-dimethyl-1H-pyrazol-4-yl)-2-methyl-1H-indol-1-yl)methyl)benzoic acid and pyridine-4-sulfonamide. MS (ES) 710.2 (M+H), tR: 1.462 min.

Example 129

Preparation of 3-((3-(3-(4-chloro-3,5-dimethylphenoxy)propyl)-2-methyl-7-(1,3,5-trimethyl-1H-pyrazol-4-yl)-1H-indol-1-yl)methyl)-N-(pyridin-3-ylsulfonyl)benzamide The title compound was prepared according to the procedure described in Example 126 using 3-((3-(3-(4-chloro-3,5-dimethylphenoxy)propyl)-7-(3,5-dimethyl-1H-pyrazol-4-yl)-2-methyl-1H-indol-1-yl)methyl)benzoic acid and pyridine-3-sulfonamide. MS (ES) 710.2 (M+H), tR: 1.497 min.

Example 130

Preparation of 4-((3-(3-(4-chloro-3,5-dimethylphenoxy)propyl)-2-methyl-7-(1,3,5-trimethyl-1H-pyrazol-4-yl)-1H-indol-1-yl)methyl)-N-(phenylsulfonyl)benzamide The title compound was prepared according to the procedure described in Example 126 using 4-((3-(3-(4-chloro-3,5-dimethylphenoxy)propyl)-7-(3,5-dimethyl-1H-pyrazol-4-yl)-2-methyl-1H-indol-1-yl)methyl)benzoic acid and benzenesulfonamide. MS (ES) 709.2 (M+H), tR: 1.602 min.

Example 131

Preparation of 4-((3-(3-(4-chloro-3,5-dimethylphenoxy)propyl)-2-methyl-7-(1,3,5-trimethyl-1H-pyrazol-4-yl)-1H-indol-1-yl)methyl)-N-(methylsulfonyl)benzamide The title compound was prepared according to the procedure described in Example 126 using 4-((3-(3-(4-chloro-3,5-dimethylphenoxy)propyl)-7-(3,5-dimethyl-1H-pyrazol-4-yl)-2-methyl-1H-indol-1-yl)methyl)benzoic acid and mathanesulfonamide. MS (ES) 647.2 (M+H).

Example 132

Preparation of 4-((3-(3-(4-chloro-3,5-dimethylphenoxy)propyl)-2-methyl-7-(1,3,5-trimethyl-1H-pyrazol-4-yl)-1H-indol-1-yl)methyl)-N-(pyridin-2-ylsulfonyl)benzamide The title compound was prepared according to the procedure described in Example 126 using 4-((3-(3-(4-chloro-3,5-dimethylphenoxy)propyl)-7-(3,5-dimethyl-1H-pyrazol-4-yl)-2-methyl-1H-indol-1-yl)methyl)benzoic acid and pyridine-2-sulfonamide. $^1$HNMR: (400 MHz) CDCl₃ δ: 1.89 (s, 3H), 2.15 (m, 2H) 2.25 (s, 3H), 2.35 (s, 3H), 2.40 (s, 6H), 2.65 (s, 3H) 3.00 (t, 2H), 3.70 (s, 3H), 3.87 (t, 2H) 5.00 (d, 2H), 6.45 (d, 2H) 6.65 (s, 2H) 6.70 (d, 1H), 7.1 (t, 1H), 7.55 (m, 4H), 8.0 (t, 1H), 8.3 (d, 1H), 8.65 (d, 1H); MS (ES) 710.2 (M+H), tR: 1.489 min.

Example 133

Preparation of 3-(3-(3-(4-chloro-3,5-dimethylphenoxy)propyl)-7-(3,5-dimethyl-1-(pyridin-3-ylmethyl)-1H-pyrazol-4-yl)-2-methyl-1H-indol-1-yl)propanoic acid Title compound was prepared (9.0 mg, 0.015 mmol) according to procedures described in Example 105 by using 3-(3-(3-(4-chloro-3,5-dimethylphenoxy)propyl)-7-(3,5-dimethyl-1H-pyrazol-4-yl)-2-methyl-1H-indol-1-yl)propanoic acid (25 mg, 0.05 mmol) and 2-(bromomethyl)pyridine hydrobromide (38 mg, 0.15 mmol). MS (ES) 585.3 (M+H), tR: 1.368 min.

Example 134

Preparation of 6-((6-chloro-3-(3-(4-chloro-3,5-dimethylphenoxy)propyl)-2-methyl-7-(1,3,5-trimethyl-1H-pyrazol-4-yl)-1H-indol-1-yl)methyl)nicotinic acid The title compound was prepared according to procedures described in Example 102 Step B using 6-chloro-3-(3-(4- chloro-3,5-dimethylphenoxy)propyl)-2-methyl-7-(1,3,5-trimethyl-1H-pyrazol-4-yl)-1H-indole and ethyl 6-(bromomethyl)nicotinate. LCMS (ESI) (>99%, ELSD), m/z: 605.2 (M+H).

Example 135

Preparation of 3-(3-(3-(4-chloro-3,5-dimethylphenoxy)propyl)-2-(trifluoromethyl)-1H-indol-1-yl)propanoic acid Step A Preparation of 3-(3-(4-chloro-3,5-dimethylphenoxy)propyl)-2-(trifluoromethyl)-1H-indole: To a solution of CuOAc (1.9 mg, 0.016 mmol) and 1-(trifluoromethyl)-1$\lambda^3$-benzo[d][1,2]iodaoxol-3(1H)-one (60%, 130 mg, 0.24 mmol) in MeOH (1.5 ml) was added 3-(3-(4-chloro-3,5-dimethylphenoxy)propyl)-1H-indole (50 mg, 0.16 mmol) under an Ar atmosphere at rt. The reaction mixture was stirred for 2 days, then diluted with Et$_2$O. To the mixture was added saturated NaHCO$_3$ solution (0.5 ml), and stirred for 30 min. The quenched reaction mixture was extracted with Et$_2$O. The combined organic layer was dried over MgSO$_4$, filtered and concentrated in vacuo. The residue was purified by reverse phase prep. HPLC (Phenomenex Gemini C18, H$_2$O/CH$_3$CN gradient from 50% to 95% CH$_3$CN, 0.1% TFA) to yield the title compound (46 mg, 75%) compound as a pale yellow solid. MS (ES) 382.2 (M+H).

Step B: The title compound was prepared according to procedures described in Example 101 Step D using 3-(3-(4-chloro-3,5-dimethylphenoxy)propyl)-2-(trifluoromethyl)-1H-indole and ethyl acrylate. MS (ES) 482.2 (M+H).

Example 136

Assays for Bcl-2 Family Proteins Activity

The in vitro modulation of Bcl-2 family proteins was determined as follows.
Bak Peptide Binding Assay
General
The compounds of the present invention can be demonstrated to compete for binding with fluorescently labeled pro-apoptotic peptides from relevant BH3 domains and exhibit selectivity for Mcl-1 over Bcl-xL and Bcl-2.
Assay
Compound affinity was measured using a fluorescence polarization anisotropy competition assay. Anisotropy measurements were carried out in 384-well, black, flat-bottom plates (Greiner Bio-one, Monroe, N.C., USA). The assay was run using a fluorescein isothiocyanate-labeled BH3 peptide derived from Bak (FITC-AHx-GQVGRQLAIIGD-DINR-NH$_2$) that was purchased from GenScript (Piscataway, N.J.) at >95% purity and used without further purification. 10 nM FITC-Bak peptide and 14 nM recombinant Mcl-1 (residues 172-327) were added to assay buffer (3 mM dithiothreitol, 50 mM NaCl, 20 mM Tris, pH 7.5). For selectivity assays, 40 nM Bcl-2 (residues 1-207$^{A96T, G110R}$, $\Delta$35-91, replaced with Bcl-xL$_{35-50}$) or 4 nM Bcl-xL (residues 1-209, loop 45-86 deleted) were incubated with 10 nM FITC-Bak in assay buffer.

Compounds are diluted in DMSO in a 10-point, 3-fold serial dilution scheme. 2.5 uL compound is added to 47.5 uL of assay buffer containing FITC-Bak and protein, for a final DMSO concentration of 5% and a top concentration of 20 uM. A FITC-Bak peptide alone (100% inhibition) and peptide plus protein (0% inhibition) control is included on each assay plate. The plate was mixed and incubated for 90 minutes at room temperature. Anisotropy is measured at excitation wavelength 480 nm and emission wavelength 535 nm using an EnVision Multi-label plate reader (PerkinElmer, Wellesley, Mass., USA). Fluorescence anisotropy is plotted against compound concentration to generate an IC$_{50}$ (inhibitor concentration at which 50% of bound peptide is displaced) by fitting the data to a 4-parameter logistic model using XLFit software (Guildford, Surrey, UK). IC$_{50}$ is converted to a binding dissociation constant (K$_i$ value) according to the formula of Wang Z. FEBS Lett (1996) 3, 245:

$$K_i = [I]_{50}/([L]_{50}/K_d + [P]_0/K_d + 1)$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, K$_d$ represents the dissociation constant of the FITC peptide probe. The results for representative compounds are shown in Tables 3 and 4.

These data demonstrate the utility of representative compounds having Formula I or Formula II as inhibitors of the activity of Mcl-1, Bcl-xL and Bcl-2 proteins to bind peptides from relevant BH3 domains.

TABLE 3. K$_i$ For Representative Compounds Having Formula I or Formula II For Inhibition of Mcl-I Protein

TABLE 3

| K$_i$'s for representative compounds for inhibition of Mcl-1 | |
|---|---|
| Examples | K$_i$ |
| 2 | 10 μM-50 μM |
| 1, 3, 4, 6, 8, 10, 11, 16, 17, 18, 19, 22, 23, 24, 26, 27, 28, 47, 50, 54, 61, 62, 97, 110, 119 | 1 μM-9.99 μM |
| 5, 9, 12, 15, 21, 33, 48, 49, 51, 52, 53, 55, 56, 59, 60, 112 | 501 nM-999 nM |
| 7, 14, 29, 31, 34, 38, 39, 40, 42, 58, 69, 109 | 301 nM-500 nM |
| 13, 20, 25, 30, 32, 35, 36, 37, 41, 43, 44, 45, 57, 64, 65, 66, 67, 68, 101, 107, 108, 115, 116, 128, 129 | 101 nM-299 nM |
| 46, 70, 71, 72, 73, 74, 75, 76, 77, 78, 79, 80, 81, 82, 83, 84, 85, 86, 87, 88, 89, 90, 91, 92, 93, 94, 95, 96, 98, 99, 100, 102, 103, 104, 105, 106, 111, 113, 114, 117, 118, 120, 121, 122, 123, 124, 125, 126, 127, 130, 131, 132, 133, 134, 135 | ≤100 nM |

TABLE 4. K$_i$ For Representative Compounds Having Formula I or Formula II For Inhibitory selectivity of Mcl-I Protein over Bcl-xL and Bcl-2 proteins.

TABLE 4

| K$_i$'s (in μM) for representative compounds for inhibition of Bcl-2 family proteins | | | |
|---|---|---|---|
| Example | Mcl-1 | Bcl-2 | Bcl-xL |
| 20 | 0.36 | | 10 |
| 44 | 0.17 | | 7.9 |
| 76 | 0.007 | 7.1 | 7.9 |
| 99 | 0.011 | 2.9 | 9.3 |
| 100 | 0.010 | 1.2 | 4.7 |

Cellular Viability of a Human Tumor Cell Lines

Human cancer cell lines NCI-H23, K562, NCI-H929, and MV-4-11 were cultured in media supplemented with 10% fetal bovine serum (FBS). To evaluate compound effect on cellular proliferation, cells were plated at 1,000 cells/well in 96-well tissue culture plates in a total volume of 90 uL medium supplemented with 10% FBS (Sigma, Saint Louis, Mo.). 24 hours later, 10 uL of compound (in a 2-fold serial dilution) is added to the cells for a top concentration of 50 uM and a final DMSO concentration <1%. After 72 hours, cell number was measured using the CellTiter-Glo Luminescent assay according to manufacturer's recommendations (Promega, Madison, Wis.). A viability assay in reduced serum was also conducted. Cells were plated at 5,000 cells/well in 96-well plates in a total volume of 100 uL medium supplemented with 10% FBS (Sigma, Saint Louis, Mo.). 24 hours later, the medium was replaced with 90 uL medium containing 1% FBS and the assay conducted as described. $EC_{50}$ values were determined by plotting growth against compound concentration in a 4-parameter logisitic model in XLFit.

TABLE 5

$EC_{50}$'s (in µM) for representative compounds on cellular proliferation of human cancer cell lines

| | K562 | NCI-H929 | NV-4-11 | NCI-H23 |
|---|---|---|---|---|
| Example 74 | 21.2 | | 11.5 | 19.8 |
| Example 76 | 17.1 | | 16.2 | |
| Example 78 | 10.0 | | 12.9 | |
| Example 104 | 24.8 | 20 | | |
| Example 117 | 14.8 | 8.8 | | |

TABLE 6

$EC_{50}$'s (in µM) for representative compounds on cellular viability of human cancer cell lines

| | K562 | NV-4-11 | NCI-H23 |
|---|---|---|---|
| Example 70 | 4.1 | | 5.8 |
| Example 71 | 7.0 | | 9.9 |
| Example 74 | 2.0 | | 5.4 |
| Example 76 | | 2.8 | |
| Example 83 | | 1.9 | |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A compound of formula II:

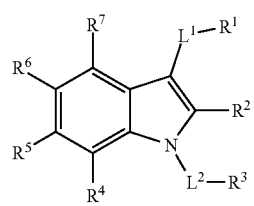

or a pharmaceutically acceptable salt thereof, wherein:

$L^1$ is a bivalent $C_{1-6}$ hydrocarbon chain;

$R^1$ is —C(O)OH or —C(O)NHS(O)$_2$R;

$R^2$ is hydrogen, —CN, —CH$_3$, or —CF$_3$;

R is optionally substituted $C_{1-6}$ aliphatic or phenyl;

$L^2$ is an unsubstituted bivalent $C_{3-6}$ hydrocarbon chain wherein one or two methylene units of $L^2$ are optionally and independently replaced with —O—, —S—, or —NR'—;

each R' is independently hydrogen or optionally substituted $C_{1-4}$ alkyl;

$R^3$ is 3,5-dimethyl-4-chlorophenyl or naphthyl;

each of $R^4$, $R^5$, $R^6$, and $R^7$ is independently selected from hydrogen and halo.

2. The compound of claim 1, or a pharmaceutically acceptable salt thereof, wherein $L^2$ is —(CH$_2$)$_3$O—.

3. The compound of claim 1, selected from the group consisting of

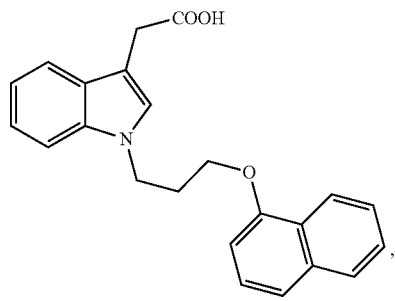

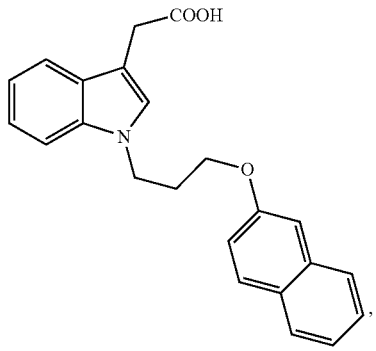

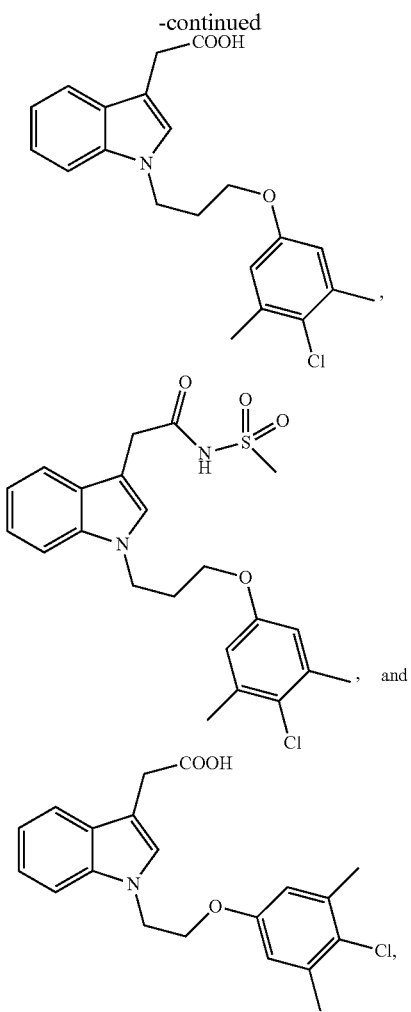

or a pharmaceutically acceptable salt thereof.

4. A pharmaceutical composition comprising a therapeutically effective amount of a compound of claim 1, or a pharmaceutically acceptable salt thereof, and optionally a pharmaceutically acceptable carrier.

5. The pharmaceutical composition of claim 4 further comprising one or more other therapeutically active agents selected from the group of anti-cancer agents consisting of alkylating agents, angiogenesis inhibitors, antibodies, antimetabolites, antimitotics, antiproliferatives, aurora kinase inhibitors, Bcl-2 family protein inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis proteins (IAPB), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids, deltoids, plant alkaloids, and topoisomerase inhibitors.

6. A method of inhibiting a protein selected from Mcl-1, Bcl-xL, and Bcl-2, comprising administering to a mammalian patient in need thereof a therapeutically effective amount of at least one compound of claim 1, or a pharmaceutically acceptable salt thereof, and, optionally, an additional therapeutic agent selected from the group of anti-cancer agents consisting of alkylating agents, angiogenesis inhibitors, antibodies, antimetabolites, antimitotics, antiproliferatives, aurora kinase inhibitors, Bcl-2 family protein inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis proteins (IAPB), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids, deltoids, plant alkaloids, and topoisomerase inhibitors.

7. A method for treating a disease or disorder associated with the expression or over-expression of Mcl-1, comprising administering to a subject in need thereof, a therapeutically effective amount of a compound of claim 1, or a pharmaceutically acceptable salt thereof, wherein:
the disease or disorder is selected from the group consisting of leukemia, lung cancer, and myeloma.

8. A method for treating a disease or disorder associated with the expression or over-expression of anti-apoptotic Bcl-2 family protein members, comprising administering to a mammalian patient in need of treatment a therapeutically effective amount of at least one compound of claim 1, and, optionally, an additional therapeutic agent wherein:
(a) the disease or disorder is selected from the group consisting of leukemia, lung cancer, and myeloma; and
(b) the additional therapeutic agent is selected from the group of anti-cancer agents consisting of alkylating agents, angiogenesis inhibitors, antibodies, antimetabolites, antimitotics, antiproliferatives, aurora kinase inhibitors, Bcl-2 family protein inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (1APs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids, deltoids, plant alkaloids, and topoisomerase inhibitors.

9. The compound of claim 1, or a pharmaceutically acceptable salt thereof, wherein
$R^4$, $R^5$, $R^6$, and $R^7$ are hydrogen.

10. The compound of claim 9, or a pharmaceutically acceptable salt thereof, wherein:

R is $C_{1-6}$ aliphatic.

11. The compound of claim 9, or a pharmaceutically acceptable salt thereof, wherein:

$L^1$ is —$CH_2$—.

12. The compound of claim 9, or a pharmaceutically acceptable salt thereof, wherein:

$L^2$ is —$(CH_2)_3O$—.

13. The compound of claim 1, or a pharmaceutically acceptable salt thereof, wherein $L^1$ is a bivalent $C_{1-3}$ hydrocarbon chain.

14. The compound of claim 1, or a pharmaceutically acceptable salt thereof, wherein $L^2$ is an unsubstituted bivalent $C_{3-6}$ hydrocarbon chain wherein one methylene unit of $L^2$ is replaced with —O—.

15. The compound of claim 9, or a pharmaceutically acceptable salt thereof, wherein $L^1$ is a bivalent $C_{1-3}$ hydrocarbon chain.

16. The compound of claim 9, or a pharmaceutically acceptable salt thereof, wherein $L^2$ is an unsubstituted bivalent $C_{3-6}$ hydrocarbon chain wherein one methylene unit of $L^2$ is replaced with —O—.

17. The compound of claim 15, or a pharmaceutically acceptable salt thereof, wherein $L^2$ is an unsubstituted bivalent $C_{3-6}$ hydrocarbon chain wherein one methylene unit of $L^2$ is replaced with —O—.

18. The compound of claim 17, or a pharmaceutically acceptable salt thereof, wherein $R^1$ is C(O)OH.

19. The compound of claim 18, or a pharmaceutically acceptable salt thereof, wherein $R^2$ is hydrogen.

* * * * *